US009796761B2

(12) United States Patent
Narimatsu et al.

(10) Patent No.: US 9,796,761 B2
(45) Date of Patent: Oct. 24, 2017

(54) GLYCAN MARKERS AS MEASURE OF DISEASE STATE OF HEPATIC DISEASES

(75) Inventors: Hisashi Narimatsu, Ibaraki (JP); Jun Hirabayashi, Ibaraki (JP); Yuzuru Ikehara, Ibaraki (JP); Takashi Angata, Ibaraki (JP); Hiroyuki Kaji, Ibaraki (JP); Atsushi Kuno, Ibaraki (JP); Takashi Ohkura, Ibaraki (JP); Toshihide Shikanai, Ibaraki (JP); Maki Sogabe, Ibaraki (JP); Akira Togayachi, Ibaraki (JP); Makoto Ochou, Ibaraki (JP); Yasuhito Tanaka, Aichi (JP); Masashi Mizokami, Chiba (JP)

(73) Assignees: NATIONAL INSTITUTE OF ADVANCED INDUSTRIAL SCIENCE AND TECHNOLOGY, Tokyo (JP); PUBLIC UNIVERSITY CORPORATION NAGOYA CITY UNIVERSITY, Aichi (JP); NATIONAL CENTER FOR GLOBAL HEALTH AND MEDICINE, Tokyo (JP); GLYCOBIOMARKER LEADING INNOVATION CO., LTD., Ibaraki (JP)

(*) Notice: Subject to any disclaimer, the term of this patent is extended or adjusted under 35 U.S.C. 154(b) by 0 days.

(21) Appl. No.: 13/384,031

(22) PCT Filed: Jul. 12, 2010

(86) PCT No.: PCT/JP2010/061791
§ 371 (c)(1),
(2), (4) Date: Mar. 27, 2012

(87) PCT Pub. No.: WO2011/007764
PCT Pub. Date: Jan. 20, 2011

(65) Prior Publication Data
US 2012/0190576 A1    Jul. 26, 2012

(30) Foreign Application Priority Data
Jul. 14, 2009    (JP) .................................. 2009-165795

(51) Int. Cl.
| C40B 30/04 | (2006.01) |
| C07K 14/00 | (2006.01) |
| C07K 9/00 | (2006.01) |
| C07K 14/47 | (2006.01) |
| G01N 33/574 | (2006.01) |

(52) U.S. Cl.
CPC ............... *C07K 9/00* (2013.01); *C07K 14/47* (2013.01); *G01N 33/57438* (2013.01); *G01N 33/57469* (2013.01); *G01N 2400/02* (2013.01); *G01N 2800/085* (2013.01)

(58) Field of Classification Search
USPC ....................................................... 530/300
See application file for complete search history.

(56) References Cited

U.S. PATENT DOCUMENTS

| 5,460,974 A | 10/1995 | Kozak et al. |
| 2002/0081312 A1 | 6/2002 | Priest et al. |
| 2002/0107179 A1 | 8/2002 | Potts et al. |
| 2004/0058409 A1 | 3/2004 | Antoine et al. |
| 2006/0040345 A1 | 2/2006 | Hoesel et al. |
| 2006/0141528 A1* | 6/2006 | Aebersold .......... G01N 33/6842 435/7.1 |
| 2007/0037221 A1 | 2/2007 | Block et al. |
| 2007/0059782 A1 | 3/2007 | Graham et al. |
| 2009/0117591 A1 | 5/2009 | Corrales Izquierdo et al. |
| 2009/0166224 A1 | 7/2009 | Yang et al. |

FOREIGN PATENT DOCUMENTS

| CN | 200680031338 | | 6/2006 | |
| EP | 1918715 A1 | | 5/2008 | |
| JP | 08-184594 A | | 7/1996 | |
| JP | 10-026622 A | | 1/1998 | |
| JP | 2007-161633 A | | 6/2007 | |
| JP | 2009-500597 A | | 1/2009 | |
| WO | WO 00/47611 | * | 8/2000 | ............. C07K 14/00 |
| WO | WO 01/35105 A1 | | 5/2001 | |
| WO | WO 2006/121892 A2 | | 11/2006 | |
| WO | WO 2007/120252 A2 | | 10/2007 | |
| WO | WO 2008/021290 | * | 2/2008 | ............... C12Q 1/00 |

OTHER PUBLICATIONS

Zhu et al., Journal of Clinical Oncology (2008) vol. 26, No. 16, 2707-2716.*
Kvale et al., J. Clin. Pathol. (1992) 45, 568-571.*
Subject Matter Eligibility Examples: Life Sciences; available at https://www.uspto.gov/sites/default/files/documents/ieg-may-2016-ex.pdf.*
Basili, Stefania et al., "Lipoprotein (a) serum levels in patients with hepatocarcinoma," Clinica Chimica Acta, vol. 262, pp. 53-60.
Block, Timothy M. et al., "Use of targeted glycoproteomics to identify serum glycoproteins that correlate with liver cancer in woodchucks and humans," PNAS, Jan. 2005, vol. 102, No. 3, pp. 779-784.
Hachem, Houda et al., "Serum Apolipoproteins A-I, A-II and B in Hepatic Metastases Comparison with other Liver Diseases: Hepatomas and Cirrhosis," J. Clin Chem. Clin. Biochem., vol. 24, 1986, pp. 161-166.

(Continued)

*Primary Examiner* — Marcela M Cordero Garcia
*Assistant Examiner* — Catherine Mader
(74) *Attorney, Agent, or Firm* — Brinks Gilson & Lione

(57) ABSTRACT

The present invention is directed to developing a glycan markers capable of detecting a hepatic disease, and more specifically to developing a glycan marker indicating a hepatic disease-state. Furthermore, the present invention is also directed to developing a glycan marker capable of distinguishing hepatic disease-states with the progress of hepatocarcinoma. The present inventors identified, among the serum glycoproteins, glycopeptides and glycoproteins in which a glycan structure specifically changes due to a hepatic diseases including hepatocarcinoma and provide these as novel glycan markers (glycopeptide and glycoprotein) specific to hepatic disease-states.

5 Claims, 35 Drawing Sheets
(7 of 35 Drawing Sheet(s) Filed in Color)

(56) References Cited

OTHER PUBLICATIONS

Harazono, Akira et al., "Site-specific glycosylation analysis of human apolipoprotein B100 using LC/ESI MS/MS," Glycobiology, 2005, vol. 15, No. 5, pp. 447-462.

Ikehara, Yuzuru et al., "Search for Glycan Biomarker for Hepatocellular Carcinoma," Biotechnology Symposium Proceedings, 2008, vol. 26, pp. 21-26 (17 pages with English translation).

Ito, Hiromi et al., "Strategy for Glycoproteomics: Identification of Glyco-Alteration Using Multiple Glycan Profiling Tools," Journal of Proteome Research, 2009, vol. 8, pp. 1358-1367.

Kaji, Hiroyuki et al., "Glycoproteomics in Strategy for Searching Disease Biomarker," Biotechnology Symposium Proceedings, 2008, vol. 26, pp. 125-126 (7 pages with English translation).

Morelle, Willy et al., "Mass spectrometric approach for screening modifications of total serum N-glycome in human diseases: application to cirrhosis," Glycobiology, 2006, vol. 16, No. 4, pp. 281-293.

Tarantino, G. et al., "Serum APO B Levels in Hepatocellular Failure," 1983, Clinica, Medica, University of Medicine and Surgery, Naples, Italy, pp. 7S-18S.

International Search Report for International Application No. PCT/JP2010/061791, dated Sep. 28, 2010, 4 pages.

International Preliminary Report on Patentability for International Application No. PCT/JP2010/061791, dated Mar. 13, 2012, 6 pages.

Inohara, Hidenori et al., "Interactions between Galectin-3 and Mac-2-Binding Protein Mediate Cell-Cell Adhesion," *Cancer Research*, Oct. 1, 1996, 56, pp. 4530-4534.

Lee, Eun Young et al., "Development of a rapid, immunochromatographic strip test for serum asialo α1-acid glycoprotein in patients with hepatic disease," *Journal of Immunological Methods*, 308, 2006, pp. 116-123.

Liljeblad, Mathias et al., "A Lectin Immunosensor Technique for Determination of α1-Acid Glycoprotein Fucosylation," *Analytical Biochemistry*, 288, 2001, pp. 216-224.

Matsumura, Kengo et al., "Carbohydrate Binding Specificity of a Fucose-specific Lectin from *Aspergillus oryzae*," *The Journal of Biological Chemistry*, vol. 282, No. 21, May 25, 2007, pp. 15700-15708.

Piller, Veronique et al., "Comparison of the carbohydrate-binding specificities of seven N-acetyl-D-galactosamine-recognizing lectins," Jul. 1990, *European Journal of Biochemistry*, vol. 191, Issue 2, pp. 461-466.

Ryden, Ingvar et al., "Diagnostic Accuracy of α1-Acid Glycoprotein Fucosylation for Liver Cirrhosis in Paitents Undergoing Hepatic Biopsy," *Clinical Chemistry*, 48:12, 2002, pp. 2195-2201.

International Search Report for International Application No. PCT/JP2010/061891, dated Sep. 21, 2010, 4 pages.

Matsuda, Atsushi et al., "Development of an all-in-one technology for glycan profiling targeting formalin-embedded tissue sections," Biochemical and Biophysical Research Communications, vol. 370, 2008, pp. 259-263.

Extended European Search Report for European Application No. 10799855.1, dated Dec. 18, 2012, 3 pages.

Jin-Bin Jia, Wen-Quan Wang, Hui-Chuan Sun, Xiao-Dong Zhu, Liang Liu, Peng-Yuan Zhuang, Ju-BoZhang, Wei Zhang, Hua-Xiang Xu, Ling-Qun Kong, Lu Lu, Wei-Zhon Wu, Lu Wang, and Zhao-You Tang; *High Expression of Macrophage Colong-Stimulating factor-1 Receptor in Peritumoral Liver Tissue is Associated with Poor Outcome in Hepatocellular Carcinoma After Curative Resection*, The Oncologist 2010;15:732-743 www.TheOncologist.com.

Chinese Office Action with English Translation of Application No. 201080040972.3, Dec. 2, 2013.

National Center for Biotechnology Information, macrophage colony-stimulating factor 1 receptor precursor [*Homo sapiens*], NCBI Reference Sequence: NP_005202.2, Dec. 19, 2002, available at the internet address <http://www.ncbi.nlm.nih.gov/protein/NP_005202>, 8 pages.

Third Office Action, and English language translation thereof, in Corresponding Chinese Application No. 201080040973.8, dated Oct. 11, 2014, 6 pages.

Cui, J. et al., "Methylation Status of c-fms Oncogene in HCC and its Relationship With Clinical Pathology", *World Journal of Gastroenterology*, vol. 7, No. 1, 2001, pp. 136-139.

Nakagawa, T. et al., "Fucosylation of N-Glycans Regulates the Secretion of Hepatic Glycoproteins into Bile Ducts", *The Journal of Biological Chemistry*, vol. 281, No. 40, Oct. 6, 2006, pp. 29797-29806.

Yang, D. et al., "The Relationship Between Point Mutation and Abnormal Expression of c-fms Oncogene in Hepatocellular Carcinoma", *Heparobiliary and Pancreatic Disease International*, vol. 3, No. 1, Feb. 15, 2004, pp. 86-89.

Li, J. et al., "Evidence for the Glycosylation of the Granulocyte Colony-Stimulating Factor Receptor", *Biochemical and Biophysical Research Communications*, vol. 205, No. 1, Nov. 30, 1994, pp. 238-244.

Song, Y. et al., "Immunohistochemical Observation of Macrophage Colony Stimulating Factor and Its Receptor in Breast Cancer and Hepatoma Tissues", *Chinese Journal of Cancer Research*, vol. 13, No. 1, Mar. 2001, pp. 1-4.

Yang, W. et al., "Co-Expression of Macrophage Colony-Stimulating Factor With Its Receptor in Human Hepatoma Cells and Its Potential Roles", *Chinese Journal of Cancer Research*, vol. 11, No. 2, Jun. 1999, pp. 79-84.

Lundy et al., An antibody-lectin sandwich assay for quantifying protein glycoforms, Molecular biotechnology, 12, (1999) 4 pgs.

Sasaki et al., Mac-2 binding protein is a cell-adhesive protein of the extracellular matrix which self-assembles into ring-like structures and binds β1 integrins, collagens and fibronectin, The EMBO Journal, 17(6) 1998, 8 pgs.

Ozaki et al., Expression and immunogenicity of a Tumor-Associated Antigen, 90K/Mac-2 Binding Protein, In Lung Carcinoma, American Cancer Society, 95(9), (2002), 9 pgs.

Office Action for U.S. Appl. No. 14/051,729 dated Feb. 4, 2016, 3 pgs.

\* cited by examiner

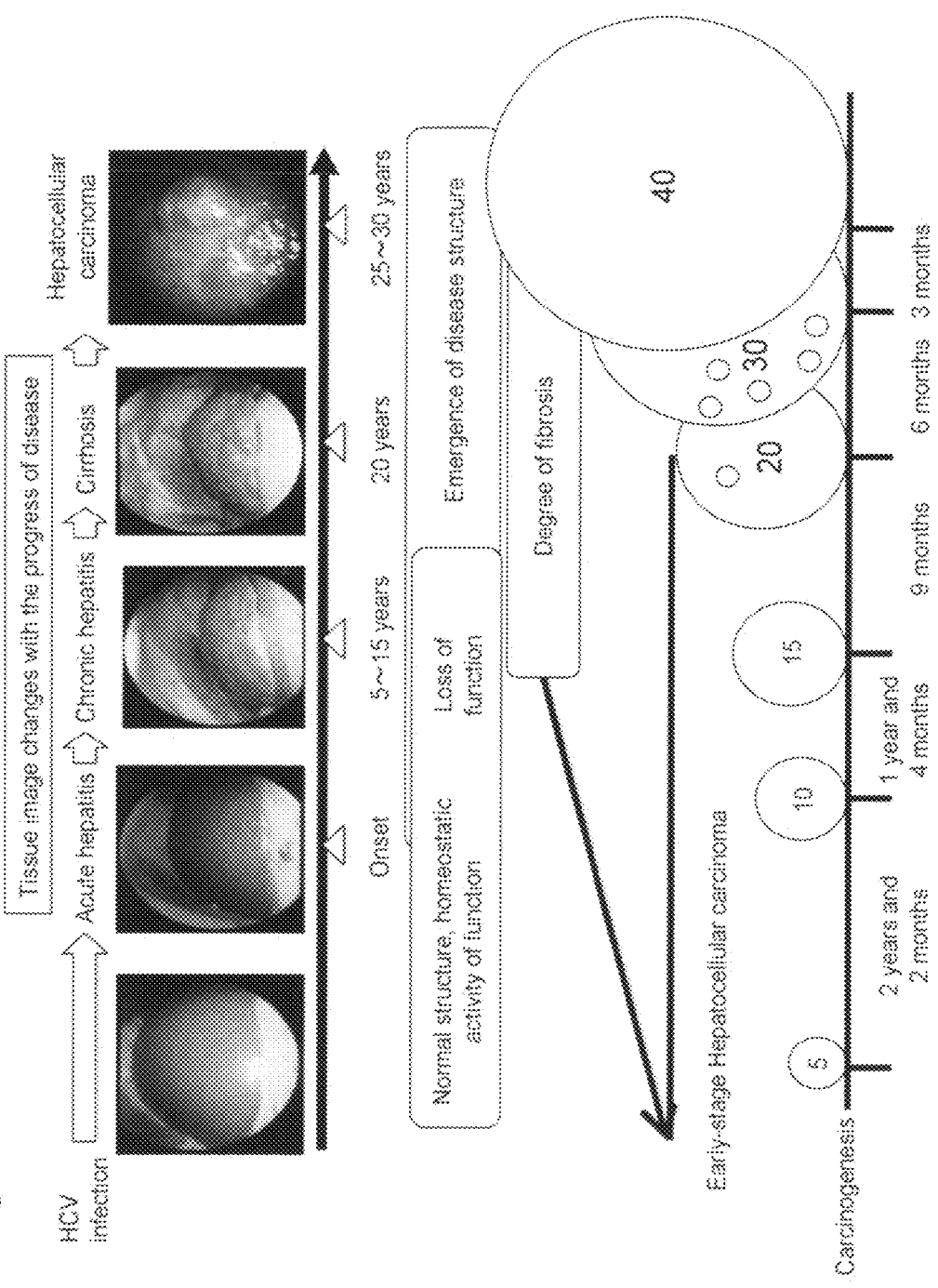

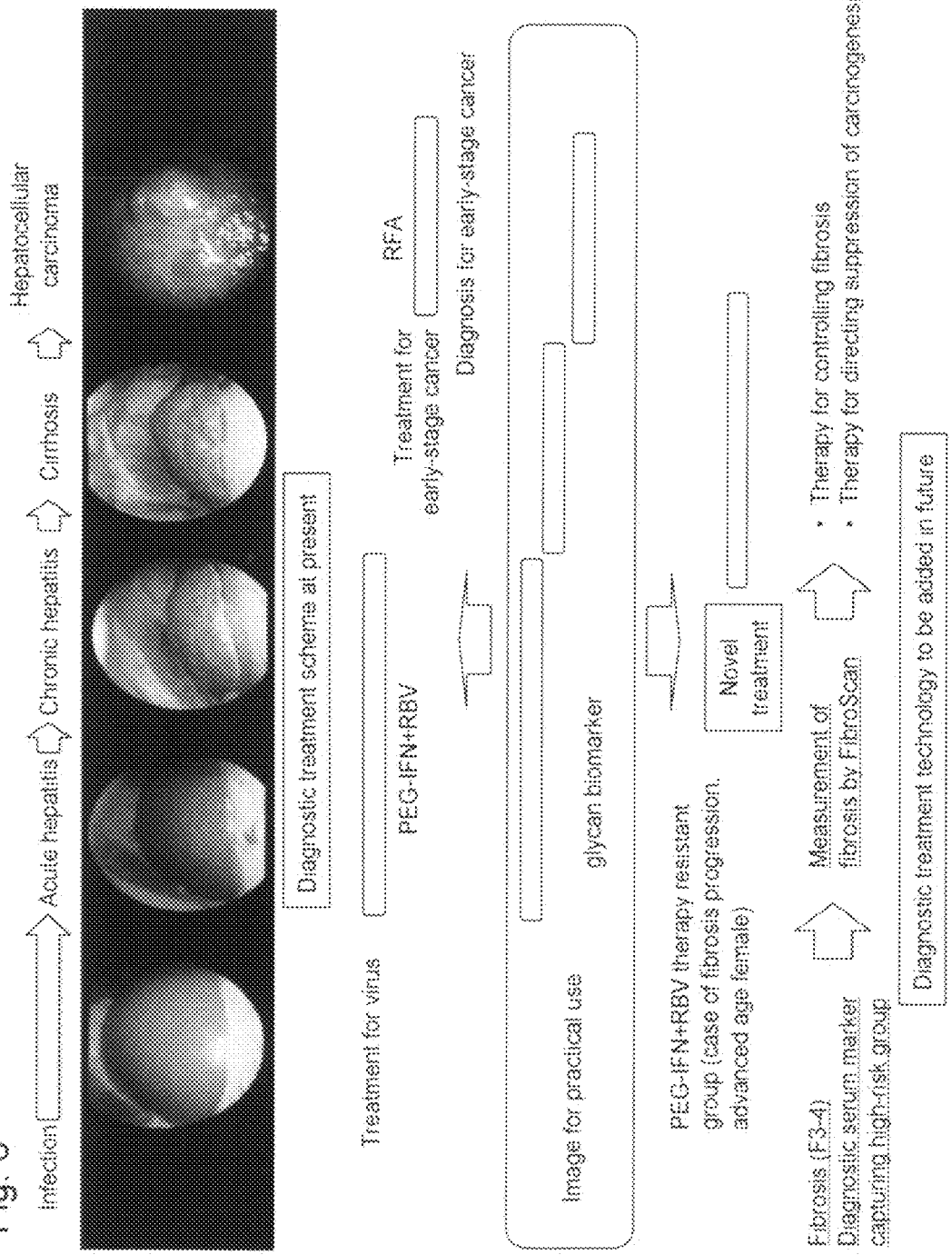

Peptide No. 26:
FQSPAGTEALFELHNISVADSANYSCVYVDLKPPFGGSAPSER; m/z=1159.436 : z=4+

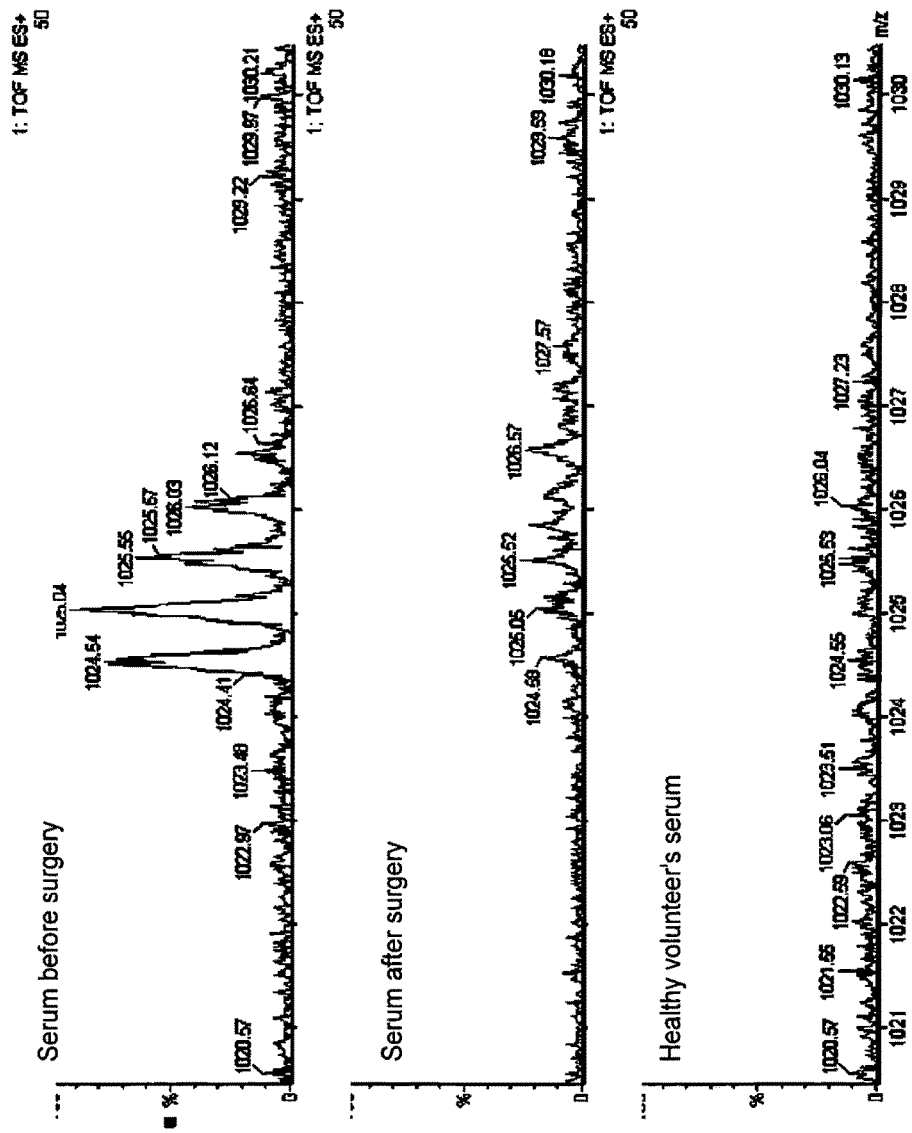

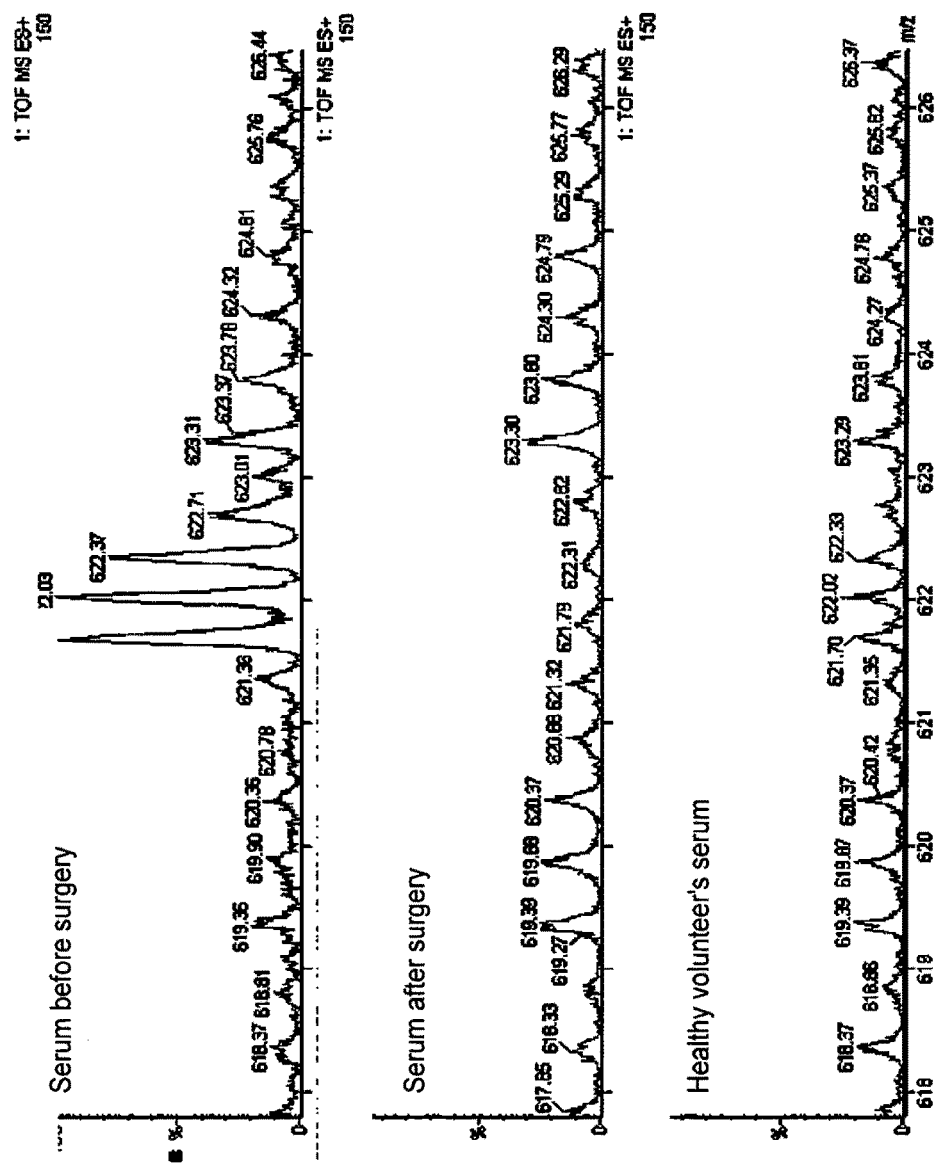
Fig. 9-3    Peptide No. 118: GNESALWDCKHDGWGK:m/z=621.6887,z=3+

Peptide No. 19: TLFCNASKEWDNTTECR : m/z=747.0729, z=3+

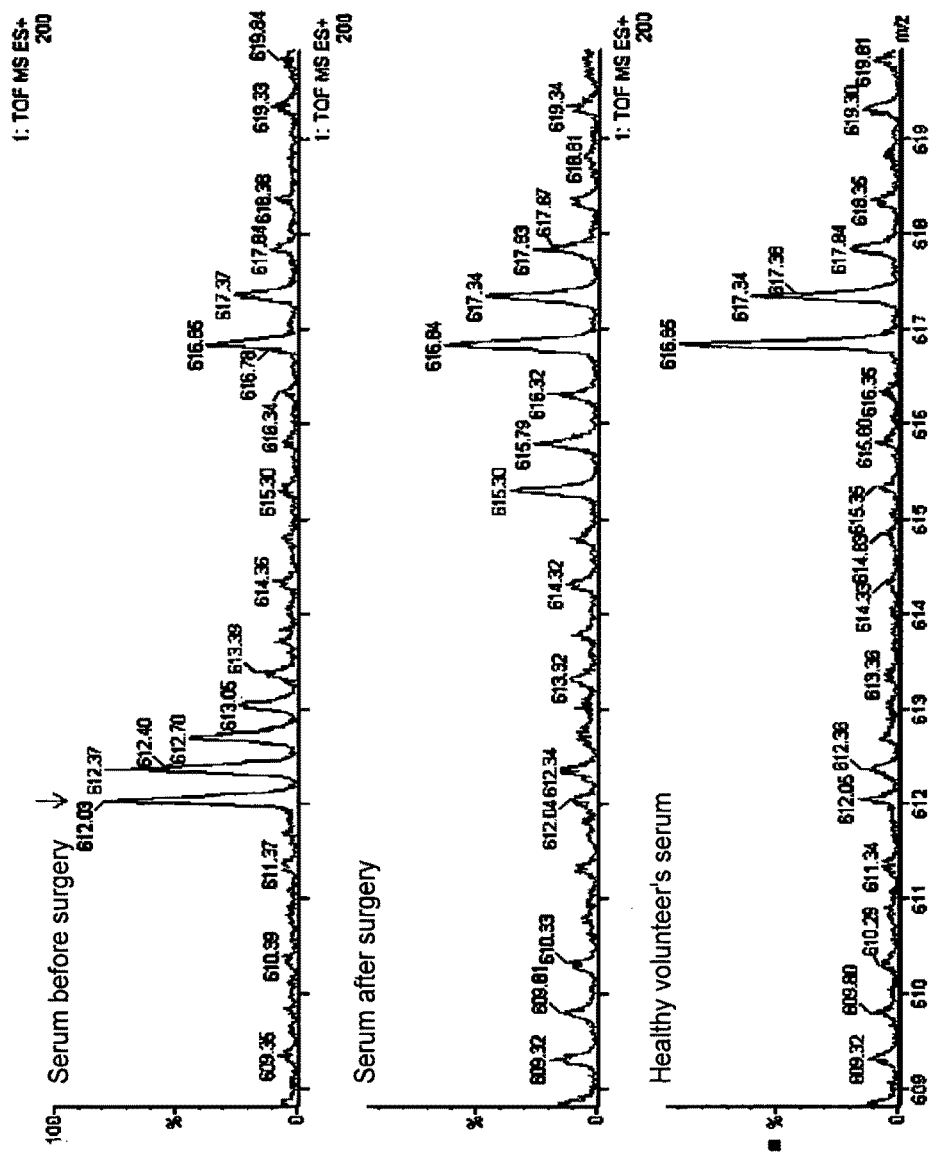

SEQUENCE LISTING

<160> NUMBER OF SEQ ID NOS: 183

<210> SEQ ID NO 1
<211> LENGTH: 15
<212> TYPE: PRT
<213> ORGANISM: Homo sapiens

```
<220> FEATURE:
<221> NAME/KEY: CARBOHYD
<222> LOCATION: (2)..(2)
<223> OTHER INFORMATION: N-LINKED (Asn) (Experimental)

<400> SEQUENCE: 1

Phe Asn Ser Ser Tyr Leu Gln Gly Thr Asn Gln Ile Thr Gly Arg
1               5                   10                  15

<210> SEQ ID NO 2
<211> LENGTH: 12
<212> TYPE: PRT
<213> ORGANISM: Homo sapiens
<220> FEATURE:
<221> NAME/KEY: CARBOHYD
<222> LOCATION: (3)..(3)
<223> OTHER INFORMATION: N-LINKED (Asn) (Experimental)

<400> SEQUENCE: 2

Val Ser Asn Val Ser Cys Gln Ala Ser Val Ser Arg
1               5                   10

<210> SEQ ID NO 3
<211> LENGTH: 19
<212> TYPE: PRT
<213> ORGANISM: Homo sapiens
<220> FEATURE:
<221> NAME/KEY: CARBOHYD
<222> LOCATION: (18)..(18)
<223> OTHER INFORMATION: N-LINKED (Asn) (Experimental)

<400> SEQUENCE: 3

Gly Thr Ala Gly Asn Ala Leu Met Asp Gly Ala Ser Gln Leu Met Gly
1               5                   10                  15

Glu Asn Arg

<210> SEQ ID NO 4
<211> LENGTH: 16
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Methionine sulfoxide ?Oxidation)
<220> FEATURE:
<221> NAME/KEY: CARBOHYD
<222> LOCATION: (8)..(8)
<223> OTHER INFORMATION: N-LINKED (Asn) (Experimental)

<400> SEQUENCE: 4

His Glu Glu Gly His Met Leu Asn Cys Thr Cys Phe Gly Gln Gly Arg
1               5                   10                  15

<210> SEQ ID NO 5
<211> LENGTH: 17
<212> TYPE: PRT
<213> ORGANISM: Homo sapiens
<220> FEATURE:
<221> NAME/KEY: CARBOHYD
<222> LOCATION: (9)..(9)
<223> OTHER INFORMATION: N-LINKED (Asn) (Experimental)

<400> SEQUENCE: 5

Arg His Glu Glu Gly His Met Leu Asn Cys Thr Cys Phe Gly Gln Gly
1               5                   10                  15

Arg
```

```
<210> SEQ ID NO 6
<211> LENGTH: 8
<212> TYPE: PRT
<213> ORGANISM: Homo sapiens
<220> FEATURE:
<221> NAME/KEY: CARBOHYD
<222> LOCATION: (2)..(2)
<223> OTHER INFORMATION: N-LINKED (Asn) (Experimental)

<400> SEQUENCE: 6

Val Asn Phe Thr Glu Ile Gln Lys
1               5

<210> SEQ ID NO 7
<211> LENGTH: 21
<212> TYPE: PRT
<213> ORGANISM: Homo sapiens
<220> FEATURE:
<221> NAME/KEY: CARBOHYD
<222> LOCATION: (7)..(7)
<223> OTHER INFORMATION: N-LINKED (Asn) (Experimental)
<220> FEATURE:
<221> NAME/KEY: CARBOHYD
<222> LOCATION: (18)..(18)
<223> OTHER INFORMATION: N-LINKED (Asn) (Experimental)

<400> SEQUENCE: 7

Leu Tyr Leu Gly Ser Asn Asn Leu Thr Ala Leu His Pro Ala Leu Phe
1               5                   10                  15

Gln Asn Leu Ser Lys
            20

<210> SEQ ID NO 8
<211> LENGTH: 11
<212> TYPE: PRT
<213> ORGANISM: Homo sapiens
<220> FEATURE:
<221> NAME/KEY: CARBOHYD
<222> LOCATION: (3)..(3)
<223> OTHER INFORMATION: N-LINKED (Asn) (Experimental)

<400> SEQUENCE: 8

Gly Leu Asn Val Thr Leu Ser Ser Thr Gly Arg
1               5                   10

<210> SEQ ID NO 9
<211> LENGTH: 13
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Methionine sulfoxide ?Oxidation)
<220> FEATURE:
<221> NAME/KEY: CARBOHYD
<222> LOCATION: (6)..(6)
<223> OTHER INFORMATION: N-LINKED (Asn) (Experimental)

<400> SEQUENCE: 9

Met Asp Gly Ala Ser Asn Val Thr Cys Ile Asn Ser Arg
1               5                   10

<210> SEQ ID NO 10
<211> LENGTH: 16
<212> TYPE: PRT
<213> ORGANISM: Homo sapiens
<220> FEATURE:
<221> NAME/KEY: CARBOHYD
<222> LOCATION: (8)..(8)
<223> OTHER INFORMATION: N-LINKED (Asn) (Experimental)
```

```
<400> SEQUENCE: 10

His Glu Glu Gly His Met Leu Asn Cys Thr Cys Phe Gly Gln Gly Arg
1               5                   10                  15

<210> SEQ ID NO 11
<211> LENGTH: 33
<212> TYPE: PRT
<213> ORGANISM: Homo sapiens
<220> FEATURE:
<221> NAME/KEY: CARBOHYD
<222> LOCATION: (16)..(16)
<223> OTHER INFORMATION: N-LINKED (Asn) (Experimental)

<400> SEQUENCE: 11

Gln Val Phe Pro Gly Leu Asn Tyr Cys Thr Ser Gly Ala Tyr Ser Asn
1               5                   10                  15

Ala Ser Ser Thr Asp Ser Ala Ser Tyr Tyr Pro Leu Thr Gly Asp Thr
            20                  25                  30

Arg

<210> SEQ ID NO 12
<211> LENGTH: 18
<212> TYPE: PRT
<213> ORGANISM: Homo sapiens
<220> FEATURE:
<221> NAME/KEY: CARBOHYD
<222> LOCATION: (13)..(13)
<223> OTHER INFORMATION: N-LINKED (Asn) (Experimental)

<400> SEQUENCE: 12

Asp Gln Cys Ile Val Asp Asp Ile Thr Tyr Asn Val Asn Asp Thr Phe
1               5                   10                  15

His Lys

<210> SEQ ID NO 13
<211> LENGTH: 14
<212> TYPE: PRT
<213> ORGANISM: Homo sapiens
<220> FEATURE:
<221> NAME/KEY: CARBOHYD
<222> LOCATION: (6)..(6)
<223> OTHER INFORMATION: N-LINKED (Asn) (Experimental)

<400> SEQUENCE: 13

Gly Ala Phe Ile Ser Asn Phe Ser Met Thr Val Asp Gly Lys
1               5                   10

<210> SEQ ID NO 14
<211> LENGTH: 14
<212> TYPE: PRT
<213> ORGANISM: Homo sapiens
<220> FEATURE:
<221> NAME/KEY: CARBOHYD
<222> LOCATION: (6)..(6)
<223> OTHER INFORMATION: N-LINKED (Asn) (Experimental)
<220> FEATURE:
<221> NAME/KEY: MOD_RES
<222> LOCATION: (9)..(9)
<223> OTHER INFORMATION: Methionine sulfoxide ?Oxidation)

<400> SEQUENCE: 14

Gly Ala Phe Ile Ser Asn Phe Ser Met Thr Val Asp Gly Lys
1               5                   10
```

```
<210> SEQ ID NO 15
<211> LENGTH: 21
<212> TYPE: PRT
<213> ORGANISM: Homo sapiens
<220> FEATURE:
<221> NAME/KEY: CARBOHYD
<222> LOCATION: (9)..(9)
<223> OTHER INFORMATION: N-LINKED (Asn) (Experimental)

<400> SEQUENCE: 15

Gly Phe Gly Val Ala Ile Val Gly Asn Tyr Thr Ala Ala Leu Pro Thr
1               5                   10                  15

Glu Ala Ala Leu Arg
            20

<210> SEQ ID NO 16
<211> LENGTH: 23
<212> TYPE: PRT
<213> ORGANISM: Homo sapiens
<220> FEATURE:
<221> NAME/KEY: CARBOHYD
<222> LOCATION: (5)..(5)
<223> OTHER INFORMATION: N-LINKED (Asn) (Experimental)
<220> FEATURE:
<221> NAME/KEY: MOD_RES
<222> LOCATION: (12)..(12)
<223> OTHER INFORMATION: Methionine sulfoxide ?Oxidation)

<400> SEQUENCE: 16

Leu Gly Ala Cys Asn Asp Thr Leu Gln Gln Leu Met Glu Val Phe Lys
1               5                   10                  15

Phe Asp Thr Ile Ser Glu Lys
            20

<210> SEQ ID NO 17
<211> LENGTH: 24
<212> TYPE: PRT
<213> ORGANISM: Homo sapiens
<220> FEATURE:
<221> NAME/KEY: CARBOHYD
<222> LOCATION: (9)..(9)
<223> OTHER INFORMATION: N-LINKED (Asn) (Experimental)

<400> SEQUENCE: 17

Leu Lys Glu Leu Pro Gly Val Cys Asn Glu Thr Met Met Ala Leu Trp
1               5                   10                  15

Glu Glu Cys Lys Pro Cys Leu Lys
            20

<210> SEQ ID NO 18
<211> LENGTH: 23
<212> TYPE: PRT
<213> ORGANISM: Homo sapiens
<220> FEATURE:
<221> NAME/KEY: CARBOHYD
<222> LOCATION: (13)..(13)
<223> OTHER INFORMATION: N-LINKED (Asn) (Experimental)

<400> SEQUENCE: 18

Gln Leu Val Glu Ile Glu Lys Val Val Leu His Pro Asn Tyr Ser Gln
1               5                   10                  15

Val Asp Ile Gly Leu Ile Lys
            20
```

```
<210> SEQ ID NO 19
<211> LENGTH: 18
<212> TYPE: PRT
<213> ORGANISM: Homo sapiens
<220> FEATURE:
<221> NAME/KEY: CARBOHYD
<222> LOCATION: (5)..(5)
<223> OTHER INFORMATION: N-LINKED (Asn) (Experimental)
<220> FEATURE:
<221> NAME/KEY: CARBOHYD
<222> LOCATION: (12)..(12)
<223> OTHER INFORMATION: N-LINKED (Asn) (Experimental)

<400> SEQUENCE: 19

Thr Leu Phe Cys Asn Ala Ser Lys Glu Trp Asp Asn Thr Thr Thr Glu
1               5                   10                  15

Cys Arg

<210> SEQ ID NO 20
<211> LENGTH: 19
<212> TYPE: PRT
<213> ORGANISM: Homo sapiens
<220> FEATURE:
<221> NAME/KEY: CARBOHYD
<222> LOCATION: (10)..(10)
<223> OTHER INFORMATION: N-LINKED (Asn) (Experimental)

<400> SEQUENCE: 20

Ile Ile Val Pro Leu Asn Asn Arg Glu Asn Ile Ser Asp Pro Thr Ser
1               5                   10                  15

Pro Leu Arg

<210> SEQ ID NO 21
<211> LENGTH: 15
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Methionine sulfoxide ?Oxidation)
<220> FEATURE:
<221> NAME/KEY: CARBOHYD
<222> LOCATION: (7)..(7)
<223> OTHER INFORMATION: N-LINKED (Asn) (Experimental)

<400> SEQUENCE: 21

Met Glu Ala Cys Met Leu Asn Gly Thr Val Ile Gly Pro Gly Lys
1               5                   10                  15

<210> SEQ ID NO 22
<211> LENGTH: 16
<212> TYPE: PRT
<213> ORGANISM: Homo sapiens
<220> FEATURE:
<221> NAME/KEY: CARBOHYD
<222> LOCATION: (3)..(3)
<223> OTHER INFORMATION: N-LINKED (Asn) (Experimental)

<400> SEQUENCE: 22

Cys Gly Asn Cys Ser Leu Thr Thr Leu Lys Asp Glu Asp Phe Cys Lys
1               5                   10                  15

<210> SEQ ID NO 23
<211> LENGTH: 23
<212> TYPE: PRT
<213> ORGANISM: Homo sapiens
```

```
<220> FEATURE:
<221> NAME/KEY: CARBOHYD
<222> LOCATION: (9)..(9)
<223> OTHER INFORMATION: N-LINKED (Asn) (Experimental)

<400> SEQUENCE: 23

Ile Thr Tyr Ser Ile Val Gln Thr Asn Cys Ser Lys Glu Asn Phe Leu
1               5                   10                  15

Phe Leu Thr Pro Asp Cys Lys
            20

<210> SEQ ID NO 24
<211> LENGTH: 12
<212> TYPE: PRT
<213> ORGANISM: Homo sapiens
<220> FEATURE:
<221> NAME/KEY: CARBOHYD
<222> LOCATION: (6)..(6)
<223> OTHER INFORMATION: N-LINKED (Asn) (Experimental)

<400> SEQUENCE: 24

Ala Val Leu Val Asn Asn Ile Thr Thr Gly Glu Arg
1               5                   10

<210> SEQ ID NO 25
<211> LENGTH: 29
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Methionine sulfoxide ?Oxidation)
<220> FEATURE:
<221> NAME/KEY: CARBOHYD
<222> LOCATION: (21)..(21)
<223> OTHER INFORMATION: N-LINKED (Asn) (Experimental)

<400> SEQUENCE: 25

Ala Arg Glu Asp Ile Phe Met Glu Thr Leu Lys Asp Ile Val Glu Tyr
1               5                   10                  15

Tyr Asn Asp Ser Asn Gly Ser His Val Leu Gln Gly Arg
            20                  25

<210> SEQ ID NO 26
<211> LENGTH: 43
<212> TYPE: PRT
<213> ORGANISM: Homo sapiens
<220> FEATURE:
<221> NAME/KEY: CARBOHYD
<222> LOCATION: (15)..(15)
<223> OTHER INFORMATION: N-LINKED (Asn) (Experimental)
<220> FEATURE:
<221> NAME/KEY: CARBOHYD
<222> LOCATION: (23)..(23)
<223> OTHER INFORMATION: N-LINKED (Asn) (Experimental)

<400> SEQUENCE: 26

Phe Gln Ser Pro Ala Gly Thr Glu Ala Leu Phe Glu Leu His Asn Ile
1               5                   10                  15

Ser Val Ala Asp Ser Ala Asn Tyr Ser Cys Val Tyr Val Asp Leu Lys
            20                  25                  30

Pro Pro Phe Gly Gly Ser Ala Pro Ser Glu Arg
            35                  40
```

```
<210> SEQ ID NO 27
<211> LENGTH: 15
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: pyrrolidone carboxylic acid (pyro-Glu)
<220> FEATURE:
<221> NAME/KEY: CARBOHYD
<222> LOCATION: (7)..(7)
<223> OTHER INFORMATION: N-LINKED (Asn) (Experimental)

<400> SEQUENCE: 27

Gln Asn Gln Cys Phe Tyr Asn Ser Ser Tyr Leu Asn Val Gln Arg
1               5                   10                  15

<210> SEQ ID NO 28
<211> LENGTH: 16
<212> TYPE: PRT
<213> ORGANISM: Homo sapiens
<220> FEATURE:
<221> NAME/KEY: CARBOHYD
<222> LOCATION: (6)..(6)
<223> OTHER INFORMATION: N-LINKED (Asn) (Experimental)
<220> FEATURE:
<221> NAME/KEY: MOD_RES
<222> LOCATION: (12)..(12)
<223> OTHER INFORMATION: Methionine sulfoxide ?Oxidation)

<400> SEQUENCE: 28

Ser Leu Glu Ala Ile Asn Gly Ser Gly Leu Gln Met Gly Leu Gln Arg
1               5                   10                  15

<210> SEQ ID NO 29
<211> LENGTH: 33
<212> TYPE: PRT
<213> ORGANISM: Homo sapiens
<220> FEATURE:
<221> NAME/KEY: CARBOHYD
<222> LOCATION: (4)..(4)
<223> OTHER INFORMATION: N-LINKED (Asn) (Experimental)
<220> FEATURE:
<221> NAME/KEY: CARBOHYD
<222> LOCATION: (27)..(27)
<223> OTHER INFORMATION: N-LINKED (Asn) (Experimental)

<400> SEQUENCE: 29

Ala His Leu Asn Val Ser Gly Ile Pro Cys Ser Val Leu Leu Ala Asp
1               5                   10                  15

Val Glu Asp Leu Ile Gln Gln Gln Ile Ser Asn Asp Thr Val Ser Pro
            20                  25                  30

Arg

<210> SEQ ID NO 30
<211> LENGTH: 11
<212> TYPE: PRT
<213> ORGANISM: Homo sapiens
<220> FEATURE:
<221> NAME/KEY: CARBOHYD
<222> LOCATION: (5)..(5)
<223> OTHER INFORMATION: N-LINKED (Asn) (Experimental)

<400> SEQUENCE: 30

Phe Thr Lys Val Asn Phe Thr Glu Ile Gln Lys
1               5                   10
```

```
<210> SEQ ID NO 31
<211> LENGTH: 17
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Methionine sulfoxide ?Oxidation)
<220> FEATURE:
<221> NAME/KEY: CARBOHYD
<222> LOCATION: (9)..(9)
<223> OTHER INFORMATION: N-LINKED (Asn) (Experimental)

<400> SEQUENCE: 31

Arg His Glu Glu Gly His Met Leu Asn Cys Thr Cys Phe Gly Gln Gly
1               5                   10                  15

Arg

<210> SEQ ID NO 32
<211> LENGTH: 18
<212> TYPE: PRT
<213> ORGANISM: Homo sapiens
<220> FEATURE:
<221> NAME/KEY: CARBOHYD
<222> LOCATION: (7)..(7)
<223> OTHER INFORMATION: N-LINKED (Asn) (Experimental)
<220> FEATURE:
<221> NAME/KEY: CARBOHYD
<222> LOCATION: (10)..(10)
<223> OTHER INFORMATION: N-LINKED (Asn) (Experimental)

<400> SEQUENCE: 32

Asp Ile Val Glu Tyr Tyr Asn Asp Ser Asn Gly Ser His Val Leu Gln
1               5                   10                  15

Gly Arg

<210> SEQ ID NO 33
<211> LENGTH: 19
<212> TYPE: PRT
<213> ORGANISM: Homo sapiens
<220> FEATURE:
<221> NAME/KEY: CARBOHYD
<222> LOCATION: (14)..(14)
<223> OTHER INFORMATION: N-LINKED (Asn) (Experimental)

<400> SEQUENCE: 33

Thr Leu Tyr Glu Thr Glu Val Phe Ser Thr Asp Phe Ser Asn Ile Ser
1               5                   10                  15

Ala Ala Lys

<210> SEQ ID NO 34
<211> LENGTH: 15
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: pyrrolidone carboxylic acid (pyro-Glu)
<220> FEATURE:
<221> NAME/KEY: CARBOHYD
<222> LOCATION: (7)..(7)
<223> OTHER INFORMATION: N-LINKED (Asn) (Experimental)

<400> SEQUENCE: 34

Gln Asp Gln Cys Ile Tyr Asn Thr Thr Tyr Leu Asn Val Gln Arg
1               5                   10                  15
```

```
<210> SEQ ID NO 35
<211> LENGTH: 22
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: pyrrolidone carboxylic acid (pyro-Glu)
<220> FEATURE:
<221> NAME/KEY: CARBOHYD
<222> LOCATION: (7)..(7)
<223> OTHER INFORMATION: N-LINKED (Asn) (Experimental)
<220> FEATURE:
<221> NAME/KEY: CARBOHYD
<222> LOCATION: (17)..(17)
<223> OTHER INFORMATION: N-LINKED (Asn) (Experimental)

<400> SEQUENCE: 35

Gln Asp Gln Cys Ile Tyr Asn Thr Thr Tyr Leu Asn Val Gln Arg Glu
1               5                   10                  15

Asn Gly Thr Ile Ser Arg
            20

<210> SEQ ID NO 36
<211> LENGTH: 12
<212> TYPE: PRT
<213> ORGANISM: Homo sapiens
<220> FEATURE:
<221> NAME/KEY: CARBOHYD
<222> LOCATION: (3)..(3)
<223> OTHER INFORMATION: N-LINKED (Asn) (Experimental)
<220> FEATURE:
<221> NAME/KEY: MOD_RES
<222> LOCATION: (6)..(6)
<223> OTHER INFORMATION: Methionine sulfoxide ?Oxidation)

<400> SEQUENCE: 36

Phe Leu Asn Asp Thr Met Ala Val Tyr Glu Ala Lys
1               5                   10

<210> SEQ ID NO 37
<211> LENGTH: 20
<212> TYPE: PRT
<213> ORGANISM: Homo sapiens
<220> FEATURE:
<221> NAME/KEY: CARBOHYD
<222> LOCATION: (3)..(3)
<223> OTHER INFORMATION: N-LINKED (Asn) (Experimental)
<220> FEATURE:
<221> NAME/KEY: MOD_RES
<222> LOCATION: (13)..(13)
<223> OTHER INFORMATION: Methionine sulfoxide ?Oxidation)
<220> FEATURE:
<221> NAME/KEY: MOD_RES
<222> LOCATION: (17)..(17)
<223> OTHER INFORMATION: Methionine sulfoxide ?Oxidation)

<400> SEQUENCE: 37

Thr Leu Asn Gln Ser Ser Asp Glu Leu Gln Leu Ser Met Gly Asn Ala
1               5                   10                  15

Met Phe Val Lys
            20

<210> SEQ ID NO 38
<211> LENGTH: 17
<212> TYPE: PRT
<213> ORGANISM: Homo sapiens
<220> FEATURE:
<221> NAME/KEY: CARBOHYD
<222> LOCATION: (9)..(9)
<223> OTHER INFORMATION: N-LINKED (Asn) (Experimental)
```

```
<400> SEQUENCE: 38

Phe Glu Val Asp Ser Pro Val Tyr Asn Ala Thr Trp Ser Ala Ser Leu
1               5                   10                  15

Lys

<210> SEQ ID NO 39
<211> LENGTH: 21
<212> TYPE: PRT
<213> ORGANISM: Homo sapiens
<220> FEATURE:
<221> NAME/KEY: CARBOHYD
<222> LOCATION: (5)..(5)
<223> OTHER INFORMATION: N-LINKED (Asn) (Experimental)

<400> SEQUENCE: 39

Ser Pro Tyr Tyr Asn Val Ser Asp Glu Ile Ser Phe His Cys Tyr Asp
1               5                   10                  15

Gly Tyr Thr Leu Arg
            20

<210> SEQ ID NO 40
<211> LENGTH: 23
<212> TYPE: PRT
<213> ORGANISM: Homo sapiens
<220> FEATURE:
<221> NAME/KEY: CARBOHYD
<222> LOCATION: (5)..(5)
<223> OTHER INFORMATION: N-LINKED (Asn) (Experimental)

<400> SEQUENCE: 40

Leu Gly Ala Cys Asn Asp Thr Leu Gln Gln Leu Met Glu Val Phe Lys
1               5                   10                  15

Phe Asp Thr Ile Ser Glu Lys
            20

<210> SEQ ID NO 41
<211> LENGTH: 31
<212> TYPE: PRT
<213> ORGANISM: Homo sapiens
<220> FEATURE:
<221> NAME/KEY: CARBOHYD
<222> LOCATION: (4)..(4)
<223> OTHER INFORMATION: N-LINKED (Asn) (Experimental)

<400> SEQUENCE: 41

Tyr Thr Gly Asn Ala Ser Ala Leu Phe Ile Leu Pro Asp Gln Asp Lys
1               5                   10                  15

Met Glu Glu Val Glu Ala Met Leu Leu Pro Glu Thr Leu Lys Arg
            20                  25                  30

<210> SEQ ID NO 42
<211> LENGTH: 27
<212> TYPE: PRT
<213> ORGANISM: Homo sapiens
<220> FEATURE:
<221> NAME/KEY: CARBOHYD
<222> LOCATION: (16)..(16)
<223> OTHER INFORMATION: N-LINKED (Asn) (Experimental)

<400> SEQUENCE: 42

Val Leu Thr Leu Asn Leu Asp Gln Val Asp Phe Gln His Ala Gly Asn
1               5                   10                  15

Tyr Ser Cys Val Ala Ser Asn Val Gln Gly Lys
            20                  25
```

<210> SEQ ID NO 43
<211> LENGTH: 22
<212> TYPE: PRT
<213> ORGANISM: Homo sapiens
<220> FEATURE:
<221> NAME/KEY: CARBOHYD
<222> LOCATION: (7)..(7)
<223> OTHER INFORMATION: N-LINKED (Asn) (Experimental)
<220> FEATURE:
<221> NAME/KEY: MOD_RES
<222> LOCATION: (11)..(11)
<223> OTHER INFORMATION: Methionine sulfoxide ?Oxidation)

<400> SEQUENCE: 43

Glu Leu Pro Gly Val Cys Asn Glu Thr Met Met Ala Leu Trp Glu Glu
1               5                   10                  15

Cys Lys Pro Cys Leu Lys
            20

<210> SEQ ID NO 44
<211> LENGTH: 20
<212> TYPE: PRT
<213> ORGANISM: Homo sapiens
<220> FEATURE:
<221> NAME/KEY: CARBOHYD
<222> LOCATION: (3)..(3)
<223> OTHER INFORMATION: N-LINKED (Asn) (Experimental)
<220> FEATURE:
<221> NAME/KEY: MOD_RES
<222> LOCATION: (17)..(17)
<223> OTHER INFORMATION: Methionine sulfoxide ?Oxidation)

<400> SEQUENCE: 44

Thr Leu Asn Gln Ser Ser Asp Glu Leu Gln Leu Ser Met Gly Asn Ala
1               5                   10                  15

Met Phe Val Lys
            20

<210> SEQ ID NO 45
<211> LENGTH: 33
<212> TYPE: PRT
<213> ORGANISM: Homo sapiens
<220> FEATURE:
<221> NAME/KEY: CARBOHYD
<222> LOCATION: (12)..(12)
<223> OTHER INFORMATION: N-LINKED (Asn) (Experimental)

<400> SEQUENCE: 45

Cys Gly Leu Val Pro Val Leu Ala Glu Asn Tyr Asn Lys Ser Asp Asn
1               5                   10                  15

Cys Glu Asp Thr Pro Glu Ala Gly Tyr Phe Ala Val Ala Val Val Lys
            20                  25                  30

Lys

<210> SEQ ID NO 46
<211> LENGTH: 31
<212> TYPE: PRT
<213> ORGANISM: Homo sapiens
<220> FEATURE:
<221> NAME/KEY: CARBOHYD
<222> LOCATION: (4)..(4)
<223> OTHER INFORMATION: N-LINKED (Asn) (Experimental)
<220> FEATURE:
<221> NAME/KEY: MOD_RES
<222> LOCATION: (17)..(17)
<223> OTHER INFORMATION: Methionine sulfoxide ?Oxidation)

```
<400> SEQUENCE: 46

Tyr Thr Gly Asn Ala Ser Ala Leu Phe Ile Leu Pro Asp Gln Asp Lys
1               5                   10                  15

Met Glu Glu Val Glu Ala Met Leu Leu Pro Glu Thr Leu Lys Arg
                20                  25                  30

<210> SEQ ID NO 47
<211> LENGTH: 27
<212> TYPE: PRT
<213> ORGANISM: Homo sapiens
<220> FEATURE:
<221> NAME/KEY: CARBOHYD
<222> LOCATION: (1)..(1)
<223> OTHER INFORMATION: N-LINKED (Asn) (Experimental)

<400> SEQUENCE: 47

Asn Ile Ser Asp Gly Phe Asp Gly Ile Pro Asp Asn Val Asp Ala Ala
1               5                   10                  15

Leu Ala Leu Pro Ala His Ser Tyr Ser Gly Arg
                20                  25

<210> SEQ ID NO 48
<211> LENGTH: 23
<212> TYPE: PRT
<213> ORGANISM: Homo sapiens
<220> FEATURE:
<221> NAME/KEY: CARBOHYD
<222> LOCATION: (8)..(8)
<223> OTHER INFORMATION: N-LINKED (Asn) (Experimental)
<220> FEATURE:
<221> NAME/KEY: MOD_RES
<222> LOCATION: (17)..(17)
<223> OTHER INFORMATION: Methionine sulfoxide ?Oxidation)

<400> SEQUENCE: 48

His Gly Ile Gln Tyr Phe Asn Asn Thr Gln His Ser Ser Leu Phe
1               5                   10                  15

Met Leu Asn Glu Val Lys Arg
                20

<210> SEQ ID NO 49
<211> LENGTH: 21
<212> TYPE: PRT
<213> ORGANISM: Homo sapiens
<220> FEATURE:
<221> NAME/KEY: CARBOHYD
<222> LOCATION: (15)..(15)
<223> OTHER INFORMATION: N-LINKED (Asn) (Experimental)

<400> SEQUENCE: 49

Ser His Glu Ile Trp Thr His Ser Cys Pro Gln Ser Pro Gly Asn Gly
1               5                   10                  15

Thr Asp Ala Ser His
                20

<210> SEQ ID NO 50
<211> LENGTH: 28
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Methionine sulfoxide ?Oxidation)
<220> FEATURE:
<221> NAME/KEY: CARBOHYD
<222> LOCATION: (24)..(24)
<223> OTHER INFORMATION: N-LINKED (Asn) (Experimental)
```

<400> SEQUENCE: 50

Asn Pro Pro Met Gly Gly Asn Val Val Ile Phe Asp Thr Val Ile Thr
1               5                   10                  15

Asn Gln Glu Glu Pro Tyr Gln Asn His Ser Gly Arg
            20                  25

<210> SEQ ID NO 51
<211> LENGTH: 23
<212> TYPE: PRT
<213> ORGANISM: Homo sapiens
<220> FEATURE:
<221> NAME/KEY: CARBOHYD
<222> LOCATION: (19)..(19)
<223> OTHER INFORMATION: N-LINKED (Asn) (Experimental)

<400> SEQUENCE: 51

Gln Ile Gly Leu Tyr Pro Val Leu Val Ile Asp Ser Ser Gly Tyr Val
1               5                   10                  15

Asn Pro Asn Tyr Thr Gly Arg
            20

<210> SEQ ID NO 52
<211> LENGTH: 20
<212> TYPE: PRT
<213> ORGANISM: Homo sapiens
<220> FEATURE:
<221> NAME/KEY: CARBOHYD
<222> LOCATION: (3)..(3)
<223> OTHER INFORMATION: N-LINKED (Asn) (Experimental)
<220> FEATURE:
<221> NAME/KEY: MOD_RES
<222> LOCATION: (13)..(13)
<223> OTHER INFORMATION: Methionine sulfoxide ?Oxidation)

<400> SEQUENCE: 52

Thr Leu Asn Gln Ser Ser Asp Glu Leu Gln Leu Ser Met Gly Asn Ala
1               5                   10                  15

Met Phe Val Lys
            20

<210> SEQ ID NO 53
<211> LENGTH: 36
<212> TYPE: PRT
<213> ORGANISM: Homo sapiens
<220> FEATURE:
<221> NAME/KEY: CARBOHYD
<222> LOCATION: (13)..(13)
<223> OTHER INFORMATION: N-LINKED (Asn) (Experimental)
<220> FEATURE:
<221> NAME/KEY: CARBOHYD
<222> LOCATION: (35)..(35)
<223> OTHER INFORMATION: N-LINKED (Asn) (Experimental)

<400> SEQUENCE: 53

Leu Ser Val Asp Lys Asp Gln Tyr Val Glu Pro Glu Asn Val Thr Ile
1               5                   10                  15

Gln Cys Asp Ser Gly Tyr Gly Val Val Gly Pro Gln Ser Ile Thr Cys
            20                  25                  30

Ser Gly Asn Arg
        35

<210> SEQ ID NO 54
<211> LENGTH: 32
<212> TYPE: PRT
<213> ORGANISM: Homo sapiens

```
<220> FEATURE:
<221> NAME/KEY: CARBOHYD
<222> LOCATION: (12)..(12)
<223> OTHER INFORMATION: N-LINKED (Asn) (Experimental)

<400> SEQUENCE: 54

Cys Gly Leu Val Pro Val Leu Ala Glu Asn Tyr Asn Lys Ser Asp Asn
1               5                   10                  15

Cys Glu Asp Thr Pro Glu Ala Gly Tyr Phe Ala Val Ala Val Val Lys
            20                  25                  30

<210> SEQ ID NO 55
<211> LENGTH: 23
<212> TYPE: PRT
<213> ORGANISM: Homo sapiens
<220> FEATURE:
<221> NAME/KEY: CARBOHYD
<222> LOCATION: (5)..(5)
<223> OTHER INFORMATION: N-LINKED (Asn) (Experimental)

<400> SEQUENCE: 55

Gly Leu Lys Phe Asn Leu Thr Glu Thr Ser Glu Ala Glu Ile His Gln
1               5                   10                  15

Ser Phe Gln His Leu Leu Arg
            20

<210> SEQ ID NO 56
<211> LENGTH: 33
<212> TYPE: PRT
<213> ORGANISM: Homo sapiens
<220> FEATURE:
<221> NAME/KEY: CARBOHYD
<222> LOCATION: (6)..(6)
<223> OTHER INFORMATION: N-LINKED (Asn) (Experimental)

<400> SEQUENCE: 56

Ser Leu Gly Asn Val Asn Phe Thr Val Ser Ala Glu Ala Leu Glu Ser
1               5                   10                  15

Gln Glu Leu Cys Gly Thr Glu Val Pro Ser Val Pro Glu His Gly Arg
            20                  25                  30

Lys

<210> SEQ ID NO 57
<211> LENGTH: 18
<212> TYPE: PRT
<213> ORGANISM: Homo sapiens
<220> FEATURE:
<221> NAME/KEY: CARBOHYD
<222> LOCATION: (7)..(7)
<223> OTHER INFORMATION: N-LINKED (Asn) (Experimental)

<400> SEQUENCE: 57

Asp Ile Val Glu Tyr Tyr Asn Asp Ser Asn Gly Ser His Val Leu Gln
1               5                   10                  15

Gly Arg

<210> SEQ ID NO 58
<211> LENGTH: 24
<212> TYPE: PRT
<213> ORGANISM: Homo sapiens
<220> FEATURE:
<221> NAME/KEY: CARBOHYD
<222> LOCATION: (7)..(7)
<223> OTHER INFORMATION: N-LINKED (Asn) (Experimental)

<400> SEQUENCE: 58
```

```
Glu His Glu Ala Gln Ser Asn Ala Ser Leu Asp Val Phe Leu Gly His
1               5                  10                 15

Thr Asn Val Glu Glu Leu Met Lys
            20

<210> SEQ ID NO 59
<211> LENGTH: 19
<212> TYPE: PRT
<213> ORGANISM: Homo sapiens
<220> FEATURE:
<221> NAME/KEY: CARBOHYD
<222> LOCATION: (16)..(16)
<223> OTHER INFORMATION: N-LINKED (Asn) (Experimental)

<400> SEQUENCE: 59

Asp Val Gln Ile Ile Val Phe Pro Glu Asp Gly Ile His Gly Phe Asn
1               5                  10                 15

Phe Thr Arg

<210> SEQ ID NO 60
<211> LENGTH: 18
<212> TYPE: PRT
<213> ORGANISM: Homo sapiens
<220> FEATURE:
<221> NAME/KEY: CARBOHYD
<222> LOCATION: (2)..(2)
<223> OTHER INFORMATION: N-LINKED (Asn) (Experimental)

<400> SEQUENCE: 60

Trp Asn Asn Thr Gly Cys Gln Ala Leu Pro Ser Gln Asp Glu Gly Pro
1               5                  10                 15

Ser Lys

<210> SEQ ID NO 61
<211> LENGTH: 15
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Methionine sulfoxide ?Oxidation)
<220> FEATURE:
<221> NAME/KEY: MOD_RES
<222> LOCATION: (5)..(5)
<223> OTHER INFORMATION: Methionine sulfoxide ?Oxidation)
<220> FEATURE:
<221> NAME/KEY: CARBOHYD
<222> LOCATION: (7)..(7)
<223> OTHER INFORMATION: N-LINKED (Asn) (Experimental)

<400> SEQUENCE: 61

Met Glu Ala Cys Met Leu Asn Gly Thr Val Ile Gly Pro Gly Lys
1               5                  10                 15

<210> SEQ ID NO 62
<211> LENGTH: 22
<212> TYPE: PRT
<213> ORGANISM: Homo sapiens
<220> FEATURE:
<221> NAME/KEY: CARBOHYD
<222> LOCATION: (8)..(8)
<223> OTHER INFORMATION: N-LINKED (Asn) (Experimental)

<400> SEQUENCE: 62

His Gly Ile Gln Tyr Phe Asn Asn Asn Thr Gln His Ser Ser Leu Phe
1               5                  10                 15
```

Met Leu Asn Glu Val Lys
            20

<210> SEQ ID NO 63
<211> LENGTH: 24
<212> TYPE: PRT
<213> ORGANISM: Homo sapiens
<220> FEATURE:
<221> NAME/KEY: CARBOHYD
<222> LOCATION: (15)..(15)
<223> OTHER INFORMATION: N-LINKED (Asn) (Experimental)

<400> SEQUENCE: 63

Ser Val Gln Glu Ile Gln Ala Thr Phe Phe Tyr Phe Thr Pro Asn Lys
1               5                   10                  15

Thr Glu Asp Thr Ile Phe Leu Arg
            20

<210> SEQ ID NO 64
<211> LENGTH: 15
<212> TYPE: PRT
<213> ORGANISM: Homo sapiens
<220> FEATURE:
<221> NAME/KEY: CARBOHYD
<222> LOCATION: (14)..(14)
<223> OTHER INFORMATION: N-LINKED (Asn) (Experimental)

<400> SEQUENCE: 64

Asp Leu Gln Ser Leu Glu Asp Ile Leu His Gln Val Glu Asn Lys
1               5                   10                  15

<210> SEQ ID NO 65
<211> LENGTH: 19
<212> TYPE: PRT
<213> ORGANISM: Homo sapiens
<220> FEATURE:
<221> NAME/KEY: CARBOHYD
<222> LOCATION: (3)..(3)
<223> OTHER INFORMATION: N-LINKED (Asn) (Experimental)

<400> SEQUENCE: 65

Phe Leu Asn Asp Ser Ile Val Asp Pro Val Asp Ser Glu Trp Phe Gly
1               5                   10                  15

Phe Tyr Arg

<210> SEQ ID NO 66
<211> LENGTH: 19
<212> TYPE: PRT
<213> ORGANISM: Homo sapiens
<220> FEATURE:
<221> NAME/KEY: CARBOHYD
<222> LOCATION: (15)..(15)
<223> OTHER INFORMATION: N-LINKED (Asn) (Experimental)

<400> SEQUENCE: 66

Phe Leu Ser Ser Ser Pro His Leu Pro Pro Ser Ser Tyr Phe Asn Ala
1               5                   10                  15

Ser Gly Arg

<210> SEQ ID NO 67
<211> LENGTH: 28
<212> TYPE: PRT
<213> ORGANISM: Homo sapiens
<220> FEATURE:
<221> NAME/KEY: CARBOHYD
<222> LOCATION: (19)..(19)
<223> OTHER INFORMATION: N-LINKED (Asn) (Experimental)

<400> SEQUENCE: 67

Gly Gly Asn Ser Asn Gly Ala Leu Cys His Phe Pro Phe Leu Tyr Asn
1               5                   10                  15

Asn His Asn Tyr Thr Asp Cys Thr Ser Glu Gly Arg
            20                  25

<210> SEQ ID NO 68
<211> LENGTH: 27
<212> TYPE: PRT
<213> ORGANISM: Homo sapiens
<220> FEATURE:
<221> NAME/KEY: CARBOHYD
<222> LOCATION: (7)..(7)
<223> OTHER INFORMATION: N-LINKED (Asn) (Experimental)
<220> FEATURE:
<221> NAME/KEY: CARBOHYD
<222> LOCATION: (17)..(17)
<223> OTHER INFORMATION: N-LINKED (Asn) (Experimental)

<400> SEQUENCE: 68

Gly Leu Leu His Leu Glu Asn Ala Ser Tyr Gly Ile Glu Pro Leu Gln
1               5                   10                  15

Asn Ser Ser His Phe Glu His Ile Ile Tyr Arg
            20                  25

<210> SEQ ID NO 69
<211> LENGTH: 31
<212> TYPE: PRT
<213> ORGANISM: Homo sapiens
<220> FEATURE:
<221> NAME/KEY: CARBOHYD
<222> LOCATION: (28)..(28)
<223> OTHER INFORMATION: N-LINKED (Asn) (Experimental)

<400> SEQUENCE: 69

Asn Glu Leu Val Gln Leu Tyr Gln Val Gly Glu Val Arg Pro Phe Tyr
1               5                   10                  15

Tyr Gly Leu Cys Thr Pro Cys Gln Ala Pro Thr Asn Tyr Ser Arg
            20                  25                  30

<210> SEQ ID NO 70
<211> LENGTH: 16
<212> TYPE: PRT
<213> ORGANISM: Homo sapiens
<220> FEATURE:
<221> NAME/KEY: CARBOHYD
<222> LOCATION: (1)..(1)
<223> OTHER INFORMATION: N-LINKED (Asn) (Experimental)
<220> FEATURE:
<221> NAME/KEY: CARBOHYD
<222> LOCATION: (15)..(15)
<223> OTHER INFORMATION: N-LINKED (Asn) (Experimental)

<400> SEQUENCE: 70

Asn Met Thr Phe Asp Leu Pro Ser Asp Ala Thr Val Val Leu Asn Arg
1               5                   10                  15

<210> SEQ ID NO 71
<211> LENGTH: 16
<212> TYPE: PRT
<213> ORGANISM: Homo sapiens
<220> FEATURE:
<221> NAME/KEY: CARBOHYD
<222> LOCATION: (1)..(1)
<223> OTHER INFORMATION: N-LINKED (Asn) (Experimental)
<220> FEATURE:
<221> NAME/KEY: MOD_RES
<222> LOCATION: (2)..(2)
<223> OTHER INFORMATION: Methionine sulfoxide ?Oxidation)
<220> FEATURE:
<221> NAME/KEY: CARBOHYD
<222> LOCATION: (15)..(15)
<223> OTHER INFORMATION: N-LINKED (Asn) (Experimental)

<400> SEQUENCE: 71

Asn Met Thr Phe Asp Leu Pro Ser Asp Ala Thr Val Val Leu Asn Arg
1               5                   10                  15

<210> SEQ ID NO 72
<211> LENGTH: 18
<212> TYPE: PRT
<213> ORGANISM: Homo sapiens
<220> FEATURE:
<221> NAME/KEY: CARBOHYD
<222> LOCATION: (4)..(4)
<223> OTHER INFORMATION: N-LINKED (Asn) (Experimental)

<400> SEQUENCE: 72

Thr Asn Ile Asn Ser Ser Arg Asp Pro Asp Asn Ile Ala Ala Trp Tyr
1               5                   10                  15

Leu Arg

<210> SEQ ID NO 73
<211> LENGTH: 14
<212> TYPE: PRT
<213> ORGANISM: Homo sapiens
<220> FEATURE:
<221> NAME/KEY: CARBOHYD
<222> LOCATION: (2)..(2)
<223> OTHER INFORMATION: N-LINKED (Asn) (Experimental)

<400> SEQUENCE: 73

Thr Asn Ser Thr Phe Val Gln Ala Leu Val Glu His Val Lys
1               5                   10

<210> SEQ ID NO 74
<211> LENGTH: 28
<212> TYPE: PRT
<213> ORGANISM: Homo sapiens
<220> FEATURE:
<221> NAME/KEY: CARBOHYD
<222> LOCATION: (5)..(5)
<223> OTHER INFORMATION: N-LINKED (Asn) (Experimental)
<220> FEATURE:
<221> NAME/KEY: CARBOHYD
<222> LOCATION: (19)..(19)
<223> OTHER INFORMATION: N-LINKED (Asn) (Experimental)

<400> SEQUENCE: 74

Val Ala Ala Ala Asn Val Ser Val Thr Gln Pro Glu Ser Thr Gly Asp
1               5                   10                  15

Pro Asn Asn Met Thr Leu Leu Ala Glu Glu Ala Arg
            20                  25

<210> SEQ ID NO 75
<211> LENGTH: 29
<212> TYPE: PRT
<213> ORGANISM: Homo sapiens
<220> FEATURE:
<221> NAME/KEY: CARBOHYD
<222> LOCATION: (5)..(5)
<223> OTHER INFORMATION: N-LINKED (Asn) (Experimental)
<220> FEATURE:
<221> NAME/KEY: CARBOHYD
<222> LOCATION: (19)..(19)
<223> OTHER INFORMATION: N-LINKED (Asn) (Experimental)

-continued

<400> SEQUENCE: 75

Val Ala Ala Ala Asn Val Ser Val Thr Gln Pro Glu Ser Thr Gly Asp
1               5                   10                  15

Pro Asn Asn Met Thr Leu Leu Ala Glu Glu Ala Arg Lys
            20                  25

<210> SEQ ID NO 76
<211> LENGTH: 22
<212> TYPE: PRT
<213> ORGANISM: Homo sapiens
<220> FEATURE:
<221> NAME/KEY: CARBOHYD
<222> LOCATION: (13)..(13)
<223> OTHER INFORMATION: N-LINKED (Asn) (Experimental)

<400> SEQUENCE: 76

Val Ala Gln Pro Gly Ile Asn Tyr Ala Leu Gly Thr Asn Val Ser Tyr
1               5                   10                  15

Pro Asn Asn Leu Leu Arg
            20

<210> SEQ ID NO 77
<211> LENGTH: 18
<212> TYPE: PRT
<213> ORGANISM: Homo sapiens
<220> FEATURE:
<221> NAME/KEY: CARBOHYD
<222> LOCATION: (3)..(3)
<223> OTHER INFORMATION: N-LINKED (Asn) (Experimental)
<220> FEATURE:
<221> NAME/KEY: CARBOHYD
<222> LOCATION: (15)..(15)
<223> OTHER INFORMATION: N-LINKED (Asn) (Experimental)

<400> SEQUENCE: 77

Val Leu Asn Ala Ser Thr Leu Ala Leu Ala Leu Ala Asn Leu Asn Gly
1               5                   10                  15

Ser Arg

<210> SEQ ID NO 78
<211> LENGTH: 22
<212> TYPE: PRT
<213> ORGANISM: Homo sapiens
<220> FEATURE:
<221> NAME/KEY: CARBOHYD
<222> LOCATION: (7)..(7)
<223> OTHER INFORMATION: N-LINKED (Asn) (Experimental)
<220> FEATURE:
<221> NAME/KEY: CARBOHYD
<222> LOCATION: (17)..(17)
<223> OTHER INFORMATION: N-LINKED (Asn) (Experimental)

<400> SEQUENCE: 78

Gln Asn Gln Cys Phe Tyr Asn Ser Ser Tyr Leu Asn Val Gln Arg Glu
1               5                   10                  15

Asn Gly Thr Val Ser Arg
            20

<210> SEQ ID NO 79
<211> LENGTH: 20
<212> TYPE: PRT
<213> ORGANISM: Homo sapiens
<220> FEATURE:
<221> NAME/KEY: CARBOHYD
<222> LOCATION: (10)..(10)
<223> OTHER INFORMATION: N-LINKED (Asn) (Experimental)

<400> SEQUENCE: 79

Glu His Glu Gly Ala Ile Tyr Pro Asp Asn Thr Thr Asp Phe Gln Arg
1               5                   10                  15

Ala Asp Asp Lys
            20

<210> SEQ ID NO 80
<211> LENGTH: 19
<212> TYPE: PRT
<213> ORGANISM: Homo sapiens
<220> FEATURE:
<221> NAME/KEY: CARBOHYD
<222> LOCATION: (2)..(2)
<223> OTHER INFORMATION: N-LINKED (Asn) (Experimental)

<400> SEQUENCE: 80

Glu Asn Gly Thr Asp Thr Val Gln Glu Glu Glu Ser Pro Ala Glu
1               5                   10                  15

Gly Ser Lys

<210> SEQ ID NO 81
<211> LENGTH: 10
<212> TYPE: PRT
<213> ORGANISM: Homo sapiens
<220> FEATURE:
<221> NAME/KEY: CARBOHYD
<222> LOCATION: (3)..(3)
<223> OTHER INFORMATION: N-LINKED (Asn) (Experimental)

<400> SEQUENCE: 81

Gly Glu Asn Phe Thr Glu Thr Asp Val Lys
1               5                   10

<210> SEQ ID NO 82
<211> LENGTH: 10
<212> TYPE: PRT
<213> ORGANISM: Homo sapiens
<220> FEATURE:
<221> NAME/KEY: CARBOHYD
<222> LOCATION: (4)..(4)
<223> OTHER INFORMATION: N-LINKED (Asn) (Experimental)

<400> SEQUENCE: 82

Gly Ile Gly Asn Tyr Ser Cys Ser Tyr Arg
1               5                   10

<210> SEQ ID NO 83
<211> LENGTH: 13
<212> TYPE: PRT
<213> ORGANISM: Homo sapiens
<220> FEATURE:
<221> NAME/KEY: CARBOHYD
<222> LOCATION: (2)..(2)
<223> OTHER INFORMATION: N-LINKED (Asn) (Experimental)

<400> SEQUENCE: 83

Gly Asn Glu Thr Ile Val Asn Leu Ile His Ser Thr Arg
1               5                   10

<210> SEQ ID NO 84
<211> LENGTH: 18
<212> TYPE: PRT
<213> ORGANISM: Homo sapiens
<220> FEATURE:
<221> NAME/KEY: CARBOHYD
<222> LOCATION: (8)..(8)

<223> OTHER INFORMATION: N-LINKED (Asn) (Experimental)

<400> SEQUENCE: 84

Ile Leu Leu Thr Cys Ser Leu Asn Asp Ser Ala Thr Glu Val Thr Gly
1               5                   10                  15

His Arg

<210> SEQ ID NO 85
<211> LENGTH: 30
<212> TYPE: PRT
<213> ORGANISM: Homo sapiens
<220> FEATURE:
<221> NAME/KEY: CARBOHYD
<222> LOCATION: (8)..(8)
<223> OTHER INFORMATION: N-LINKED (Asn) (Experimental)
<220> FEATURE:
<221> NAME/KEY: CARBOHYD
<222> LOCATION: (24)..(24)
<223> OTHER INFORMATION: N-LINKED (Asn) (Experimental)

<400> SEQUENCE: 85

Leu Asp Val Asp Gln Ala Leu Asn Arg Ser His Glu Ile Trp Thr His
1               5                   10                  15

Ser Cys Pro Gln Ser Pro Gly Asn Gly Thr Asp Ala Ser His
            20                  25                  30

<210> SEQ ID NO 86
<211> LENGTH: 29
<212> TYPE: PRT
<213> ORGANISM: Homo sapiens
<220> FEATURE:
<221> NAME/KEY: CARBOHYD
<222> LOCATION: (14)..(14)
<223> OTHER INFORMATION: N-LINKED (Asn) (Experimental)
<220> FEATURE:
<221> NAME/KEY: CARBOHYD
<222> LOCATION: (18)..(18)
<223> OTHER INFORMATION: N-LINKED (Asn) (Experimental)

<400> SEQUENCE: 86

Asn Cys Gln Asp Ile Asp Glu Cys Val Thr Gly Ile His Asn Cys Ser
1               5                   10                  15

Ile Asn Glu Thr Cys Phe Asn Ile Gln Gly Gly Phe Arg
            20                  25

<210> SEQ ID NO 87
<211> LENGTH: 9
<212> TYPE: PRT
<213> ORGANISM: Homo sapiens
<220> FEATURE:
<221> NAME/KEY: CARBOHYD
<222> LOCATION: (1)..(1)
<223> OTHER INFORMATION: N-LINKED (Asn) (Experimental)
<220> FEATURE:
<221> NAME/KEY: MOD_RES
<222> LOCATION: (5)..(5)
<223> OTHER INFORMATION: Methionine sulfoxide ?Oxidation)

<400> SEQUENCE: 87

Asn Arg Thr Pro Met Gly His Met Lys
1               5

<210> SEQ ID NO 88
<211> LENGTH: 9
<212> TYPE: PRT
<213> ORGANISM: Homo sapiens
<220> FEATURE:
<221> NAME/KEY: CARBOHYD

```
<222> LOCATION: (3)..(3)
<223> OTHER INFORMATION: N-LINKED (Asn) (Experimental)

<400> SEQUENCE: 88

Gln Tyr Asn Ser Thr Gly Asp Tyr Arg
1               5

<210> SEQ ID NO 89
<211> LENGTH: 14
<212> TYPE: PRT
<213> ORGANISM: Homo sapiens
<220> FEATURE:
<221> NAME/KEY: CARBOHYD
<222> LOCATION: (4)..(4)
<223> OTHER INFORMATION: N-LINKED (Asn) (Experimental)
<220> FEATURE:
<221> NAME/KEY: MOD_RES
<222> LOCATION: (9)..(9)
<223> OTHER INFORMATION: Methionine sulfoxide ?Oxidation)
<220> FEATURE:
<221> NAME/KEY: CARBOHYD
<222> LOCATION: (13)..(13)
<223> OTHER INFORMATION: N-LINKED (Asn) (Experimental)

<400> SEQUENCE: 89

Ser His Thr Asn Thr Ser His Val Met Gln Tyr Gly Asn Lys
1               5                   10

<210> SEQ ID NO 90
<211> LENGTH: 16
<212> TYPE: PRT
<213> ORGANISM: Homo sapiens
<220> FEATURE:
<221> NAME/KEY: CARBOHYD
<222> LOCATION: (12)..(12)
<223> OTHER INFORMATION: N-LINKED (Asn) (Experimental)

<400> SEQUENCE: 90

Ser Leu Ser Cys Gln Met Ala Ala Leu Gln Gly Asn Gly Ser Glu Arg
1               5                   10                  15

<210> SEQ ID NO 91
<211> LENGTH: 16
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Methionine sulfoxide ?Oxidation)
<220> FEATURE:
<221> NAME/KEY: CARBOHYD
<222> LOCATION: (12)..(12)
<223> OTHER INFORMATION: N-LINKED (Asn) (Experimental)

<400> SEQUENCE: 91

Ser Leu Ser Cys Gln Met Ala Ala Leu Gln Gly Asn Gly Ser Glu Arg
1               5                   10                  15

<210> SEQ ID NO 92
<211> LENGTH: 12
<212> TYPE: PRT
<213> ORGANISM: Homo sapiens
<220> FEATURE:
<221> NAME/KEY: CARBOHYD
<222> LOCATION: (3)..(3)
<223> OTHER INFORMATION: N-LINKED (Asn) (Experimental)

<400> SEQUENCE: 92

Thr Tyr Asn Gly Thr Asn Pro Asp Ala Ala Ser Arg
1               5                   10
```

<210> SEQ ID NO 93
<211> LENGTH: 28
<212> TYPE: PRT
<213> ORGANISM: Homo sapiens
<220> FEATURE:
<221> NAME/KEY: CARBOHYD
<222> LOCATION: (5)..(5)
<223> OTHER INFORMATION: N-LINKED (Asn) (Experimental)
<220> FEATURE:
<221> NAME/KEY: CARBOHYD
<222> LOCATION: (19)..(19)
<223> OTHER INFORMATION: N-LINKED (Asn) (Experimental)
<220> FEATURE:
<221> NAME/KEY: MOD_RES
<222> LOCATION: (20)..(20)
<223> OTHER INFORMATION: Methionine sulfoxide ?Oxidation)

<400> SEQUENCE: 93

Val Ala Ala Ala Asn Val Ser Val Thr Gln Pro Glu Ser Thr Gly Asp
1               5                   10                  15

Pro Asn Asn Met Thr Leu Leu Ala Glu Glu Ala Arg
            20                  25

<210> SEQ ID NO 94
<211> LENGTH: 11
<212> TYPE: PRT
<213> ORGANISM: Homo sapiens
<220> FEATURE:
<221> NAME/KEY: CARBOHYD
<222> LOCATION: (8)..(8)
<223> OTHER INFORMATION: N-LINKED (Asn) (Experimental)

<400> SEQUENCE: 94

Val Cys Glu Ile His Glu Asp Asn Ser Thr Arg
1               5                   10

<210> SEQ ID NO 95
<211> LENGTH: 12
<212> TYPE: PRT
<213> ORGANISM: Homo sapiens
<220> FEATURE:
<221> NAME/KEY: CARBOHYD
<222> LOCATION: (7)..(7)
<223> OTHER INFORMATION: N-LINKED (Asn) (Experimental)

<400> SEQUENCE: 95

Val Val Asp Asp Val Ser Asn Gln Thr Ser Cys Arg
1               5                   10

<210> SEQ ID NO 96
<211> LENGTH: 16
<212> TYPE: PRT
<213> ORGANISM: Homo sapiens
<220> FEATURE:
<221> NAME/KEY: CARBOHYD
<222> LOCATION: (9)..(9)
<223> OTHER INFORMATION: N-LINKED (Asn) (Experimental)

<400> SEQUENCE: 96

His Thr Gly Asn Val Val Ile Thr Asn Cys Ser Ala Ala His Ser Arg
1               5                   10                  15

<210> SEQ ID NO 97
<211> LENGTH: 25
<212> TYPE: PRT
<213> ORGANISM: Homo sapiens
<220> FEATURE:
<221> NAME/KEY: CARBOHYD

```
<222> LOCATION: (24)..(24)
<223> OTHER INFORMATION: N-LINKED (Asn) (Experimental)

<400> SEQUENCE: 97

Ile Asn Leu Ala Gly Asp Val Ala Ala Leu Asn Ser Gly Leu Ala Thr
1               5                   10                  15
Glu Ala Phe Ser Ala Tyr Gly Asn Lys
            20                  25

<210> SEQ ID NO 98
<211> LENGTH: 21
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: pyrrolidone carboxylic acid (pyro-Glu)
<220> FEATURE:
<221> NAME/KEY: CARBOHYD
<222> LOCATION: (9)..(9)
<223> OTHER INFORMATION: N-LINKED (Asn) (Experimental)

<400> SEQUENCE: 98

Gln Gln Gln His Leu Phe Gly Ser Asn Val Thr Asp Cys Ser Gly Asn
1               5                   10                  15
Phe Cys Leu Phe Arg
            20

<210> SEQ ID NO 99
<211> LENGTH: 33
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: pyrrolidone carboxylic acid (pyro-Glu)
<220> FEATURE:
<221> NAME/KEY: CARBOHYD
<222> LOCATION: (16)..(16)
<223> OTHER INFORMATION: N-LINKED (Asn) (Experimental)

<400> SEQUENCE: 99

Gln Val Phe Pro Gly Leu Asn Tyr Cys Thr Ser Gly Ala Tyr Ser Asn
1               5                   10                  15
Ala Ser Ser Thr Asp Ser Ala Ser Tyr Tyr Pro Leu Thr Gly Asp Thr
            20                  25                  30
Arg

<210> SEQ ID NO 100
<211> LENGTH: 10
<212> TYPE: PRT
<213> ORGANISM: Homo sapiens
<220> FEATURE:
<221> NAME/KEY: CARBOHYD
<222> LOCATION: (6)..(6)
<223> OTHER INFORMATION: N-LINKED (Asn) (Experimental)

<400> SEQUENCE: 100

Ser Ala Glu Phe Phe Asn Tyr Thr Val Arg
1               5                   10

<210> SEQ ID NO 101
<211> LENGTH: 16
<212> TYPE: PRT
<213> ORGANISM: Homo sapiens
<220> FEATURE:
<221> NAME/KEY: CARBOHYD
```

```
<222> LOCATION: (7)..(7)
<223> OTHER INFORMATION: N-LINKED (Asn) (Experimental)

<400> SEQUENCE: 101

Ser Asp Leu Asn Pro Ala Asn Gly Ser Tyr Pro Phe Lys Ala Leu Arg
1               5                   10                  15

<210> SEQ ID NO 102
<211> LENGTH: 16
<212> TYPE: PRT
<213> ORGANISM: Homo sapiens
<220> FEATURE:
<221> NAME/KEY: CARBOHYD
<222> LOCATION: (8)..(8)
<223> OTHER INFORMATION: N-LINKED (Asn) (Experimental)

<400> SEQUENCE: 102

Thr Val Ser Cys Gln Val Gln Asn Gly Ser Glu Thr Val Val Gln Arg
1               5                   10                  15

<210> SEQ ID NO 103
<211> LENGTH: 24
<212> TYPE: PRT
<213> ORGANISM: Homo sapiens
<220> FEATURE:
<221> NAME/KEY: CARBOHYD
<222> LOCATION: (8)..(8)
<223> OTHER INFORMATION: N-LINKED (Asn) (Experimental)
<220> FEATURE:
<221> NAME/KEY: CARBOHYD
<222> LOCATION: (14)..(14)
<223> OTHER INFORMATION: N-LINKED (Asn) (Experimental)

<400> SEQUENCE: 103

Val Ile Ser Val Asp Glu Leu Asn Asp Thr Ile Ala Ala Asn Leu Ser
1               5                   10                  15

Asp Thr Glu Phe Tyr Gly Ala Lys
            20

<210> SEQ ID NO 104
<211> LENGTH: 25
<212> TYPE: PRT
<213> ORGANISM: Homo sapiens
<220> FEATURE:
<221> NAME/KEY: CARBOHYD
<222> LOCATION: (9)..(9)
<223> OTHER INFORMATION: N-LINKED (Asn) (Experimental)
<220> FEATURE:
<221> NAME/KEY: MOD_RES
<222> LOCATION: (22)..(22)
<223> OTHER INFORMATION: Methionine sulfoxide ?Oxidation)

<400> SEQUENCE: 104

Val Tyr Ser Leu Pro Gly Arg Glu Asn Tyr Ser Ser Val Asp Ala Asn
1               5                   10                  15

Gly Ile Gln Ser Gln Met Leu Ser Arg
            20                  25

<210> SEQ ID NO 105
<211> LENGTH: 21
<212> TYPE: PRT
<213> ORGANISM: Homo sapiens
<220> FEATURE:
<221> NAME/KEY: MOD_RES
<222> LOCATION: (17)..(17)
<223> OTHER INFORMATION: Methionine sulfoxide ?Oxidation)
<220> FEATURE:
<221> NAME/KEY: CARBOHYD
<222> LOCATION: (20)..(20)
```

<223> OTHER INFORMATION: N-LINKED (Asn) (Experimental)

<400> SEQUENCE: 105

Tyr Arg Gly Thr Ala Gly Asn Ala Leu Met Asp Gly Ala Ser Gln Leu
1               5                   10                  15
Met Gly Glu Asn Arg
            20

<210> SEQ ID NO 106
<211> LENGTH: 13
<212> TYPE: PRT
<213> ORGANISM: Homo sapiens
<220> FEATURE:
<221> NAME/KEY: CARBOHYD
<222> LOCATION: (4)..(4)
<223> OTHER INFORMATION: N-LINKED (Asn) (Experimental)

<400> SEQUENCE: 106

Tyr Ser Ser Asn His Thr Glu His Ser Gln Asn Leu Arg
1               5                   10

<210> SEQ ID NO 107
<211> LENGTH: 11
<212> TYPE: PRT
<213> ORGANISM: Homo sapiens
<220> FEATURE:
<221> NAME/KEY: CARBOHYD
<222> LOCATION: (3)..(3)
<223> OTHER INFORMATION: N-LINKED (Asn) (Experimental)

<400> SEQUENCE: 107

Tyr Tyr Asn Tyr Thr Leu Ser Ile Asn Gly Lys
1               5                   10

<210> SEQ ID NO 108
<211> LENGTH: 19
<212> TYPE: PRT
<213> ORGANISM: Homo sapiens
<220> FEATURE:
<221> NAME/KEY: CARBOHYD
<222> LOCATION: (5)..(5)
<223> OTHER INFORMATION: N-LINKED (Asn) (Experimental)

<400> SEQUENCE: 108

Ser Leu Thr Phe Asn Glu Thr Tyr Gln Asp Ile Ser Glu Leu Val Tyr
1               5                   10                  15
Gly Ala Lys

<210> SEQ ID NO 109
<211> LENGTH: 22
<212> TYPE: PRT
<213> ORGANISM: Homo sapiens
<220> FEATURE:
<221> NAME/KEY: CARBOHYD
<222> LOCATION: (4)..(4)
<223> OTHER INFORMATION: N-LINKED (Asn) (Experimental)

<400> SEQUENCE: 109

Ala Phe Glu Asn Val Thr Asp Leu Gln Trp Leu Ile Leu Asp His Asn
1               5                   10                  15
Leu Leu Glu Asn Ser Lys
            20

<210> SEQ ID NO 110
<211> LENGTH: 10
<212> TYPE: PRT

```
<213> ORGANISM: Homo sapiens
<220> FEATURE:
<221> NAME/KEY: CARBOHYD
<222> LOCATION: (3)..(3)
<223> OTHER INFORMATION: N-LINKED (Asn) (Experimental)

<400> SEQUENCE: 110

Cys Arg Asn Leu Ser Gly Gln Thr Asp Lys
1               5                   10

<210> SEQ ID NO 111
<211> LENGTH: 18
<212> TYPE: PRT
<213> ORGANISM: Homo sapiens
<220> FEATURE:
<221> NAME/KEY: CARBOHYD
<222> LOCATION: (5)..(5)
<223> OTHER INFORMATION: N-LINKED (Asn) (Experimental)

<400> SEQUENCE: 111

Asp Phe Thr Leu Asn Glu Thr Val Asn Ser Ile Phe Ala Gln Gly Ala
1               5                   10                  15

Pro Arg

<210> SEQ ID NO 112
<211> LENGTH: 12
<212> TYPE: PRT
<213> ORGANISM: Homo sapiens
<220> FEATURE:
<221> NAME/KEY: CARBOHYD
<222> LOCATION: (2)..(2)
<223> OTHER INFORMATION: N-LINKED (Asn) (Experimental)

<400> SEQUENCE: 112

Asp Asn Tyr Thr Asp Leu Val Ala Ile Gln Asn Lys
1               5                   10

<210> SEQ ID NO 113
<211> LENGTH: 27
<212> TYPE: PRT
<213> ORGANISM: Homo sapiens
<220> FEATURE:
<221> NAME/KEY: CARBOHYD
<222> LOCATION: (9)..(9)
<223> OTHER INFORMATION: N-LINKED (Asn) (Experimental)

<400> SEQUENCE: 113

Glu Leu His His Leu Gln Glu Gln Asn Val Ser Asn Ala Phe Leu Asp
1               5                   10                  15

Lys Gly Glu Phe Tyr Ile Gly Ser Lys Tyr Lys
            20                  25

<210> SEQ ID NO 114
<211> LENGTH: 19
<212> TYPE: PRT
<213> ORGANISM: Homo sapiens
<220> FEATURE:
<221> NAME/KEY: CARBOHYD
<222> LOCATION: (5)..(5)
<223> OTHER INFORMATION: N-LINKED (Asn) (Experimental)

<400> SEQUENCE: 114

Glu Pro Gly Ser Asn Val Thr Met Ser Val Asp Ala Glu Cys Val Pro
1               5                   10                  15

Met Val Arg
```

-continued

```
<210> SEQ ID NO 115
<211> LENGTH: 25
<212> TYPE: PRT
<213> ORGANISM: Homo sapiens
<220> FEATURE:
<221> NAME/KEY: CARBOHYD
<222> LOCATION: (20)..(20)
<223> OTHER INFORMATION: N-LINKED (Asn) (Experimental)

<400> SEQUENCE: 115

Phe Leu Asn Asp Val Lys Thr Leu Tyr Glu Thr Glu Val Phe Ser Thr
1               5                   10                  15

Asp Phe Ser Asn Ile Ser Ala Ala Lys
            20                  25

<210> SEQ ID NO 116
<211> LENGTH: 30
<212> TYPE: PRT
<213> ORGANISM: Homo sapiens
<220> FEATURE:
<221> NAME/KEY: CARBOHYD
<222> LOCATION: (15)..(15)
<223> OTHER INFORMATION: N-LINKED (Asn) (Experimental)

<400> SEQUENCE: 116

Phe Ser Leu Leu Gly His Ala Ser Ile Ser Cys Thr Val Glu Asn Glu
1               5                   10                  15

Thr Ile Gly Val Trp Arg Pro Ser Pro Pro Thr Cys Glu Lys
            20                  25                  30

<210> SEQ ID NO 117
<211> LENGTH: 35
<212> TYPE: PRT
<213> ORGANISM: Homo sapiens
<220> FEATURE:
<221> NAME/KEY: CARBOHYD
<222> LOCATION: (9)..(9)
<223> OTHER INFORMATION: N-LINKED (Asn) (Experimental)
<220> FEATURE:
<221> NAME/KEY: CARBOHYD
<222> LOCATION: (23)..(23)
<223> OTHER INFORMATION: N-LINKED (Asn) (Experimental)
<220> FEATURE:
<221> NAME/KEY: MOD_RES
<222> LOCATION: (28)..(28)
<223> OTHER INFORMATION: Methionine sulfoxide ?Oxidation)

<400> SEQUENCE: 117

Gly Asn Glu Ala Asn Tyr Tyr Ser Asn Ala Thr Thr Asp Glu His Gly
1               5                   10                  15

Leu Val Gln Phe Ser Ile Asn Thr Thr Asn Val Met Gly Thr Ser Leu
            20                  25                  30

Thr Val Arg
        35

<210> SEQ ID NO 118
<211> LENGTH: 16
<212> TYPE: PRT
<213> ORGANISM: Homo sapiens
<220> FEATURE:
<221> NAME/KEY: CARBOHYD
<222> LOCATION: (2)..(2)
<223> OTHER INFORMATION: N-LINKED (Asn) (Experimental)

<400> SEQUENCE: 118

Gly Asn Glu Ser Ala Leu Trp Asp Cys Lys His Asp Gly Trp Gly Lys
1               5                   10                  15
```

<210> SEQ ID NO 119
<211> LENGTH: 12
<212> TYPE: PRT
<213> ORGANISM: Homo sapiens
<220> FEATURE:
<221> NAME/KEY: CARBOHYD
<222> LOCATION: (2)..(2)
<223> OTHER INFORMATION: N-LINKED (Asn) (Experimental)

<400> SEQUENCE: 119

Gly Asn Glu Thr Leu His Tyr Glu Thr Phe Gly Lys
1               5                   10

<210> SEQ ID NO 120
<211> LENGTH: 38
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Methionine sulfoxide ?Oxidation)
<220> FEATURE:
<221> NAME/KEY: MOD_RES
<222> LOCATION: (24)..(24)
<223> OTHER INFORMATION: Methionine sulfoxide ?Oxidation)
<220> FEATURE:
<221> NAME/KEY: CARBOHYD
<222> LOCATION: (37)..(37)
<223> OTHER INFORMATION: N-LINKED (Asn) (Experimental)

<400> SEQUENCE: 120

His Leu Gln Met Asp Ile His Ile Phe Glu Pro Gln Gly Ile Ser Phe
1               5                   10                  15

Leu Glu Thr Glu Ser Thr Phe Met Thr Asn Gln Leu Val Asp Ala Leu
                20                  25                  30

Thr Thr Trp Gln Asn Lys
            35

<210> SEQ ID NO 121
<211> LENGTH: 23
<212> TYPE: PRT
<213> ORGANISM: Homo sapiens
<220> FEATURE:
<221> NAME/KEY: CARBOHYD
<222> LOCATION: (3)..(3)
<223> OTHER INFORMATION: N-LINKED (Asn) (Experimental)

<400> SEQUENCE: 121

His Asn Asn Asp Thr Gln His Ile Trp Glu Ser Asp Ser Asn Glu Phe
1               5                   10                  15

Ser Val Ile Ala Asp Pro Arg
            20

<210> SEQ ID NO 122
<211> LENGTH: 43
<212> TYPE: PRT
<213> ORGANISM: Homo sapiens
<220> FEATURE:
<221> NAME/KEY: CARBOHYD
<222> LOCATION: (25)..(25)
<223> OTHER INFORMATION: N-LINKED (Asn) (Experimental)

<400> SEQUENCE: 122

His Tyr Tyr Ile Ala Ala Glu Glu Ile Ile Trp Asn Tyr Ala Pro Ser
1               5                   10                  15

Gly Ile Asp Ile Phe Thr Lys Glu Asn Leu Thr Ala Pro Gly Ser Asp
                20                  25                  30

```
Ser Ala Val Phe Phe Glu Gln Gly Thr Thr Arg
        35                  40

<210> SEQ ID NO 123
<211> LENGTH: 18
<212> TYPE: PRT
<213> ORGANISM: Homo sapiens
<220> FEATURE:
<221> NAME/KEY: CARBOHYD
<222> LOCATION: (17)..(17)
<223> OTHER INFORMATION: N-LINKED (Asn) (Experimental)

<400> SEQUENCE: 123

Ile Asp Gly Ser Gly Asn Phe Gln Val Leu Leu Ser Asp Arg Tyr Phe
1               5                   10                  15

Asn Lys

<210> SEQ ID NO 124
<211> LENGTH: 17
<212> TYPE: PRT
<213> ORGANISM: Homo sapiens
<220> FEATURE:
<221> NAME/KEY: CARBOHYD
<222> LOCATION: (3)..(3)
<223> OTHER INFORMATION: N-LINKED (Asn) (Experimental)

<400> SEQUENCE: 124

Ile Ser Asn Ser Ser Asp Thr Val Glu Cys Glu Cys Ser Glu Asn Trp
1               5                   10                  15

Lys

<210> SEQ ID NO 125
<211> LENGTH: 18
<212> TYPE: PRT
<213> ORGANISM: Homo sapiens
<220> FEATURE:
<221> NAME/KEY: CARBOHYD
<222> LOCATION: (4)..(4)
<223> OTHER INFORMATION: N-LINKED (Asn) (Experimental)

<400> SEQUENCE: 125

Lys Ala Glu Asn Ser Ser Asn Glu Glu Glu Thr Ser Ser Glu Gly Asn
1               5                   10                  15

Met Arg

<210> SEQ ID NO 126
<211> LENGTH: 23
<212> TYPE: PRT
<213> ORGANISM: Homo sapiens
<220> FEATURE:
<221> NAME/KEY: CARBOHYD
<222> LOCATION: (15)..(15)
<223> OTHER INFORMATION: N-LINKED (Asn) (Experimental)

<400> SEQUENCE: 126

Lys Thr Thr Cys Asn Pro Cys Pro Leu Gly Tyr Lys Glu Glu Asn Asn
1               5                   10                  15

Thr Gly Glu Cys Cys Gly Arg
            20

<210> SEQ ID NO 127
<211> LENGTH: 20
<212> TYPE: PRT
<213> ORGANISM: Homo sapiens
<220> FEATURE:
```

```
<221> NAME/KEY: CARBOHYD
<222> LOCATION: (11)..(11)
<223> OTHER INFORMATION: N-LINKED (Asn) (Experimental)

<400> SEQUENCE: 127
```

Leu Asp Ala Pro Thr Asn Leu Gln Phe Val Asn Glu Thr Asp Ser Thr
1               5                   10                  15

Val Leu Val Arg
            20

```
<210> SEQ ID NO 128
<211> LENGTH: 35
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Methionine sulfoxide ?Oxidation)
<220> FEATURE:
<221> NAME/KEY: CARBOHYD
<222> LOCATION: (23)..(23)
<223> OTHER INFORMATION: N-LINKED (Asn) (Experimental)

<400> SEQUENCE: 128
```

Leu Glu Pro Glu Gly Pro Ala Pro His Met Leu Gly Leu Val Ala Gly
1               5                   10                  15

Trp Gly Ile Ser Asn Pro Asn Val Thr Val Asp Glu Ile Ile Ser Ser
                20                  25                  30

Gly Thr Arg
        35

```
<210> SEQ ID NO 129
<211> LENGTH: 17
<212> TYPE: PRT
<213> ORGANISM: Homo sapiens
<220> FEATURE:
<221> NAME/KEY: CARBOHYD
<222> LOCATION: (6)..(6)
<223> OTHER INFORMATION: N-LINKED (Asn) (Experimental)

<400> SEQUENCE: 129
```

Leu Asn Ala Glu Asn Asn Ala Thr Phe Tyr Phe Lys Ile Asp Asn Val
1               5                   10                  15

Lys

```
<210> SEQ ID NO 130
<211> LENGTH: 17
<212> TYPE: PRT
<213> ORGANISM: Homo sapiens
<220> FEATURE:
<221> NAME/KEY: CARBOHYD
<222> LOCATION: (11)..(11)
<223> OTHER INFORMATION: N-LINKED (Asn) (Experimental)

<400> SEQUENCE: 130
```

Leu Gln Gln Asp Val Leu Gln Phe Gln Lys Asn Gln Thr Asn Leu Glu
1               5                   10                  15

Arg

```
<210> SEQ ID NO 131
<211> LENGTH: 30
<212> TYPE: PRT
<213> ORGANISM: Homo sapiens
<220> FEATURE:
<221> NAME/KEY: CARBOHYD
<222> LOCATION: (17)..(17)
```

<223> OTHER INFORMATION: N-LINKED (Asn) (Experimental)

<400> SEQUENCE: 131

Leu Ser His Asn Glu Leu Ala Asp Ser Gly Ile Pro Gly Asn Ser Phe
1               5                   10                  15

Asn Val Ser Ser Leu Val Glu Leu Asp Leu Ser Tyr Asn Lys
            20                  25                  30

<210> SEQ ID NO 132
<211> LENGTH: 15
<212> TYPE: PRT
<213> ORGANISM: Homo sapiens
<220> FEATURE:
<221> NAME/KEY: CARBOHYD
<222> LOCATION: (3)..(3)
<223> OTHER INFORMATION: N-LINKED (Asn) (Experimental)

<400> SEQUENCE: 132

Leu Ser Asn Ile Ser His Leu Asn Tyr Cys Glu Pro Asp Leu Arg
1               5                   10                  15

<210> SEQ ID NO 133
<211> LENGTH: 20
<212> TYPE: PRT
<213> ORGANISM: Homo sapiens
<220> FEATURE:
<221> NAME/KEY: CARBOHYD
<222> LOCATION: (10)..(10)
<223> OTHER INFORMATION: N-LINKED (Asn) (Experimental)
<220> FEATURE:
<221> NAME/KEY: CARBOHYD
<222> LOCATION: (14)..(14)
<223> OTHER INFORMATION: N-LINKED (Asn) (Experimental)

<400> SEQUENCE: 133

Leu Thr Asp Thr Ile Cys Gly Val Gly Asn Met Ser Ala Asn Ala Ser
1               5                   10                  15

Asp Gln Glu Arg
            20

<210> SEQ ID NO 134
<211> LENGTH: 34
<212> TYPE: PRT
<213> ORGANISM: Homo sapiens
<220> FEATURE:
<221> NAME/KEY: CARBOHYD
<222> LOCATION: (28)..(28)
<223> OTHER INFORMATION: N-LINKED (Asn) (Experimental)

<400> SEQUENCE: 134

Arg Glu Gly Asp His Glu Phe Leu Glu Val Pro Glu Ala Gln Glu Asp
1               5                   10                  15

Val Glu Ala Thr Phe Pro Val His Gln Pro Gly Asn Tyr Ser Cys Ser
            20                  25                  30

Tyr Arg

<210> SEQ ID NO 135
<211> LENGTH: 20
<212> TYPE: PRT
<213> ORGANISM: Homo sapiens
<220> FEATURE:
<221> NAME/KEY: CARBOHYD
<222> LOCATION: (5)..(5)
<223> OTHER INFORMATION: N-LINKED (Asn) (Experimental)
<220> FEATURE:
<221> NAME/KEY: CARBOHYD
<222> LOCATION: (19)..(19)

<223> OTHER INFORMATION: N-LINKED (Asn) (Experimental)

<400> SEQUENCE: 135

Ser Gly Pro Lys Asn Met Thr Phe Asp Leu Pro Ser Asp Ala Thr Val
1               5                   10                  15

Val Leu Asn Arg
            20

<210> SEQ ID NO 136
<211> LENGTH: 22
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Methionine sulfoxide ?Oxidation)
<220> FEATURE:
<221> NAME/KEY: CARBOHYD
<222> LOCATION: (9)..(9)
<223> OTHER INFORMATION: N-LINKED (Asn) (Experimental)

<400> SEQUENCE: 136

Thr Tyr Asn Val Leu Asp Met Lys Asn Thr Thr Cys Gln Asp Leu Gln
1               5                   10                  15

Ile Glu Val Thr Val Lys
            20

<210> SEQ ID NO 137
<211> LENGTH: 19
<212> TYPE: PRT
<213> ORGANISM: Homo sapiens
<220> FEATURE:
<221> NAME/KEY: CARBOHYD
<222> LOCATION: (10)..(10)
<223> OTHER INFORMATION: N-LINKED (Asn) (Experimental)

<400> SEQUENCE: 137

Val Ala Ser Val Ile Asn Ile Asn Pro Asn Thr Thr His Ser Thr Gly
1               5                   10                  15

Ser Cys Arg

<210> SEQ ID NO 138
<211> LENGTH: 21
<212> TYPE: PRT
<213> ORGANISM: Homo sapiens
<220> FEATURE:
<221> NAME/KEY: CARBOHYD
<222> LOCATION: (15)..(15)
<223> OTHER INFORMATION: N-LINKED (Asn) (Experimental)

<400> SEQUENCE: 138

Val Thr Val Gln Ser Leu Leu Thr Val Glu Thr Leu Glu His Asn Gln
1               5                   10                  15

Thr Tyr Glu Cys Arg
            20

<210> SEQ ID NO 139
<211> LENGTH: 11
<212> TYPE: PRT
<213> ORGANISM: Homo sapiens
<220> FEATURE:
<221> NAME/KEY: CARBOHYD
<222> LOCATION: (3)..(3)
<223> OTHER INFORMATION: N-LINKED (Asn) (Experimental)

<400> SEQUENCE: 139

Trp Val Asn Tyr Ser Cys Leu Asp Gln Ala Arg
1               5                   10

<210> SEQ ID NO 140
<211> LENGTH: 21
<212> TYPE: PRT
<213> ORGANISM: Homo sapiens
<220> FEATURE:
<221> NAME/KEY: CARBOHYD
<222> LOCATION: (14)..(14)
<223> OTHER INFORMATION: N-LINKED (Asn) (Experimental)

<400> SEQUENCE: 140

Tyr Lys Val Asp Tyr Glu Ser Gln Ser Thr Asp Thr Gln Asn Phe Ser
1               5                   10                  15

Ser Glu Ser Lys Arg
            20

<210> SEQ ID NO 141
<211> LENGTH: 22
<212> TYPE: PRT
<213> ORGANISM: Homo sapiens
<220> FEATURE:
<221> NAME/KEY: CARBOHYD
<222> LOCATION: (9)..(9)
<223> OTHER INFORMATION: N-LINKED (Asn) (Experimental)

<400> SEQUENCE: 141

Gly Cys Val Leu Leu Ser Tyr Leu Asn Glu Thr Val Thr Val Ser Ala
1               5                   10                  15

Ser Leu Glu Ser Val Arg
            20

<210> SEQ ID NO 142
<211> LENGTH: 29
<212> TYPE: PRT
<213> ORGANISM: Homo sapiens
<220> FEATURE:
<221> NAME/KEY: CARBOHYD
<222> LOCATION: (15)..(15)
<223> OTHER INFORMATION: N-LINKED (Asn) (Experimental)

<400> SEQUENCE: 142

Ala Leu Val Leu Glu Gln Leu Thr Pro Ala Leu His Ser Thr Asn Phe
1               5                   10                  15

Ser Cys Val Leu Val Asp Pro Glu Gln Val Val Gln Arg
            20                  25

<210> SEQ ID NO 143
<211> LENGTH: 15
<212> TYPE: PRT
<213> ORGANISM: Homo sapiens
<220> FEATURE:
<221> NAME/KEY: CARBOHYD
<222> LOCATION: (14)..(14)
<223> OTHER INFORMATION: N-LINKED (Asn) (Experimental)

<400> SEQUENCE: 143

Trp Phe Tyr Ile Ala Ser Ala Phe Arg Asn Glu Glu Tyr Asn Lys
1               5                   10                  15

<210> SEQ ID NO 144
<211> LENGTH: 30
<212> TYPE: PRT
<213> ORGANISM: Homo sapiens
<220> FEATURE:
<221> NAME/KEY: CARBOHYD -continued

```
<222> LOCATION: (5)..(5)
<223> OTHER INFORMATION: N-LINKED (Asn) (Experimental)

<400> SEQUENCE: 144

Ser Glu Gly Thr Asn Ser Thr Leu Thr Leu Ser Pro Val Ser Phe Glu
1               5                   10                  15

Asn Glu His Ser Tyr Leu Cys Thr Val Thr Cys Gly His Lys
            20                  25                  30

<210> SEQ ID NO 145
<211> LENGTH: 22
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: pyrrolidone carboxylic acid (pyro-Glu)
<220> FEATURE:
<221> NAME/KEY: CARBOHYD
<222> LOCATION: (7)..(7)
<223> OTHER INFORMATION: N-LINKED (Asn) (Experimental)
<220> FEATURE:
<221> NAME/KEY: CARBOHYD
<222> LOCATION: (17)..(17)
<223> OTHER INFORMATION: N-LINKED (Asn) (Experimental)

<400> SEQUENCE: 145

Gln Asn Gln Cys Phe Tyr Asn Ser Ser Tyr Leu Asn Val Gln Arg Glu
1               5                   10                  15

Asn Gly Thr Val Ser Arg
            20

<210> SEQ ID NO 146
<211> LENGTH: 14
<212> TYPE: PRT
<213> ORGANISM: Homo sapiens
<220> FEATURE:
<221> NAME/KEY: CARBOHYD
<222> LOCATION: (8)..(8)
<223> OTHER INFORMATION: N-LINKED (Asn) (Experimental)

<400> SEQUENCE: 146

Val Asp Leu Glu Asp Phe Glu Asn Asn Thr Ala Tyr Ala Lys
1               5                   10

<210> SEQ ID NO 147
<211> LENGTH: 19
<212> TYPE: PRT
<213> ORGANISM: Homo sapiens
<220> FEATURE:
<221> NAME/KEY: CARBOHYD
<222> LOCATION: (7)..(7)
<223> OTHER INFORMATION: N-LINKED (Asn) (Experimental)

<400> SEQUENCE: 147

Ile Gly Glu Ala Asp Phe Asn Arg Ser Lys Glu Phe Met Glu Glu Val
1               5                   10                  15

Ile Gln Arg

<210> SEQ ID NO 148
<211> LENGTH: 21
<212> TYPE: PRT
<213> ORGANISM: Homo sapiens
<220> FEATURE:
<221> NAME/KEY: CARBOHYD
<222> LOCATION: (10)..(10)
<223> OTHER INFORMATION: N-LINKED (Asn) (Experimental)
```

```
<400> SEQUENCE: 148

Ser His Ala Ala Ser Asp Ala Pro Glu Asn Leu Thr Leu Leu Ala Glu
1               5                   10                  15

Thr Ala Asp Ala Arg
            20

<210> SEQ ID NO 149
<211> LENGTH: 11
<212> TYPE: PRT
<213> ORGANISM: Homo sapiens
<220> FEATURE:
<221> NAME/KEY: CARBOHYD
<222> LOCATION: (7)..(7)
<223> OTHER INFORMATION: N-LINKED (Asn) (Experimental)

<400> SEQUENCE: 149

Asp Phe Tyr Val Asp Glu Asn Thr Thr Val Arg
1               5                   10

<210> SEQ ID NO 150
<211> LENGTH: 13
<212> TYPE: PRT
<213> ORGANISM: Homo sapiens
<220> FEATURE:
<221> NAME/KEY: CARBOHYD
<222> LOCATION: (3)..(3)
<223> OTHER INFORMATION: N-LINKED (Asn) (Experimental)

<400> SEQUENCE: 150

Val Gln Asn Val Thr Glu Phe Asp Asp Ser Leu Leu Arg
1               5                   10

<210> SEQ ID NO 151
<211> LENGTH: 21
<212> TYPE: PRT
<213> ORGANISM: Homo sapiens
<220> FEATURE:
<221> NAME/KEY: CARBOHYD
<222> LOCATION: (14)..(14)
<223> OTHER INFORMATION: N-LINKED (Asn) (Experimental)

<400> SEQUENCE: 151

His Gly Val Ile Ile Ser Ser Thr Val Asp Thr Tyr Glu Asn Gly Ser
1               5                   10                  15

Ser Val Glu Tyr Arg
            20

<210> SEQ ID NO 152
<211> LENGTH: 31
<212> TYPE: PRT
<213> ORGANISM: Homo sapiens
<220> FEATURE:
<221> NAME/KEY: CARBOHYD
<222> LOCATION: (4)..(4)
<223> OTHER INFORMATION: N-LINKED (Asn) (Experimental)
<220> FEATURE:
<221> NAME/KEY: MOD_RES
<222> LOCATION: (23)..(23)
<223> OTHER INFORMATION: Methionine sulfoxide ?Oxidation)

<400> SEQUENCE: 152

Tyr Thr Gly Asn Ala Ser Ala Leu Phe Ile Leu Pro Asp Gln Asp Lys
1               5                   10                  15

Met Glu Glu Val Glu Ala Met Leu Leu Pro Glu Thr Leu Lys Arg
            20                  25                  30
```

```
<210> SEQ ID NO 153
<211> LENGTH: 18
<212> TYPE: PRT
<213> ORGANISM: Homo sapiens
<220> FEATURE:
<221> NAME/KEY: CARBOHYD
<222> LOCATION: (14)..(14)
<223> OTHER INFORMATION: N-LINKED (Asn) (Experimental)

<400> SEQUENCE: 153

Ala Phe Gly Gln Phe Phe Ser Pro Gly Glu Val Ile Tyr Asn Lys Thr
1               5                   10                  15

Asp Arg

<210> SEQ ID NO 154
<211> LENGTH: 13
<212> TYPE: PRT
<213> ORGANISM: Homo sapiens
<220> FEATURE:
<221> NAME/KEY: CARBOHYD
<222> LOCATION: (7)..(7)
<223> OTHER INFORMATION: N-LINKED (Asn) (Experimental)

<400> SEQUENCE: 154

Glu Ala Pro Tyr Phe Tyr Asn Asp Thr Val Thr Phe Lys
1               5                   10

<210> SEQ ID NO 155
<211> LENGTH: 24
<212> TYPE: PRT
<213> ORGANISM: Homo sapiens
<220> FEATURE:
<221> NAME/KEY: CARBOHYD
<222> LOCATION: (7)..(7)
<223> OTHER INFORMATION: N-LINKED (Asn) (Experimental)
<220> FEATURE:
<221> NAME/KEY: MOD_RES
<222> LOCATION: (23)..(23)
<223> OTHER INFORMATION: Methionine sulfoxide ?Oxidation)

<400> SEQUENCE: 155

Glu His Glu Ala Gln Ser Asn Ala Ser Leu Asp Val Phe Leu Gly His
1               5                   10                  15

Thr Asn Val Glu Glu Leu Met Lys
            20

<210> SEQ ID NO 156
<211> LENGTH: 17
<212> TYPE: PRT
<213> ORGANISM: Homo sapiens
<220> FEATURE:
<221> NAME/KEY: CARBOHYD
<222> LOCATION: (11)..(11)
<223> OTHER INFORMATION: N-LINKED (Asn) (Experimental)

<400> SEQUENCE: 156

Glu Leu Asp Arg Glu Val Tyr Pro Trp Tyr Asn Leu Thr Val Glu Ala
1               5                   10                  15

Lys

<210> SEQ ID NO 157
<211> LENGTH: 21
<212> TYPE: PRT
<213> ORGANISM: Homo sapiens
<220> FEATURE:
<221> NAME/KEY: CARBOHYD
<222> LOCATION: (9)..(9)
<223> OTHER INFORMATION: N-LINKED (Asn) (Experimental)
```

```
<400> SEQUENCE: 157

Leu Gly Ser Tyr Pro Val Gly Gly Asn Val Ser Phe Glu Cys Glu Asp
1               5                   10                  15

Gly Phe Ile Leu Arg
            20

<210> SEQ ID NO 158
<211> LENGTH: 25
<212> TYPE: PRT
<213> ORGANISM: Homo sapiens
<220> FEATURE:
<221> NAME/KEY: CARBOHYD
<222> LOCATION: (9)..(9)
<223> OTHER INFORMATION: N-LINKED (Asn) (Experimental)
<220> FEATURE:
<221> NAME/KEY: CARBOHYD
<222> LOCATION: (24)..(24)
<223> OTHER INFORMATION: N-LINKED (Asn) (Experimental)

<400> SEQUENCE: 158

Gly Cys Val Leu Leu Ser Tyr Leu Asn Glu Thr Val Thr Val Ser Ala
1               5                   10                  15

Ser Leu Glu Ser Val Arg Gly Asn Arg
            20                  25

<210> SEQ ID NO 159
<211> LENGTH: 13
<212> TYPE: PRT
<213> ORGANISM: Homo sapiens
<220> FEATURE:
<221> NAME/KEY: CARBOHYD
<222> LOCATION: (8)..(8)
<223> OTHER INFORMATION: N-LINKED (Asn) (Experimental)

<400> SEQUENCE: 159

Val Tyr Lys Pro Ser Ala Gly Asn Asn Ser Leu Tyr Arg
1               5                   10

<210> SEQ ID NO 160
<211> LENGTH: 17
<212> TYPE: PRT
<213> ORGANISM: Homo sapiens
<220> FEATURE:
<221> NAME/KEY: CARBOHYD
<222> LOCATION: (1)..(1)
<223> OTHER INFORMATION: N-LINKED (Asn) (Experimental)
<220> FEATURE:
<221> NAME/KEY: CARBOHYD
<222> LOCATION: (7)..(7)
<223> OTHER INFORMATION: N-LINKED (Asn) (Experimental)
<220> FEATURE:
<221> NAME/KEY: MOD_RES
<222> LOCATION: (16)..(16)
<223> OTHER INFORMATION: Methionine sulfoxide ?Oxidation)

<400> SEQUENCE: 160

Asn Gly Thr Gly His Gly Asn Ser Thr His His Gly Pro Glu Tyr Met
1               5                   10                  15

Arg

<210> SEQ ID NO 161
<211> LENGTH: 17
<212> TYPE: PRT
<213> ORGANISM: Homo sapiens
<220> FEATURE:
<221> NAME/KEY: CARBOHYD
<222> LOCATION: (1)..(1)
```

<223> OTHER INFORMATION: N-LINKED (Asn) (Experimental)
<220> FEATURE:
<221> NAME/KEY: CARBOHYD
<222> LOCATION: (7)..(7)
<223> OTHER INFORMATION: N-LINKED (Asn) (Experimental)

<400> SEQUENCE: 161

Asn Gly Thr Gly His Gly Asn Ser Thr His His Gly Pro Glu Tyr Met
1               5                   10                  15

Arg

<210> SEQ ID NO 162
<211> LENGTH: 13
<212> TYPE: PRT
<213> ORGANISM: Homo sapiens
<220> FEATURE:
<221> NAME/KEY: CARBOHYD
<222> LOCATION: (10)..(10)
<223> OTHER INFORMATION: N-LINKED (Asn) (Experimental)

<400> SEQUENCE: 162

Ala Ala Ile Pro Ser Ala Leu Asp Thr Asn Ser Ser Lys
1               5                   10

<210> SEQ ID NO 163
<211> LENGTH: 11
<212> TYPE: PRT
<213> ORGANISM: Homo sapiens
<220> FEATURE:
<221> NAME/KEY: CARBOHYD
<222> LOCATION: (3)..(3)
<223> OTHER INFORMATION: N-LINKED (Asn) (Experimental)
<220> FEATURE:
<221> NAME/KEY: MOD_RES
<222> LOCATION: (7)..(7)
<223> OTHER INFORMATION: Methionine sulfoxide ?Oxidation)

<400> SEQUENCE: 163

Leu Gly Asn Trp Ser Ala Met Pro Ser Cys Lys
1               5                   10

<210> SEQ ID NO 164
<211> LENGTH: 21
<212> TYPE: PRT
<213> ORGANISM: Homo sapiens
<220> FEATURE:
<221> NAME/KEY: CARBOHYD
<222> LOCATION: (9)..(9)
<223> OTHER INFORMATION: N-LINKED (Asn) (Experimental)

<400> SEQUENCE: 164

Val Val Gly Val Pro Tyr Gln Gly Asn Ala Thr Ala Leu Phe Ile Leu
1               5                   10                  15

Pro Ser Glu Gly Lys
            20

<210> SEQ ID NO 165
<211> LENGTH: 12
<212> TYPE: PRT
<213> ORGANISM: Homo sapiens
<220> FEATURE:
<221> NAME/KEY: CARBOHYD
<222> LOCATION: (3)..(3)
<223> OTHER INFORMATION: N-LINKED (Asn) (Experimental)

<400> SEQUENCE: 165

Gly Leu Asn Leu Thr Glu Asp Thr Tyr Lys Pro Arg
1               5                   10

```
<210> SEQ ID NO 166
<211> LENGTH: 26
<212> TYPE: PRT
<213> ORGANISM: Homo sapiens
<220> FEATURE:
<221> NAME/KEY: CARBOHYD
<222> LOCATION: (16)..(16)
<223> OTHER INFORMATION: N-LINKED (Asn) (Experimental)

<400> SEQUENCE: 166

Ser Ile Pro Ala Cys Val Pro Trp Ser Pro Tyr Leu Phe Gln Pro Asn
1               5                   10                  15

Asp Thr Cys Ile Val Ser Gly Trp Gly Arg
            20                  25

<210> SEQ ID NO 167
<211> LENGTH: 15
<212> TYPE: PRT
<213> ORGANISM: Homo sapiens
<220> FEATURE:
<221> NAME/KEY: CARBOHYD
<222> LOCATION: (5)..(5)
<223> OTHER INFORMATION: N-LINKED (Asn) (Experimental)

<400> SEQUENCE: 167

Tyr Asn Ser Gln Asn Gln Ser Asn Asn Gln Phe Val Leu Tyr Arg
1               5                   10                  15

<210> SEQ ID NO 168
<211> LENGTH: 14
<212> TYPE: PRT
<213> ORGANISM: Homo sapiens
<220> FEATURE:
<221> NAME/KEY: CARBOHYD
<222> LOCATION: (9)..(9)
<223> OTHER INFORMATION: N-LINKED (Asn) (Experimental)

<400> SEQUENCE: 168

Lys Leu Pro Pro Gly Leu Leu Ala Asn Phe Thr Leu Leu Arg
1               5                   10

<210> SEQ ID NO 169
<211> LENGTH: 11
<212> TYPE: PRT
<213> ORGANISM: Homo sapiens
<220> FEATURE:
<221> NAME/KEY: CARBOHYD
<222> LOCATION: (3)..(3)
<223> OTHER INFORMATION: N-LINKED (Asn) (Experimental)

<400> SEQUENCE: 169

Leu Gly Asn Trp Ser Ala Met Pro Ser Cys Lys
1               5                   10

<210> SEQ ID NO 170
<211> LENGTH: 17
<212> TYPE: PRT
<213> ORGANISM: Homo sapiens
<220> FEATURE:
<221> NAME/KEY: CARBOHYD
<222> LOCATION: (7)..(7)
<223> OTHER INFORMATION: N-LINKED (Asn) (Experimental)

<400> SEQUENCE: 170

Leu His Ile Asn His Asn Asn Leu Thr Glu Ser Val Gly Pro Leu Pro
1               5                   10                  15

Lys
```

```
<210> SEQ ID NO 171
<211> LENGTH: 9
<212> TYPE: PRT
<213> ORGANISM: Homo sapiens
<220> FEATURE:
<221> NAME/KEY: CARBOHYD
<222> LOCATION: (4)..(4)
<223> OTHER INFORMATION: N-LINKED (Asn) (Experimental)

<400> SEQUENCE: 171

Gly Ile Cys Asn Ser Ser Asp Val Arg
1               5

<210> SEQ ID NO 172
<211> LENGTH: 14
<212> TYPE: PRT
<213> ORGANISM: Homo sapiens
<220> FEATURE:
<221> NAME/KEY: CARBOHYD
<222> LOCATION: (11)..(11)
<223> OTHER INFORMATION: N-LINKED (Asn) (Experimental)

<400> SEQUENCE: 172

His Glu Arg Asp Ala Gly Val Val Cys Thr Asn Glu Thr Arg
1               5                   10

<210> SEQ ID NO 173
<211> LENGTH: 17
<212> TYPE: PRT
<213> ORGANISM: Homo sapiens
<220> FEATURE:
<221> NAME/KEY: CARBOHYD
<222> LOCATION: (9)..(9)
<223> OTHER INFORMATION: N-LINKED (Asn) (Experimental)

<400> SEQUENCE: 173

Ala Ser Pro Pro Ser Ser Ser Cys Asn Ile Ser Ser Gly Glu Met Gln
1               5                   10                  15

Lys

<210> SEQ ID NO 174
<211> LENGTH: 14
<212> TYPE: PRT
<213> ORGANISM: Homo sapiens
<220> FEATURE:
<221> NAME/KEY: CARBOHYD
<222> LOCATION: (6)..(6)
<223> OTHER INFORMATION: N-LINKED (Asn) (Experimental)

<400> SEQUENCE: 174

Lys Glu Asp Ala Leu Asn Glu Thr Arg Glu Ser Glu Thr Lys
1               5                   10

<210> SEQ ID NO 175
<211> LENGTH: 32
<212> TYPE: PRT
<213> ORGANISM: Homo sapiens
<220> FEATURE:
<221> NAME/KEY: CARBOHYD
<222> LOCATION: (23)..(23)
<223> OTHER INFORMATION: N-LINKED (Asn) (Experimental)

<400> SEQUENCE: 175

Glu Ser Lys Pro Leu Thr Ala Gln Gln Thr Thr Lys Leu Asp Ala Pro
1               5                   10                  15

Thr Asn Leu Gln Phe Val Asn Glu Thr Asp Ser Thr Val Leu Val Arg
                20                  25                  30
```

```
<210> SEQ ID NO 176
<211> LENGTH: 11
<212> TYPE: PRT
<213> ORGANISM: Homo sapiens
<220> FEATURE:
<221> NAME/KEY: CARBOHYD
<222> LOCATION: (5)..(5)
<223> OTHER INFORMATION: N-LINKED (Asn) (Experimental)

<400> SEQUENCE: 176

Glu Ile Arg His Asn Ser Thr Gly Cys Leu Arg
1               5                   10

<210> SEQ ID NO 177
<211> LENGTH: 34
<212> TYPE: PRT
<213> ORGANISM: Homo sapiens
<220> FEATURE:
<221> NAME/KEY: CARBOHYD
<222> LOCATION: (3)..(3)
<223> OTHER INFORMATION: N-LINKED (Asn) (Experimental)
<220> FEATURE:
<221> NAME/KEY: CARBOHYD
<222> LOCATION: (23)..(23)
<223> OTHER INFORMATION: N-LINKED (Asn) (Experimental)

<400> SEQUENCE: 177

Met Leu Asn Thr Ser Ser Leu Leu Glu Gln Leu Asn Glu Gln Phe Asn
1               5                   10                  15

Trp Val Ser Arg Leu Ala Asn Leu Thr Gln Gly Glu Asp Gln Tyr Tyr
            20                  25                  30

Leu Arg

<210> SEQ ID NO 178
<211> LENGTH: 10
<212> TYPE: PRT
<213> ORGANISM: Homo sapiens
<220> FEATURE:
<221> NAME/KEY: CARBOHYD
<222> LOCATION: (1)..(1)
<223> OTHER INFORMATION: N-LINKED (Asn) (Experimental)

<400> SEQUENCE: 178

Asn Phe Thr Glu Asn Asp Leu Leu Val Arg
1               5                   10

<210> SEQ ID NO 179
<211> LENGTH: 34
<212> TYPE: PRT
<213> ORGANISM: Homo sapiens
<220> FEATURE:
<221> NAME/KEY: CARBOHYD
<222> LOCATION: (28)..(28)
<223> OTHER INFORMATION: N-LINKED (Asn) (Experimental)

<400> SEQUENCE: 179

Asn Leu Ala Ser Arg Pro Tyr Thr Phe His Ser His Gly Ile Thr Tyr
1               5                   10                  15

Tyr Lys Glu His Glu Gly Ala Ile Tyr Pro Asp Asn Thr Thr Asp Phe
            20                  25                  30

Gln Arg

<210> SEQ ID NO 180
<211> LENGTH: 25
<212> TYPE: PRT
<213> ORGANISM: Homo sapiens
```

```
<220> FEATURE:
<221> NAME/KEY: CARBOHYD
<222> LOCATION: (15)..(15)
<223> OTHER INFORMATION: N-LINKED (Asn) (Experimental)

<400> SEQUENCE: 180

Tyr Pro Pro Thr Val Ser Met Val Glu Gly Gln Gly Glu Lys Asn Val
1               5                   10                  15

Thr Phe Trp Gly Arg Pro Leu Pro Arg
            20                  25

<210> SEQ ID NO 181
<211> LENGTH: 15
<212> TYPE: PRT
<213> ORGANISM: Homo sapiens
<220> FEATURE:
<221> NAME/KEY: CARBOHYD
<222> LOCATION: (5)..(5)
<223> OTHER INFORMATION: N-LINKED (Asn) (Experimental)

<400> SEQUENCE: 181

Phe Cys Arg Asp Asn Tyr Thr Asp Leu Val Ala Ile Gln Asn Lys
1               5                   10                  15

<210> SEQ ID NO 182
<211> LENGTH: 15
<212> TYPE: PRT
<213> ORGANISM: Homo sapiens
<220> FEATURE:
<221> NAME/KEY: CARBOHYD
<222> LOCATION: (2)..(2)
<223> OTHER INFORMATION: N-LINKED (Asn) (Experimental)

<400> SEQUENCE: 182

Ile Asn Ala Thr Asp Ala Asp Glu Pro Asn Thr Leu Asn Ser Lys
1               5                   10                  15

<210> SEQ ID NO 183
<211> LENGTH: 19
<212> TYPE: PRT
<213> ORGANISM: Homo sapiens
<220> FEATURE:
<221> NAME/KEY: CARBOHYD
<222> LOCATION: (10)..(10)
<223> OTHER INFORMATION: N-LINKED (Asn) (Experimental)

<400> SEQUENCE: 183

Thr Val Val Thr Tyr His Ile Pro Gln Asn Ser Ser Leu Glu Asn Val
1               5                   10                  15

Asp Ser Arg
```

GLYCAN MARKERS AS MEASURE OF DISEASE STATE OF HEPATIC DISEASES

This application is a National Stage of International Application PCT/JP2010/061791 filed Jul.12, 2010, which claims the benefit of the filing date of Japanese Patent Application No. 2009-165795, filed Jul. 14, 2009. The entirety of both applications is hereby incorporated by reference.

TECHNICAL FIELD

The present invention relates to at least one hepatic disease-state-indicating glycan marker having glycan(s), and more specifically to a marker serving as an indicator for hepatic disease-state based on glycosylation change on a peptide and a protein. The present invention also relates to a marker capable of detecting the underlying state of the liver such as hepatocarcinoma and inflammation/fibrosis based on difference in sugar chain.

BACKGROUND ART

Hepatocarcinoma is roughly divided into a primary hepatocarcinoma developed in the liver and a metastatic hepatocarcinoma. Ninety percent of the primary hepatocarcinoma is said to be hepatocellular carcinoma.

Hepatocellular carcinoma patients often have hepatitis C virus or hepatitis B virus infection as an underlying disease. Acute viral hepatitis is developed into chronic viral hepatitis and further into cirrhosis. Likewise, in most cases, canceration occurs for the first time after a long period of time from the onset of viral hepatitis. In cirrhosis, inflammation and regeneration repeatedly occur, with the result that the number of normal hepatic cells reduces and the liver changes into an organ constituted of fibrous tissue. For example, the number of hepatitis C patients is 3,000,000 in Japan and said to be 10,000,000 or more in China and Africa. Furthermore, in the cases of hepatitis B and C patients, an incidence of cancer from chronic hepatitis, more specifically, an incidence of cancer from mild chronic hepatitis (F1) is 0.8% each year and an incidence of cancer from moderate chronic hepatitis (F2) is 0.9% each year. In contrast, an incidence of cancer from severe chronic hepatitis (F3) becomes 3.5% each year and moreover, the rate of carcinogenesis from cirrhosis (F4) increases up to 7% each year (FIGS. 2, 3). Also, the histology of the hepatic disease changes according to the progression of the state. First, in chronic hepatitis, the function of the liver starts to disappear, and in cirrhosis, a pathological structure appears and fibrosis of the liver advances (FIG. 1).

In cancer therapy, it is important to find cancer in the early stage.
Also in the case of hepatocellular carcinoma, early detection of cancer has a significant effect upon therapy and postoperative prognosis. The 5-year survival rate of partial hepatectomy is 80% in stage-I hepatocarcinoma and only 38% in stage-IV hepatocarcinoma.

As hepatocarcinoma markers, up to present, a-fetoprotein (AFP) and a protein induced by Vitamin K absence or antagonist-II (PIVKA-II) have been known (Patent Literatures 1, 2); however, neither specificity nor sensitivity thereof are sufficient. For this reason, in medical examination presently carried out for early detection of hepatocarcinoma, a hepatocarcinoma marker is used in combination with imaging inspection such as ultrasonographic examination, computed tomography (CT) and nuclear magnetic resonance imaging (MRI).

CITATION LIST

Patent Literatures

Patent Literature 1: JP Patent Publication (Kokai) No. 10-26622 A
Patent Literature 2: JP Patent Publication (Kokai) No. 8-184594 A

SUMMARY OF INVENTION

Technical Problem

The present invention is directed to developing glycan markers capable of detecting hepatic diseases, and more specifically to developing glycan markers indicating hepatic disease-state. Furthermore, the present invention is also directed to developing glycan markers capable of distinguishing hepatic disease-states associated with the progress of hepatocellular carcinoma. Moreover, the present invention is directed to developing hepatic disease-state-indicating glycan markers including glycan markers for hepatocellular carcinoma, liver cirrhosis, chronic hepatitis and hepatic fibrosis. In the case of hepatitis C, the rate of developing hepatocellular carcinoma from liver cirrhosis is said to be approximately 7% each year. Presently, to detect canceration, the cirrhosis patients must undergo an examination about once per three months. To simplify examination for canceration from cirrhosis, providing a hepatocarcinoma marker capable of detecting canceration, for example, by a blood test is also an object of the present invention.

Furthermore, in conventional cancer markers made of a protein, determination is made by checking an increase of an expression level thereof in cancer; however most of the proteins are expressed in normal cells. Therefore, it has been often not easy to determine canceration by comparing degrees of expression levels. Then, providing a simple hepatocarcinoma marker not solely based on comparison between degrees of expression levels is also an object of the invention.

In addition, it is expected that if the disease background underlying progression into hepatocellular carcinoma can be specified, progression into the cancer can be suppressed. Then, providing a hepatic disease-state marker capable of specifying a disease states underlying hepatocarcinoma is another object.

Furthermore, in searching a disease-state-indicating marker such as a conventional cancer related glycan marker by proteomics, there are problems: (i) a technique to enrich a protein having glycan(s) specific to a disease-state such as cancer from a cell or a histological section and (ii) a technique to analyze the structure of glycan of an identified marker candidate protein have not yet been established. Then, searching hepatic disease-state-indicating glycan markers by a glycoproteomics-based method to search disease-marker is another object.

Moreover, the present invention is directed to develop markers indicating degree of hepatic disease-state progression, in particular, to develop hepatic fibrosis markers capable of distinguishing hepatic-disease group of stages of F1 and F2 from those of F3 and F4 or cirrhosis markers capable of distinguishing those of stages of F1, F2, and F3 from that of F4 (FIG. 4).

Solution to Problem

The present inventors identified the serum glycoproteins whose glycan structure are altered specifically associated with hepatic diseases including hepatocellular carcinoma by using glycoproteomics, and provide those glycopeptides and glycoproteins as nobel glycan markers specific to hepatic disease-states.

The present inventors further provide methods to specify hepatic disease-state underlying hepatocellular carcinoma and markers to perform the method, by comparative glycan analyses for the glycan markers by means of mass spectrometry and lectin array.

Advantageous Effects of Invention

The hepatic disease-state-indicating glycan markers of the present invention make it possible to detect hepatic disease-states such as hepatocellular carcinoma easily and with high reliability by examining blood sample such as serum. Thus, the invention produces such an excellent effect. Furthermore, the hepatic disease-state-indicating glycan markers of the present invention enable to specify disease-state underlying hepatocellular carcinoma by comparative glycan analysis of them.

In addition to capability to monitor hepatic disease-state progression, the markers can evaluate the improvement of inflammation and liver fibrosis by anti-viral treatments with e.g. interferon. This is due to that the technology monitoring hepatic fibrosis progression leads a diagnosis more accurate than that by conventional serum marker and requires small amount of serum to diagnose.

BRIEF DESCRIPTION OF DRAWINGS

The patent or application file contains at least one drawing executed in color. Copies of this patent or patent application publication with color drawing(s) will be provided by the Office upon request and payment of the necessary fee.

Disappearance of a normal structure and function for homeostatic activity are observed at this time and simultaneously, a pathological structure characterized by fibrosis appears. It is known that the hepatocellular carcinoma cells in the early stage develop into the classical hepatocellular carcinoma cells, and the feature of cells changes. When the size of carcinoma cells exceeds 2 cm, classical hepatocellular carcinoma cells appear in early-stage hepatocellular carcinoma.

Figures 1, 9:
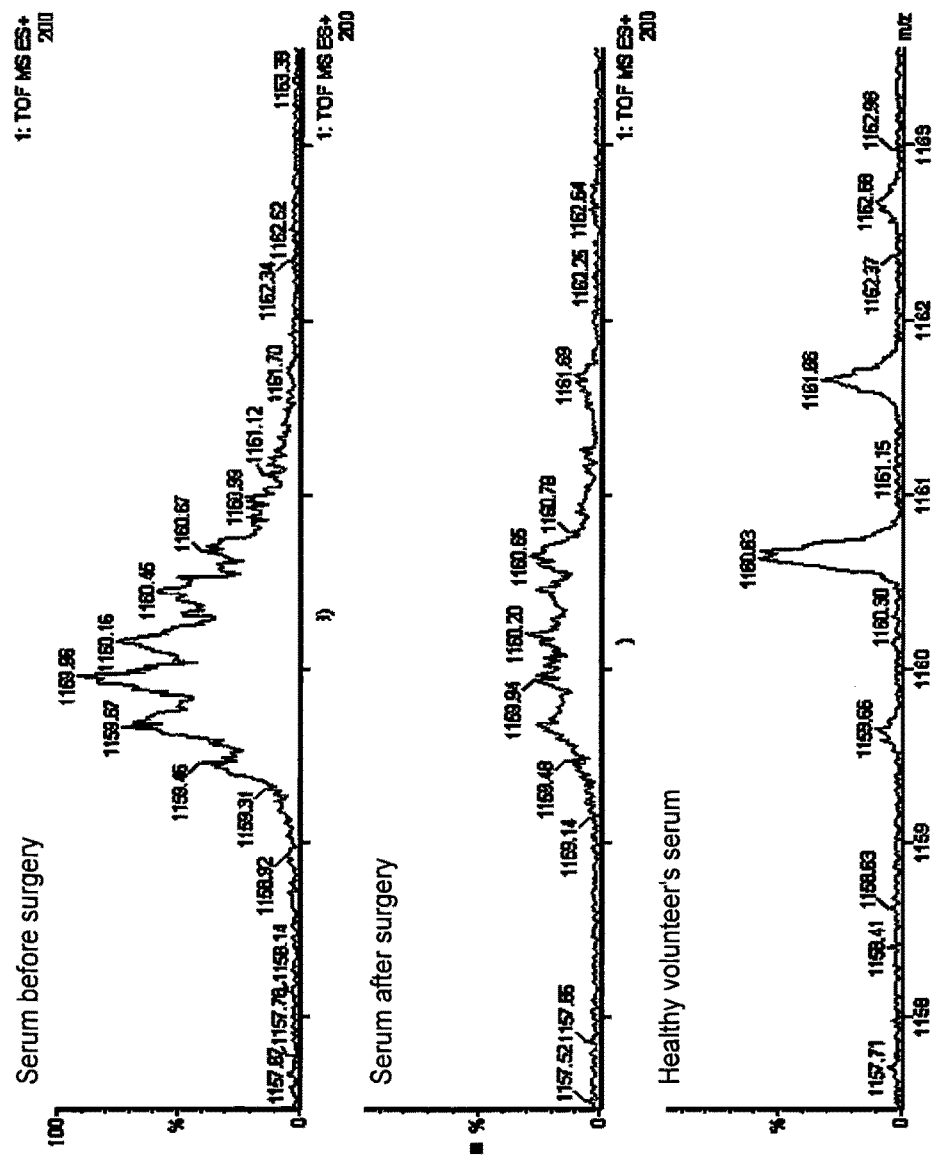
Figures 4, 9:
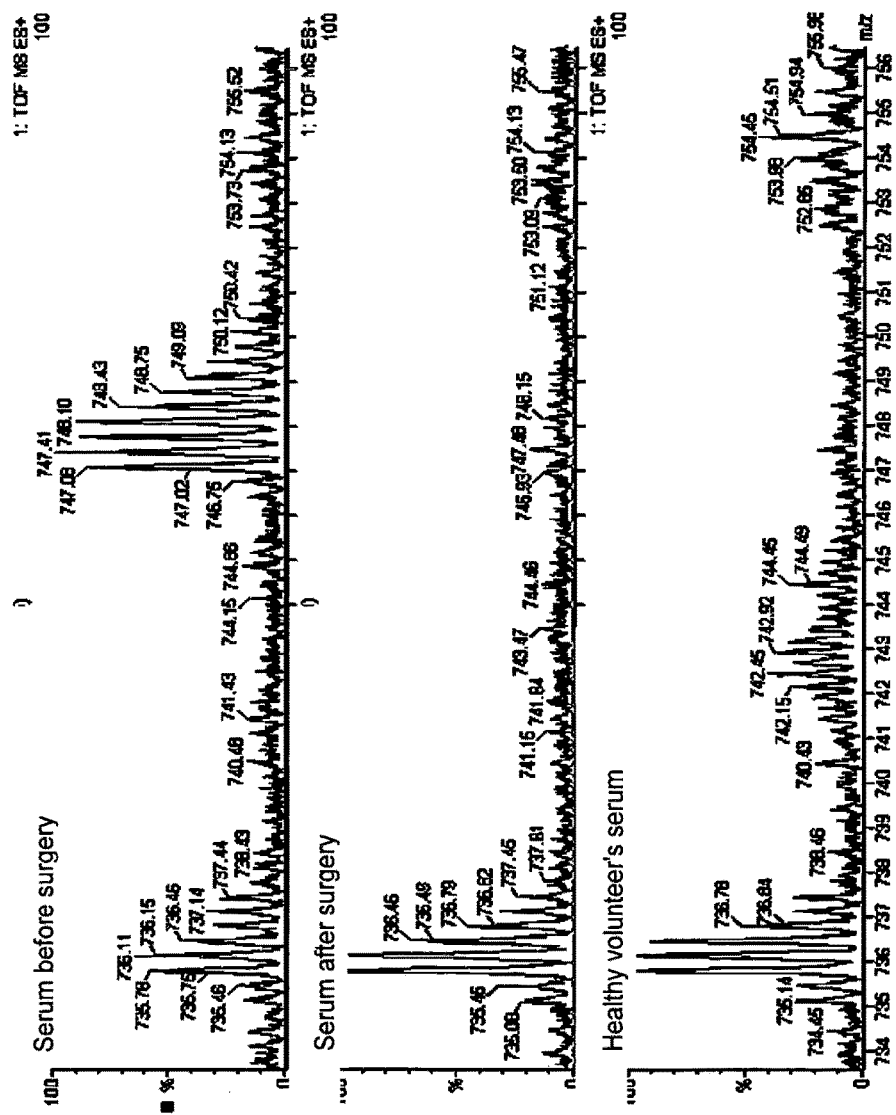
Figures 5, 9:
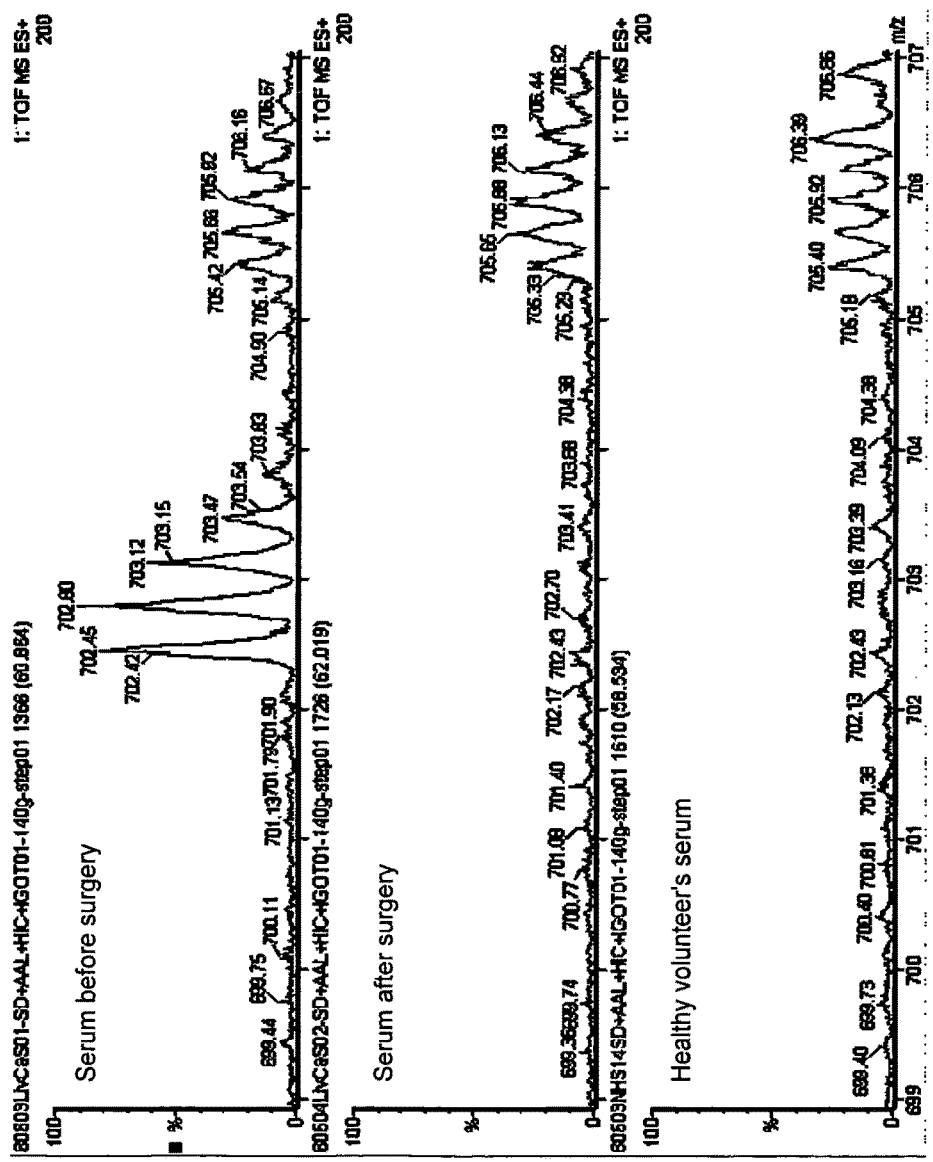
FIG. 5 Infection leads to carcinogenesis with the passage of time.
Figures 6, 9:
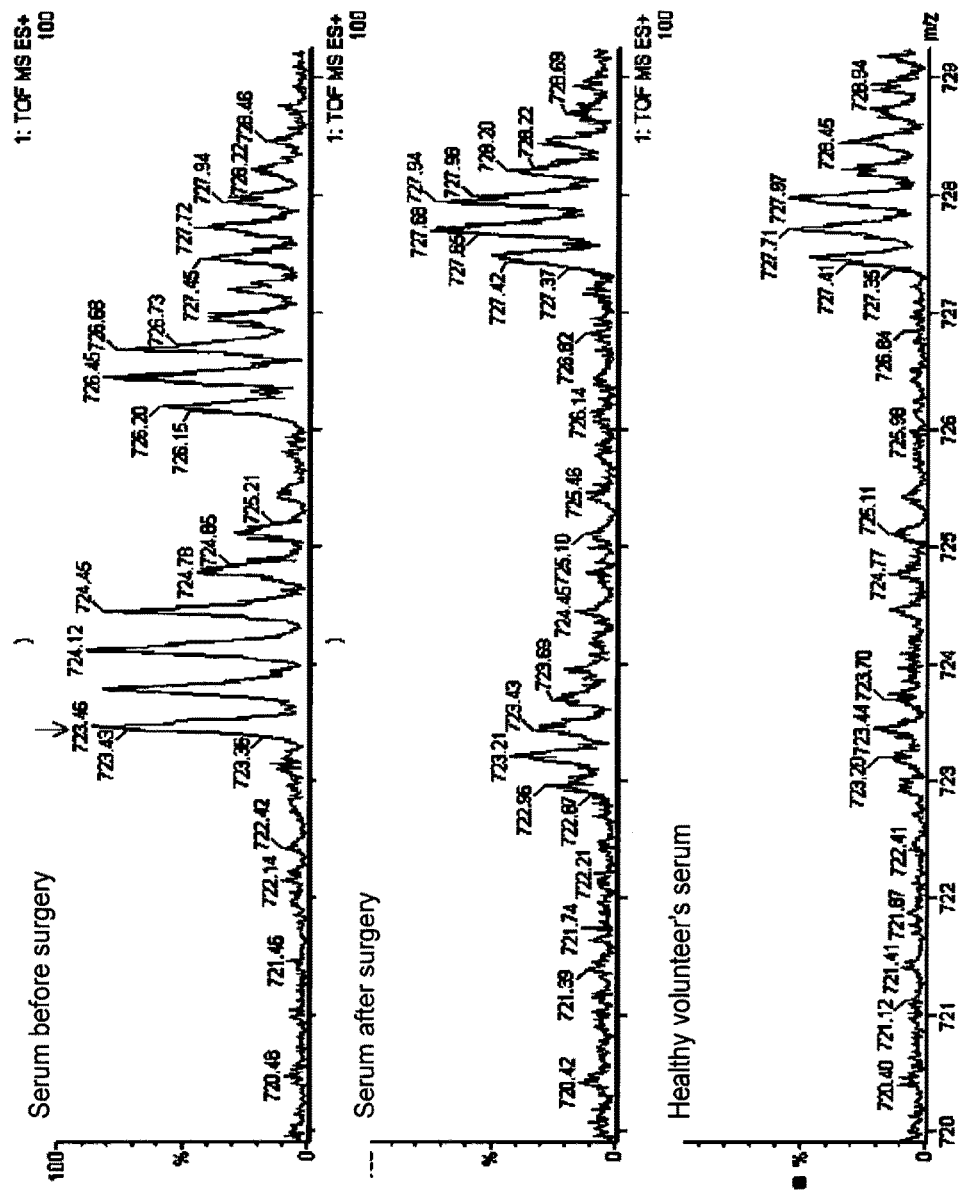
Figures 7, 9:
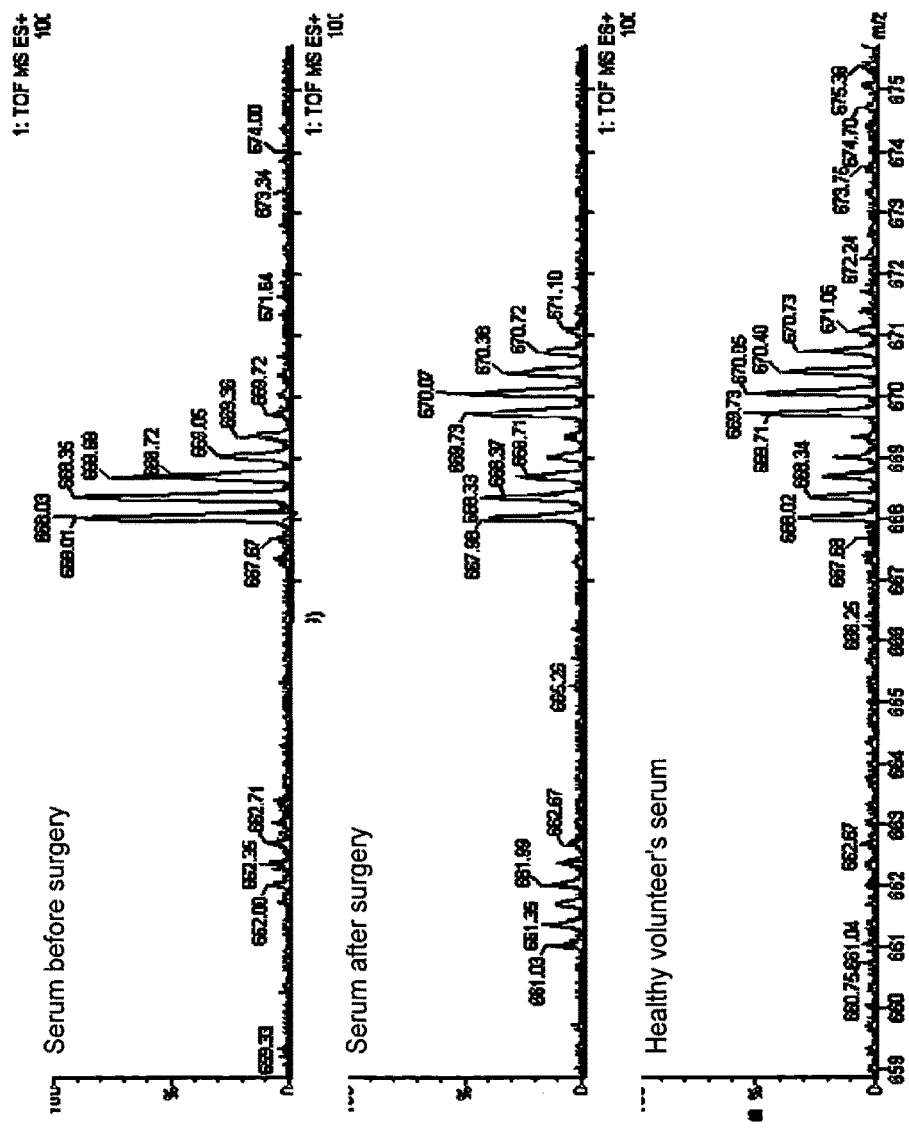

FIG. 6 Chronic hepatitis is treated by a peginterferon/ribavirin combination therapy (PEG-IFN+RBV therapy); whereas early-stage hepatocellular carcinoma is treated with radiofrequency ablation (RFA). Neither a diagnostic detection method nor an effective therapy is known for treating cirrhosis. Because the biomarkers of the present invention can distinguish the states of chronic hepatitis, cirrhosis, and hepatocellular carcinoma, the biomarker can serve as a reference to develop a novel therapy for cirrhosis. Furthermore, if the biomarker is used in combination with fibroscan, quantitative evaluation of fibrosis can be expected. Fibrosis (F3 to 4) cases can be enriched by the diagnostic serum marker. This means that the serum biomarker is expectedly used not only for quantitative diagnosis of fibrosis but also for evaluation of the therapeutic effect of a therapy on the clinical introduction of the therapy aimed at suppression of hepatic fibrosis progression and carcinogenesis.

Figure 7:
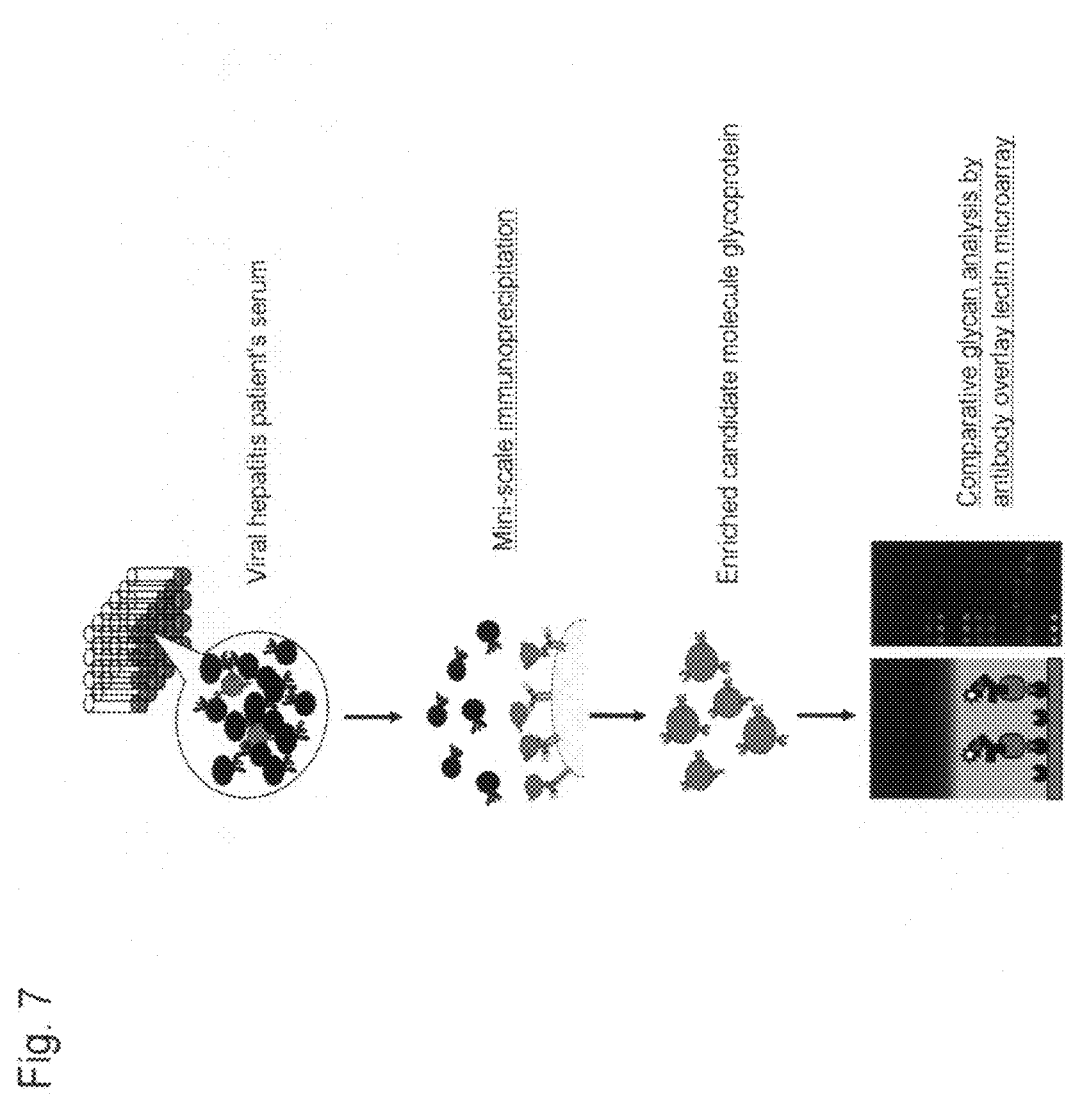

FIG. 7 is an illustration showing a strategy for a verification test of a biomarker candidate molecule based on lectin microarray. The hepatic disease-state-indicating marker is screened from glycoproteins present in the serum. Therefore, a target specimen for analysis is the serum. A comparative glycan analysis is carried out for the marker candidate molecules identified from the sera of hepatitis virus-infected patients by large-scale analysis. The candidate molecule is enriched easily by an immunoprecipitation method using an antibody against candidate core protein. The lectin microarray is a highly sensitive means for comparative glycan analysis. The preparation about 100 nanograms of protein is sufficient for the analysis. Therefore, the aforementioned pretreatment can be made in a mini-scale. The enriched candidate molecule is quickly added to the lectin microarray and reacted for a predetermined time. Then, by the antibody overlay lectin microarray method, the glycan profile of the candidate molecule is obtained. At this time, the amount of protein to be added to the lectin array varies depending upon the type of protein; however it is approximately nanogram to several tens of nanograms. The number of samples sufficient for statistical analysis was subjected to the array analyses and thereafter the data set was subjected to a two-group comparative analysis such as Student-T test and Mann-Whitney U-test. In this manner, it is possible to objectively screen lectins showing a signal with a significant difference due to the difference of disease-states.

Figure 8:
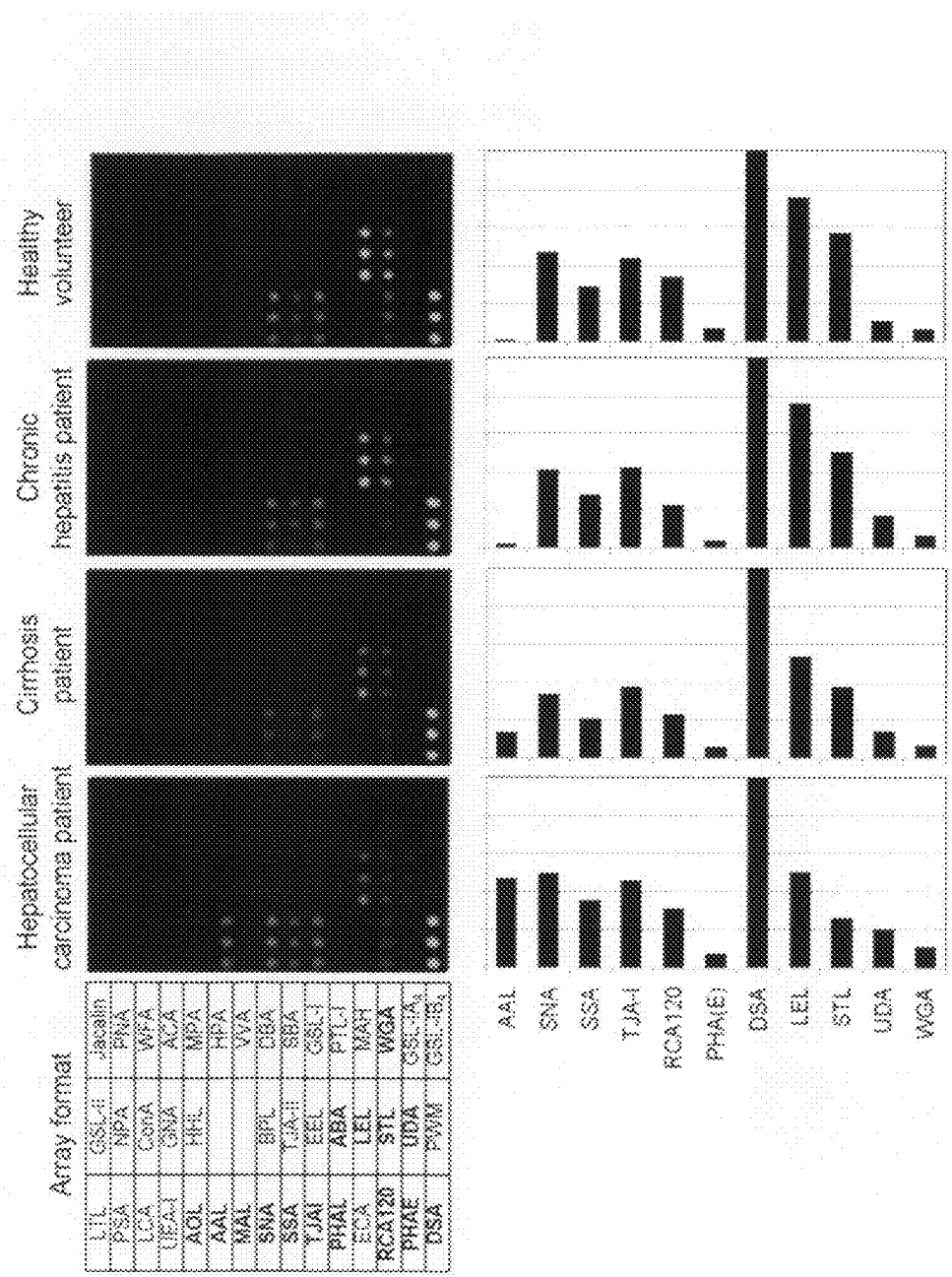

FIG. 8 shows the results of comparative glycan analysis of one of hepatic disease-state-indicating marker molecules, namely Carboxypeptidase N, polypeptide 2 (CPN2), by the antibody overlay lectin microarray method. The arrangement of lectins on the lectin microarray is shown in the upper left panel of the figure. The lectins showing a significant signal obtained by this experiment are shown by boldface. Signals were obtained from 11 types of lectins. Typical scan images of CPN2 derived from the sera of patients with hepatocellular carcinoma, cirrhosis and chronic hepatitis and the sera of healthy volunteers are shown in upper right panel of the figure. The signals from the 11 types of lectins are converted into numerical values from the scan data by use of array analysis software and shown in the graphs in the lower panel. It is found that signal intensity changes (increase or decrease) depending upon the severity of the disease-state.

Figure 1:
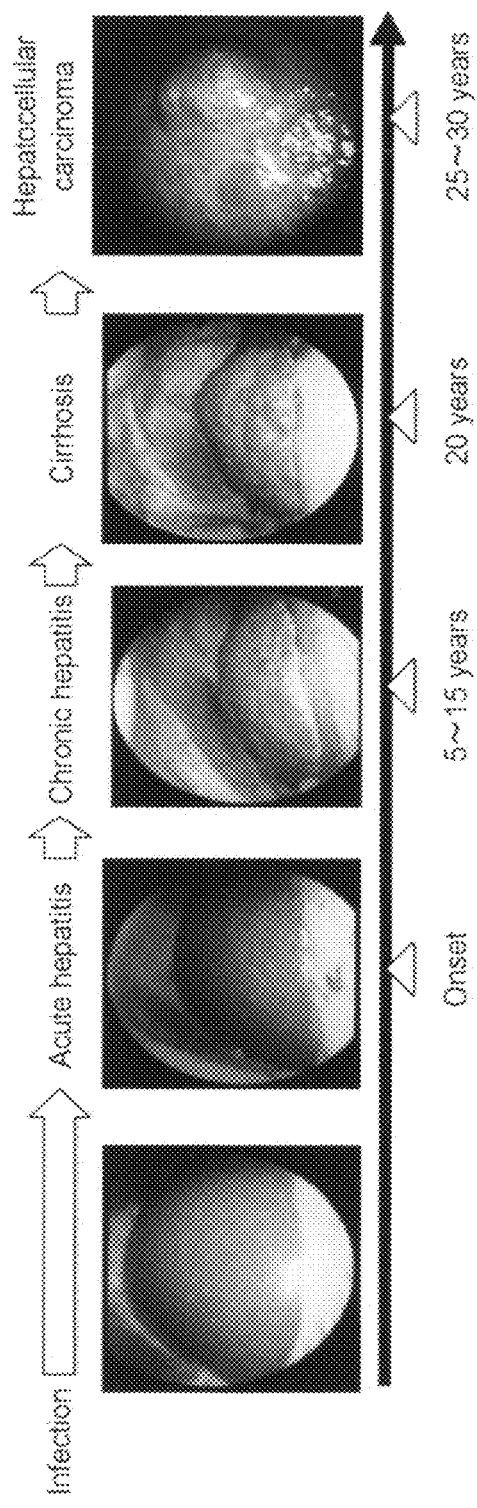
FIG. 1 Hepatitis C becomes chronic over 5 to 15 years after infection, developes into cirrhosis 20 years after infection, and reaches hepatocellular carcinoma after 25 to 30 years. Although the speed of progression varies between individuals; however a risk of developing into hepatocellular carcinoma increases with the passage of time.

FIG. 9-1 From peptide mixtures prepared from the sera of healthy volunteers and a patient of hepatocellular carcinoma obtained before and after surgery, glycopeptides were collected by a probe lectin and labeled by isotope-coded glycosylation site-specific tagging (IGOT) method. Using the equal amount of total glycopeptides, each glycopeptide sample was separately subjected to LC/MS analysis. Based on the mass to charge ratio (m/z) and retention time of the identified marker peptides, ions of each marker peptide were selected and their spectra were shown. The cases where the signal intensity of the marker peptide obtained from sera before surgery is significantly higher than those of others are shown in FIGS. 9-1 to 9-8.

FIG. 9-1 shows the spectra of Peptide No. 26 listed in the following Table 1.

Figure 2:
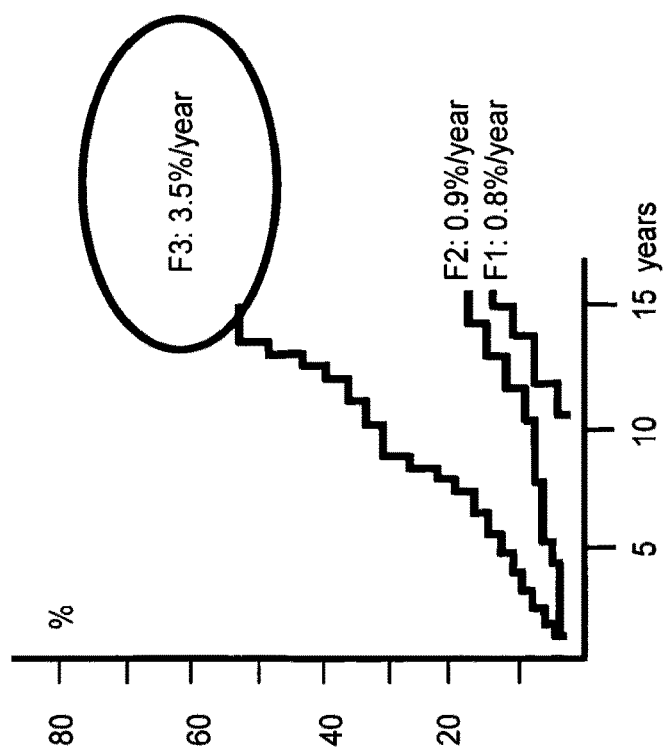
FIG. 2 is a graph showing the rate of incidence of hepatocellular carcinoma from chronic hepatitis. The stages of F1 to F3 of hepatic fibrosis are classified into chronic hepatitis. The lower stages of fibrosis shows the lower rate of incidence of hepatocellular carcinoma. The rate from F1 is 0.8% each year, 0.9% each year from F2, whereas it is 3.5% each year from F3.

FIG. 9-2 shows the spectra of Peptide No. 124 listed in the following Table 1.

Figure 3:
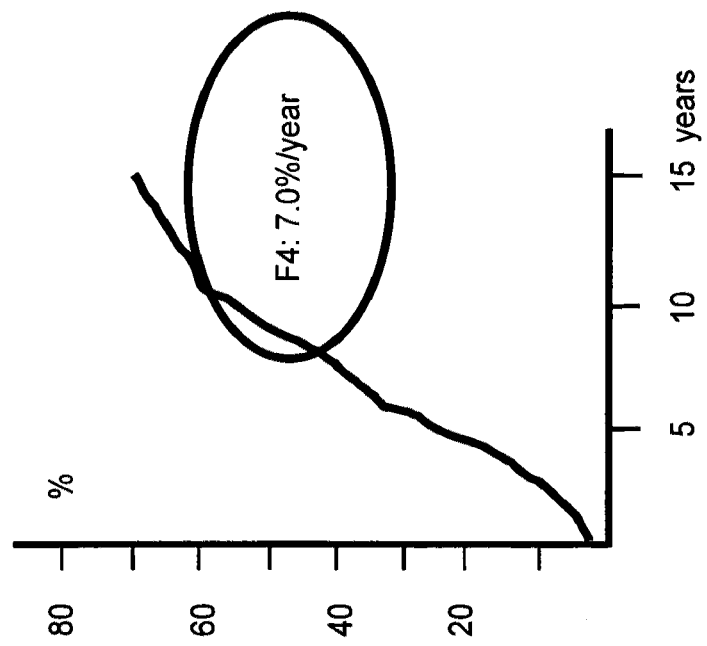
FIG. 3 is a graph showing the rate of incidence of hepatocellular carcinoma from cirrhosis. The stage of fibrosis is determined by histopathological diagnosis on a liver biopsy specimen. If the stage of fibrosis is F4, the rate of incidence of the cancer reaches 7.0% each year.

FIG. 9-3 shows the spectra of Peptide No. 118 listed in the following Table 1.

Figure 4:
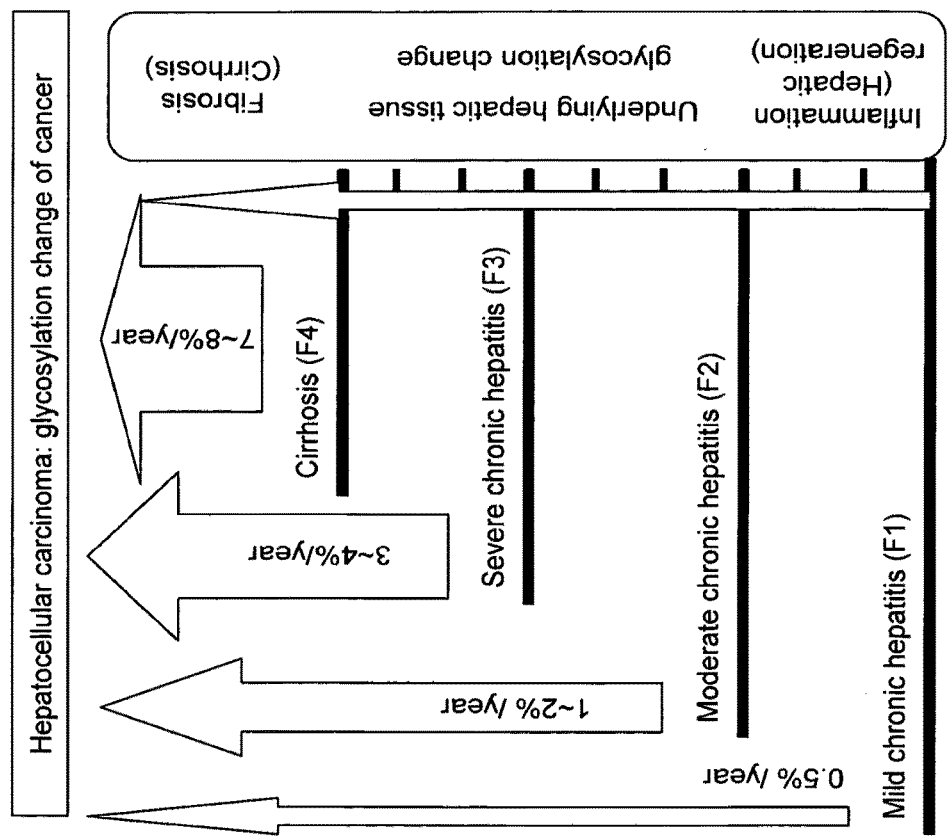
FIG. 4 Infection of the liver with hepatitis C virus causes regeneration of damaged hepatic cells and fibrosis as repairing scar. As fibrosis of the liver progresses, a risk of carcinogenesis increases. Therefore, "degree of fibrosis" becomes an index of risk of carcinogenesis. In the underlying liver tissue developing into cancer, constituting cells are altered, thus glycan structure is expected to be altered associated with the progression of fibrosis.

FIG. 9-4 shows the spectra of Peptide No. 19 listed in the following Table 1.

FIG. 9-5 shows the spectra of Peptide No. 130 listed in the following Table 1.

FIG. 9-6 shows the spectra of Peptide No. 135 listed in the following Table 1.

FIG. 9-7 shows the spectra of Peptide No. 125 listed in the following Table 1.

FIG. 9-8 shows the spectra of Peptide No. 132 listed in the following Table 1.

Figure 10:
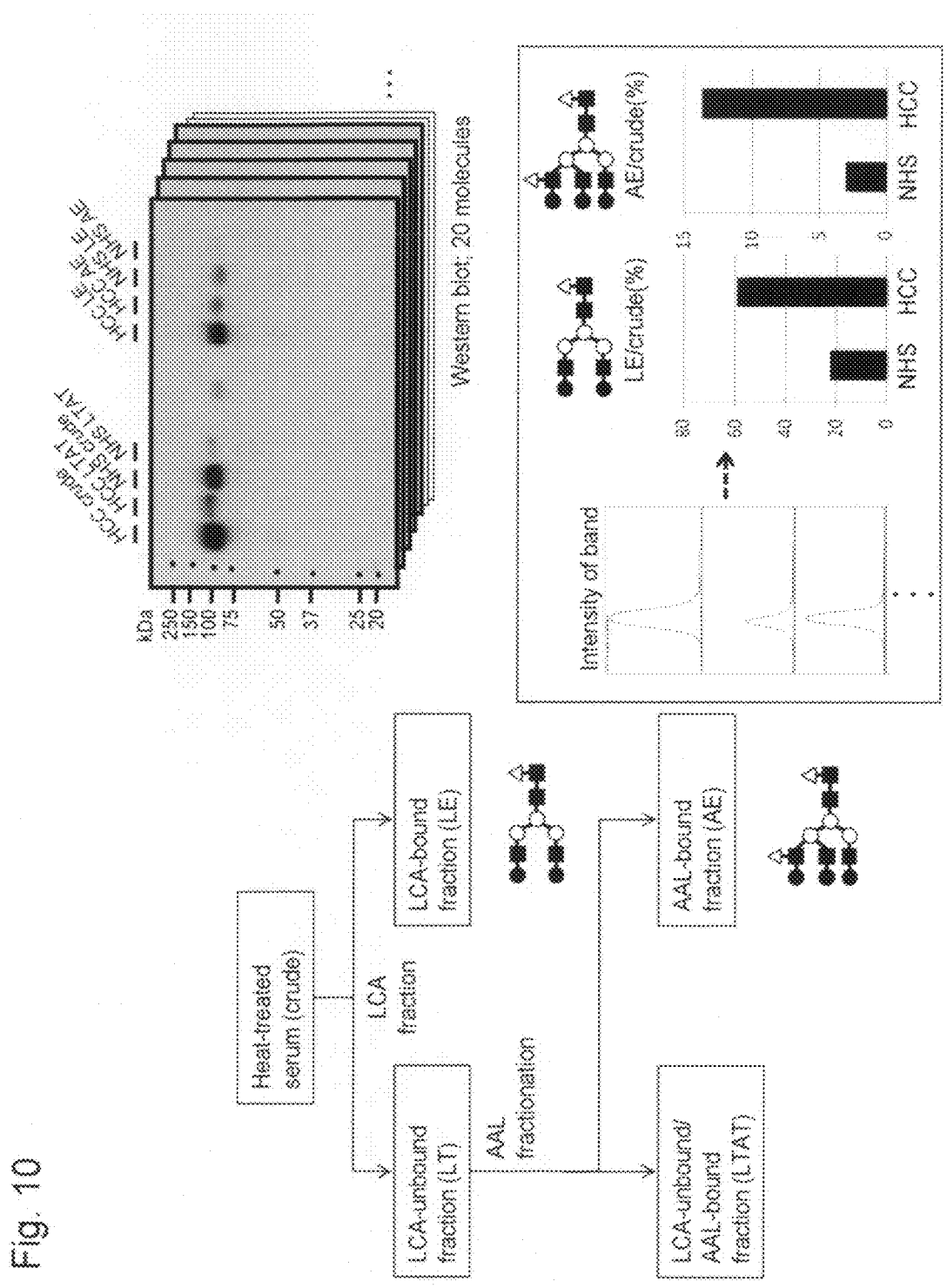

FIG. 10 schematically shows a fractionation procedure of serum proteins by serial lectin column chromatography and quantification and analysis of a band by Western blotting method. Each human serum was heated at 100° C. for 15 min under presence of 0.2% SDS, and used for following analysis as a heat-treated serum. The heat-treated serum is applied to LCA column to separate to an LCA-bound fraction (LE) and an LCA-unbound (through) fraction (LT). Subsequently, the LCA-unbound fraction is applied to AAL column to separate to an AAL-bound fraction (AE) and an LCAJAAL-unbound fraction (LTAT). Note that ■ represents GlcNAc (N-acetyl glucosamine); ○ represents Man (mannose); ● represents Gal (galactose); and Δ represents Fuc (fucose).

Figure 11:
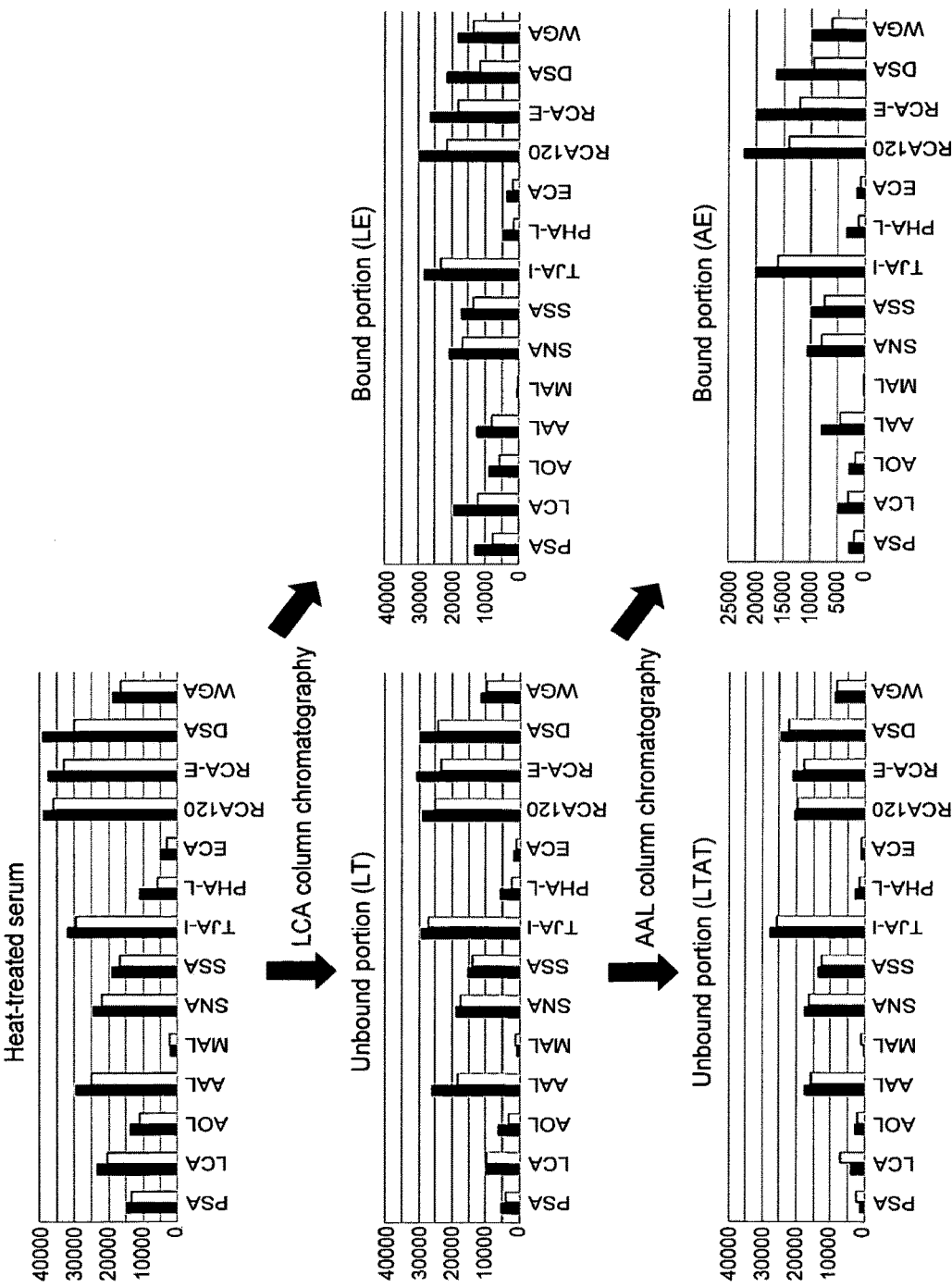

FIG. 11 is graphs showing the results of lectin array analyses of each fraction obtained by LCA-AAL serial lectin column chromatography. In this figure, the signals obtained from 14 lectins are shown by bar charts. The vertical axis indicates Net intensity. Data of healthy volunteers' pooled serum (NHS) are indicated by open bars; whereas the data of HCC patients' pooled serum (HCC) are indicated by solid bars.

Figure 12:
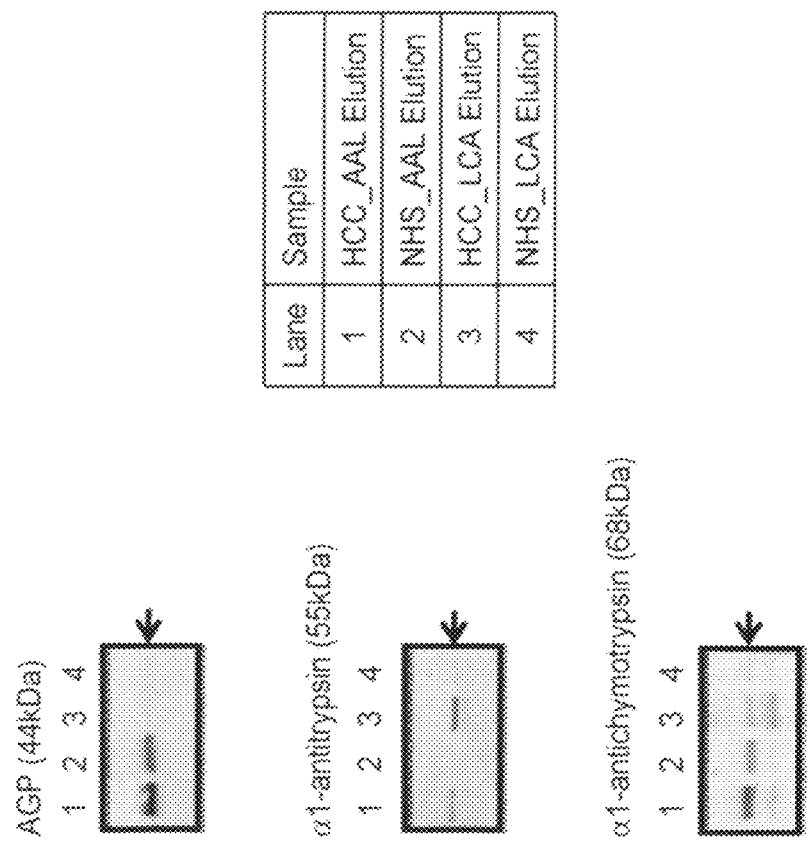

FIG. 12 shows the results of detection analysis of particular glycoproteins AGP, AAT and ACT in each fraction obtained by the serial lectin column chromatography. These proteins were reported already that their fucosylation were increased associated with hepatic diseases such as liver fibrosis and hepatocarcinoma. In the figure, molecular groups fucosylated differentially are compared. More specifically, an LCA-bound molecules (LCA elution, LE) and an LCA-unbound/AAL-bound molecules (AAL elution, AE) are compared. Note that quantitative comparison was made by western blotting method.

Figure 13A:
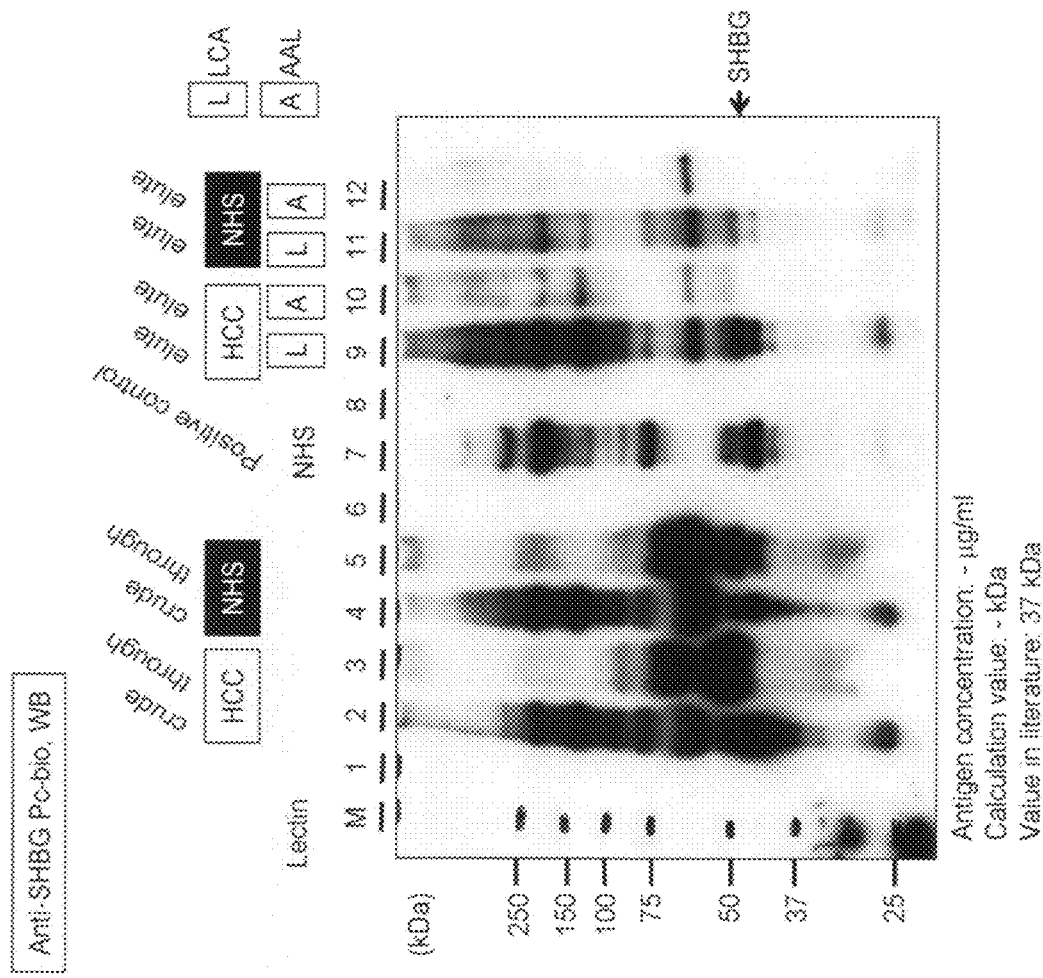

FIG. 13A shows the screening results of a hepatocarcinoma-state-indicating glycan marker candidate. Specimens were prepared from a healthy volunteers' pooled serum and a hepatocellular carcinoma patients' pooled serum by serial lectin column chromatography as described in Examples 3 and 4, and subjected to western blotting to analyze the amount of a glycoprotein (SHBG) in each fraction.

Figure 13B:
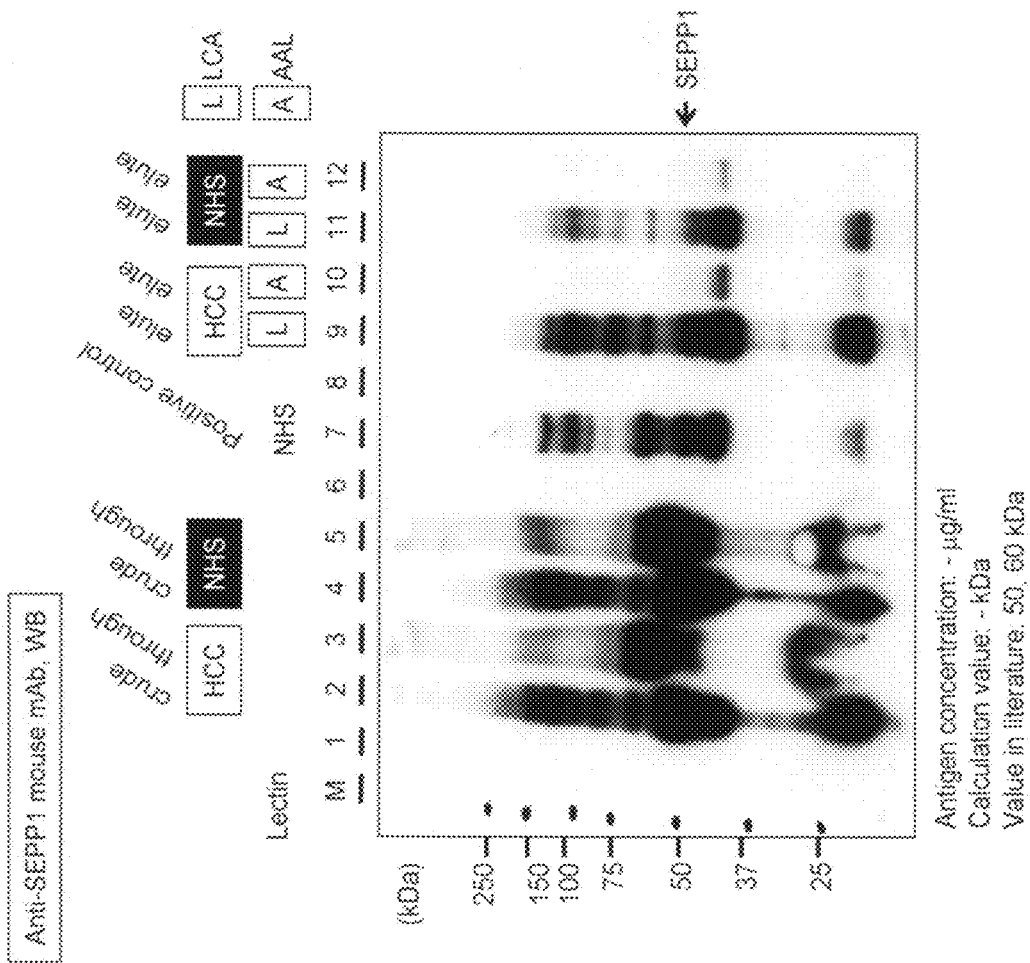

FIG. 13B shows the screening results of a hepatocarcinoma-state-indicating glycan marker candidate. Specimens were prepared from a healthy volunteers' pooled serum and a hepatocellular carcinoma patients' pooled serum by serial lectin column chromatography as described in Examples 3 and 4, and subjected to western blotting to analyze the amount of a glycoprotein (SEPP1) in each fraction.

Figure 13C:
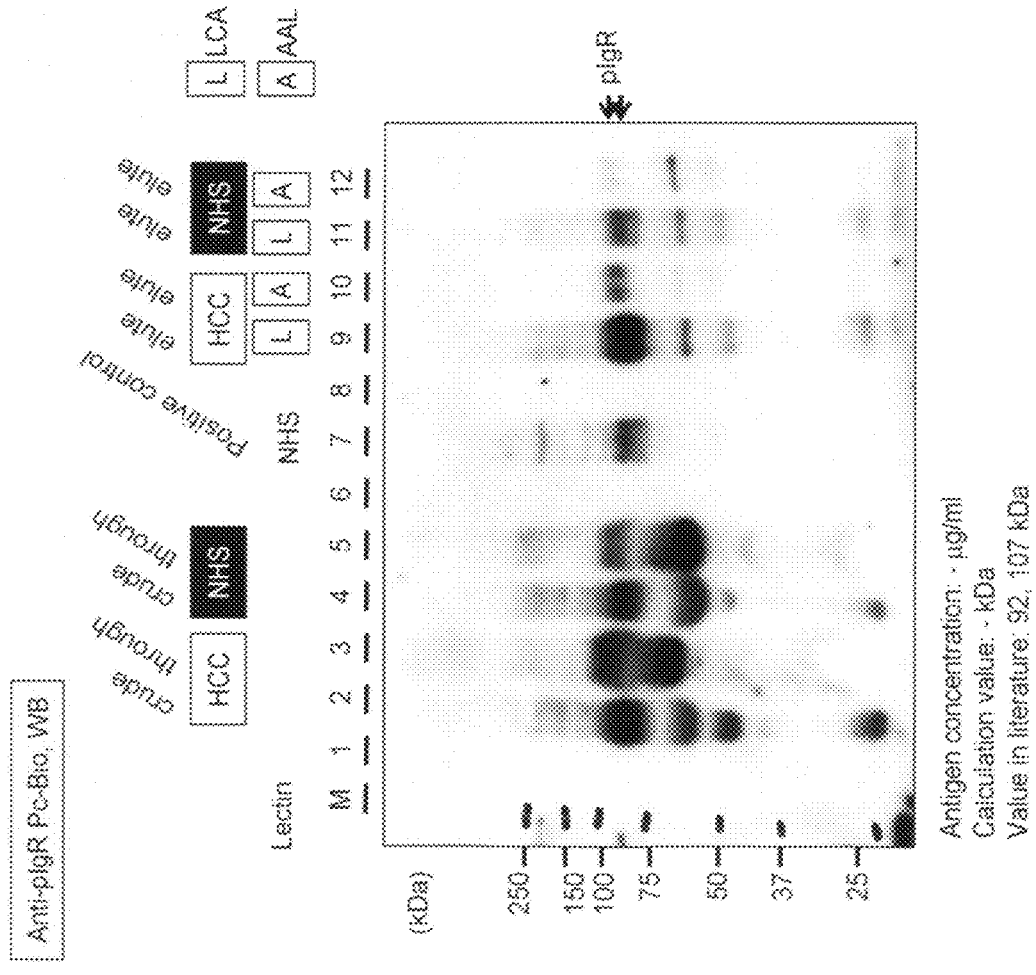

FIG. 13C shows the screening results of a hepatocarcinoma-state-indicating glycan marker candidate. Specimens were prepared from a healthy volunteers' pooled serum and a hepatocellular carcinoma patients' pooled serum by serial lectin column chromatography as described in Examples 3 and 4, and subjected to western blotting to analyze the amount of a glycoprotein (pIgR) in each fraction.

Figure 13D:
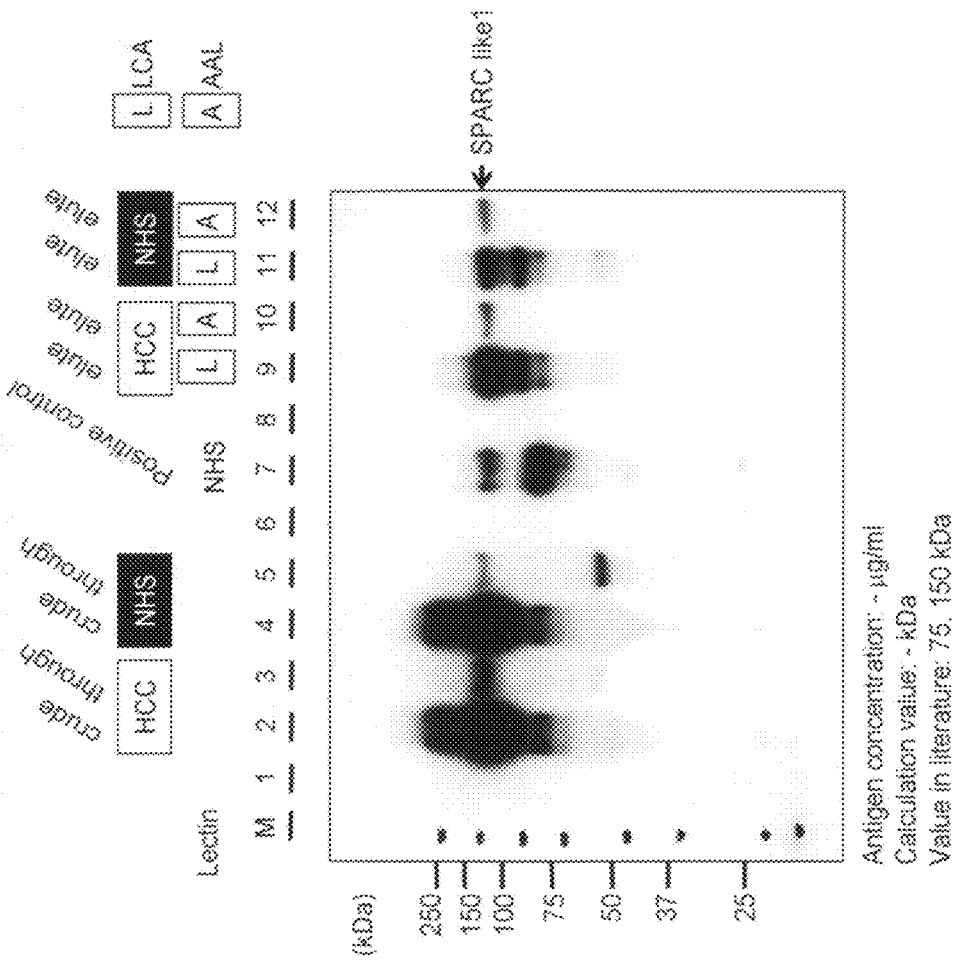

FIG. 13D shows the screening results of a hepatocarcinoma-state-indicating glycan marker candidate. Specimens were prepared from a healthy volunteers' pooled serum and a hepatocellular carcinoma patients' pooled serum by serial lectin column chromatography as described in Examples 3 and 4, and subjected to western blotting to analyze the amount of a glycoprotein (SPARCL1) in each fraction.

Figure 13E:
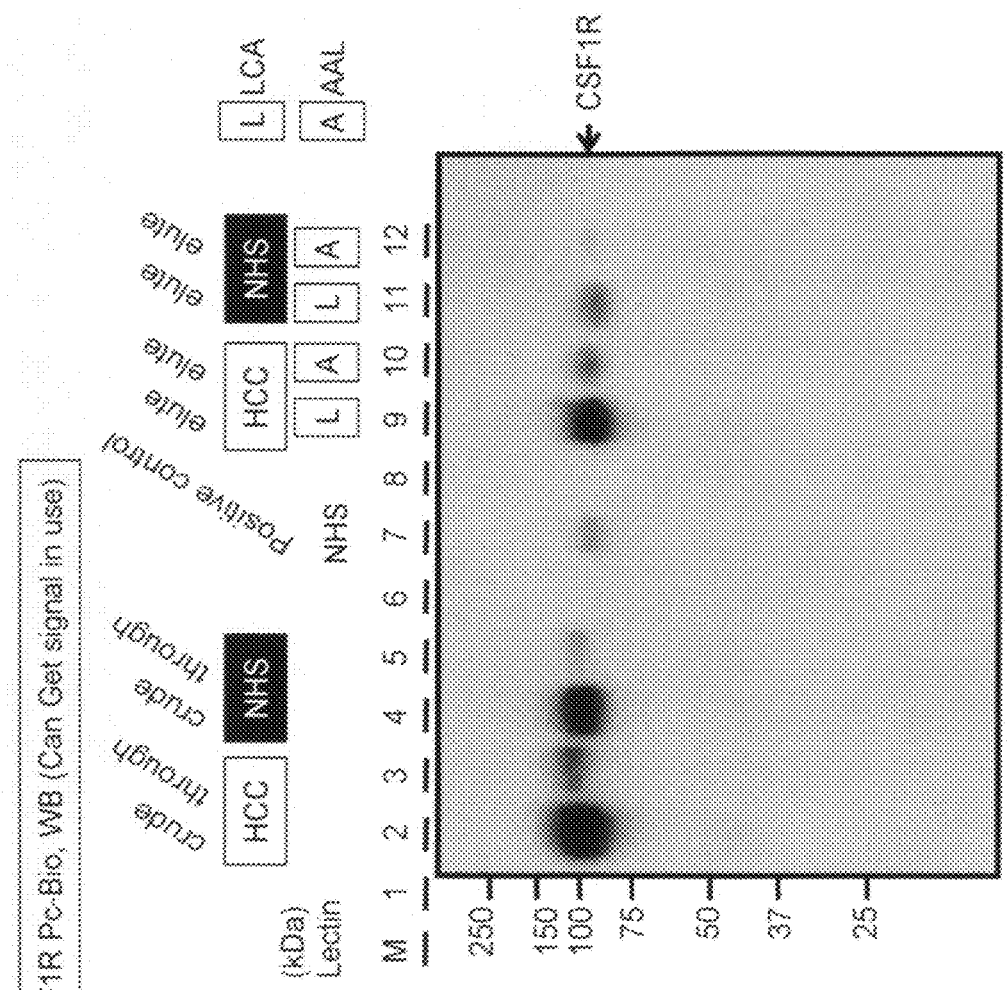

FIG. 13E shows the screening results of a hepatocarcinoma-state-indicating glycan marker candidate. Specimens were prepared from a healthy volunteers' pooled serum and a hepatocellular carcinoma patients' pooled serum by serial lectin column chromatography as described in Examples 3 and 4, and subjected to western blotting to analyze the amount of a glycoprotein (CSF1R) in each fraction.

Figure 13F:
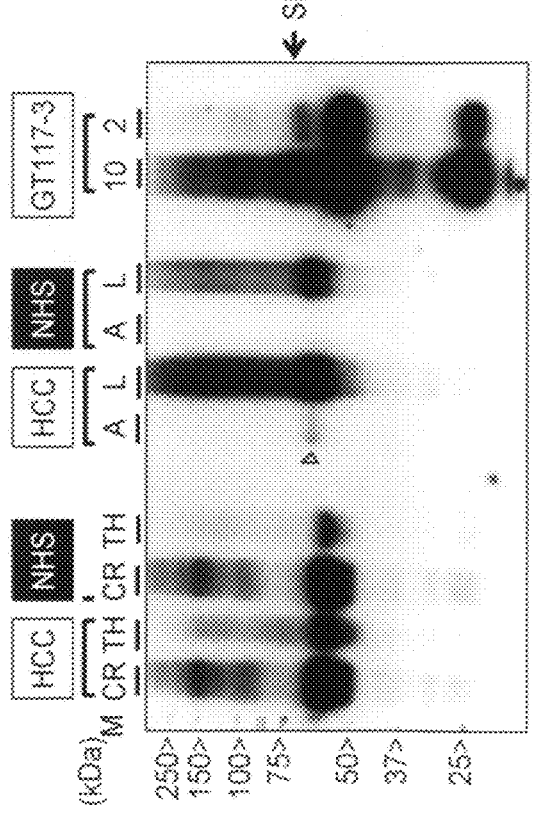

FIG. 13F shows the screening results of a hepatocarcinoma-state-indicating glycan marker candidate. Specimens were prepared from a healthy volunteers' pooled serum and a hepatocellular carcinoma patients' pooled serum by serial lectin column chromatography as described in Examples 3 and 4, and subjected to western blotting to analyze the amount of a glycoprotein (SERPINA7) in each fraction.

Figure 14:
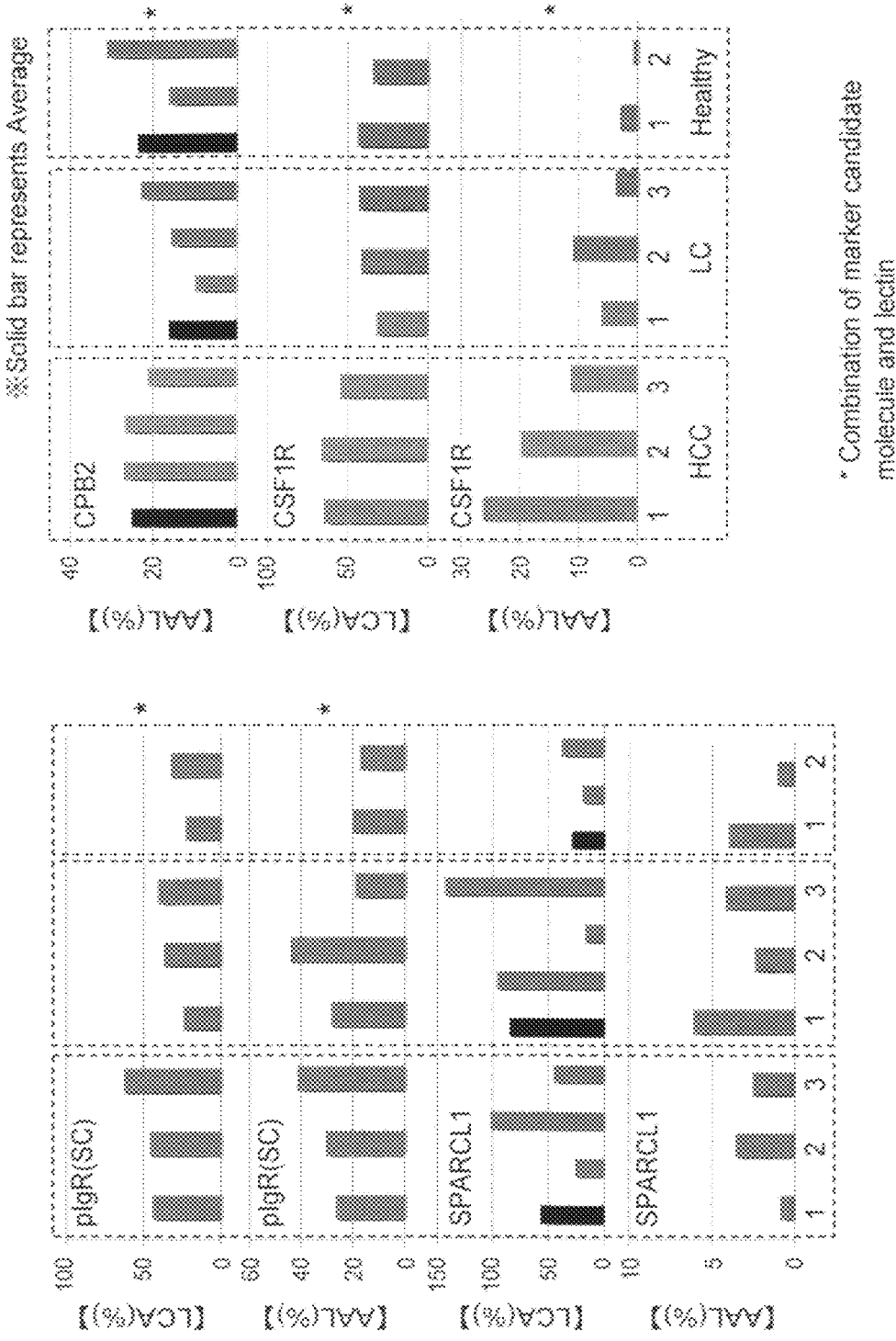

FIG. 14 The glycoproteins of each of three healthy persons, three cirrhosis patients and three hepatocellular carcinoma patients were analyzed by serial lectin column chromatography followed by western blotting to analyze their amounts in each lectin fraction of the sera. In this figure, the amounts of glycoproteins present in lectin fractions which show difference of the amount of proteins are different are indicated by bar charts.

Vertical axis AAL % indicates the ratio of the protein amount of target molecule A contained in a bound fraction of AAL column chromatography for that in the serum before chromatographic treatment (100%). LCA % is also similarly defined. As a result, the amount of CPB2 present in an AAL-bound fraction (AE), the amount of pIgR in an LCA-bound fraction (LE), the amount of pIgR present in the AAL-bound fraction (AE), the amount of CSF1R present in the LCA-bound fraction (LE), the amount of CSF1R in the AAL-bound fraction (AE), etc. were significantly high in hepatocellular carcinoma patients. By quantitation or comparison of glycan alteration on these molecules (molecule complex), especially for LCA- or AAL-bound glycans, the disease state of the liver, in particular, hepatocellular carcinoma, is expected to be predictable.

Figure 15:
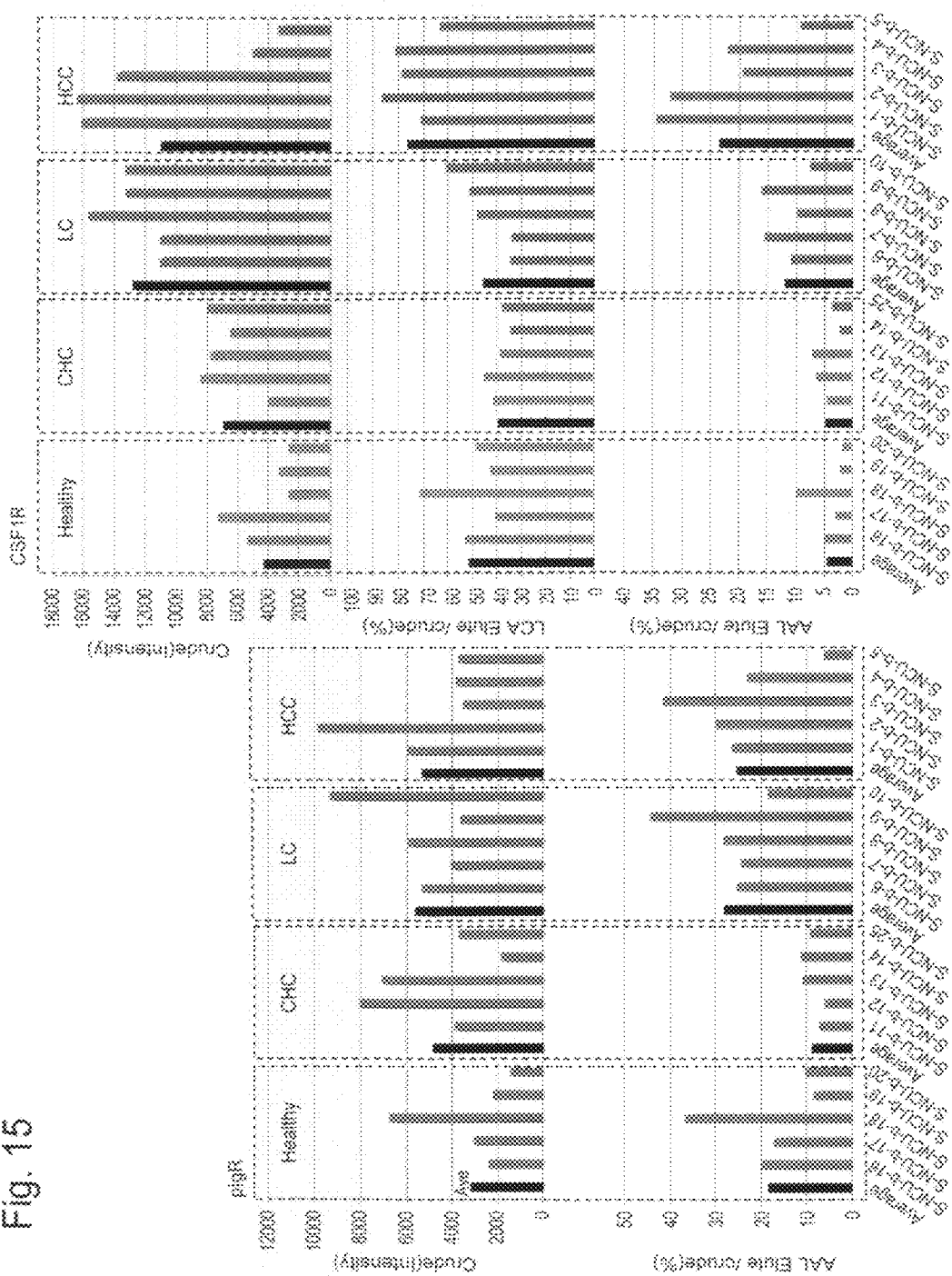

FIG. 15 The glycoproteins of each of five healthy volunteers, five chronic hepatitis patients, five hepatic cirrhosis patients and five hepatocarcinoma patients were subjected to lectin continuous chromatography and Western blot analysis to analyze the amounts thereof present in each lectin fraction of the sera. In this figure, the amounts of glycoproteins present in a LCA-bound fraction and an AAL-bound fraction are indicated by bar charts. As a result, in the amount of pIgR present in the LCA-bound fraction (LE) and the amount of pIgR present in the AAL-bound fraction (AE), the present ratios thereof in hepatic cirrhosis and hepatocarcinoma patients were higher than in healthy volunteers. In contrast, the present ratio of CSF1R in the LCA-bound fraction (LE) was significantly high only in hepatocarcinoma patients compared that in healthy volunteers. Furthermore, the present ratio of CSF1R (the amount of CSF1R present) in the AAL-bound fraction (AE) was high in hepatic cirrhosis patients and further high in hepatocarcinoma patients compared to those in healthy volunteers and chronic hepatitis patients.

Figure 16:
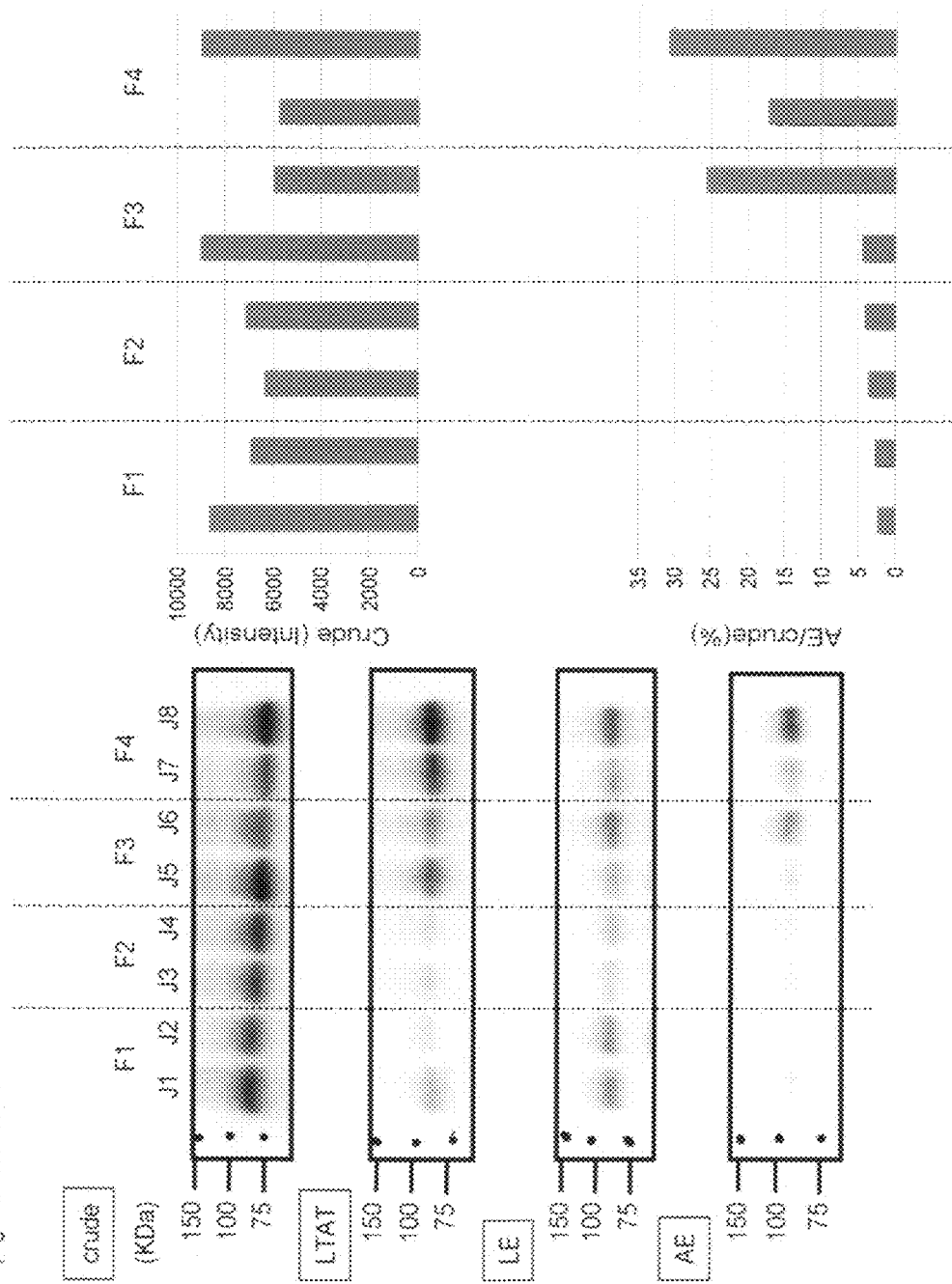

FIG. 16 shows the correlation between the present ratio (present amount) of pIgR in the fractions obtained by serial lectin column chromatography/Western blot analysis and the progression of hepatic fibrosis. Herein, it is shown that when the progression of fibrosis is F3 or F4 (particularly F4), the amount of pIgR in the AAL-bound fraction (AE) increases. These facts suggest the possibility that cancer cells grow with the progress of the fibrosis.

Figure 17:
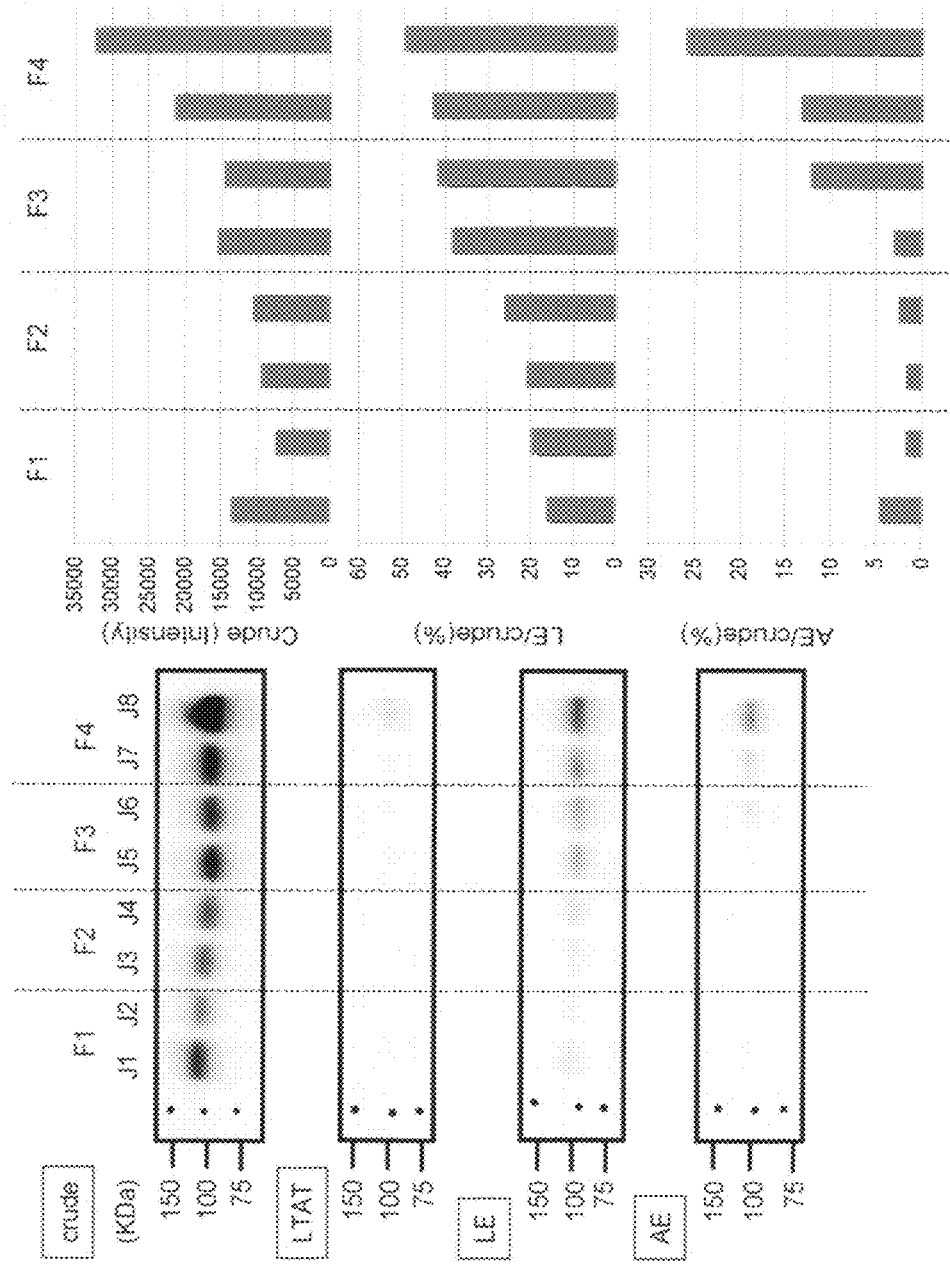

FIG. 17 shows the correlation between the present ratio (present amount) of CSF1R in the fractions obtained by serial lectin column chromatography/Western blot analysis and the progression of hepatic fibrosis. It is shown that CSF1R in the LCA-bound fraction (LE) increases in proportional to the progression (F1 to F4) of fibrosis. In addition, it is shown that when the progression of fibrosis is F3 or F4 (particularly F4), CSF1R in the AAL-bound fraction (AE) abruptly increases. These facts suggest the possibility that cancer cells grow with the progress of the hepatic fibrosis.

Figure 18:
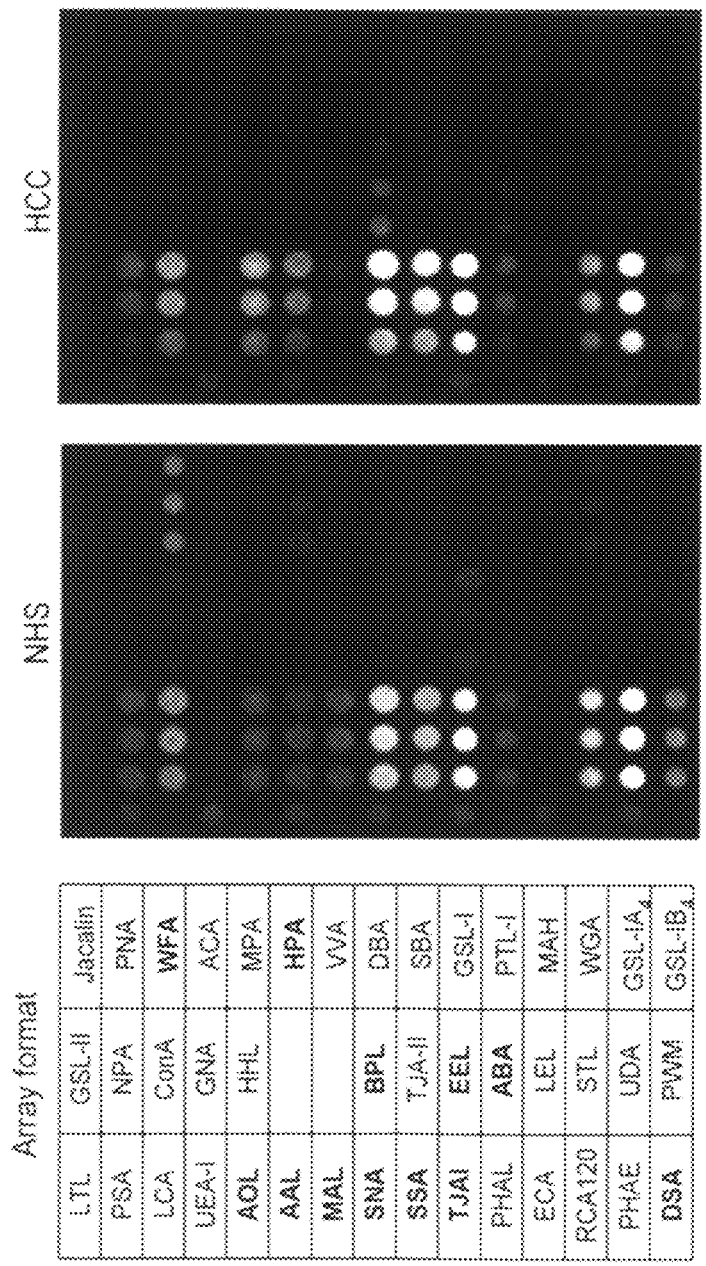

FIG. 18 shows the results of comparative sugar-chain analysis of a hepatic disease-state-indicating marker candidate molecule, pIgR, by an antibody overlay lectin microarray. The analysis was performed by using pIgR (corresponding to 10 ng) concentrated and purified from the serum by an immunoprecipitation method. The arrangement of lectins on the lectin microarray is shown in the left side of the figure. The lectins emitting a significant signal obtained by this experiment are shown by boldface. Signal was obtained from 19 types of lectins. Typical scan images of pIgR derived from the sera of a hepatocarcinoma patient and a healthy volunteer are shown on the right side of the figure. As a result, in pIgR derived from hepatocarcinoma patient's serum compared to pIgR derived from the healthy volunteer's serum, the signals emitted from 7 types of lectins (AOL, AAL, SNA, SSA, TJA-I, BPL, ABA) increased; whereas signals emitted from 5 types of lectins (MAL, DSA, EEL, WFA, HPA) decreased.

Figure 19:
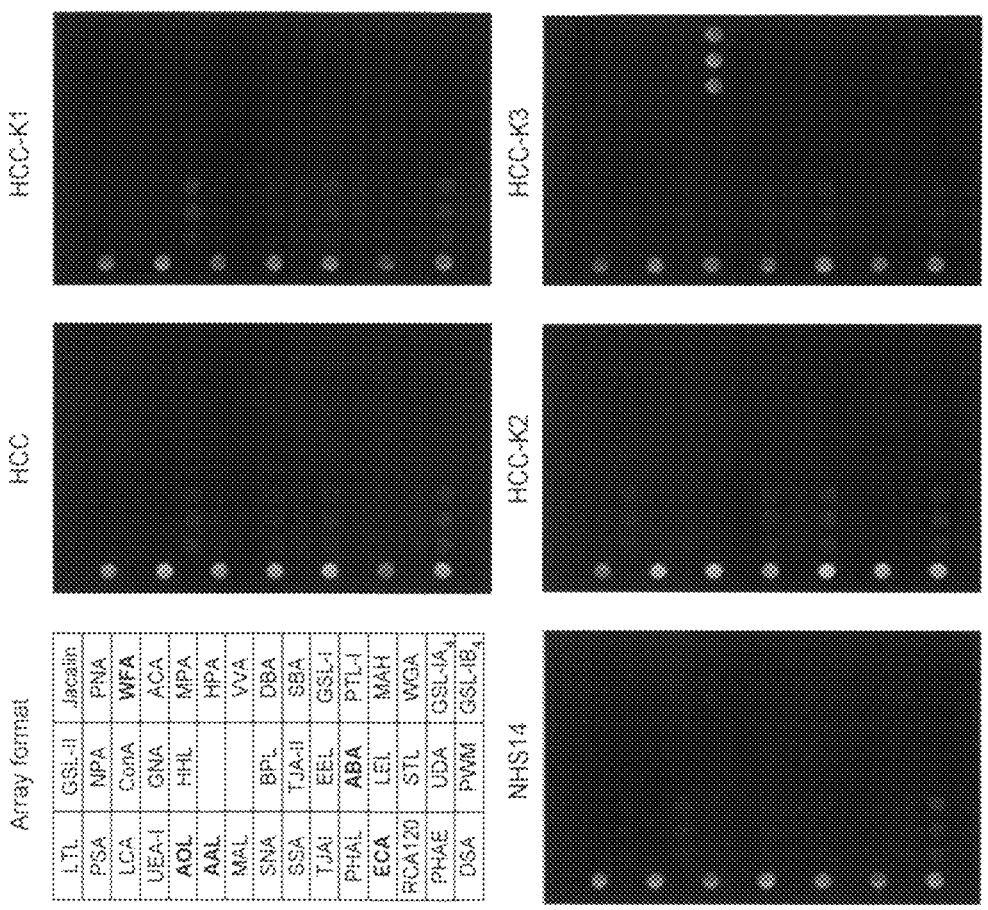

FIG. 19 shows the results of comparative glycan analysis of a hepatic disease-state-indicating marker candidate molecule, pIgR, by an antibody overlay lectin microarray. The analysis was performed by use of healthy volunteers' pooled sera (NHS: sera of 14 individuals) and pooled sera of a plurality of types of hepatocarcinoma patients (HCC: sera of 5 individuals, HCC-K1: sera of 2 individuals, HCC-K2: sera of 6 individuals, HCC-K3: sera of 2 individuals). Using pIgR (corresponding to 10 ng) concentrated and purified from these sera by an immunoprecipitation method, the analysis was performed by lectin array. In pIgR derived from hepatocarcinoma patients' sera, compared to the pIgR derived from the healthy volunteers' sera, the singles emitted from 7 types of lectins (AOL, AAL, SNA, SSA, TJA-I, BPL, ABA) increased, whereas signals emitted from 5 types of lectins (MAL, DSA, EEL, WFA, HPA) decreased.

Figure 20:
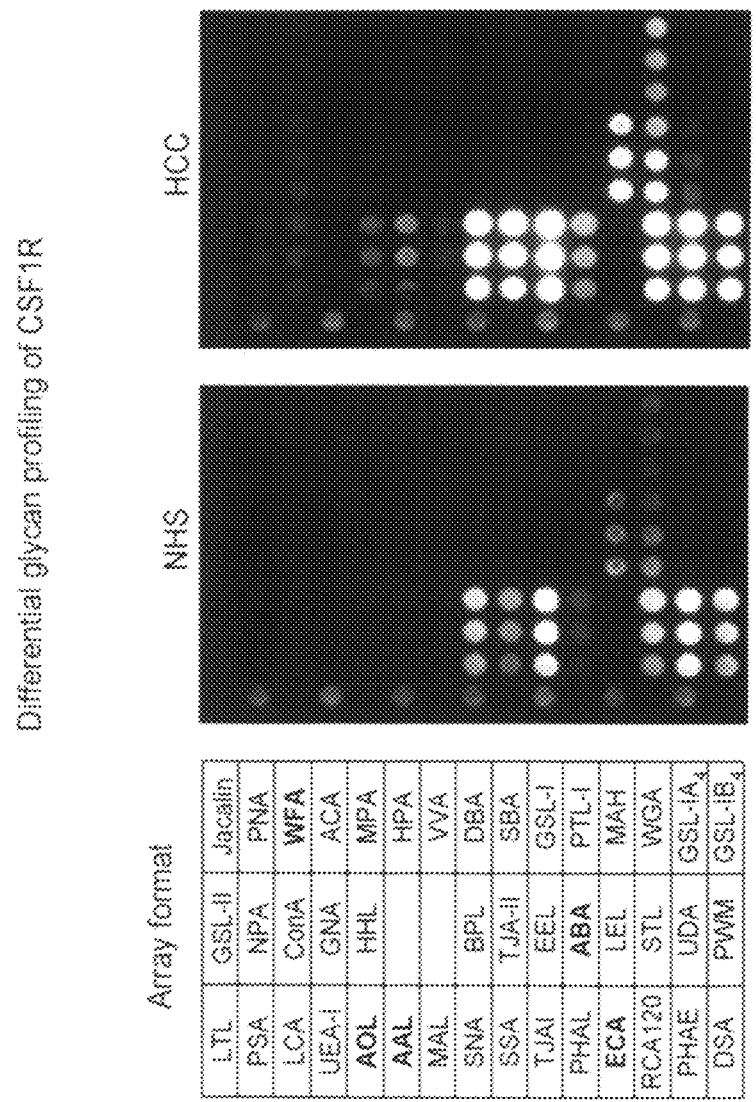

FIG. 20 shows the results of comparative glycan analysis of a hepatic disease-state-indicating marker candidate molecule, CSF1R, by an antibody overlay lectin microarray. Using CSF1R (corresponding to 2 ng) concentrated and purified from the serum by an immunoprecipitation method, the analysis was performed. The arrangement of lectins on the lectin microarray is shown in the left side of the figure. The lectins emitting a significant signal obtained by this experiment are shown by boldface. Signals were obtained from 20 types of lectins. Typical scan images of CSF1R derived from the sera of a hepatocarcinoma patient and a healthy volunteer are shown on the right side of the figure. As a result, in CSF1R derived from the hepatocarcinoma patient's serum compared to CSF1R derived from the healthy volunteer's serum, the signals emitted from 5 types of lectins (AOL, AAL, ECA, ABA, WFA)) increased.

Figures 1, 21:
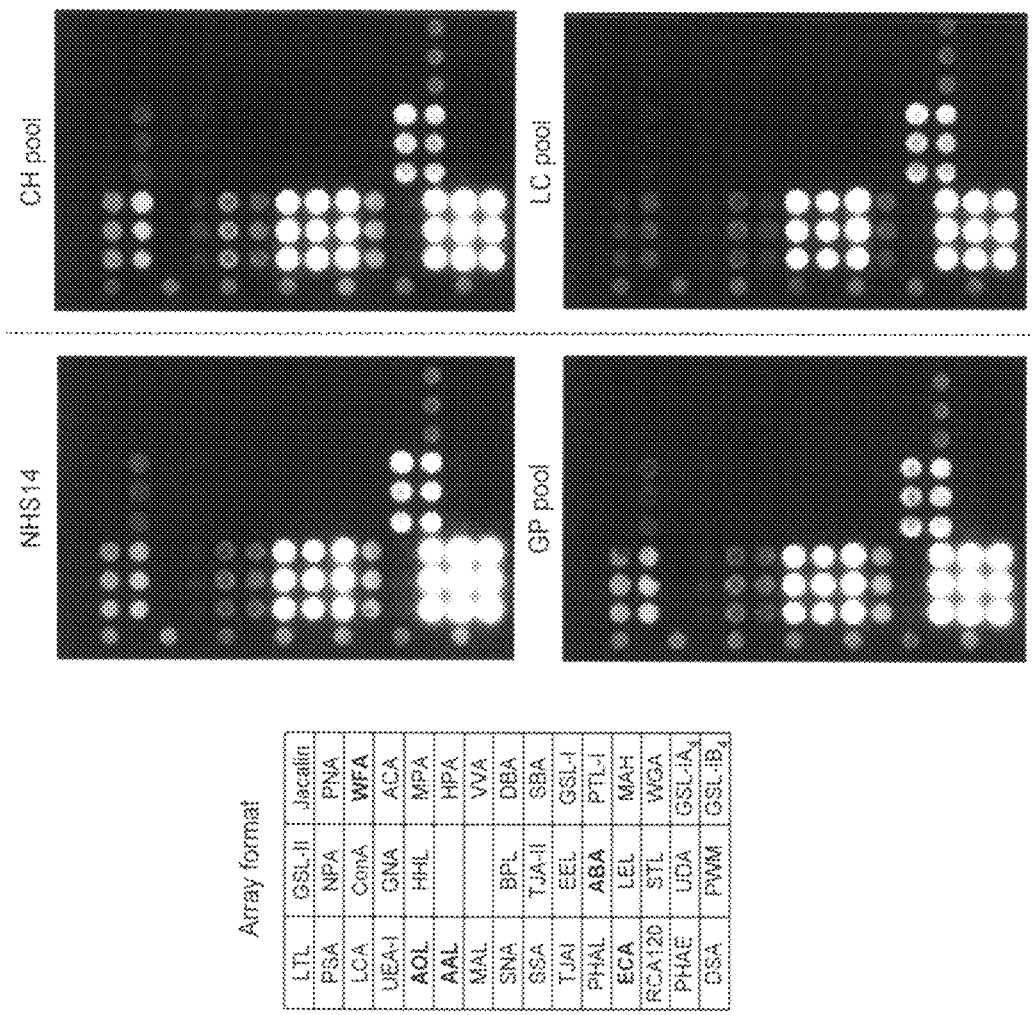
Figures 2, 21:
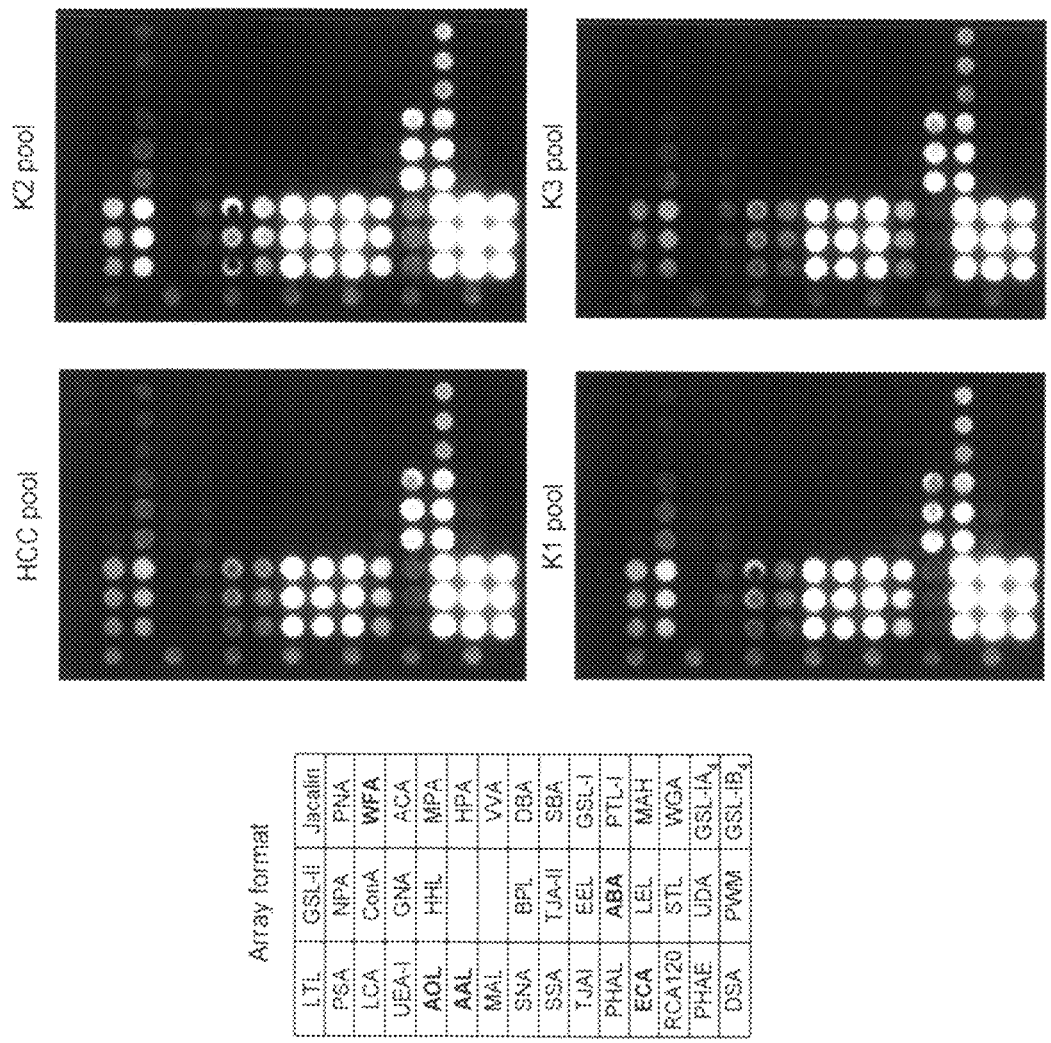

FIG. 21-1 shows the results of comparative glycan analysis of a hepatic disease-state-indicating marker candidate molecule, CSF1R, by an antibody overlay lectin microarray. Using CSF1R (corresponding to 2 ng) concentrated and purified from the serum by an immunoprecipitation method, the analysis was performed. More specifically, using the pooled sera of healthy volunteers (NHS: sera of 14 individuals), relatively advanced-age healthy volunteers (GP: sera of 5 individuals), (viral) hepatitis patients (CH: sera of 5 individuals), hepatic cirrhosis patients (LC: sera of 5 individuals) and hepatocarcinoma patients (HCC: sera of 5 individuals, K1: sera of 2 individuals, K2: sera of 6 individuals, K3: sera of 2 individuals), CSF1R protein was purified and concentrated in the same manner and subjected to the analysis of a glycan profile of CSF1R protein (an anti-CSF1R antibody precipitate). In lectins of AOL, AAL, ECA, ABA and WFA, it was found that signal derived from hepatocellular carcinoma patients (HCC) increases compared to that derived from healthy volunteers (NHS). Particularly, WFA signal was rarely detected in healthy volunteers (NHS), relatively advanced-age healthy volunteers (GP), (viral) hepatitis patients (CH) and hepatic cirrhosis patients (LC), whereas significant WFA signal was observed in the sera (HCC, K1, K2, K3) derived from hepatocellular carcinoma patients (HCC).

FIG. 21-2 shows the results of comparative glycan analysis continued from FIG. 21-1.

Figure 22:
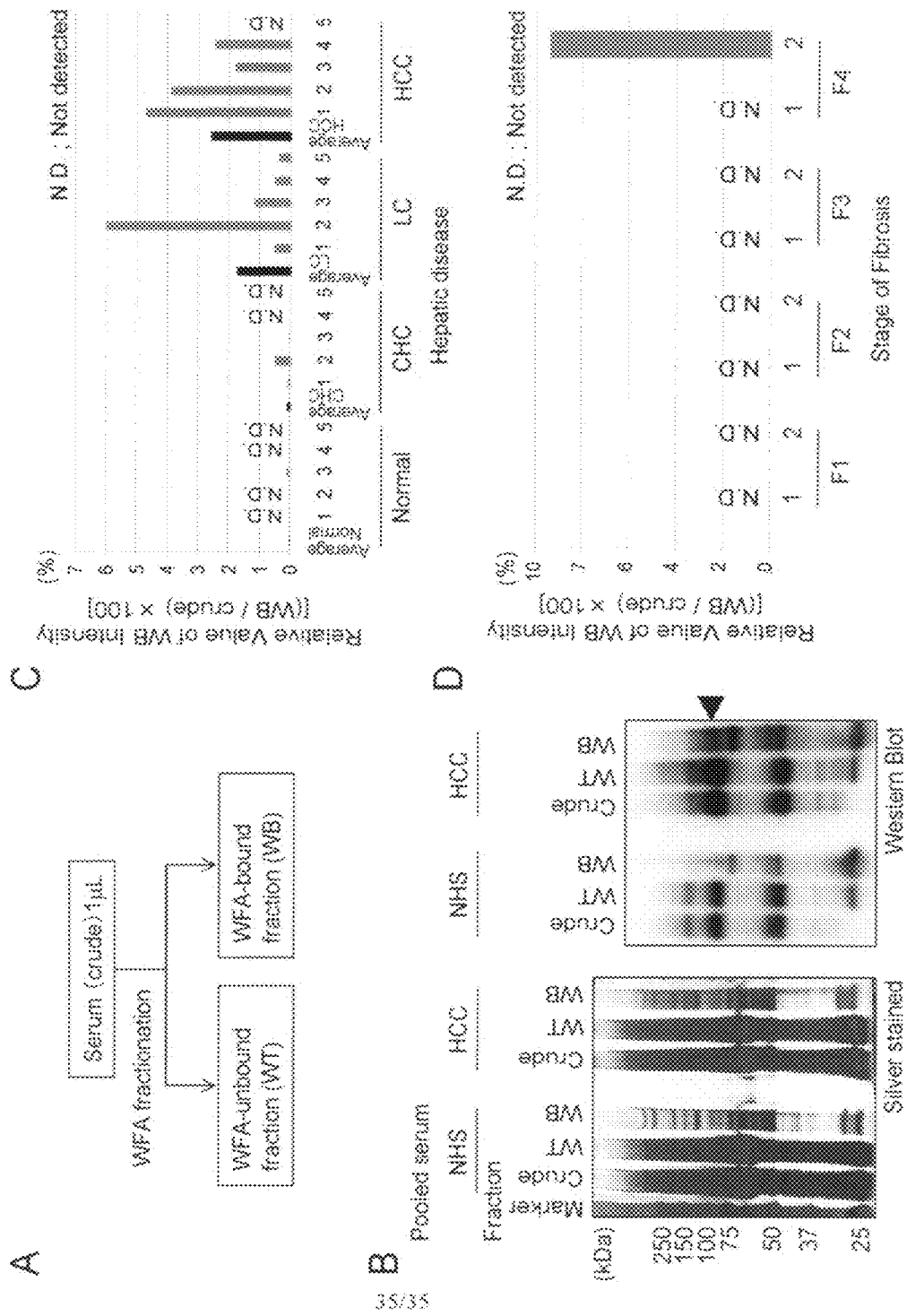

FIG. 22 (A) schematically shows a procedure of batch-system fractionation with WFA from the serum. (B) The pooled sera of a healthy volunteer (NHS) and a hepatocellular carcinoma patient (HCC) were subjected to immunoprecipitation with WFA lectin and then to Western blot analysis using an anti-CSF1R antibody. In this manner, the amount of CSF1R present in the serum and having a WFA-bound glycan was checked. As a result, it was elucidated that the signal of WFA lectin is high in CSFR1 derived from a hepatocellular carcinoma patient (HCC). The signal of WFA-bound CSFR1 derived from NHS was rarely detected. (C) Using the sera from five healthy volunteers (Normal), five (viral) hepatitis patients (CHC), five hepatic cirrhosis patients (LC) and five hepatocellular carcinoma patients (HCC) as a sample set, the amounts of WFA-bound CSF1R present in the sera were checked. In the results, the intensity of a band obtained by Western blot was quantified and shown as a bar chart. The average value of each disease is shown in the leftmost side of the disease. As a result, it was elucidated that the present amount of WFA-bound CSF1R in the hepatic cirrhosis patients (LC) is high compared to those of the healthy volunteers (Normal) and (viral) hepatitis patients (CHC). Furthermore, in the hepatocellular carcinoma patients (HCC), the amount of WFA-bound CSF1R is significantly high compared to those of the healthy volunteers (Normal), (viral) hepatitis patients (CHC) and even hepatic cirrhosis patients (LC). (D) To validate the relation with progression of fibrosis, using the sera of mild chronic hepatitis (F1), moderate chronic hepatitis (F2), severe chronic hepatitis (F3), hepatic cirrhosis (F4) patients as a sample set, the amount of WFA-bound CSF1R in the sera was checked in accordance with the aforementioned method (first, crude sera was analyzed without fractionation). CSF1R of WFA fraction was rarely detected in F1 to F3, and detected in F4 patient's serum. The intensity of WFA-bound CSF1R obtained by Western blot was quantified and shown as a bar chart.

DESCRIPTION OF EMBODIMENTS

1. Current Situation of Chronic Hepatic Disease
1-1. Disease-State of Hepatic Disease When a person is infected with hepatitis B virus or hepatitis C virus, the person suffers an acute-stage inflammation, which proceeds into a chronic-stage inflammation over 5 to 15 years. Particularly, hepatitis C once enters the chronic-stage is rarely cured naturally, with the result that deterioration of the liver function proceeds and hepatic cirrhosis occurs. The disease-states from chronic hepatitis to hepatic cirrhosis are defined pathomorphologically based on fibrous change observed in the Glisson region of the liver and the liver lobules and classified into a mild phase (F1), a moderate phase (F2), a severe phase (F3) and a hepatic cirrhosis phase (F4). Progression of fibrosis is correlated with an increase of risk of developing hepatocarcinoma. The cancer incidence in F1 or F2 is 1% or less per year, whereas, the incidence increases to 3-4% per year in F3. In the hepatic cirrhosis (F4) diagnosed based on observation of a tissue image where the degree of fibrosis is more advanced, hepatocarcinoma occurs with a probability of about 7% per year. Therefore, to efficiently find hepatocarcinoma and treat it, it is important to screen patients particularly in F3 and F4 stages in a simple manner and follow them up as subjects to be placed under detailed examination.

The medical benefit system for hepatitis B and hepatitis C patients in Japan is exclusively directed to patients of F1 to F3 degrees of fibrosis, determined based on histopathological diagnosis on a liver biopsy specimen. In contrast, patients diagnosed as F4 are classified into hepatic cirrhosis. Therefore, only a part of them are treated as aid recipients for interferon therapy by the medical benefit system for hepatitis B and hepatitis C patients; however satisfactory therapeutic results have not yet been obtained.

1-2. Evaluation of Fibrosis Suppression by Antiviral Therapy

To chronic hepatitis C, a PEG-IFN+RBV therapy is applied, whereas single administration of interferon is applied to hepatic cirrhosis C compensation phase. On the other hand, hepatitis B (chronic hepatitis, hepatic cirrhosis) is primarily treated with a nucleic-acid analogue. Thus, it seems to be essential to use markers for evaluating inflammation and fibrosis. Particularly, a serum biomarker is expected to be clinically applied for a wide variety of diagnostic and evaluate purposes.

1-3. Hepatocarcinoma

It has been considered that a microbiological factor such as infection with hepatitis B virus or hepatitis C virus and an environmental factor significantly and alternately work on the onset of hepatocarcinoma. In Japan, it is known that about nine out of ten hepatocarcinoma patients are previously infected with hepatitis B or C virus and hepatocarcinoma occurs in chronic hepatitis and hepatic cirrhosis patients. As a risk factor of developing hepatocarcinoma, other than the viruses, male, advanced age, heavy use of alcohol, tobacco, mycotoxin such as aflatoxin, etc., are pointed out (hepatoma medical care guideline, the International Medical Information Center foundation).

1-4. Early Diagnosis of Hepatocarcinoma

In detection of hepatocarcinoma, measurement of a hepatoma marker such as AFP and PIVKA-II in the serum sample taken from a subject and diagnostic imaging primarily represented by ultrasonographic examination (echo check) are mostly used at present. As the check by diagnostic imaging, first, ultrasonographic examination or CT is used. If any abnormality is found in the first check, usually MRI and angiography are further carried out.

1-5. Capturing High Carcinogenic Risk Group in View of Hepatocarcinoma Prevention In Japan, about nine out of ten hepatocarcinoma patients are derived from patients with hepatitis due to infection with hepatitis B virus or hepatitis C virus. Therefore, it is possible to catch patients to be placed under detailed examination by using viral infection and deterioration of the liver function as an indicator.

However, even for a hepatic cirrhosis patient (F4) who may have hepatocarcinoma with a probability of about 7% per year, taking expensive and highly invasive detailed examination repeatedly every three months for finding and treating early-stage cancer, is inevitably a large burden economically and physically. Needless to say, the same is true in a patient with F3 having a cancer incidence of 3-4% per year. Furthermore, in consideration that a successful virus treatment rate of hepatitis C with interferon is about five out of ten, a great many chronic hepatitis patients remain unsuccessfully treated with interferon. It is therefore necessary to inform exactly where the chronic hepatitis patients are positioned in the process leading to hepatic cirrhosis and hepatocarcinoma and clinically follow them up. In other words, in present treatment for a disease process from hepatitis to hepatocarcinoma, it is necessary to weigh a carcinogenic risk in hepatitis to hepatic cirrhosis patients by a simple test such as a blood test and apply a diagnostic treatment of hepatocarcinoma in accordance with the carcinogenic risk.

The degree of fibrosis is clinicopathologically correlated with risks of developing into hepatic cirrhosis and hepatocarcinoma. Therefore, we consider that if a testing technique is developed for serologically and quantitatively measuring the progress of fibrosis, such a problem can be solved.

2. Acquisition of Novel Hepatic Disease-State-Indicating Glycan Marker Represented by a Novel Glycan Marker for Hepatocarcinoma 2-1. Novel Hepatic Disease-State-Indicating Glycan Marker Including a Glycanmarker for Hepatocarcinoma The glycan marker for hepatocarcinoma of the present invention is sometimes described as a glycan related tumor marker or a tumor-specific glycan marker. Either one refers to a hepatocarcinoma specific glycan structure of a glycoprotein. Glycoproteins having such glycans are included.

The composition and structural diversity of a glycan on a protein secreted from a cell are controlled on the basis of expression balance of several hundreds of glycan related genes and varied depending upon the degree of cell differentiation and development of cancer. The glycoprotein whose glycan structure varies can be used as a disease-state-indicating marker including a tumor marker. Then, a glycan related tumor marker has been searched by using proteomics as a base. In a marker search pipeline based on proteomics, candidate molecules are identified by a large-scale analysis in Phase-1. In Phase-2, the candidate molecules are verified and narrowed by quantitative analysis. Further, in Phase-3, a validation test is carried out. A glycan related marker is similarly searched based on glycoproteomics basically through the above pipeline.

Furthermore, the present invention includes a novel hepatic disease-state-indicating glycan marker. Of the aforementioned glycan markers for hepatocarcinoma, a glycan-marker showing a change, which characterizes onset of a disease caused by viral infection, chronic hepatitis, hepatic cirrhosis and hepatocarcinoma developed therefrom, is found as a candidate. Such a marker which can specifies a hepatic disease-state based on a glycan change with the progress of the disease-state of a viral hepatic disease refers to a hepatic disease-state-indicating glycan marker.

The novel hepatic disease-state-indicating glycan marker of the present invention is pathognomonic to each disease-state of a viral hepatic disease, more specifically, hepatocarcinoma, hepatic cirrhosis, hepatic fibrosis (F3 and F4 markers) or chronic hepatitis, and effectively distinguishes individual diseases.

Furthermore, the novel hepatic disease-state-indicating glycan marker of the present invention includes a hepatic disease-state-indicating glycan marker glycopeptide and a hepatic disease-state-indicating glycan marker glycoprotein. For example, a glycopeptide specifically identified in a specimen of a hepatocarcinoma patient or a hepatic-disease patient, or a cancer cell-line and a healthy volunteer's specimen by the lectin catch IGOT method, is determined as a candidate glycopeptide for a hepatocarcinoma marker or a hepatic disease-state-indicating glycan marker. This glycopeptide is validated by a glycopeptide comparative glycan analysis technique, represented by comparative glycoproteomics method for a stable isotope introduced glycopeptide, using 100 patient specimens (or patient specimens corresponding to individual stages of a disease (20 samples for each stage)) versus 100 healthy volunteer's specimens. In the validation, a glycopeptide whose efficacy is strongly suggested can be determined as the marker glycopeptide. Furthermore, a glycoprotein containing the sequence of a hepatic disease-state-indicating glycan marker candidate glycopeptide is validated by a comparative glycan analysis technique represented by an antibody overlay lectin microarray method. In the validation, the glycoprotein whose efficacy is strongly suggested can be determined as the marker glycoprotein.

2-2. Method for Acquiring Hepatic Disease-State-Indicating Glycanmarker 2-2-1. Large-Scale Identification of Glycoprotein Large-scale selective collection and concentration methods of glycopeptides to be used herein are roughly divided into (i) a method of using a probe having affinity for a glycan, (ii) a method for using a chemical reaction with a glycan (Zhang H. et al. Nat Biotechnol 21, 660-666 (2003)) and (iii) a method for introducing an affinity tag into a glycan. Any one of the methods can be used. Preferably, a method of using a probe can be used. Now, the method of using a probe will be more specifically described below.

(1) Collection by probe: As the probe, a lectin and an anti-glycan antibody can be used. To describe more specifically, first, from the supernatant of a medium culturing a cell-line derived from hepatocarcinoma, a glycoprotein is collected with a probe lectin or an antibody probe. Then, from the serum of a healthy volunteer, a glycoprotein is collected with the probe lectin or the antibody probe; at the same time, glycoproteins are exhaustively collected by lectins except a probe lectin.

(2) The probe lectin can be selected principally through statistical analysis of glycan profile by using the aforementioned lectin microarray. Alternatively, the probe lectin can be selected in consideration of an expression profile (results of real time quantitative PCR) of a glycan gene and literature information (information based on which the probe lectin to be used can be predicted such as acceleration of fucosylation with cancerous change). Basically, the probe lectin is selected through the statistical analysis of a profile and adequacy of the selected lectin is determined based on the binding specificity. When hepatocarcinoma is targeted, for example, a lectin (AAL) derived from *Aleuria aurantia* capable of detecting fucosylation and lectin (DSA) derived from *Datura stramonium* capable of detecting a hyperbranch of a glycan can be used.

An antibody probe may be prepared after the structure of an antigen (glycan) is elucidated; but the structural determination is not a requisite condition. Thus, the antibody probe may be prepared without determining the structure of an antigen glycan (or a glycopeptide).

(3) Lectins for use in exclusive collection vary depending upon the distribution of a glycan structure in a target specimen in narrowing biomarkers. For example, when the serum is used as a target, most of the glycans on the serum glycoprotein have been known to be sialylated bi-antennary glycans. Because of this, if treated with sialidase, it is considered that most of the serum glycoproteins (peptides) are exhaustively collected with lectins (RCA120) derived from *Ricinus communis*. Thus, RCA120 can be used. Note that a lectin recognizing sialic acid is not used. This is to avoid effect produced by elimination of sialic acid by man-made operation and deterioration of a specimen with the passage of time. When a target specimen is not the serum, for example, is other body fluid, other lectins can be selected. Furthermore, glycoproteins can be exhaustively collected by hydrophilic interaction chromatography and gel filtration in place of a lectin.

2-2-2. Identification of Glycopeptide or Glycoprotein

The collected glycoproteins are analyzed, for example, by Lectin-IGOT-LC/MS method to identify the candidate glycopeptides as described in JP Patent Publication (Kokai) No. 2004-233303 A (JP Patent No. 4220257); and Kaji H, et al., Mass spectrometric identification of N-linked glycopeptides using lectin-mediated affinity capture and glycosylation site-specific stable isotope tagging, Nature Protocols 1, 3019-3027 (2006).

(1) Glycan Excision and Stable Isotope Tagging of the Glycosylated Sites

The glycopeptide subsets of specimens are recollected from the protease digests of the glycoproteins captured with a probe using the same probe; or directly collected using the probe from a protease digest (peptide mixture) of crude specimen without any protein separation. The obtained glycopeptides are treated with an enzyme such as glycopeptidase to remove glycans in water labeled with a stable isotope oxygen (18O). Owing to the treatment, asparagine at a glycosylated site is converted to aspartic acid. Then, isotopic oxygen atom (18O) of water is incorporated into the peptide. This method to label glycosylated site with stable isotope is called "isotope-coded glycosylation site-specific tagging (IGOT)".

(2) LC/MS Shotgun Analysis of Labeled Peptides

The peptides labeled by IGOT method are separated by LC and introduced into MS to perform tandem mass spectrometry. In this manner, the sequences of the peptides are comprehensively identified.

(3) Identification of Peptide

Database search (MS/MS ion search method) can be made for the obtained MS/MS measurement results (spectra) of the peptide mixture, in which obtained MS/MS spectra are compared with those in the database; as described in the Standard Technology Collection (edited by Japan Patent Office), mass spectrometry, 3-6-2-2 amino acid sequence analysis. In the search, the following modifications of an amino acid are taken into consideration (oxidation of methionine residue side-chain, deamination or cyclization of amino-terminal glutamine, deamination of an amino terminal carbamidomethylcysteine, deamination of asparagine residue side-chain (however, a stable isotope oxygen is incorporated therein)).

(4) Identification of Glycosylated Site

Among the peptides identified by the MS/MS ion search method, peptides having both deamidated asparagine residue(s) incorporating a stable isotope oxygen and consensus sequence(s) for N-glycosylation (Asn-Xaa-[Ser/Thr], but Xaa is not Pro) are employed as candidate glycopeptide (in the case where Xaa is Lys/Arg and an identified peptide sequence is cleaved at this site, if the next residue to Xaa can be confirmed to be [Ser/Thr], referring to the entire amino acid sequence of the protein, this peptide is included). Then the asparagine residue of the consensus sequence of the glycopeptide is defined as a glycosylated site. In the case there are multiple consensus sequences in a peptide and the number of deamidated (stable isotope lebeled) asparagine is less than that of consensus sequence, and the position of deamidated asparagine cannot be specified by the MS/MS spectrum, all sites (consensus sites) are described together and noted with the fact that they could not be distinguished.

(5) Notation System of Glycopeptide

The peptides listed in Table 1 of the claims and Table 1 below are based on the results identified by the IGOT-LC/MS method in consideration of the presence or absence of modification in the identification process by this method described in the above section (3). Accordingly, the marker glycopeptide is not only defined simply by an amino acid sequence but also defined in consideration of modification of a functional group actually contained in a peptide. The actual status of modifications is described by a digit sequence, as follows. (1) The amino acid sequence of a peptide moiety is described by an array of single-letter abbreviations of amino acids. (2) The position and type of modifications are expressed by a digit sequence.

The initial position of a digit sequence represents the terminal amino group of a peptide and the end position thereof represents the terminal carboxyl group. The digits between them represent positions of individual side chain of each amino acid residue. Furthermore, numerical values represent types of modifications. "0" means not modified; "1" represents deamination or cyclization of an amino-terminal glutamine residue; "2" represents oxidation of a methionine residue side-chain; "3" represents deamination or cyclization of the amino-terminal carbamidomethylated cysteine residue and "4" represents deamidation of an asparagine residue (IGOT label), more specifically represents a glycosylated site. Note that the sequence list was prepared based on Table 1 below.

2-2-3. Further Selection of the Candidate Glycopeptides of Hepatic Disease-State-Indicating Glycan Markers The candidate glycopeptides of hepatic disease-state-indicating glycan markers are collected with a cancer probe (a lectin) from (i) a hepatoma-derived cell-line culture medium and (ii) the serum of hepatocellular carcinoma patient (taken before and after a surgery of the cancer) and identified by the large-scale glycopeptide identification methods described in the above sections 2-2-1 and 2-2-2. The identified glycopeptide can be defined as an initial candidate of the glycan marker.

Next, glycopeptides collected from (iii) sera of healthy volunteers with the same probe lectin and with other lectin enabling comprehensive identification, are identified by the same procedure and used as a reference for selection of a marker candidate glycopeptide. More specifically, among candidate glycopeptides, the peptides identified from the healthy volunteer's serum using the cancer probe are ranked lower. On the contrary, the peptides identified with lectin for comprehensive identification are thought to be relatively abundant in the serum and thus evaluated as easily detectable candidates.

Furthermore, glycopeptides identified from (iv) sera taken from hepatocellular carcinoma patients after surgery, using the probe lectin and other lectins in the same manner, are used as a reference to select marker candidates for distinct stage of the hepatic disease. To describe more specifically, the glycopeptide identified from the specimen before the surgery but not identified from the sera of a post-operative patients and healthy volunteers can be regarded as a marker implicating the presence of hepatocellular carcinoma; whereas, a glycopeptide identified from the patients' sera regardless before and after surgery but not identified from the healthy volunteers' sera can be regarded as a marker candidate for background underlying hepatocellular carcinoma (namely, hepatitis and fibrosis leading to hepatic cirrhosis). At this time, an approximate amount of glycoprotein in the serum and a change thereof can be estimated based on comparison of signal intensity of the labeled peptides in LC/MS analysis.

The marker candidate glycopeptides thus selected can be used as candidate glycopeptides of hepatic disease-state-indicating glycan marker through verification tests. Furthermore, a glycoprotein containing the peptide sequence can be used as a glycan biomarker indicating hepatic disease-state through verification tests performed in the state of protein.

2-2-4. Candidate Glycopeptides for a Glycan Biomarker Indicating Hepatic Disease-State The candidate glycopeptides for a glycan biomarker indicating hepatic disease-state, which are selected by the aforementioned steps, are shown in Table 1 below.

TABLE 1

Hepatic disease-state indicating marker glycopeptide
Peptide sequence and modification information
The initial position of a sequence of numbers represents the terminal amino group and
the end position thereof represents the terminal carboxyl group. The numerals between
them represent modification states of residue side-chains. "0" means not modified: "1"
represents deamidation or cyclization of an N-terminal Gln: "2" represents oxidation of

| SEQ. ID. No.: | Peptide No. | a Met side-chain: "3" represents deamidation or cyclization of an N-terminal carbamidemethylated Cys: "4" represents a glycosylation site (Asn label) |
|---|---|---|
| 1 | 1 | FNSSYLQGTNQITGR/00400000000000000 |
| 2 | 2 | VSNVSCQASVSR/000400000000000 |

TABLE 1-continued

Hepatic disease-state indicating marker glycopeptide
Peptide sequence and modification information
The initial position of a sequence of numbers represents the terminal amino group and
the end position thereof represents the terminal carboxyl group. The numerals between
them represent modification states of residue side-chains. "0" means not modified: "1"
represents deamidation or cyclization of an N-terminal Gln: "2" represents oxidation of
a Met side-chain: "3" represents deamidation or cyclization of an N-terminal
carbamidemethylated Cys: "4" represents a glycosylation site (Asn label)

| SEQ. ID. No.: | Peptide No. | |
|---|---|---|
| 3 | 3 | GTAGNALMDGASQLMGENR/0000000000000000400 |
| 4 | 4 | HEEGHMLNCTCFGQGR/000000204000000000 |
| 5 | 5 | RHEEGHMLNCTCFGQGR/00000000004000000000 |
| 6 | 6 | VNFTEIQK/0040000000 |
| 7 | 7 | LYLGSNNLTALHPALFQNLSK/000000040000000000040000 |
| 8 | 8 | GLNVTLSSTGR/0004000000000 |
| 9 | 9 | MDGASNVTCINSR/020000400000000 |
| 10 | 10 | HEEGHMLNCTCFGQGR/000000004000000000 |
| 11 | 11 | QVFPGLNYCTSGAYSNASSTDSASYYPLTGDTR/0000000000000004000000000000000000 |
| 12 | 12 | DQCIVDDITYNVNDTFHK/00000000000004000000 |
| 13 | 13 | GAFISNFSMTVDGK/0000004000000000 |
| 14 | 14 | GAFISNFSMTVDGK/0000004002000000 |
| 15 | 15 | GFGVAIVGNYTAALPTEAALR/000000004000000000000 |
| 16 | 16 | LGACNDTLQQLMEVFKFDTISEK/000004000000200000000000 |
| 17 | 17 | LKELPGVCNETMMALWEECKPCLK/0000000040000000000000000 |
| 18 | 18 | QLVEIEKVVLHPNYSQVDIGLIK/000000000000040000000000 |
| 19 | 19 | TLFCNASKEWDNTTTECR/00000400000040000000 |
| 20 | 20 | IIVPLNNRENISDPTSPLR/00000000000400000000000 |
| 21 | 21 | MEACMLNGTVIGPGK/00000204000000000 |
| 22 | 22 | CGNCSLTTLKDEDFCK/00040000000000000 |
| 23 | 23 | ITYSIVQTNCSKENFLFLTPDCK/000000000040000000000000 |
| 24 | 24 | AVLVNNITTGER/00000040000000 |
| 25 | 25 | AREDIFMETLKDIVEYYNDSNGSHVLQGR/0000000200000000000004000000000 |
| 26 | 26 | FQSPAGTEALFELHNISVADSANYSCVYVDLKPPFGGSAPSER/000000000000004000000400000000000000000000 |
| 27 | 27 | QNQCFYNSSYLNVQR/10000000400000000 |
| 28 | 28 | SLEAINGSGLQMGLQR/000000400000200000 |
| 29 | 29 | AHLNVSGIPCSVLLADVEDLIQQQISNDTVSPR/000040000000000000000000000040000000 |
| 30 | 30 | FTKVNFTEIQK/0000040000000 |
| 31 | 31 | RHEEGHMLNCTCFGQGR/0000000204000000000 |
| 32 | 32 | DIVEYYNDSNGSHVLQGR/000000040040000000000 |
| 33 | 33 | TLYETEVFSTDFSNISAAK/000000000000000400000000 |
| 34 | 34 | QDQCIYNTTYLNVQR/10000004000000000 |
| 35 | 35 | QDQCIYNTTYLNVQRENGTISR/1000000400000000004000000 |
| 36 | 36 | FLNDTMAVYEAK/00040020000000 |
| 37 | 37 | TLNQSSDELQLSMGNAMFVK/00040000000002000200000 |
| 38 | 38 | FEVDSPVYNATWSASLK/0000000004000000000 |

TABLE 1-continued

Hepatic disease-state indicating marker glycopeptide
Peptide sequence and modification information
The initial position of a sequence of numbers represents the terminal amino group and the end position thereof represents the terminal carboxyl group. The numerals between them represent modification states of residue side-chains. "0" means not modified: "1" represents deamidation or cyclization of an N-terminal Gln: "2" represents oxidation of a Met side-chain: "3" represents deamidation or cyclization of an N-terminal carbamidemethylated Cys: "4" represents a glycosylation site (Asn label)

| SEQ. ID. No.: | Peptide No. | |
|---|---|---|
| 39 | 39 | SPYYNVSDEISFHCYDGYTLR/00000400000000000000 |
| 40 | 40 | LGACNDTLQQLMEVFKFDTISEK/00000040000000000000000 |
| 41 | 41 | YTGNASALFILPDQDKMEEVEAMLLPETLKR/000040000000000000000000000000 |
| 42 | 42 | VLTLNLDQVDFQHAGNYSCVASNVQGK/00000000000000400000000000 |
| 43 | 43 | ELPGVCNETMMALWEECKPCLK/000000040002000000000 |
| 44 | 44 | TLNQSSDELQLSMGNAMFVK/0004000000000000020000 |
| 45 | 45 | CGLVPVLAENYNKSDNCEDTPEAGYFAVAVVKK/000000000004000000000000000000000 |
| 46 | 46 | YTGNASALFILPDQDKMEEVEAMLLPETLKR/000040000000000020000000000000 |
| 47 | 47 | NISDGFDGIPDNVDAALALPAHSYSGR/04000000000000000000000000 |
| 48 | 48 | HGIQYFNNNTQHSSLFMLNEVKR/000000040000000020000000 |
| 49 | 49 | SHEIWTHSCPQSPGNGTDASH/000000000000000400000000 |
| 50 | 50 | NPPMGGNVVIFDTVITNQEEPYQNHSGR/0000200000000000000000000400000 |
| 51 | 51 | QIGLYPVLVIDSSGYVNPNYTGR/00000000000000000400000 |
| 52 | 52 | TLNQSSDELQLSMGNAMFVK/0004000000000200000000 |
| 53 | 53 | LSVDKDQYVEPENVTIQCDSGYGVVGPQSITCSGNR/000000000004000000000000000000000400 |
| 54 | 54 | CGLVPVLAENYNKSDNCEDTPEAGYFAVAVVK/00000000000400000000000000000000 |
| 55 | 55 | GLKFNLTETSEAEIHQSFQHLLR/0000040000000000000000 |
| 56 | 56 | SLGNVNFTVSAEALESQELCGTEVPSVPEHGRK/000000400000000000000000000000000 |
| 57 | 57 | DIVEYYNDSNGSHVLQGR/000000040000000000 |
| 58 | 58 | EHEAQSNASLDVFLGHTNVEELMK/00000000400000000000000 |
| 59 | 59 | DVQIIVFPEDGIHGFNFTR/00000000000000040000 |
| 60 | 60 | WNNTGCQALPSQDEGPSK/004000000000000000 |
| 61 | 61 | MEACMLNGTVIGPGK/020002040000000 |
| 62 | 62 | HGIQYFNNNTQHSSLFMLNEVK/00000000400000000000000 |
| 63 | 63 | SVQEIQATFFYFTPNKTEDTIFLR/000000000000000400000000 |
| 64 | 64 | DLQSLEDILHQVENK/00000000000000400 |
| 65 | 65 | FLNDSIVDPVDSEWFGFYR/0004000000000000000 |
| 66 | 66 | FLSSSPHLPPSSYFNASGR/0000000000000000400 |
| 67 | 67 | GGNSNGALCHFPFLYNNHNYTDCTSEGR/0000000000000000000004000000 |
| 68 | 68 | GLLHLENASYGIEPLQNSSHFEHIIYR/000000400000000004000000000 |
| 69 | 69 | NELVQLYQVGEVRPFYYGLCTPCQAPTNYSR/0000000000000000000000000000040 |
| 70 | 70 | NMTFDLPSDATVVLNR/0400000000000400 |
| 71 | 71 | NMTFDLPSDATVVLNR/0420000000000400 |
| 72 | 72 | TNINSSRDPDNIAAWYLR/000040000000000000 |
| 73 | 73 | TNSTFVQALVEHVK/00400000000000 |
| 74 | 74 | VAAANVSVTQPESTGDPNNMILLAEEAR/000004000000000040000000000 |

TABLE 1-continued

Hepatic disease-state indicating marker glycopeptide
Peptide sequence and modification information
The initial position of a sequence of numbers represents the terminal amino group and the end position thereof represents the terminal carboxyl group. The numerals between them represent modification states of residue side-chains. "0" means not modified: "1" represents deamidation or cyclization of an N-terminal Gln: "2" represents oxidation of a Met side-chain: "3" represents deamidation or cyclization of an N-terminal carbamidemethylated Cys: "4" represents a glycosylation site (Asn label)

| SEQ. ID. No.: | Peptide No. | |
|---|---|---|
| 75 | 75 | VAAANVSVTQPESTGDPNNMTLLAEEARK/000004000000000004000000000000 |
| 76 | 76 | VAQPGINYALGINVSYPNNUR/00000000000004000000000 |
| 77 | 77 | VLNASTLALALANLNGSR/000400000000000040000 |
| 78 | 78 | QNQCFYNSSYLNVQRENGTVSR/000000040000000004000000 |
| 79 | 79 | EHEGAIYPDNUDFQRADDK/00000000000400000000000 |
| 80 | 80 | ENGTDTVQEEEESPAEGSK/0040000000000000000000 |
| 81 | 81 | GENFTETDVK/000400000000 |
| 82 | 82 | GIGNYSCSYR/000040000000 |
| 83 | 83 | GNETIVNLIHSTR/00400000000000 |
| 84 | 84 | ILLTCSLNDSATEVTGHR/000000004000000000000 |
| 85 | 85 | LDVDQALNRSHEIWTHSCPQSPGNGTDASH/00000000400000000000000040000000 |
| 86 | 86 | NCQDIDECVTGIHNCSINETCFNIQGGFR/00000000000004000040000000000000 |
| 87 | 87 | NRTPMGHMK/040002000000 |
| 88 | 88 | QYNSTGDYR/00040000000 |
| 89 | 89 | SHTNTSHVMQYGNK/0000400002000400 |
| 90 | 90 | SLSCQMAALQGNGSER/000000000000400000 |
| 91 | 91 | SLSCQMAALQGNGSER/000000200000400000 |
| 92 | 92 | TYNGTNPDAASR/000400000000000 |
| 93 | 93 | VAAANVSVTQPESTGDPNNMTLLAEEAR/000004000000000000042000000000 |
| 94 | 94 | VCEIHEDNSTR/0000000040000 |
| 95 | 95 | VVDDVSNQTSCR/00000004000000 |
| 96 | 96 | HTGNVVITNCSAAHSR/0000000004000000000 |
| 97 | 97 | INLAGDVAALNSGLATEAFSAYGNK/000000000000000000000000400 |
| 98 | 98 | QQQHLFGSNVTDCSGNFCLFR/10000000040000000000000 |
| 99 | 99 | QVFPGLNYCTSGAYSNASSTDSASYYPLTGDTR/100000000000000040000000000000000 |
| 100 | 100 | SAEFFNYTVR/000000400000 |
| 101 | 101 | SDLNPANGSYPFKALR/000000040000000000 |
| 102 | 102 | TVSCQVQNGSETVVQR/000000004000000000 |
| 103 | 103 | VISVDELNDTIAANLSDTEFYGAK/00000000400000400000000000 |
| 104 | 104 | VYSLPGRENYSSVDANGIQSQMLSR/0000000004000000000000020000 |
| 105 | 105 | YRGTAGNALMDGASQLMGENR/00000000000000000200400 |
| 106 | 106 | YSSNHTEHSQNLR/000040000000000 |
| 107 | 107 | YYNYTLSINGK/0004000000000 |
| 108 | 108 | SLTFNETYQDISELVYGAK/000004000000000000000 |
| 109 | 109 | AFENVIDLQWLILDHNLLENSK/000040000000000000000000 |
| 110 | 110 | CRNLSGQTDK/000400000000 |

TABLE 1-continued

Hepatic disease-state indicating marker glycopeptide
Peptide sequence and modification information
The initial position of a sequence of numbers represents the terminal amino group and the end position thereof represents the terminal carboxyl group. The numerals between them represent modification states of residue side-chains. "0" means not modified: "1" represents deamidation or cyclization of an N-terminal Gln: "2" represents oxidation of a Met side-chain: "3" represents deamidation or cyclization of an N-terminal carbamidemethylated Cys: "4" represents a glycosylation site (Asn label)

| SEQ. ID. No.: | Peptide No. | |
|---|---|---|
| 111 | 111 | DFTLNETVNSIFAQGAPR/000004000000000000 |
| 112 | 112 | DNYTDLVAIQNK/00400000000000 |
| 113 | 113 | ELHHLQEQNVSNAFLDKGEFYIGSKYK/00000000040000000000000000000 |
| 114 | 114 | EPGSNVTMSVDAECVPMVR/0000040000000000000000 |
| 115 | 115 | FLNDVKTLYETEVFSTDFSNISAAK/000000000000000000004000000 |
| 116 | 116 | FSLLGHASISCTVENETIGVWRPSPPTCEK/0000000000000040000000000000000 |
| 117 | 117 | GNEANYYSNATTDEHGLVQFSINTINVMGTSLTVR/000000004000000000000400002000000 |
| 118 | 118 | GNESALWDCKHDGWGK/004000000000000000 |
| 119 | 119 | GNETLHYETFGK/00400000000000 |
| 120 | 120 | HLQMDIHIFEPQGISFLETESTFMTNQLVDALTTWQNK/00002000000000000000000020000000000000400 |
| 121 | 121 | HNNDTQHIWESQSNEFSVIADPR/000400000000000000000000 |
| 122 | 122 | HYYIAAEEIIWNYAPSGIDIFTKENLTAPGSDSAVFFEQGTTR/000000000000000000000000004000000000000000000 |
| 123 | 123 | IDGSGNFQVLLSDRYFNK/00000000000000000400 |
| 124 | 124 | ISNSSDTVECECSENWK/00040000000000000000 |
| 125 | 125 | KAENSSNEEETSSEGNMR/000040000000000000 |
| 126 | 126 | KTTCNPCPLGYKEENNTGECCGR/0000000000000004000000000 |
| 127 | 127 | LDAPTNLQFVNETDSTVLVR/00000000004000000000 |
| 128 | 128 | LEPEGPAPHMLGLVAGWGISNPNVTVDEIISSGTR/000000000200000000000004000000000000 |
| 129 | 129 | LNAENNATFYFKIDNVK/00000040000000000 |
| 130 | 130 | LQQDVLQFQKNQTNLER/0000000000040000000 |
| 131 | 131 | LSHNELADSGIPGNSFNVSSLVELDLSYNK/000000000000000004000000000000 |
| 132 | 132 | LSNISHLNYCEPDLR/00040000000000000 |
| 133 | 133 | LTDTICGVGNMSANASDQER/00000000004000400000 |
| 134 | 134 | REGDHEFLEVPEAQEDVEATFPVHQPGNYSCSYR/000000000000000000000000000040000000 |
| 135 | 135 | SGPKNMTFDLPSDATVVLNR/00000400000000000000400 |
| 136 | 136 | TYNVLDMKNTTCQDLQIEVTVK/000000020400000000000000 |
| 137 | 137 | VASVININPNTTHSTGSCR/0000000000040000000000 |
| 138 | 138 | VTVQSLLTVETLEHNQTYECR/000000000000000040000000 |
| 139 | 139 | WVNYSCLDQAR/0004000000000 |
| 140 | 140 | YKVDYESQSTDTQNFSSESKR/00000000000000400000000 |
| 141 | 141 | GCVLLSYLNETVTVSASLESVR/00000000040000000000000 |
| 142 | 142 | ALVLEQLTPALHSTNFSCVLVDPEQVVQR/000000000000000004000000000000 |
| 143 | 143 | WFYIASAFRNEEYNK/000000000000000400 |
| 144 | 144 | SEGTNSTLTLSPVSFENEHSYLCTVTCGHK/00000400000000000000000000000000 |
| 145 | 145 | QNQCFYNSSYLNVQRENGTVSR/10000000400000000004000000 |
| 146 | 146 | VDLEDFENNTAYAK/0000000040000000 |

TABLE 1-continued

Hepatic disease-state indicating marker glycopeptide
Peptide sequence and modification information
The initial position of a sequence of numbers represents the terminal amino group and
the end position thereof represents the terminal carboxyl group. The numerals between
them represent modification states of residue side-chains. "0" means not modified: "1"
represents deamidation or cyclization of an N-terminal Gln: "2" represents oxidation of
a Met side-chain: "3" represents deamidation or cyclization of an N-terminal
carbamidemethylated Cys: "4" represents a glycosylation site (Asn label)

| SEQ. ID. No.: | Peptide No. | |
|---|---|---|
| 147 | 147 | IGEADFNRSKEFMEEVIQR/0000000040000000000000 |
| 148 | 148 | SHAASDAPENLTLLAETADAR/000000000040000000000000 |
| 149 | 149 | DFYVDENTTVR/0000000400000 |
| 150 | 150 | VQNVTEFDDSLLR/000400000000000 |
| 151 | 151 | HGVIISSTVDTYENGSSVEYR/00000000000004000000000 |
| 152 | 152 | YTGNASALFILPDQDKMEEVEAMLLPETLKR/00004000000000000000002000000000 |
| 153 | 153 | AFGQFFSPGEVIYNKTDR/0000000000000040000000 |
| 154 | 154 | EAPYFYNDTVTFK/0000000400000000 |
| 155 | 155 | EHEAQSNASLDVFLGHTNVEELMK/0000000400000000000000200 |
| 156 | 156 | ELDREVYPWYNLTVEAK/00000000004000000 |
| 157 | 157 | LGSYPVGGNVSFECEDGFILR/000000000400000000000 |
| 158 | 158-LR | GCVLLSYLNETVTVSASLESVRGNR/00000000004000000000000400 |
| 159 | 159-LR | VYKPSAGNNSLYR/000000040000000 |
| 160 | 160-LR | NUGHGNSTHHGPEYMR/04000004000000000200 |
| 161 | 161-LR | NGTGHGNSTHHGPEYMR/040000040000000000000 |
| 162 | 162-LR | AAIPSALDTNSSK/00000000004000 |
| 163 | 163-LR | LGNWSAMPSCK/00040002000000 |
| 164 | 164-LR | VVGVPYQGNATALFILPSEGK/000000000400000000000 |
| 165 | 165-LR | GLNLTEDTYKPR/0000400000000000 |
| 166 | 166-LR | SIPACVPWSPYLFQPNUCIVSGWGR/0000000000000004000000000000 |
| 167 | 167-LR | YNSQNQSNNQFVLYR/000040000000000 |
| 168 | 168-LR | KLPPGLLANFTLLR/0000000004000000 |
| 169 | 169-LR | LGNWSAMPSCK/00040000000000 |
| 170 | 170-LR | LHINHNNLTESVGPLPK/000000040000000000 |
| 171 | 171-LR | GICNSSDVR/000040000000 |
| 172 | 172-LR | HERDAGVVCTNETR/00000000000040000 |
| 173 | 173-LR | ASPPSSSCNISSGEMQK/00000000004000000000 |
| 174 | 174-LR | KEDALNETRESETK/0000004000000000 |
| 175 | 175-LR | ESKPLTAQQTTKLDAPTNLQFVNETDSTVLVR/0000000000000000000000040000000000 |
| 176 | 176-LR | EIRHNSTGCLR/0000040000000 |
| 177 | 177-LR | MLNTSSLLEQLNEQFNWVSRLANLTQGEDQYYLR/000400000000000000000004000000000000 |
| 178 | 178-LR | NFTENDLLVR/0400000000000 |
| 179 | 179-LR | NLASRPYTFHSHGITYYKEHEGAIYPDNITDFQR/000000000000000000000000000000040000000 |
| 180 | 180-LR | YPPTVSMVEGQGEKNVTFWGRPLPR/00000000000000004000000000000 |
| 181 | 181-LR | FCRDNYTDLVAIQNK/00000400000000000 |

TABLE 1-continued

Hepatic disease-state indicating marker glycopeptide
Peptide sequence and modification information
The initial position of a sequence of numbers represents the terminal amino group and
the end position thereof represents the terminal carboxyl group. The numerals between
them represent modification states of residue side-chains. "0" means not modified; "1"
represents deamidation or cyclization of an N-terminal Gln; "2" represents oxidation of
a Met side-chain; "3" represents deamidation or cyclization of an N-terminal
carbamidemethylated Cys; "4" represents a glycosylation site (Asn label)

| SEQ. ID. No.: | Peptide No. | |
|---|---|---|
| 182 | 182-LR | INATDADEPNTLNSK/00400000000000000 |
| 183 | 183-LR | TVVTYHIPQNSSLENVDSR/000000000040000000000 |

Moreover, glycoproteins containing the marker candidate glycopeptides selected in the aforementioned steps are shown in Table 2 below (with the proviso that Protein No. 97 and 98 (AGP) and 65 (M2BP) listed in Table 2 below are eliminated).

TABLE 2

| Protein No. | Marker protein |
|---|---|
| 1 | ADAM metallopeptidase domain 9 isoform 1 precursor |
| 2 | ADAM metallopeptidase domain 9 isoform 2 precursor |
| 3 | ADAM metallopeptidase with thrombospondin type 1 motif, 13 isoform 1 preproprotein |
| 4 | ADAM metallopeptidase with thrombospondin type 1 motif, 13 isoform 2 preproprotein |
| 5 | ADAM metallopeptidase with thrombospondin type 1 motif, 13 isoform 3 preproprotein |
| 6 | ADAM metallopeptidase with thrombospondin type 1 motif, 9 preproprotein |
| 7 | ADAMTS-like 2 |
| 8 | alpha 1B-glycoprotein |
| 9 | alpha-2-glycoprotein 1, zinc |
| 10 | alpha-2-macroglobulin precursor |
| 11 | alpha-2-macroglobulin-like 1 |
| 12 | alpha-fetoprotein precursor |
| 13 | apolipoprotein B precursor |
| 14 | asialoglycoprotein receptor 1 |
| 15 | attractin isoform 1 |
| 16 | attractin isoform 2 |
| 17 | basigin isoform 1 |
| 18 | basigin isoform 2 |
| 19 | biotinidase precursor |
| 20 | cadherin 5, type 2 preproprotein |
| 21 | carboxypeptidase E precursor |
| 22 | carboxypeptidase N, polypeptide 2, 83 kD |
| 23 | cat eye syndrome critical region protein 1 isoform a precursor |
| 24 | CD163 antigen isoform a |
| 25 | CD163 antigen isoform b |
| 26 | ceruloplasmin precursor |
| 27 | clusterin isoform 1 |
| 28 | clusterin isoform 2 |
| 29 | coagulation factor C homolog, cochlin precursor |
| 30 | coagulation factor V precursor |
| 31 | coagulation factor XIII B subunit precursor |
| 32 | colony stimulating factor 1 receptor precursor |
| 33 | complement component (3d/Epstein Barr virus) receptor 2 isoform 1 |
| 34 | complement component (3d/Epstein Barr virus) receptor 2 isoform 2 |
| 35 | complement component 1, q subcomponent, A chain precursor |
| 36 | complement component 1, r subcomponent |
| 37 | complement component 2 precursor |
| 38 | complement component 4 binding protein, alpha chain precursor |
| 39 | complement component 4 binding protein, beta chain isoform 1 precursor |
| 40 | complement component 4 binding protein, beta chain isoform 1 precursor |
| 41 | complement component 4 binding protein, beta chain isoform 1 precursor |
| 42 | complement component 4 binding protein, beta chain isoform 2 precursor |
| 43 | complement component 4 binding protein, beta chain isoform 2 precursor |
| 44 | complement component 4A preproprotein |
| 45 | complement component 4B preproprotein |
| 46 | complement factor B preproprotein |
| 47 | complement factor H isoform a precursor |
| 48 | cytokine receptor-like factor 1 |
| 49 | dopamine beta-hydroxylase precursor |
| 50 | EMI domain containing 2 |
| 51 | fibrinogen, beta chain preproprotein |
| 52 | fibrinogen, gamma chain isoform gamma-A precursor |
| 53 | fibrinogen, gamma chain isoform gamma-B precursor |
| 54 | fibronectin 1 isoform 1 preproprotein |

TABLE 2-continued

| Protein No. | Marker protein |
|---|---|
| 55 | fibronectin 1 isoform 2 preproprotein |
| 56 | fibronectin 1 isoform 3 preproprotein |
| 57 | fibronectin 1 isoform 4 preproprotein |
| 58 | fibronectin 1 isoform 5 preproprotein |
| 59 | fibronectin 1 isoform 6 preproprotein |
| 60 | fibronectin 1 isoform 7 preproprotein |
| 61 | fibulin 1 isoform A precursor |
| 62 | fibulin 1 isoform B precursor |
| 63 | fibulin 1 isoform C precursor |
| 64 | fibulin 1 isoform D |
| 65 | galectin 3 binding protein |
| 66 | glucosamine (N-acetyl)-6-sulfatase precursor |
| 67 | golgi phosphoprotein 2 |
| 68 | golgi phosphoprotein 2 |
| 69 | haptoglobin |
| 70 | hypothetical protein LOC196463 |
| 71 | immunoglobulin J chain |
| 72 | immunoglobulin superfamily, member 1 isoform 1 |
| 73 | insulin-like growth factor binding protein 3 isoform a precursor |
| 74 | insulin-like growth factor binding protein 3 isoform b precursor |
| 75 | inter-alpha (globulin) inhibitor H4 |
| 76 | inter-aloha globulin inhibitor H2 polypeptide |
| 77 | intercellular adhesion molecule 2 precursor |
| 78 | interleukin 18 binding protein precursor |
| 79 | interleukin 18 binding protein precursor |
| 80 | interleukin 18 binding protein precursor |
| 81 | kininogen 1 |
| 82 | laminin, gamma 1 precursor |
| 83 | legumain preproprotein |
| 84 | legumain preproprotein |
| 85 | lumican precursor |
| 86 | lunatic fringe isoform a |
| 87 | lunatic fringe isoform b |
| 88 | lysosomal-associated membrane protein 1 |
| 89 | lysosomal-associated membrane protein 2 precursor |
| 90 | lysosomal-associated membrane protein 2 precursor |
| 91 | mannan-binding lectin serine protease 1 isoform 2 precursor |
| 92 | mannosidase, alpha, class 2B, member 2 |
| 93 | MHC class I chain-related gene A protein |
| 94 | microfibrillar-associated protein 4 |
| 95 | neuronal cell adhesion molecule isoform A precursor |
| 96 | neuronal cell adhesion molecule isoform B precursor |
| 97 | orosomucoid 1 precursor |
| 98 | orosomucoid 2 |
| 99 | oxygen regulated protein precursor |
| 100 | palmitoyl-protein thioesterase 1 (ceroid-lipofuscinosis, neuronal 1, infantile) |
| 101 | peptidoglycan recognition protein 2 precursor |
| 102 | phospholipid transfer protein isoform a precursor |
| 103 | plasma carboxypeptidase B2 isoform a preproprotein |
| 104 | plasma carboxypeptidase B2 isoform b |
| 105 | polymeric immunoglobulin receptor |
| 106 | PREDICTED: similar to ADAMTS-like 2 |
| 107 | PREDICTED: similar to Carboxypeptidase N subunit 2 precursor (Carboxypeptidase N polypeptide 2) |
| 108 | PREDICTED: similar to HEG homolog 1 |
| 109 | PREDICTED: similar to HEG homolog 1 |
| 110 | PREDICTED: similar to Mucin-5B precursor (Mucin 5 subtype B, tracheobronchial) (High molecular weight salivary mucin MG1) (Sublingual gland mucin) |
| 111 | PREDICTED: similar to Mucin-5B precursor (Mucin 5 subtype B, tracheobronchial) (High molecular weight salivary mucin MG1) (Sublingual gland mucin) (4390) |
| 112 | prion protein preproprotein |
| 113 | prion protein preproprotein |
| 114 | prion protein preproprotein |
| 115 | prion protein preproprotein |
| 116 | prion protein preproprotein |
| 117 | procollagen-lysine, 2-oxoglutarate 5-dioxygenase 3 precursor |
| 118 | prosaposin isoform a preproprotein |
| 119 | prosaposin isoform b preproprotein |
| 120 | prosaposin isoform c preproprotein |
| 121 | selectin L precursor |
| 122 | selenoprotein P isoform 1 precursor |
| 123 | selenoprotein P isoform 1 precursor |
| 124 | selenoprotein P isoform 2 |
| 125 | serine (or cysteine) proteinase inhibitor, clade A (alpha-1 antiproteinase, antitrypsin), member 4 |
| 126 | serine (or cysteine) proteinase inhibitor, clade A, member 7 |
| 127 | serine (or cysteine) proteinase inhibitor, clade C (antithrombin), member 1 |
| 128 | serpin peptidase inhibitor, clade A, member 3 precursor |

TABLE 2-continued

| Protein No. | Marker protein |
|---|---|
| 129 | sex hormone-binding globulin |
| 130 | SPARC-like 1 |
| 131 | TP53-target gene 5 protein |
| 132 | transferrin |
| 133 | transmembrane 4 superfamily member 6 |
| 134 | transmembrane 4 superfamily member 8 isoform 1 |
| 135 | transmembrane 4 superfamily member 8 isoform 2 |
| 136 | tripeptidyl-peptidase I preproprotein |
| 137 | tumor rejection antigen (gp96) 1 |
| 138 | UDP-GlcNAc: betaGal beta-1,3-N-acetylglucosaminyltransferase 1 |
| 139 | UDP-GlcNAc: betaGal beta-1,3-N-acetylglucosaminyltransferase 2 |
| 140 | vascular cell adhesion molecule 1 isoform a precursor |
| 141 | vitronectin precursor |
| 142 | von Willebrand factor preproprotein |
| 143-LR | apolipoprotein H precursor |
| 144-LR | coagulation factor II precursor |
| 145-LR | complement factor I |
| 146-LR | complement factor properdin |
| 147-LR | desmoglein 2 preproprotein |
| 148-LR | hemopexin |
| 149-LR | inducible T-cell co-stimulator ligand |
| 150-LR | leucine-rich alpha-2-glycoprotein 1 |
| 151-LR | serine (or cysteine) proteinase inhibitor, clade A (alpha-1 antiproteinase, antitrypsin), member 5 |

2-2-5. Verification of the Candidate Glycopeptides of Glycan Biomarker Indicating Hepatic Disease-State For example, various novel glycopeptides described in the above section "2-2-4. Candidate glycopeptides of glycan biomarker indicating hepatic disease-state" are subjected to multiple verification tests described below, to select and verify marker candidate glycopeptides for individual hepatic disease-states. More specifically, examples of the verification tests include i) Comparison of signal intensity of IGOT-labeled peptides in LC/MS analyses for glycopeptides of the hepatocellular carcinoma patients' sera taken before and after surgery, and for the sera of healthy volunteers, which peptides are obtained with a probe lectin; ii) Comparative quantitative proteomics using stable isotope(s) which methods are known in the art, for glycoproteins of the hepatocellular carcinoma patients' sera taken before and after surgery, and for the sera of healthy volunteers, which proteins are obtained with a probe lectin, iii) Quantitative detection using an antibody for each candidate glycoproteins (glycoproteins containing the sequence of glycopeptides described in the above section 2-2-4), which proteins are collected from the hepatocellular carcinoma patients' sera before and after surgery, and the sera of healthy volunteers with a probe lectin; and iv) Comparative glycan profiling by the an antibody overlay lectin microarray method etc. for glycoproteins (glycoproteins containing the sequences of glycopeptides described in the above section 2-2-4) obtained from the sera of (viral) hepatitis patients, hepatic cirrhosis patients and hepatocellular carcinoma patients.

The aforementioned verification tests will be more specifically described as follows.

Re: i) Comparison of signal intensity of IGOT-labeled peptides in LC/MS analyses for glycopeptides of the hepatocellular carcinoma patients' sera taken before and after surgery, and for the sera of healthy volunteers, which peptides are obtained with a probe lectin: The aforementioned specimen (the serum) proteins are separately subjected to S-reduction and alkylation and then digested with trypsin. The resultant peptide mixture is subjected to affinity-chromatography using a probe lectin to collect glycopeptides. These are labeled in accordance with the aforementioned IGOT method. The total amounts thereof are approximately equalized and the glycopeptides are individually subjected to LC/MS analysis. With reference to the mass to charge ratio and elution position of the glycopeptide identified, the spectra of the labeled peptides are obtained. The signal intensities of them are compared. The peptides remarkably present only before surgery and the peptides remarkably present before and after surgery can be selected.

Re: ii) Comparative quantitative proteomics using stable isotope(s) which methods are known in the art, for glycoproteins of the hepatocellular carcinoma patients' sera taken before and after surgery, and for the serum of healthy volunteers, which proteins are obtained with a probe lectin: Glycoproteins collected from the serum specimens with a probe lectin are subjected to S-reduction and alkylation and then digested with trypsin. The resultant peptides are differentially labeled with stable isotopes (guanidination reaction of a Lys side-chain amino group using methylisourea double-labeled with 13C/15N) and then subjected to LC/MS analysis. The spectra of the peptides identified are analyzed and the signal intensities are compared. In this way, change between specimens can be quantitatively estimated. From the quantitative alteration of proteins having cancerous glycans, significance of marker candidates can be verified for each disease-state and then selected candidates for further tests.

Re: iii) Quantitative detection using an antibody for each candidate glycoproteins (glycoproteins containing the sequence of glycopeptides described in the above section 2-2-4), which proteins are collected from the hepatocellular carcinoma patients' sera before and after surgery, and the sera of healthy volunteers with a probe lectin: Glycoproteins collected from the serum specimens with a probe lectin are subjected to, for example, SDS-PAGE, transferred to a membrane and immunologically detected by western blot. The signal intensities of the obtained bands are compared quantitatively to estimate change between the specimens. From the quantitative change of proteins having a cancerous glycans, significance of marker candidates can be verified for each disease-state and then selected candidates for further tests. The antibodies listed in Table 3 can be used for the immunological detection.

Re: iv) Comparative glycan profiling by the an antibody overlay lectin microarray method etc. for glycoproteins (glycoproteins containing the sequences of glycopeptides described in the above section 2-2-4) obtained from the sera of (viral) hepatitis patients, hepatic cirrhosis patients and hepatocellular carcinoma patients. Blood samples are collected from (viral) hepatitis patients, chronic hepatitis patients, hepatic cirrhosis patients and hepatocellular carcinoma patients. From each collected blood sample, candidate glycoproteins of glycan biomarker indicating a hepatic disease-state are enriched and purified by immunoprecipitation method using an antibody and subjected to an antibody-overlay lectin array analyses to select candidates of the glycan biomarker (FIG. 7). As the lectin microarray, for example, a lectin microarray in which multiple lectins, which include whole or part of lectins shown in Table 4 (described later), are immobilized onto a solid phase can be used. More specifically, the lectin microarray described in Kuno A., et al. Nat. Methods 2, 851-856 (2005) or LecChip manufactured by GP Bioscience Ltd. can be used. As the antibody, the antibodies listed in Table 3 can be used.

TABLE 3

| Name of candidate protein | Antibody (vender, catalog No.) |
|---|---|
| alpha-1-B glycoprotein (A1BG) | mouse monoclonal, clone 54B12 (AbFrontier, LFMA0185) |
| | rabbit polyclonal (GenWay Biotech, 18-003-42440) |
| alpha-2-glycoprotein 1, zinc-binding (AZGP1) | rabbit polyclonal (Biovendor Lab. Med., RD181093100) |
| carboxypeptidase B2 (CPB2) | mouse monoclonal, clone 13H4 (Genetex, GTX14757) |
| carboxypeptidase N, polypeptide 2 (CPN2) | mouse monoclonal, clone 36A1 (AbFrontier, LFMA0203) |
| complement factor H (CFH) | rabbit polyclonal (Santa Cruz Biotech., sc-33156) |
| | mouse monoclonal, clone OX-24 (Affinity Bioreagents, MA1-70057) |
| complement factor I (CFI) | sheep polyclonal (The Binding Site, PC031) |
| Alpha-1-antitrypsin | mouse monoclonal, clone 202808 (R&D Systems, MAB1268) |
| | mouse monoclonal, clone B9 (Abcam, ab9399) |
| | goat polyclonal (Abcam, ab7634) |
| Alpha-2-antiplasmin | mouse monoclonal, clone 236122 (R&D Systems, MAB1470) |
| | rabbit polyclonal (AssayPro, 13081-05025) |
| Alpha-2-HS-glycoprotein (Fetuin A) | mouse monoclonal, clone 112922 (R&D Systems, MAB1184) |
| | rabbit polyclonal (AssayPro, 12031-05025) |
| Alpha-2-macroglobulin | mouse monoclonal, clone 3D1 (AbFrontier, LFMA0139) |
| | mouse monoclonal, clone 9A3 (AbFrontier, LFMA0138) |
| | goat polyclonal (Abcam, ab7338) |
| Apolipoprotein C-III | mouse monoclonal, clone 68/7 (Chemicon (Millipore), MAB002687) |
| | goat polyclonal (GeneTex, GTX41024) |
| Ceruloplasmin | mouse monoclonal, clone 3B11 (Santa Cruz Biotech, sc-69767) |
| | rabbit polyclonal (Abcam, ab48650) |
| Clusterin (Apo-J) | mouse monoclonal, clone 78E (Santa Cruz Biotech, sc-32264) |
| | goat polyclonal (Chemicon (Millipore), AB825) |
| Complement C1s subcomponent | mouse monoclonal, clone M241 (Santa Cruz Biotech, sc-52627) |
| | sheep polyclonal (R&D Systems, BAF2060) |
| Complement C3 | mouse monoclonal, clone B-9 (Santa Cruz Biotech, sc-28294) |
| | rabbit polyclonal (Abcam, ab48342) |
| Complement C4 | mouse monoclonal, clone HYB162-02 (Antibodyshop A/S, HYB162-02-02) |
| | rabbit polyclonal (AssayPro, 11231-05025) |
| Complement factor B | mouse monoclonal, clone M20/6 (Santa Cruz Biotech, sc-47680) |
| | mouse monoclonal, clone M13/12 (Santa Cruz Biotech, sc-47682) |
| | goat polyclonal (R&D Systems, BAF2739) |
| Hemopexin | mouse monoclonal, clone ABS 013-32 (Santa Cruz Biotech, sc-59556) |
| | rabbit polyclonal (AssayPro, 12131-05025) |
| Kininogen | mouse monoclonal, clone 207025 (R&D Systems, MAB1569) |
| | goat polyclonal (R&D Systems, BAF1396) |
| Prothrombin | mouse monoclonal, clone 200710 (R&D Systems, MAB1473) |
| | rabbit polyclonal (AssayPro, 11581-05025) |
| Serotransferrin | mouse monoclonal, clone HTF-14 (Sanbio BV, MON5016) |
| | rabbit polyclonal (Rockland, 209-4634) |
| Transthyretin (Prealbumin) | mouse monoclonal, clone 10E1 (Santa Cruz Biotech, sc-69794) |
| | rabbit polyclonal (Abcam, ab48323) |

TABLE 3-continued

| Name of candidate protein | Antibody (vender, catalog No.) |
|---|---|
| apolipoprotein B | mouse monoclonal, clone C1.4 (Santa Cruz Biotech, SC13538) |
| | goat polyclonal (Rockland, 600-101-111) |
| attractin | mouse monoclonal, clone 9H8 (Lab Frontier, LFMA0146) |
| | goat polyclonal (Santa Cruz Biotech, SC9327) |
| CD163 | mouse monoclonal, clone RM3/1 (Hycult Biotechnology, HM2157) |
| | rabbit polyclonal (Santa Cruz Biotech, SC33559) |
| coagulation factor V | mouse monoclonal, clone 6A5 (Santa Cruz Biotech, SC13512) |
| | sheep polyclonal (Affinity BioReagents, PA1-43041) |
| complement component 4 binding protein, beta | rabbit polyclonal (Aviva Systems Biology, ARP33814_P050) |
| complement factor properdin | mouse monoclonal, clone 3B10 (AntibodyShop, HYB039-06-02) |
| | rabbit polyclonal (Santa Cruz Biotech, SC68366) |
| golgi membrane protein 1 | mouse monoclonal, clone 5B10 (Abnova, H00051280-M06) |
| | rabbit polyclonal (Imgenex, IMG-5280A) |
| leucine-rich alpha-2-glycoprotein 1 | mouse monoclonal, clone 2E3 (Abnova, H00116844-M01) |
| lysosomal-associated membrane protein 1 | mouse monoclonal, clone H5G11 (Santa Cruz Biotech, SC18821) |
| | rabbit polyclonal (Santa Cruz Biotech, SC5570) |
| lysosomal-associated membrane protein 2 | mouse monoclonal, clone H4B4 (Santa Cruz Biotech, SC18822) |
| | rabbit polyclonal (Santa Cruz Biotech, SC5571) |
| UDP-GlcNAc: betaGal beta-1,3-N-acetylglucosaminyltransferase 2 | goat polyclonal (Everest Biotech, EB08038) |
| ADAMTS-like 2 | Rabbit polyclonal (Sigma, A6352) |
| Apolipoprotein D | Mouse monoclonal clone 36C6 (abnova, ab49447) |
| Butyrylcholinesterase | Mouse polyclonal (abnova, H00000590-A01) |
| | Rabbit polyclonal (AVIVA systems biology, ARP44208_T100 |
| Colony stimulating factor 1 receptor | Biotinilated Goat polyclonal (R&D, BAF329) |
| | Mouse monoclonal (abnova, clone 1G4) |
| Complement component (3d/Epstein Barr virus) receptor 2 | Rabbit monoclonal clone EP3093 (abcam, ab75985) Rabbit monoclonal clone EP3093 (EPITOMICS, 2546-1) |
| Dopamine beta-hydroxylase | Sheep polyclonal (R&D, PPS067) |
| | Rabbit polyclonal (Thermo scientific, PA1-4655) |
| Fibronectin 1 | Rabbit polyclonal (Santa cruz biotechnology, inc., sc-9068) Goat polyclonal (Santa cruz biotechnology, inc., sc-6952) |
| Inducible T-cell co-stimulator ligand | Biotinilated rat monoclonal (abcam, ab21240) |
| | Biotinilated goat poly (R&D, BAF165) |
| Insulin-like growth factor binding protein 3 | Biotinilated goat polyclonal (R&D, BAF675) |
| Intercellular adhesion molecule 2 | Goat polyclonal (R&D, AF244) |
| Mannan-binding lectin serine protease 1 (MASP3) (Same sequence as MASP1 from 1 through 435) | Rabbit polyclonal (Santa cruz biotechnology, inc., sc-48749) Goat polyclonal (R&D, BAF1724) |
| Polymeric immunoglobulin receptor | Biotinilated Goat polyclonal (R&D, BAF2717) |
| | Mouse monoclonal clone GA-1 (Sigma, I6635) |
| Mucin-5B (Mucin 5 subtype B, tracheobronchial) (High molecular weight salivary mucin MG1) (Sublingual gland mucin) | Rabbit polyclonal (Sigma, HPA008246) |
| Prostaglandin H2 D-isomerase | Mouse polyclonal (abnova, H00005730-B01) |
| Selenoprotein P | Mouse monoclonal (abnova, MAB0761) |
| Serine (or cysteine) proteinase inhibitor, clade A, member 7 | Mouse monoclonal (Lifespan, LS-C18098) Rabbit polyclonal (Sigma, HPA002803) |
| Serine (or cysteine) proteinase inhibitor, clade C (antithrombin), member 1 | Mouse monoclonal clone BDI205 (abcam, ab20933) Biotinilated goat polyclonal (R&D, BAF1267) |
| Sex hormone-binding globulin | Biotinilated goat polyclonal (R&D, BAF2656) |
| SPARC-like 1 | Biotinilated goat polyclonal (R&D, BAF2728) |
| Tumor rejection antigen 1 | Rabbit polyclonal (Proteintech group, inc., 10979-1-AP) Mouse monoclonal clone 2H3 (Novus, NBP1-04346) |
| ADAM metallopeptidase domain9 | Biotinilated Goat polyclonal (R&D, BAF939) |
| prosaposin | Mouse polyclonal (Abnova, H00005660-A01) |
| UDP-GlcNAc: betaGal beta-1,3-N-acetylglucosaminyltransferase1 | Mouse monoclonal clone 1A8 (Abnova, H00010678-M05) |
| cytokine receptor-like factor 1 | Mouse monoclonal clone 4F4 (Abnova, H00009244-M01) |

TABLE 3-continued

| Name of candidate protein | Antibody (vender, catalog No.) |
|---|---|
| tripeptidyl-peptidase | biotinilated Goat polyclonal (R&D, BAF2237) |
| palmitoyl-protein thioesterase 1 | rabbit polyclonal (Proteintech Group Inc. 10887-1-AP) |
| basigin | Biotinilated Goat polyclonal (R&D, BAF972) |
| oxygen regulated protein | Goat polyclonal (R&D, AF5558) |
| MHC class 1 chain-related gene A protein | Biotinilated goat polyclonal (R&D, BAF1300) |
| prion protein | Mouse monoclonal (Sigma, P0110) |
| legumain | Biotinilated Goat polyclonal (R&D, BAF2199) |
| asialoglycoprotein receptor 1 | Rabbit polyclonal (Lifespan, C30704-100) |
| carboxypeptidase E | Goat polyclonal (R&D, AF3587) |
| procollagen-lysine, 2-oxoglutarate 5-dioxygenase 3 | rabbit polyclonal (Proteintech Group Inc. 11027-1-AP) |
| glucosamine (N-acetyl)-6-sulfatase | Goat polyclonal (R&D, AF2484) |
| EMI domain containing 2 | Rabbit polyclonal (Lifespan, C82705-50) |
| mannosidase, alpha, class 2B, member 2 | rabbit polyclonal (Proteintech Group Inc. 17697-1-AP) |
| Glycosyl phosphatidyl inositol-specific phospholipase D | Mouse monoclonal clone 38A1(GenWay bio, 20-007-280085) |

As described above, the glycan structures of glycopeptides or glycoproteins are comprehensively analyzed to check whether the glycan structures change or not between a (viral) hepatitis patient, chronic hepatitis patients, hepatic cirrhosis patients and hepatocellular carcinoma patients. A glycopeptide or glycoprotein, whose glycan structure changes, can be used as a glycan biomarker indicating the hepatic disease-state.

3. Detection of a Marker Glycopeptide Indicating Hepatic Disease-State and a Marker Glycoprotein Indicating Hepatic Disease-State 3-1. Mass Spectrometry A marker glycopeptide or glycoprotein indicating hepatic disease-state can be detected with a mass spectrometer as a detector for a specimen obtained with a probe lectin etc.

A marker glycopeptide collected can be detected preferably by liquid chromatography after removal of its glycan moiety, followed by mass spectrometry, in which the eluted peptides are introduced directly into a mass spectrometer on line. Mass spectrometric analysis can obtain not only its simple mass spectrum, but also its MS/MS spectrum using collision-induced dissociation (CID) as fragmentation method. Additionally, marker peptide is able to be detected as multiple fragment ions generated by CID for pre-listed ion of the marker peptide (technology called as single reaction monitoring (SRM) or multiple reaction monitoring (MRM)). In the analytical method, if a synthetic marker peptide having certain mass difference due to incorporation of stable isotope is added into the specimen, it is possible to perform absolute quantitation of the peptide by comparing their signal intensities.

A marker glycoprotein can be detected by use of various proteomic techniques known in the art. For example, a collected protein fraction is separated by one-dimensional or two-dimensional gel electrophoresis. Then, the signal intensity (dye or fluorescence staining, etc.) of the target spot can be compared to that of a reference specimen to quantify relatively. In case of use of mass spectrometer, it is possible to detect the collected glycoprotein by protease digestion followed by LC/MS analysis. Quantification can be made by various methods (e.g., ICAT, MCAT, iTRAQ, SILAC methods) using a stable isotope label and a non-labeled simple quantification method (e.g., peptide counting method, area integration method) can be used in combination with them. Furthermore, as described later, quantification can be made by the ELISA method.

3-2. Lectin Microarray 3-2-1. Glycan Profiling by Lectin Microarray (1) Lectin Microarray (Simply Referred Also to as Lectin Array)

A lectin array is prepared by immobilizing a plurality of types of probe lectins different in specificity onto a single substrate in parallel (in the form of array). The lectin array can simultaneously analyze which lectin interacts with an analysis target, i.e., a conjugated polysaccharide.

When the lectin array is used, information required for estimating a glycan structure can be obtained by a single analysis and a step from sample preparation to scanning can be quickly and simply carried out. In a glycan profiling system such as mass spectrometry, a glycoprotein cannot be directly analyzed as it is; in other words, a glycoprotein must be treated and decomposed into glycopeptides and free glycans. On the other hand, in the lectin microarray, a glycoprotein can be analyzed as it is only by introducing, for example, a fluorescent reagent, directly into a core protein moiety thereof. This is an advantage of the lectin microarray. The lectin microarray technique has been developed by the present inventors and the principle and fundamental are described, for example, in Kuno A., et al. Nat. Methods 2,851-856 (2005).

Lectins to be used in the lectin array are listed in the following Table 4.

TABLE 4

| | Lectins | Origin | Binding specificity (Sugar binding specificity) |
|---|---|---|---|
| 1 | LTL | *Lotus tetragonolobus* | Fucα1-3GlcNAc, Sia-Le$^x$ and Le$^x$ |
| 2 | PSA | *Pisum sativum* | Fucα1-6GlcNAc and α-Man |
| 3 | LCA | *Lens culinaris* | Fucα1-6GlcNAc and α-Man, α-Glc |
| 4 | UEA-I | *Ulex europaeus* | Fucα1-2LacNAc |
| 5 | AOL | *Aspergillus oryzae* | Terminal αFuc and ±Sia-Le$^x$ |

TABLE 4-continued

| Lectins | Origin | Binding specificity (Sugar binding specificity) |
|---|---|---|
| 6 AAL | *Aleuria aurantia* | Terminal αFuc and ±Sia-Le$^x$ |
| 7 MAL | *Maackia amurensis* | Siaα 2-3Gal |
| 8 SNA | *Sambucus nigra* | Siaα 2-6Gal/GalNAc |
| 9 SSA | *Sambucus sieboldiana* | Siaα 2-6Gal/GalNAc |
| 10 TJA-I | *Trichosanthes japonica* | Siaα 2-6Galβ1-4GlcNAcβ-R |
| 11 PHA(L) | *Phaseolus vulgaris* | Tri- and tetra-antennary complex oligosaccharides |
| 12 ECA | *Erythrina cristagalli* | Lac/LacNAc |
| 13 RCA120 | *Ricinus communis* | Lac/LacNAc |
| 14 PHA(E) | *Phaseolus vulgaris* | NA2 and bisecting GlcNAc |
| 15 DSA | *Datura stramonium* | (GlcNAc)$_n$, polyLacNAc and LacNAc (NA3, NA4) |
| 16 GSL-II | *Griffonia simplicifolia* | Agalactosylated N-glycan |
| 17 NPA | *Narcissus pseudonarcissus* | non-substituted α1-6Man |
| 18 ConA | *Canavalia ensiformis* | α-Man (inhibited by presence of bisecting GlcNAc) |
| 19 GNA | *Galanthus nivalis* | non-substituted α1-6Man |
| 20 HHL | *Hippeastrum hybrid* | non-substituted α1-6Man |
| 21 BPL | *Bauhinia purpurea alba* | Galβ1-3GalNAc and NA3, NA4 |
| 22 TJA-II | *Trichosanthes japonica* | Fucα1-2Gal, β-GalNAc > NA3, NA4 |
| 23 EEL | *Euonymus europaeus* | Galα1-3[Fucα1-2Gal] > Galα1-3Gal |
| 24 ABA | *Agaricus bisporus* | Galβ1-3GalNAcα-Thr/Ser (T) and sialyl-T |
| 25 LEL | *Lycopersicon esculentum* | (GlcNAc)$_n$ and polyLacNAc |
| 26 STL | *Solanum tuberosum* | (GlcNAc)$_n$ and polyLacNAc |
| 27 UDA | *Urtica dioica* | (GlcNAc)$_n$ and polyLacNAc |
| 28 PWM | *Phytolacca americana* | (GlcNAc)$_n$ and polyLacNAc |
| 29 Jacalin | *Artocarpus integrifolia* | Galβ1-3GalNAcα-Thr/Ser (T) and GalNAcα-Thr/Ser (Tn) |
| 30 PNA | *Arachis hypogaea* | Galβ1-3GalNAcα-Thr/Ser (T) |
| 31 WFA | *Wisteria floribunda* | Terminal GalNAc (e.g., GalNAcβ1-4GlcNAc) |
| 32 ACA | *Amaranthus caudatus* | Galβ1-3GalNAcα-Thr/Ser (T) |
| 33 MPA | *Maclura pomifera* | Galβ1-3GalNAcα-Thr/Ser (T) and GalNAcα-Thr/Ser (Tn) |
| 34 HPA | *Helix pomatia* | Terminal GalNAc |
| 35 VVA | *Vicia villosa* | α-, β-linked terminal GalNAc and GalNAcα-Thr/Ser (Tn) |
| 36 DBA | *Dolichos biflorus* | GalNAcα-Thr/Ser (Tn) and GalNAcα1-3GalNAc |
| 37 SBA | *Glycine max* | Terminal GalNAc (especially GalNAcα1-3Gal) |
| 38 GSL-I mixture | *Griffonia simplicifolia* | α-GalNAc, GalNAcα-Thr/Ser (Tn), α-Gal |
| 39 PTL-I | *Psophocarpus tetragonolobus* | α-GalNAc and Gal |
| 40 MAH | *Maackia amurensis* | Siaα 2-3Galβ1-3[Siaα2-6GalNAc] α-R |
| 41 WGA | *Triticum unlgaris* | (GlcNAc)n and multivalent Sia |
| 42 GSL-IA$_4$ | *Griffonia simplicifolia* | α-GalNAc, GalNAcα-Thr/Ser (Tn) |
| 43 GSL-IB$_4$ | *Griffonia simplicifolia* | α-Gal |

For example, a lectin array (LecChip, manufactured by GP Bioscience Ltd.) in which 45 types of lectins are immobilized onto a substrate is already commercially available.

(2) Statistical Analysis of Glycan Profile Obtained by Lectin Array

The lectin array has been developed, up to present, to a practical technique by which a quantitative comparative glycan profiling can be made with respect to not only a purified sample but also a mixture of specimens such as the serum and a cell lysate. Particularly, the comparative glycan profiling of a cell surface glycan has been significantly developed (Ebe, Y. et al. J. Biochem. 139, 323-327 (2006), Pilobello, K. T. et al. Proc Natl Acad Sci USA. 104, 11534-11539 (2007), Tateno, H. et al. Glycobiology 17, 1138-1146 (2007)).

Furthermore, data mining by statistical analysis of a glycan profile can be made, for example, by a method(s) described in "Kuno A, et al. J Proteomics Bioinform. 1, 68-72 (2008)." or "the Japanese Society of Carbohydrate Research 2008/8/18 development of application technique for lectin microarray~comparative glycan profiling and statistical analysis of biological specimen~Kuno A, Matsuda A, Itakura Y, Matsuzaki H, Narimatsu H, Hirabayashi J" and "Matsuda A, et al. Biochem Biophys Res Commun. 370, 259-263 (2008)".

(3) Antibody Overlay Lectin Microarray Method

The platform of a lectin microarray is basically the same as described above. An above-described subject is not directly labeled with a fluorescent reagent but by indirectly introducing a fluorescent group into a subject via an antibody. In this manner, many subjects can be simply and quickly analyzed at the same time. This is an application method (see "Kuno A, Kato Y, Matsuda A, Kaneko M K, Ito H, Amano K, Chiba Y, Narimatsu H, Hirabayashi J. Mol. Cell Proteomics. 8, 99-108 (2009)", "Hirabayashi J, Kuno A, Uchiyama N, "Development of application technology for glycan profiling using a lectin microarray", Experimental Medicine, extra number "Study for cancer diagnosis at a molecular level~challenge to clinical application", Yodosha, Vol. 25 (17) 164-171 (2007)", Kuno A, Hirabayashi J, "Application of glycan profiling system by lectin microarray to searching glycan biomarker", Genetic Medicine MOOK No. 11 "Development of clinical glycan biomarker and elucidation of glycan function", pp. 34-39, Medical Do (2008)).

For example, if a glycoprotein is a subject, the glycan moiety can be recognized by a lectin on a lectin microarray. Thus, if an antibody against a core protein moiety is overlayed on the glycoprotein, the glycoprotein can be specifically detected with a high sensitivity without labeling the subject glycoprotein or highly purifying it.

(4) Lectin Overlay Antibody Microarray Method

This is a method using an antibody microarray, which is prepared by immobilizing an antibody against a core protein onto a substrate such as a glass substrate in parallel (in the form of array), in place of a lectin microarray. The same numbers of antibodies as the number of markers to be checked are required. It is necessary to previously determine a lectin for detecting a glycan change.

3-3 Lectin-Antibody Sandwich Immunological Detection

Based on the results of a lectin array, a simple and inexpensive sandwich detection method can be designed. Basically, two types of antibodies are used in the sandwich detection method. This method can be applied simply by replacing lectin for one of the antibodies in the protocol of this method. Therefore, this method can be applied to an automatic operation using a conventional automatic immuno-detection apparatus. What is a point that should be considered is the reaction between an antibody and a lectin to be used as sandwiching substances. The antibody has at least two N-linked glycans. Therefore, when the lectin to be used recognizes a glycan on the antibody, background noise inevitably occurs in sandwich detection time due to the binding reaction thereof. To suppress generation of a noise signal, an approach of modifying a glycan moiety on the antibody and an approach of using only Fab containing no glycan moiety are conceivable. As these approaches, known methods may be employed. As the approach of modifying a glycan moiety, for example, methods described in Chen S. et al., Nat. Methods. 4, 437-44 (2007) and Comunale M A, et al., J Proteome Res. 8, 595-602 (2009), are mentioned. As the approach of using Fab, for example, a method described in Matsumoto H., et al., Clin Chem Lab Med 48, 505-512 (2010), may be mentioned.

3-4. Method Using Serial Column Chromatography

An antibody overlay lectin array is the most ideal approach for statistically detecting a lectin, which most precisely reflects a disease specific change of a glycan on a novel hepatic disease-state-indicating glycan marker candidate molecule; however, it requires an antibody which can immunologically precipitate and can be detected by an overlay method. Nevertheless, such an antibody is not always available. Accordingly, as means for using more candidate molecules in detection of a hepatic disease, generally a method of immunologically detecting the amount of target glycoprotein is applied to a glycoprotein collected by a probe lectin. To describe more specifically, SDS-PAGE is performed; a protein is transferred onto a membrane and thereafter immunologically detected by Western blot. The signal intensities of the obtained bands are compared. In this manner, changes between specimens can be quantitatively estimated. Based on quantitative change of a protein having a cancerous glycosylation, significance of each marker candidate can be validated for each disease-state and the candidates were screened. Herein, glycan marker candidate molecules, in which fucose modification increases with the progress of a hepatic disease, are validated. In this case, generally, AAL lectin, which is used in a step of identifying a candidate molecule, is also used as a probe protein in a validation step. For example, this strategy is actually employed in a report of Liu Y., et al. J Proteome Res. 9, 798-805 (2010). However, proteins in the serum are known to differ in N-linked glycan structure (degree of branching) and fucosylation (core fucose, blood group antigen, etc.) depending upon the type of protein. Even if they are the same molecules, it has been reported that they are differently modified with fucose. For example, Nakagawa T, et al. have reported, in J. Biol. Chem. 281, 29797-29806 (2006), that α1-anti-trypsin molecules are differently modified with fucose. This is because proteins are increased or not in a different timing depending upon the type of disease and degree of progress. Therefore, it is not ideal to use AAL capable of recognizing and collecting almost all fucose modifications and collect a whole of fucose-containing glycoproteins and quantitatively compare them. Then, we conceived that two different types of fucose recognizing lectins are used for separating and fractionating proteins by serial column chromatography and individual fractions are quantitatively analyzed and compared. The scheme of the technique is shown in FIG. 10. The lectin to be used herein is LCA and AAL. According to analysis so far made for lectin specificity, LCA is known to recognize a hypo-branched glycan having a core modified with fucose among the N-linked glycans. AAL can recognize core fucose having any degree of branching of the N-linked glycans and also known to be able to recognize fucose modification on the side of non-reducing end represented by ABO and Lewis antigens. In other words, LCA has high specificity and AAL has low specificity. Then, as the first step, LCA column chromatography is performed to capture a fucose-containing glycoprotein binding to LCA. This is specified as an LCA-bound fucose-containing glycoprotein. During the chromatography, a fucose-containing glycoprotein having no hypo-branched N-linked glycan with core fucose modification does not bind to an LCA column and is fractionated into an (LCA) unbound fraction. To capture such fucose-containing glycoproteins from the LCA-unbound fraction, the LCA-unbound fraction is subjected to AAL column chromatography. At this time, the glycoproteins captured by AAL is specified as LCA-unbound/AAL-bound fucose-containing glycoprotein. By the operation, an increase or decrease of fucosylation on the same protein with the progress of a disease can be probably evaluated separately depending upon the modification type.

4. Hepatic Disease-State-Indicating Glycan Marker Candidate

Several examples of a hepatic disease-state-indicating glycan marker candidate selected in the aforementioned steps will be shown below.

4-1. Examples of the Hepatic Disease-State-Indicating Glycan Marker Candidate Glycopeptide Include the Following Glycopeptides.

(1) A hepatic disease-state-indicating glycan marker glycopeptide, which is a polypeptide represented by Peptide No. 19 in Table 1.

(2) A hepatic disease-state-indicating glycan marker glycopeptide, which is a polypeptide represented by Peptide No. 26 in Table 1.

(3) A hepatic disease-state-indicating glycan marker glycopeptide, which is a polypeptide represented by Peptide No. 118 in Table 1.

(4) A hepatic disease-state-indicating glycan marker glycopeptide, which is a polypeptide represented by Peptide No. 124 in Table 1.

(5) A hepatic disease-state-indicating glycan marker glycopeptide, which is a polypeptide represented by Peptide No. 125 in Table 1.

(6) A hepatic disease-state-indicating glycan marker glycopeptide, which is a polypeptide represented by Peptide No. 130 in Table 1.

(7) A hepatic disease-state-indicating glycan marker glycopeptide, which is a polypeptide represented by Peptide No. 132 in Table 1.

(8) A hepatic disease-state-indicating glycan marker glycopeptide, which is a polypeptide represented by Peptide No. 135 in Table 1.

Note that the glycopeptides of (1) to (8) above can be used in combination with two or more.

4-2. Examples of the Hepatic Disease-State-Indicating Glycan Marker Candidate Glycoprotein Include the Following Glycoproteins:

(1) A hepatic disease-state-indicating glycan marker glycoprotein, which is a glycoprotein containing a polypeptide represented by Protein No. 22 in Table 2 above and having a glyccolylation change including fucosylation;

(2) A hepatic disease-state-indicating glycan marker glycoprotein, which is a glycoprotein containing a polypeptide represented by Protein No. 89 or 90 in Table 2 above and having a glycosylation change including fucosylation;

(3) A hepatic disease-state-indicating glycan marker glycoprotein, which is a glycoprotein containing a polypeptide represented by Protein No. 145-LR in Table 2 above and having a glycosylation change including fucosylation;

(4) A hepatic disease-state-indicating glycan marker glycoprotein, which is a glycoprotein containing a polypeptide represented by Protein No. 9 in Table 2 above and having a glycosylation change including fucosylation;

(5) A hepatic disease-state-indicating glycan marker glycoprotein, which is a glycoprotein containing a polypeptide represented by Protein No. 8 in Table 2 above and having a glycosylation change including fucosylation (6) A hepatic disease-state-indicating glycan marker glycoprotein, which is a glycoprotein containing a polypeptide represented by Protein No. 103 or 104 in Table 2 above and having a glycosylation change including fucosylation;

(7) A hepatic disease-state-indicating glycan marker glycoprotein, which is a glycoprotein containing a polypeptide represented by Protein No. 47 in Table 2 above and having a glycosylation change including fucosylation;

(8) A hepatic disease-state-indicating glycan marker glycoprotein, which is protein pIgR containing a polypeptide represented by Protein No. 105 in Table 2 above and having a glycosylation change including fucosylation;

(9) A hepatic disease-state-indicating glycan marker glycoprotein, which is protein CSF1R containing a polypeptide represented by Protein No. 32 in Table 2 above and having a glycosylation change including fucosylation;

(10) A hepatic disease-state-indicating glycan marker glycoprotein, which is protein SHBG containing a polypeptide represented by Protein No. 129 in Table 2 above and having a glycosylation change including fucosylation;

(11) A hepatic disease-state-indicating glycan marker glycoprotein, which is protein SEPP1 containing a polypeptide represented by Protein No. 122 or 123 in Table 2 above and having a glycosylation change including fucosylation;

(12) A hepatic disease-state-indicating glycan marker glycoprotein, which is protein SPARCL1 containing a polypeptide represented by Protein No. 130 in Table 2 above and having a glycosylation change including fucosylation;

(13) A hepatic disease-state-indicating glycan marker glycoprotein, which is protein SERPINA7 containing a polypeptide represented by Protein No. 126 in Table 2 above and having a glycosylation change including fucosylation; and

(14) A hepatic disease-state-indicating glycan marker glycoprotein, which is protein MANA2 containing a polypeptide represented by Protein No. 92 in Table 2 above and having a glycosylation change including fucosylation.

Note that the glycoproteins of (1) to (14) above can be used in combination with two or more.

Furthermore, the glycoproteins of (1) to (8) described in the above section 4-1. and the glycoproteins of (1) to (14) described in the above section 4-2. can be used in combination with two or more.

5. Validation of Hepatic Disease-State-Indicating Glycan Marker Candidate

The marker candidates identified above are studied on 1) how significantly a measurement value changes with the progress of a disease, 2) in which stage of disease (initial stage or late stage) the measurement value most significantly changes and 3) whether data of measurement-value change contributes to controlling a disease. Based on the study, usefulness of the marker is evaluated and which hepatic disease-state the marker is suitably used can be validated.

6. Method of Detecting and/or Identifying a Hepatic Disease by Use of a Novel Hepatic Disease-State-Indicating Glycan Marker Candidate Furthermore, the present invention includes a method of specifically detecting a hepatic disease, including detecting and/or identifying a novel hepatic disease-state-indicating glycan marker candidate listed in Table 2 above (note that, hereinafter, a lectin specifically reacting with a certain novel hepatic disease-state-indicating glycan marker candidate will be referred to as lectin "A").

For example, examples of detection means for a novel hepatic disease-state-indicating glycan marker candidate having a glycan specifically reacting with lectin "A" include the followings.

(1) a combination of means, i.e., (i) means for detecting a glycan specifically reacting with lectin "A" and (ii) means for detecting a core protein by means for detecting a portion (core protein) except the glycan of a hepatic disease-state-indicating glycan marker, and (2) an antibody, which is an antibody specific to a hepatic disease-state-indicating glycan marker having a glycan specifically binding to lectin "A" and using the vicinity of a glycan binding site as an epitope. Herein, the means for detecting a glycan specifically reacting with lectin "A" and the means for detecting a core protein may be means for measuring a glycan specifically reacting with lectin "A" and means for measuring a core protein, respectively.

For example, a patient with a hepatic disease can be distinguishably detected from a healthy volunteer by detecting a novel hepatic disease-state-indicating glycan marker candidate by use of an antibody against a core protein and lectin "A". Preferably, an antibody overlay method using a lectin array ("Kuno A, Kato Y, Matsuda A, Kaneko M K, Ito H, Amano K, Chiba Y, Narimatsu H, Hirabayashi J. Mol. Cell Proteomics. 8, 99-108 (2009)) can be used.

As a more simple detection method, a lectin-antibody sandwich immunological detection method can be used.

6-1. For Example, a Specific Method for Detecting a Hepatic Disease by Use of a Novel Hepatic Disease-State-Indicating Glycan Marker Candidate Having a Glycan Specifically Reacting with Lectin "A" Includes 1) a step of measuring a hepatic disease-state-indicating glycan marker having a glycan specifically reacting with lectin "A" in a specimen taken from a subject outside the body or a fragment thereof (a peptide containing a glycan modification site), 2) a step of measuring a hepatic disease-state-indicating glycan marker having a glycan specifically reacting with lectin "A" in a specimen taken from a healthy volunteer outside the body or a fragment thereof (a peptide containing a glycan modification site), 3) a step of measuring a hepatic disease-state-indicating glycan marker having a glycan specifically reacting with lectin "A" in a specimen taken from a patient with a hepatic disease outside the body or a fragment thereof (a peptide containing a glycan modification site), and 4) comparing the measurement results of the hepatic disease-state-indicating glycan marker having a glycan specifically reacting with lectin "A" taken from the subject or a fragment thereof (a peptide containing a glycan modification site) with the measurement results of a hepatic disease-state-indicating glycan marker having a glycan specifically reacting with lectin "A" taken from the healthy volunteer or the patient with a hepatic disease or a fragment thereof (a peptide containing a glycan modification site); and determining as being the hepatic disease if the measurement results of the subject is closer to the measurement value of the patient with a hepatic disease.

6-1-1.

1) Method for Measuring Progression of Fibrosis

In the progression of hepatitis by hepatitis viral infection, it is known that the degree of fibrosis is correlated with deterioration of liver function and a risk of developing hepatocarcinoma. Therefore, measurement of fibrosis means to evaluate deterioration of liver function and a carcinogenic risk. Furthermore, about four out of ten hepatitis patients does not respond to an interferon therapy and viral infection sustains. Whether these disease-states are developed into active disease-states is considered to be determined based on progression of fibrosis. In view of these, measuring progression of fibrosis has significant meaning in diagnostic treatment for hepatitis.

Evaluation of fibrosis presently performed is based on pathologic diagnosis on a biopsy specimen. Owing to recent introduction of FibroScan, this method is expected to be widely used. Furthermore, as a method of serologically evaluating fibrosis, Fibro Test, Forn's index, Hepatoscore, etc., are clinically used; however, they are inferior in both sensitivity and specificity to biopsy diagnosis.

With respect to the marker candidate glycopeptides and glycoproteins obtained by the present invention and listed in Tables 1 or 2, analysis is made as follows. Patient's sera different in the degree of fibrosis are subjected to an antibody overlay lectin microarray. A lectin exhibiting an increase or decrease in signal intensity correlating with the degree of fibrosis is selected. Based on the data, a sandwich assay using an antibody against a marker candidate molecule and lectin "A" whose signal intensity changes with the progress of fibrosis, for example, a lectin-antibody sandwich ELISA and an antibody overlay lectin microarray method, can be established. The sera from about 100 patients having fibrosis classified by staging based on pathological diagnosis, are collected and analyzed to set a cut-off value for each stage. In this manner, progress of hepatic fibrosis can be monitored by use of the patient's serum.

2) Detection of Hepatic Cirrhosis

Hepatic Cirrhosis is defined as a disease-state where a regeneration node in which a hepatic lobule structure disappears and a fibrous connective tissue surrounding it diffusely emerges over the liver. This is a terminal state of a progressive chronic hepatic disease with hepatic cell damage and fibrosis sustained. Liver biopsy for hepatic cirrhosis is performed for diagnosing a cause. In the most cases of early-stage hepatic cirrhosis and a large-node hepatic cirrhosis, it is difficult to make diagnosis (surgical pathology, 4th edition, from Bunkodo). In the circumstances, it is required to develop a testing technique enabling qualitative and quantitative diagnosis for hepatic cirrhosis. With respect to this purpose, if there is a set of a candidate molecule antibody and lectin that can distinguish fibrosis stage F3 from F4 in those found in the section 1) Method for measuring progression of fibrosis, such a set can be used for detecting hepatic cirrhosis.

3) Detection of Early-Stage Hepatocarcinoma

Early-stage hepatocarcinoma is defined as a highly differentiated hepatic cell of around 1.5 cm in size accompanying pathologic interstitial infiltrate. This is a pathological change distinguished from conventional hepatocarcinoma and regeneration node and a borderline pathological change (atypical adenomatous hyperplasia). Particularly, a borderline pathological change and highly differentiated hepatocarcinoma are considered as the same in the process reaching carcinogenesis and they are known to follow a clinical course into conventional hepatocarcinoma. In addition, highly differentiated hepatocarcinoma is considered as one of pathological changes prior to conventional hepatocarcinoma. If the pathological change is found and treated, permanent cure of the cancer can be expected.

As means for attaining this, a comparative hepatic analysis method such as lectin-antibody sandwich ELISA and antibody overlay lectin microarray is employed to examine a hepatic change of marker candidate glycopeptides and glycoproteins obtained in the present invention and listed in Table 1 or 2, by serially taking a plurality of sera of patients in fibrosis stage F4 for several years until a cancer is found. Owing to this, a set of a candidate molecule having a hepatic that significantly changes from the initial stage of hepatic cirrhosis to carcinogenesis and a lectin capable of capturing the hepatic change can be used as an early-stage hepatocarcinoma detection tool.

6-2. Detection of a Novel Hepatic Disease-State-Indicating Hepatic Marker Candidate Having a Glycan Specifically Reacting with Lectin "a" in a Specimen or a Fragment Thereof (a Peptide Containing a Glycan Modification Site)

Examples of a specimen include a biopsy specimen and a body fluid specimen, preferably, blood (the serum, blood plasma etc.).

Measurement includes both qualitative measurement and quantitative measurement.

A hepatic disease-state-indicating a glycan marker having a glycan specifically reacting with lectin "A" or a fragment thereof (a peptide containing a glycan modification site) can be measured by use of, for example, (1) means for measuring a glycan specifically reacting with lectin "A", more specifically, a lectin "A" immobilized column and array, and (2) means for measuring a novel hepatic disease-state-indicating glycan marker candidate or a fragment thereof, more specifically, use of an antibody against a novel hepatic disease-state-indicating glycan marker candidate or a fragment thereof. Preferably, a lectin-antibody sandwich ELISA and an antibody overlay lectin array method can be used.

Furthermore, the concentration of a novel hepatic disease-state-indicating glycan marker candidate having a glycan specifically reacting with lectin "A" or a fragment thereof (a peptide containing a glycan modification site) can be measured. Measurement means thereof include an antibody overlay lectin array method using a lectin array, LC-MS, an immunological measurement method, an enzyme activity measurement method and capillary electrophoresis method. Preferably, a qualitative or quantitative method can be used, which includes LC-MS, enzyme immunoassay method using a monoclonal antibody or polyclonal antibody specific to a novel glycan marker for hepatocarcinoma candidate having a glycan specifically reacting with lectin "A" or a fragment thereof, a two-antibody sandwich ELISA method, a gold colloid method, a radioimmunoassay technique, a latex aggregation immunoassay, a fluorescent immunoassay, a Western blotting method, an immunohistochemical method and a surface plasmon resonance spectroscopy (hereinafter referred to as a SPR method).

Further more specifically, semi-quantification can be performed by the Western blotting method using lectin "A" and an anti-novel disease-state-indicating glycan marker candidate antibody. In the qualitative measurement, the phrase "the case where measurement results of a subject is further high" means the case where the fact that a novel disease-state-indicating glycan marker candidate having a glycan specifically reacting with lectin "A" is present in a larger amount in the specimen from a subject than the specimen from a healthy volunteer is qualitatively demonstrated. Moreover, a lectin method and mass spectrometry serving as a direct measurement method for a glycan without using an antibody are also included.

As lectin "A" herein, whose reactivity varies in response to a change in glycan structure of AAT, ACT, pIgR, CPB2 and CSF1R with the progress of hepatic fibrosis, AAL can be mentioned. The protein amount itself of CSF1R also tends to increase with the progress of hepatic fibrosis. However, such a quantitative change occurs in another disease. Therefore, this is not a tool for accurately distinguishing the progression of fibrosis. In contrast, AAL-bound CSF1R quantitative change in response to a change of a glycan structure is not influenced by another disease. Thus, the accuracy is high. Furthermore, the accuracy of distinguishing the range of a progression stage of fibrosis of F3 to F4 is improved by adding a step of removing LCA-bound AAT, ACT, pIgR, CPB2, CSF1R as a previous step of detecting AAL-bound AAT, ACT, pIgR, CPB2, CSF1R.

As lectin "A" whose reactivity changes in response to a change in glycan structure of CSF1R with the progress of a disease from hepatic cirrhosis to hepatocarcinoma, WFA can be mentioned which is carefully selected by the antibody overlay lectin array method. As described above, since the amount of CSF1R protein in the serum increases with the progress of hepatic fibrosis, it is preferred for more accurate diagnosis that the mass of CSF1R core protein is separately measured and a WFA-bound CSF1R measurement value is normalized by the measurement value.

7. Preparation of Novel Specific Polyclonal Antibody and/or Monoclonal Antibody Using a Novel Hepatic Disease-State-Indicating Glycan Marker Candidate or a Fragment Thereof In the method of detecting hepatocarcinoma by use of a novel hepatic disease-state-indicating glycan marker, a hepatic disease-state-indicating glycan marker specific polyclonal antibody and/or monoclonal antibody can be used, if they are easily obtained. However, if they are not easily obtained, they can be prepared, for example, as follows.

7-1. Preparation of Antibody

The novel hepatic disease-state-indicating glycan marker of the present invention can be used for preparing a polyclonal antibody or monoclonal antibody for detecting a hepatic disease.

For example, an antibody against a fragment of a novel hepatic disease-state-indicating glycan marker candidate can be prepared by a method known in the art. Production of the antibody can be boosted by injecting complete Freund's adjuvant at the same time. Furthermore, a peptide containing a binding site at which a glycan of X is bonded is synthesized, allowed to covalently bond to a commercially available keyhole limpet hemocyanin (KLH) and injected to an animal. Note that if a granulocyte-macrophage colony stimulating factor (GM-CSF) is simultaneously injected herein, production of the antibody can be boosted.

Furthermore, for example, the anti-novel hepatic disease-state-indicating glycan marker candidate monoclonal antibody can be prepared by a method of Köhler and Milstein (Nature Vol. 256, pp 495-497 (1975)). More specifically, the antibody can be prepared by fusing an antibody-forming cell obtained from an animal immunized with an antigen with a myeloma cell to prepare a hybridoma and selecting a clone producing an anti-X antibody from the resultant hybridoma.

Specifically, an adjuvant is added to the obtained hepatic disease-state-indicating glycan marker candidate for an antigen. Examples of the adjuvant include complete Freund's adjuvant and incomplete Freund's adjuvant. These may be used as a mixture.

The antigen obtained as mentioned above is administered to a mammal such as a mouse, a rat, a horse, a monkey, a rabbit, a goat, a sheep. As an immunization method, any method can be employed as long as it is a conventional method; however, intravenous injection, subcutaneous injection, intraperitoneal injection, etc. are primarily employed. Furthermore, the interval between immunization operations is not particularly limited; however, immunization is performed at intervals of several days to several weeks and preferably intervals of 4 to 21 days.

Two to three days after the final immunization date, antibody-forming cells are collected. Examples of the antibody-forming cell include a spleen cell, a lymph node cell and a peripheral blood cell.

As the myeloma cell to be fused with an antibody-forming cell, established cell-lines derived from various animals such as a mouse, a rat and a human are used as long as one skilled in the art can generally obtains. Examples of the cell-line that can be used include a cell-line having a drug resistance and not surviving in a selective medium (for example, HAT medium) in an unfusion state and surviving there only in a fusion state. Generally, 8-azaguanine resistant line is used. This cell-line is defective in hypoxanthine-guanine-phosphoribosyl transferase and cannot grow in a hypoxanthine-aminopterin-thymidine (HAT) medium.

As the myeloma cell, various cell-lines known in the art are preferably used which include, for example, P3 (P3x63Ag8.653) (J. Immunol. 123, 1548-1550 1979)), P3x63Ag8U.1 (Current Topics in Microbiology and Immunology 81, 1-7 (1978)), NS-1 (Kohler, G. and Milstein, C., Eur. J. Immunol. 6, 511-519 (1976)), MPC-11 (Margulies, D. H. et al., Cell 8, 405-415 (1976)), SP2/0 (Shulman, M. et al., Nature 276, 269-270 (1978)), FO (de St. Groth, S. F. et al., J. Immunol. Methods 35, 1-21 (1980)), 5194 (Trowbridge, I. S., J. Exp. Med. 148, 313-323 (1978)) and 8210 (Galfre, G et al., Nature 277, 131-133 (1979)).

Next, the myeloma cell is fused with an antibody-forming cell. Cells are fused as follows. The myeloma cell and the antibody-forming cell are allowed to be in contact with each other in a mixing ratio of 1:1 to 1:10 in a medium for culturing an animal cell, such as MEM, DMEM and RPME-1640 medium, in the presence of a fusion promoter at 30 to 37° C. for 1 to 15 minutes. To accelerate cell fusion, a fusion promoter or a fusion virus such as a polyethylene glycol and polyvinyl alcohol having an average molecular weight of 1,000 to 6,000 or Sendai virus can be used. Furthermore, the antibody-forming cell can be fused with the myeloma cell by a commercially available cell fusion apparatus employing electrical stimulation (for example, electroporation).

After cell fusion treatment, a desired hybridoma is screened from fused cells. Examples of a screening method include a method of using a selective proliferation of cells in a selective medium. More specifically, a cell suspension solution is diluted with an appropriate medium and spread on a microtiter plate. A selective medium (HAT medium, etc.) is added to the wells and culturing is performed while replacing the selective medium with a fresh one, thereafter. The resultant growing cells can be obtained as hybridomas.

A hybridoma is screened by a limiting dilution method, fluorescence excitation cell sorter method, etc. Finally, a monoclonal antibody producing hybridoma is obtained. Examples of a method for collecting a monoclonal antibody from the obtained hybridoma include an ordinary cell culture method and an ascitic fluid forming method.

EXAMPLES

Example 1

Discovery of Glycopeptide Biomarker Candidates by Glycoproteomics (IGOT-LC/MS Method)
1. Method for Preparation of Culture Medium Supernatant (HepG2, HuH-7: -Lot. 071213)

HepG2 and Huh-7 cells were cultured in Dulbecco's modified Eagle's medium (D-MEM, containing D-glucose, 10% heat-inactivated fetal bovine serum (FBS), penicillin, streptomycin and ITS (Huh-7 only) using 14 cm dishes, and maintained at 37° C. in a humidity-controlled incubator with 5% CO2 for 3 days. The cells at 80-90% confluence were washed with the serum-free medium (10 ml/dish) (100% DMEM-high glucose, no additives) after removal of FBS-containing medium. A serum-free medium (30 ml/dish) was added and the cells were cultured for 48 hours (HepG2, HuH-7 cells will be destroyed if culturing is continued over 48 h in the serum-free medium). The media supernatant was recovered by centrifugation at 4500 g for 30 min and stored at −80° C.

The stored supernatant was thawed before use, filtrated by a 0.45 micrometer filter, and used in the following Examples. Note that NaN3 was added to the medium at final concentration of 0.1%.
2. Large-Scale Identification Method of Glycoprotein
  1) Preparation of Peptide Specimen Proteins of the serum samples (diluted and heat-denatured before use) and of cell culture media, were precipitated by adding trichloroacetic acid (TCA, 100% saturated aqueous solution) at a final concentration of 10%.

The mixture was cooled on ice for 10-60 minutes to precipitate proteins. The precipitate was recovered by high-speed centrifugation at 4° C. The precipitate was suspended with ice-cooled acetone and recovered by centrifugation to wash away TCA. The washing was repeated twice.

The precipitate was solubilized with a solubilization buffer solution (0.5 M tris-hydrochloric acid buffer, pH 8-8.5, containing 7M guanidine hydrochloride and 10 mM EDTA (ethylenediamine tetraacetate)) so that a protein concentration became about 5-10 mg/ml. The precipitate remained was removed by high-speed centrifugation. Nitrogen gas was supplied or sprayed to the protein extract to remove oxygen dissolved into the extract. Then, dithiothreitol (DTT, equal weight of protein) was added to the extract, as powder or solution in the solubilization buffer. With bubbling of nitrogen gas or under nitrogen atmosphere, disulfide bonds were reduced for 1-2 hours at room temperature. Next, iodoacetamide (2.5 weight of protein) was added to the extract and the reduced cysteine residues were alkylated for 1-2 hours at room temperature in the dark. The reaction mixture was dialyzed against a buffer solution, in general 50-100 volume of 10 mM ammonium bicarbonate, pH8.6, at 4° C. (in cold room). The external solution was exchanged three to five times at appropriate time intervals to remove the denaturing agent (guanidine hydrochloride) and excess reagents.

Although the protein partially precipitated, the suspension was directly subjected to protein quantification. Trypsin (sequence grade or more, 1/100-1/50 weight of protein) was added to digest proteins at 37° C. overnight (about 16 hours). The progression of digestion was confirmed by SDS-gel electrophoresis method. When digestion was confirmed to be sufficient, phenylmethane sulfonyl fluoride (PMSF) was added to terminate the reaction at a final concentration of 5 mM.
  2) Collection and Purification of Glycopeptides The digest (peptide mixture) was loaded in a column, in which a probe lectin was immobilized. After washing the column, glycopeptides were eluted with appropriate sugar solution dependent on the lectin specificity. To the eluate, equal volume of ethanol and 4 volumes of 1-butanol were added, then the peptide solution was loaded to Sepharose column equilibrated with a solvent, water:ethanol:1-butanol (1:1:4, v/v). After washing with the same solvent, glycopeptides were eluted with 50% ethanol (v/v). The glycopeptide fraction was transferred little by little to a microtube containing a small amount (2 microliter) of glycerol and evaporated by centrifugal vacuum concentrator to concentrate the glycopeptides and to remove solvent water.

3) Glycan Removal and Concomitant Stable Isotope Labeling (IGOT) of Glycosylation Site To the purified glycopeptides (in glycerol solution), a requisite amount of buffer solution was added. Solvent of the mixture was evaporated again by the same way, and then, water labeled with a stable isotope oxygen-18 ($H_2^{18}O$) was added to the glycerol solution (glycerol concentration was controlled to be 10% or less). Peptide-N-glycanase (glycopeptidase F, PNGase) prepared with the labeled water was added and the reaction was performed at 37° C. overnight.

4) LC/MS Shotgun Analysis of the Labeled Peptides

The reaction solution was diluted with 0.1% formic acid and subjected to LC/MS shotgun analysis. A nano flow LC system using direct nano-flow pump was used to detect peptides with high resolution, high reproducibility, and high sensitivity. Injected peptides were trapped once on a trap column (reverse phase C18 silica gel) for desalting. After washing, the peptide was separated by linear gradient of acetonitril using a frit-less spray tip column (150 micrometer inner diameter and 50 mm long) of the same resin. The eluate was ionized through an electrospray interface and directly introduced into a mass spectrometer. The peptides were analyzed by tandem mass spectrometry method (MS/MS) based on collision-induced dissociation (CID) in a data dependent mode in which maximum two intense ions were selected to be analyzed.

5) Identification of Peptide by MS/MS-Ion Search Method

Several thousands of MS/MS spectra obtained were individually treated by smoothing and changed to centroid spectra to make a peak list.

Based on the peak lists, each peptide was identified by MS/MS ion-search method using a protein sequence database. As a search engine, Mascot (Matrix Science) was used. Parameters for the identification were as follows: a fragmentation method: trypsin digestion, maximum number of missed cleavage: 2, fixed modification: carbamidomethylation of cysteine, variable modifications: deamination of an N-terminal glutamine, oxidation of methionine, 18O-incorporating deamidation of asparagine: glycosylation site, error tolerance of MS spectrum: 500 ppm, and error tolerance of MS/MS spectrum: 0.5 Da.

6) Identification of Glycopeptide

Database searching was carried out by the aforementioned conditions. The obtained results were subjected to the following identification confirmation process.

(1) Probability score (a coincidence probability: Expectation value) is 0.05 or less.

(2) The number of fragment ions contributing to identification is 4 or more.

(3) Error (ppm) is not significantly deviated from systematic error (mass error being 0.5 Da or less).

(4) The identified peptide has consensus sequences and has Asn modifications (conversion to Asp and 18O incorporation) equal to or smaller than the number of consensus sequences.

3. Selection of Marker Glycopeptide Candidates for Further Verification

1) Glycopeptides collected with a probe lectin from tryptic digests of sera of primary hepatocellular carcinoma patients who were infected by hepatitis virus, which sera were obtained before and after surgery, and digests of culture media of hepatoma cell lines, and then identified by IGOT-LC/MS method described above. The glycopeptides identified were dealt as primary candidates of glycopeptide marker for estimating the progression of liver disease. The number of detection of the candidate peptides with a probe lectin (AAL) from the samples listed in Table 5-C (medium; 2, sera; 10 (before and after surgery, 5 each) is for example represents a detection frequency with the probe.

2) Next, glycopeptides collected from sera of healthy volunteers with the same lectin were identified by the same way (Comprehensive list 2). For example, the number of detection of the peptides with the probe (AAL), which were listed in Table 5-B, represents a detection frequency with the probe lectin.

3) Furthermore, to collect glycopeptides comprehensively, peptide samples prepared from sera of healthy volunteers and patients of hepatocellular carcinoma were applied to RCA120 column after sialidase treatment, and the captured glycopeptides were identified by the same way (Comprehensive list 3). The number of detection of the peptides obtained with RCA120, for example in Table 5-F, represents the detection frequency for the lectin.

4) These glycopeptide lists were compared with each other and the glycopeptides were classified and selected the markers for further verification as follows.

(i) The initial glycopeptide list of the above section 1) was compared with those of comprehensive list 2. Among the proteins in the list 1, those not overlapped with those in list 2 were defined as marker glycopeptides. However, among overlapped glycopeptides, those which were not identified in sera of the patients (after surgery) and identified in the media and sera of the patients (before surgery), were ranked to lower rank of the marker glycopeptides (as Group 5). Glycopeptide markers including the group 5 were listed in Table 5, where the serial numbers of glycopeptides of the group 5 were marked with LR (lower ranking) at the tail end.

(ii) With respect to the peptides not overlapped, those only identified from the culture supernatant and the serum before surgery were separated and classified as, "marker glycopeptide for hepatocellular carcinoma", whereas those identified from before and after surgery were classified as "marker glycopeptide for liver fibrosis". Furthermore, these were compared with those of comprehensive list 3. The overlapped glycopeptides were ranked high as marker peptides present in a relatively higher concentration in the serum. More specifically, "marker glycopeptides for hepatocellular carcinoma" were classified into a first group and a third group based on the level (high and low) in the serum, respectively. "Marker glycopeptides for liver fibrosis" were also classified into a second group and a fourth group based on the level (high and low) in the serum.

As described above, the marker glycopeptides selected were not simply defined by only the amino acid sequence but also defined in combination with modification of the peptide moiety, particularly a glycosylation site clarified, and listed in Table 1 above.

TABLE 5

Hepatic disease-state indicating marker glycopeptide
Peptide sequence and modification information
The initial position of a sequence of numbers represents the terminal amino group and the end position there of represents the terminal carboxyl group. The numerals between them represent modification states of residue side-chains. "0" means not modified: "1" represents deamidation or cyclization of an N-terminal Gln: "2" represents oxidation of a Met side-chain: "3"
Pep- represents deamidation or cyclization of an N-tide terminal carbamidemethylated Cys: "4" represents a
No. glycosylation site (Asnlabel)

| SEQ. ID. NO. | Pep- tide No. | Heptic disease-state indicating marker glycopeptide Peptide sequence and modification information | A. The detection number with probe (AAL). (B + C = total 14) | B. The detection number with probe (AAL) from healthy serum (total 2) | C. The detection number with probe (AAL) related HCC specimen (medium 2 + serum 10) (total 12) | D. The detection number from HCC representative specimen (total 7) | E. The detection number from HCC specimen after surgery (total 5) | F. The detection number with RCA specimen (total 11) | G. The number of protein with RCA candidate derived serum derived (total 11) |
|---|---|---|---|---|---|---|---|---|---|
| | | First group: Hepatocarcinoma marker peptide (marker peptide present in a relative large amount in serum) | | | | | | | |
| 1 | 1 | FNSSYLQGTNQITGR/00400000000000000 | 2 | 0 | 2 | 2 | 0 | 11 | 1 |
| 2 | 2 | VSNVSCQASVSR/000400000000 | 2 | 0 | 2 | 2 | 0 | 10 | 1 |
| 3 | 3 | GTAGNALMDGASQLMGENR/0000000000000000400 | 2 | 0 | 2 | 2 | 0 | 7 | 1 |
| 4 | 4 | HEEGHMLNCTCFGQGR/0000000204000000000 | 2 | 0 | 2 | 2 | 0 | 3 | 7 |
| 5 | 5 | RHEEGHMLNCTCFGQGR/00000000004000000000 | 2 | 0 | 2 | 2 | 0 | 3 | 7 |
| 6 | 6 | VNFTEIQK/0040000000 | 2 | 0 | 2 | 2 | 0 | 2 | 1 |
| 7 | 7 | LYLGSNNLTALHPALFQNLSK/000000040000000000000000 | 2 | 0 | 2 | 2 | 0 | 1 | 2 |
| 8 | 8 | GLNVTLSSTGR/00040000000 | 1 | 0 | 1 | 1 | 0 | 11 | 2 |
| 9 | 9 | MDGASNVTCINSR/0200004000000000 | 1 | 0 | 1 | 1 | 0 | 11 | 1 |
| 10 | 10 | HEEGHMLNCTCFGQGR/000000000400000000 | 1 | 0 | 1 | 1 | 0 | 7 | 7 |
| 11 | 11 | QVFPGLNYCTSGAYSNASSTDSASYYPLTGDTR/0000000000000004000000000000000000 | 1 | 0 | 1 | 1 | 0 | 3 | 1 |

TABLE 5-continued

| SEQ. ID. NO.: | Pep- tide No. | Hepatic disease-state indicating marker glycopeptide Peptide sequence and modification information The initial position of a sequence of numbers represents the terminal amino group and the end position there of represents the terminal carboxyl group. The numerals between them represent modification states of residue side-chains. "0" means not modified: "1" represents deamidation or cyclization of an N-terminal Gln: "2" represents oxidation of a Met side-chain: "3" represents deamidation or cyclization of an N-terminal Gln: "4" represents a tide terminal carbamidemethylated Cys: "4" represents a No. glycosylation site (Asnlabel) | A. The de- tec- tion num- ber with probe (AAL). (B + C = total total 14) | B. The de- tec- tion num- ber with probe (AAL) from heal- thy serum (total 2) | C. The de- tec- tion num- ber with probe (AAL) from medium 2 + serum (total 12) | D. The detec- tion number from HCC relat- ed spec- imen (total 7) | E. The detec- tion number from HCC spec- imen after sur- gery (fibro- sis spec- imen) (total 5) | F. The de- tec- tion num- ber with RCA from serum (total 11) | G. The num- ber of pro- tein can- di- date de- rived |
|---|---|---|---|---|---|---|---|---|
| 12 | 12 | DQCIVDDITYNVNDTFHK/00000000000004000000 | 3 | 0 | 3 | 3 | 0 | 5 | 7 |
| 13 | 13 | GAFISNFSMTVDGK/00000004000000000 | 1 | 0 | 1 | 1 | 0 | 11 | 1 |
| 14 | 14 | GAFISNFSMTVDGK/00000004002000000 | 1 | 0 | 1 | 1 | 0 | 11 | 1 |
| 15 | 15 | GFGVAIVGNYTAALPTEAALR/000000000040000000000000 | 1 | 0 | 1 | 1 | 0 | 11 | 1 |
| 16 | 16 | LGACNDTLQQLMEVFKFDTISEK/00000400000020000000000 | 1 | 0 | 1 | 1 | 0 | 9 | 1 |
| 17 | 17 | LKELPGVCNETMMALWEECKPCLK/000000000040000000000000 | 1 | 0 | 1 | 1 | 0 | 9 | 2 |
| 18 | 18 | QLVEIEKVVLHPNYSQVDIGLIK/0000000000004000000000 | 1 | 0 | 1 | 1 | 0 | 9 | 1 |
| 19 | 19 | TLFCNASKEWDNTTTECR/0000400000040000000 | 1 | 0 | 1 | 1 | 0 | 7 | 5 |
| 20 | 20 | IIVPLNNRENISDPTSPLR/000000204000000000 | 1 | 0 | 1 | 1 | 0 | 6 | 1 |
| 21 | 21 | MEACMLNGTVIGPGK/00000020400000000 | 1 | 0 | 1 | 1 | 0 | 5 | 1 |
| 22 | 22 | CGNCSLTTLKDEDFCK/0004000000000000 | 1 | 0 | 1 | 1 | 0 | 4 | 3 |
| 23 | 23 | ITYSIVQTNCSKENFLFLTPDCK/00000000004000000000000 | 1 | 0 | 1 | 1 | 0 | 3 | 1 |
| 24 | 24 | AVLVNNITTGER/000000400000 | 1 | 0 | 1 | 1 | 0 | 2 | 2 |
| 25 | 25 | AREDIFMETLKDIVEYYNDSNGSHVLQGR/ 000000200000000000004000000000 | 1 | 0 | 1 | 1 | 0 | 1 | 1 |

TABLE 5-continued

| SEQ. ID. NO.: | Pep-tide No. | Hepatic disease-state indicating marker glycopeptide / Peptide sequence and modification information (The initial position of a sequence of numbers represents the terminal amino group and the end position there of represents the terminal carboxyl group. The numerals between them represent modification states of residue side-chains. "0" means not modified; "1" represents deamidation or cyclization of an N-terminal Gln; "2" represents oxidation of a Met side-chain; "3" represents deamidation or cyclization of an N-tide terminal carbamidemethylated Cys; "4" represents a glycosylation site (Asnlabel)) | A. The detection number with probe (AAL). (B + C = total 14) | B. The detection number with probe (AAL) from healthy serum (total 2) | C. The detection number with probe (AAL) from HCC related specimen (total 12) | D. The detection number from HCC representative specimen (total 7) | E. The detection number from HCC specimen after surgery (fibrosis specimen) (total 5) | F. The detection number with RCA from serum date (total 11) | G. The number of protein candidate derived |
|---|---|---|---|---|---|---|---|---|---|
| 26 | 26 | FQSPAGTEALFELHNISVADSANYSCVYYDLKPPFGGSAPSER/ 00000000000000004000000000000000000000000 | 1 | 0 | 1 | 1 | 0 | 1 | 1 |
| 27 | 27 | QNQCFYNSSYLNVQR/100000040000000 | 1 | 0 | 1 | 1 | 0 | 1 | 1 |
| 28 | 28 | SLEAINGSGLQMGLQR/0000000400000200000 | 1 | 0 | 1 | 1 | 0 | 1 | 1 |
|  |  | Second group: Hepatic cellfibrosis marker peptide (marker peptide presentin a relative large amount in serum) |  |  |  |  |  |  |  |
| 29 | 29 | AHLNVSGIPCSVLLADVEDLIQNISNDTVSPR/ 00004000000000000000000000000040000000 | 4 | 0 | 4 | 3 | 1 | 2 | 2 |
| 30 | 30 | FTKVNFTEIQK/00004000000 | 4 | 0 | 4 | 3 | 1 | 1 | 1 |
| 31 | 31 | RHEEGHMLNCTCFGQGR/000000020400000000000 | 3 | 0 | 3 | 2 | 1 | 3 | 7 |
| 32 | 32 | DIVEYYNDSNGSHVLQGR/00000004040000000000 | 5 | 0 | 5 | 4 | 1 | 1 | 1 |
| 33 | 33 | TLYETEVFSTDFSNISAAK/000000000000004000000 | 10 | 0 | 10 | 5 | 5 | 6 | 1 |
| 34 | 34 | QDQCIYNTTYLNVQR/100000040000000 | 9 | 0 | 9 | 4 | 5 | 3 | 1 |
| 35 | 35 | QDQCIYNTTYLNVQRENGTISR/10000040000000000040000 | 8 | 0 | 8 | 5 | 3 | 1 | 1 |
| 36 | 36 | FLNDTMAVYEAK/000402000000 | 7 | 0 | 7 | 3 | 4 | 8 | 1 |
| 37 | 37 | TLNQSDELQLSMGNAMFVK/0004000000002000200000 | 6 | 0 | 6 | 2 | 4 | 6 | 1 |

TABLE 5-continued

| SEQ. ID. NO.: | Pep- tide No. | Hepatic disease-state indicating marker glycopeptide Peptide sequence and modification information The initial position of a sequence of numbers represents the terminal amino group and the end position there of represents the terminal carboxyl group. The numerals between them represent modification states of residue side-chains. "0" means not modified: "1" represents deamidation or cyclization of an N-terminal Gln: "2" represents oxidation of a Met side-chain: "3" Pep- represents deamidation or cyclization of an N-tide terminal carbamidemethylated Cys: "4" represents a No. glycosylation site (Asnlabel) | A. The detection number with probe (AAL) (B + C = total 14) | B. The detection number with probe (AAL) from healthy serum (total 2) | C. The detection number with probe (AAL) from HCC related specimen (total 12) | D. The detection number from HCC representative specimen (total 7) | E. The detection number from HCC specimen after surgery (fibrosis specimen) (total 5) | F. The detection number with RCA from serum specimen (total 11) | G. The number of protein candidate derived |
|---|---|---|---|---|---|---|---|---|---|
| 38 | 38 | FEVDSPVYNATWSASLK/00000000400000000 | 5 | 0 | 5 | 3 | 2 | 10 | 1 |
| 39 | 39 | SPYYNVSDEISFHCYDGYTLR/000004000000000000000000 | 5 | 0 | 5 | 3 | 2 | 8 | 1 |
| 40 | 40 | LGACNDTLQQLMEVFKFDTISEK/00000400000000000000000000 | 5 | 0 | 5 | 2 | 3 | 11 | 1 |
| 41 | 41 | YTGNASALFILPDQDKMEEVEAMLLPETLKR/0000400000000000000000000000000 | 5 | 0 | 5 | 2 | 3 | 5 | 1 |
| 42 | 42 | VLTLNLDQVDFQHAGNYSCVASNVQGK/000000004000000000000000 | 5 | 0 | 5 | 2 | 3 | 1 | 1 |
| 43 | 43 | ELPGVCNETMMALWEECKPCLK/00000040020000000000 | 4 | 0 | 4 | 3 | 1 | 2 | 2 |
| 44 | 44 | TLNQSSDELQLSMGNAMFVK/000400000000020000 | 4 | 0 | 4 | 2 | 2 | 8 | 1 |
| 45 | 45 | CGLVPVLAENYNKSDNCEDTPEAGYFAVAVVKK/00000000004000000000000000000000 | 4 | 0 | 4 | 2 | 2 | 3 | 1 |
| 46 | 46 | YMNASALFILPDQQKMEEVEAMLLPETLKR/000040000000002000000000000 | 4 | 0 | 4 | 1 | 3 | 4 | 1 |
| 47 | 47 | NISDGFDGIPDNVDAALALPAHSYSGR/040000000000000000000000000 | 4 | 0 | 4 | 1 | 3 | 1 | 1 |
| 48 | 48 | HGIQYFNNNTQHSSLFMLNEVKR/00000040000000020000000 | 4 | 0 | 4 | 1 | 3 | 1 | 1 |
| 49 | 49 | SHEIWTHSCPQSPGNGTDASH/000000000000040000000 | 3 | 0 | 3 | 2 | 1 | 10 | 1 |

TABLE 5-continued

| SEQ. ID. NO.: | Pep- tide No. | Hepatic disease-state indicating marker glycopeptide Peptide sequence and modification information The initial position of a sequence of numbers represents the terminal amino group and the end position there of represents the terminal carboxyl group. The numerals between them represent modification states of residue side-chains. "0" means not modified; "1" represents deamidation or cyclization of an N-terminal Gln: "2" represents oxidation of a Met side-chain: "3" represents deamidation or cyclization of an N-terminal Gln: "4" represents terminal carbamidemethylated Cys: "/" represents a glycosylation site (Asnlabel) | A. The detection number with probe (AAL). (B+C= total 14) | B. The detection number with probe (AAL) from healthy serum (total 2) | C. The detection number with probe (AAL) from HCC related specimen (total 12) | D. The detection number from HCC representative specimen (total 7) | E. The detection number from HCC specimen after surgery (fibrosis specimen) (total 5) | F. The detection number with RCA from serum specimen (total 11) | G. The number of protein candidate derived |
|---|---|---|---|---|---|---|---|---|---|
| 50 | 50 | NPPMGGNVVIFDTVITNQEEPYQNHSGR/ 00002000000000000000400000 | 3 | 0 | 3 | 2 | 1 | 1 | 1 |
| 51 | 51 | QIGLYPVLVIDSSGYVNPNYTGR/ 00000000000000000200000000 | 3 | 0 | 3 | 1 | 2 | 10 | 1 |
| 52 | 52 | TLNQSSDELQLSMGNAMFVK/ 00040000000000200000000 | 3 | 0 | 3 | 1 | 2 | 9 | 1 |
| 53 | 53 | LSVDKDQYVEPENVTIQCDSGYGVVGPQSITCSGNR/ 000000000004000000000000000000000400 | 3 | 0 | 3 | 1 | 2 | 2 | 1 |
| 54 | 54 | CGLVPVLAENYNKSDNCEDTPEAGYFAVAVVK/ 00000000004000000000000000000000 | 3 | 0 | 3 | 1 | 2 | 1 | 1 |
| 55 | 55 | GLKFNLTETSEAEIHQSFQHLLR/ 00000400000000000000000 | 3 | 0 | 3 | 1 | 2 | 1 | 1 |
| 56 | 56 | SLGNVNFTVSAEALESQELCGTEVPSVPEHGRK/ 0000004000000000000000000000000 | 3 | 0 | 3 | 1 | 2 | 1 | 1 |
| 57 | 57 | DIVEYYNDSNGSHVLQGR/ 000000040000000000 | 3 | 0 | 3 | 1 | 2 | 1 | 1 |
| 58 | 58 | EHEAQSNASLDVFLGHTNVEELMK/ 00000004000000000000040000 | 3 | 0 | 3 | 1 | 1 | 1 | 1 |
| 59 | 59 | DVQIIVFPEDGIHGFNFTR/ 0000000000000000040000 | 2 | 0 | 2 | 1 | 1 | 8 | 1 |
| 60 | 60 | WNNTGCQALPSQDEGPSK/ 040000000000000000 | 2 | 0 | 2 | 1 | 1 | 7 | 1 |
| 61 | 61 | MEACMLNGTVIGPGK/ 020002040000000 | 2 | 0 | 2 | 1 | 1 | 2 | 1 |
| 62 | 62 | HGIQYFNNNTQHSSLFMLNEVK/ 00000004000000000000000 | 2 | 0 | 2 | 1 | 1 | 1 | 1 |

TABLE 5-continued

Hepatic disease-state indicating marker glycopeptide

Peptide sequence and modification information
The initial position of a sequence of numbers represents the terminal amino group and the end position there of represents the terminal carboxyl group. The numerals between them represent modification states of residue side-chains. "0" means not modified: "1" represents deamidation or cyclization of an N-terminal Gln: "2" represents oxidation of a Met side-chain: "3" Pep- represents deamidation or cyclization of an N-tide terminal carbamidemethylated Cys: "4" represents a No. glycosylation site (Asnlabel)

| SEQ. ID. NO.: | Pep-tide No. | Peptide sequence and modification information | A. The detection number with probe (AAL). (B + C = total 14) | B. The detection number with probe (AAL) from healthy serum (total 2) | C. The detection number with probe (AAL) from medium 2 + serum (total 10) | D. The detection number from HCC representative specimen (total 7) | E. The detection number from HCC specimen after surgery (fibrosis specimen) (total 5) | F. The detection number with RCA from serum (total 11) | G. The number of protein candidate derived |
|---|---|---|---|---|---|---|---|---|---|
| 63 | 63 | SVQEIQATFFYFTPNKTEDTIFLR/0000000000000400000000000 | 2 | | 2 | 1 | 1 | 1 | 2 |

Third group: Hepatocarcinoma marker peptide (marker peptide presentin a relative lower amount in serum)

| 64 | 64 | DLQSLEDILHQVENK/000000000000400 | 2 | 0 | 2 | 2 | 0 | 0 | 2 |
| 65 | 65 | FLNDSIVDPVDSEWFGFYR/00040000000000000000 | 2 | 0 | 2 | 2 | 0 | 0 | 1 |
| 66 | 66 | FLSSSPHLPSSYFNASGR/0000000000000400000 | 2 | 0 | 2 | 2 | 0 | 0 | 1 |
| 67 | 67 | GGNSNGALCHPFFLYNNHNYTDCTSEGR/000000000000040000000000000 | 2 | 0 | 2 | 2 | 0 | 0 | 7 |
| 68 | 68 | GLLHLENASYGIEPLQNSSHFEHIIYR/0000000040000000000000000 | 2 | 0 | 2 | 2 | 0 | 0 | 2 |
| 69 | 69 | NELVQLYQVGEVRPFYYGLCTPCQAPTNYSR/00000000000000000000000000000400 | 2 | 0 | 2 | 2 | 0 | 0 | 1 |
| 70 | 70 | NMTFDLPSDATVVLNR/04000000000000400 | 2 | 0 | 2 | 2 | 0 | 0 | 1 |
| 71 | 71 | NMTFDLPSDATVVLNR/04200000000000000 | 2 | 0 | 2 | 2 | 0 | 0 | 1 |
| 72 | 72 | TNINSSRDPDNIAAWYLR/00004000000000000 | 2 | 0 | 2 | 2 | 0 | 0 | 1 |
| 73 | 73 | TNSTFVQALVEHVK/00400000000000 | 2 | 0 | 2 | 2 | 0 | 0 | 3 |

TABLE 5-continued

Hepatic disease-state indicating marker glycopeptide

Peptide sequence and modification information

The initial position of a sequence of numbers represents the terminal amino group and the end position there of represents the terminal carboxyl group. The numerals between them represent modification states of residue side-chains. "0" means not modified; "1" represents deamidation or cyclization of an N-terminal Gln; "2" represents oxidation of a Met side-chain; "3" Pep- represents deamidation or cyclization of an N-tide terminal carbamidemethylated Cys; "4" represents a No. glycosylation site (Asnlabel)

| SEQ. ID. NO.: | Pep- tide No. | Peptide sequence and modification information | A. The detection number with probe (AAL). (B + C = total 14) | B. The detection number with probe (AAL) from healthy serum (total 2) | C. The detection number with probe (AAL) from serum (total 12) | D. The detection number from HCC representative specimen (total 7) | E. The detection number from HCC specimen after surgery (fibrosis specimen) (total 5) | F. The detection number with RCA from serum (total 11) | G. The number of protein candidate derived |
|---|---|---|---|---|---|---|---|---|---|
| 74 | 74 | VAAANVSVTQPESTGDPNNMTLLAEEAR/ 00000400000000000400000000000 | 2 | 0 | 2 | 2 | 0 | 0 | 1 |
| 75 | 75 | VAAANVSVTQPESTGDPNNMTLLAEEARK/ 000004000000000000400000000000 | 2 | 0 | 2 | 2 | 0 | 0 | 1 |
| 76 | 76 | VAQPGINYALGTNVSYPNNLLR/ 000000000000000000040000000000 | 2 | 0 | 2 | 2 | 0 | 0 | 1 |
| 77 | 77 | VLNASTLALALANLNGSR/ 00040000000000000040 | 2 | 0 | 2 | 2 | 0 | 0 | 1 |
| 78 | 78 | QNQCFYNSSYLNVQRENGTVSR/ 000000000000400000000000000000 | 3 | 0 | 3 | 3 | 0 | 0 | 1 |
| 79 | 79 | EHEGAIYPDUTDFQPRADDK/ 00000000000400000000000 | 1 | 0 | 1 | 1 | 0 | 0 | 1 |
| 80 | 80 | ENGTDTVQEEEESPAEGSK/ 0040000000000000000 | 1 | 0 | 1 | 1 | 0 | 0 | 5 |
| 81 | 81 | GENFTETDVK/0004000000000 | 1 | 0 | 1 | 1 | 0 | 0 | 1 |
| 82 | 82 | GIGNYSCSYR/000040000000 | 1 | 0 | 1 | 1 | 0 | 0 | 1 |
| 83 | 83 | GNETVNLIHSTR/004000000000 | 1 | 0 | 1 | 1 | 0 | 0 | 1 |
| 84 | 84 | ILLTCSLNDSATEVTGHR/000000000040000000000 | 1 | 0 | 1 | 1 | 0 | 0 | 2 |
| 85 | 85 | LDVDQALNRSHEIWTHSCPQSPGNGTDASH/ 00000004000000000000004000000000 | 1 | 0 | 1 | 1 | 0 | 0 | 1 |
| 86 | 86 | NCQDIDECVTGIHNCSINETCFNIQGGFR/ 0000000000004000400000000000 | 1 | 0 | 1 | 1 | 0 | 0 | 4 |

TABLE 5-continued

Hepatic disease-state indicating marker glycopeptide

Peptide sequence and modification information
The initial position of a sequence of numbers represents the terminal amino group and the end position there of represents the terminal carboxyl group. The numerals between them represent modification states of residue side-chains. "0" means not modified: "1" represents deamidation or cyclization of an N-terminal Gln: "2" represents oxidation of a Met side-chain: "3" represents deamidation or cyclization of an N-tide terminal carbamidemethylated Cys: "4" represents a Pep- No. glycosylation site (Asn1abel)

| SEQ. ID. NO.: | Pep. No. | Peptide sequence and modification information | A. The detection number with probe (AAL). (B + C = total 14) | B. The detection number with probe (AAL) from healthy serum (total 2) | C. The detection number with probe (AAL) from HCC related specimen (medium 2 + serum 10) (total 12) | D. The detection number from HCC representative specimen (total 7) | E. The detection number from HCC specimen after surgery (fibrosis specimen) (total 5) | F. The detection number with RCA from serum (total 11) | G. The number of protein candidate derived |
|---|---|---|---|---|---|---|---|---|---|
| 87 | 87 | NRTPMGHMK/04000200000 | 1 | 0 | 1 | 1 | 0 | 0 | 1 |
| 88 | 88 | QYNSTGDYR/00040000000 | 1 | 0 | 1 | 1 | 0 | 0 | 1 |
| 89 | 89 | SHTNTSHVMQYGNK/00040000200400 | 1 | 0 | 1 | 1 | 0 | 0 | 2 |
| 90 | 90 | SLSCQMAALQGNGSER/0000000000400000 | 1 | 0 | 1 | 1 | 0 | 0 | 1 |
| 91 | 91 | SLSCQMAALQGNGSER/0000020000400000 | 1 | 0 | 1 | 1 | 0 | 0 | 1 |
| 92 | 92 | TYNGTNPDAASR/004000000000 | 1 | 0 | 1 | 1 | 0 | 0 | 2 |
| 93 | 93 | VAAANVSVTQPESTGDPNNMTLLAEEAR/0000400000000000420000000000 | 1 | 0 | 1 | 1 | 0 | 0 | 1 |
| 94 | 94 | VCEIHEDNSTR/00000000040000 | 1 | 0 | 1 | 1 | 0 | 0 | 1 |
| 95 | 95 | VVDDVSNQTSCR/000000004000000 | 1 | 0 | 1 | 1 | 0 | 0 | 1 |
| 96 | 96 | HTGNVVITNCSAAHSR/00000000400000 | 1 | 0 | 1 | 1 | 0 | 0 | 2 |
| 97 | 97 | INLAGDVAALNSGLATEAFSAYGNK/00000000000000000400 | 1 | 0 | 1 | 1 | 0 | 0 | 1 |
| 98 | 98 | OOOHLFGSNVTDCSGNFCLFR/100000000400000000000000 | 1 | 0 | 1 | 1 | 0 | 0 | 1 |
| 99 | 99 | QVFPGLNYCTSGAYSNASSTDSASYYPLTGDTR/1000000000000004000000000000000 | 1 | 0 | 1 | 1 | 0 | 0 | 1 |

TABLE 5-continued

Hepatic disease-state indicating marker glycopeptide

Peptide sequence and modification information

The initial position of a sequence of numbers represents the terminal amino group and the end position there of represents the terminal carboxyl group. The numerals between them represent modification states of residue side-chains. "0" means not modified; "1" represents deamidation or cyclization of an N-terminal Gln: "2" represents oxidation of a Met side-chain: "3" represents deamidation or cyclization of an N-tide terminal carbamidemethylated Cys: "4" represents a glycosylation site (Asnlabel)

| SEQ. ID. NO. | Pep- tide No. | Sequence | A. The de- tec- tion num- ber with probe (AAL). (B + C = total (total 14) | B. The de- tec- tion num- ber with probe (AAL) from heal- thy serum spec- imen (total 2) | C. The de- tec- tion num- ber with probe (AAL) from HCC relat- ed spec- imen (me- dium 2 + serum (total 12) | D. The detec- tion number from HCC repre- sent- ative spec- imen (total 7) | E. The detec- tion number from HCC spec- imen after sur- gery (fibro- sis spec- imen) (total 5) | F. The de- tec- tion num- ber with RCA from serum (total 11) | G. The num- ber of pro- tein can- di- date de- rived |
|---|---|---|---|---|---|---|---|---|---|
| 100 | 100 | SAEFNYTVR/000000400000000 | 1 | 0 | 1 | 1 | 0 | 0 | 1 |
| 101 | 101 | SDLNPANGSYPFKALR/000000400000000000 | 1 | 0 | 1 | 1 | 0 | 0 | 1 |
| 102 | 102 | TVSCQVQNGSETVVQR/000000004000000000000 | 1 | 0 | 1 | 1 | 0 | 0 | 1 |
| 103 | 103 | VISVDELNDTIAANLSDTEFYGAK/000000000400000000000000 | 1 | 0 | 1 | 1 | 0 | 0 | 2 |
| 104 | 104 | VYSLPGRENYSSVDANGIQSQMLSR/0000000040000000000020000 | 1 | 0 | 1 | 1 | 0 | 0 | 1 |
| 105 | 105 | YRGTAGNALMDGASQLMGENR/000000000000000200400 | 1 | 0 | 1 | 1 | 0 | 0 | 1 |
| 106 | 106 | YSSNHTEHSQNLR/000040000000000 | 1 | 0 | 1 | 1 | 0 | 0 | 1 |
| 107 | 107 | YYNYTLSINGK/0004000000000 | 1 | 0 | 1 | 1 | 0 | 0 | 1 |
| 108 | 108 | SLTFNETYQDISELVYGAK/00000400000000000000 | 2 | 0 | 2 | 2 | 0 | 0 | 1 |
| 109 | 109 | AFENVTDLQWLILDHNLLENSK/0000400000000000000000 | 1 | 0 | 1 | 1 | 0 | 0 | 1 |
| 110 | 110 | CRNLSGQTDK/0004000000000 | 1 | 0 | 1 | 1 | 0 | 0 | 1 |
| 111 | 111 | DFTLNETVNSIFAQGAPR/0000040000000000000 | 1 | 0 | 1 | 1 | 0 | 0 | 2 |
| 112 | 112 | DNYTDLVAIQNK/040000000000 | 1 | 0 | 1 | 1 | 0 | 0 | 1 |

TABLE 5-continued

Hepatic disease-state indicating marker glycopeptide Peptide sequence and modification information The initial position of a sequence of numbers represents the terminal amino group and the end position there of represents the terminal carboxyl group. The numerals between them represent modification states of residue side-chains. "0" means not modified: "1" represents deamidation or cyclization of an N-terminal Gln: "2" represents oxidation of a Met side-chain: "3" represents deamidation or cyclization of an N-tide terminal carbamidemethylated Cys: "4" represents a No. glycosylation site (Asnlabel)

| SEQ. ID NO.: | Pep-tide No. | Sequence | A. The detection number with probe (AAL) (B+C = total 14) | B. The detection number with probe (AAL) from healthy serum (total 2) | C. The detection number with probe (AAL) from medium 2+ serum (total 10) | D. The detection number from HCC related specimen (total 7) | E. The detection number from HCC specimen after surgery (fibrosis specimen) (total 5) | F. The detection number with RCA from serum candidate (total 11) | G. The number of protein candidate derived |
|---|---|---|---|---|---|---|---|---|---|
| 113 | 113 | ELHHLQEQNVSNAPLDKGEFYIGSKYK/ 0000000040000000000000000 | 1 | 0 | 1 | 1 | 0 | 0 | 1 |
| 114 | 114 | EPGSNVTMSVDAECVPMVR/ 0000002040000000000000 | 1 | 0 | 1 | 1 | 0 | 0 | 1 |
| 115 | 115 | FLNDVKTLYETEVESTDFSNISAAK/ 000000000000000040000000 | 1 | 0 | 1 | 1 | 0 | 0 | 1 |
| 116 | 116 | FSLLGHASISCTVENETIGVWRPSPPTCEK/ 000000000000004000000000000000 | 1 | 0 | 1 | 1 | 0 | 0 | 1 |
| 117 | 117 | GNEANYYSNATTDEHGLVQFSINTTNVMGTSLTVR/ 0000000040000000000000002000000000 | 1 | 0 | 1 | 1 | 0 | 0 | 1 |
| 118 | 118 | GNESALWDCKHDGWGK/ 0403000000000000 | 1 | 0 | 1 | 1 | 0 | 0 | 2 |
| 119 | 119 | GNETLHYETPGK/ 040000000000 | 1 | 0 | 1 | 1 | 0 | 0 | 1 |
| 120 | 120 | HLQMDIHIFEPQGISFLETESTFMTNQLVDALTTWQNK/ 0000200000000000000000002000000000000400 | 1 | 0 | 1 | 1 | 0 | 0 | 1 |
| 121 | 121 | HNNDTQHIWESDSNEFSVIADPR/ 00040000000000000000000 | 0 | 1 | 1 | 1 | 0 | 1 | 1 |
| 122 | 122 | HYYIAAEEIIWNYAPSGIDIFTKENLTAPGSDSAVFFEQGTTR/ 000000000000000000000040000000000000000000 | 1 | 0 | 1 | 0 | 0 | 1 | 1 |
| 123 | 123 | IDGSGNFQVLLSDRYFNK/ 000000000000000400 | 1 | 0 | 1 | 1 | 0 | 0 | 1 |
| 124 | 124 | ISNSDTVECSENMK/ 00040000000000000 | 1 | 0 | 1 | 1 | 0 | 0 | 2 |

TABLE 5-continued

Hepatic disease-state indicating marker glycopeptide

Peptide sequence and modification information
The initial position of a sequence of numbers represents the terminal amino group and the end position there of represents the terminal carboxyl group. The numerals between them represent modification states of residue side-chains. "0" means not modified; "1" represents deamidation or cyclization of an N-terminal Gln; "2" represents oxidation of a Met side-chain; "3" represents deamidation or cyclization of an N-tide terminal carbamidemethylated Cys; "4" represents a No. glycosylation site (Asnlabel)

| SEQ. ID. NO.: | Pep- tide No. | Peptide sequence | A. The detection number with probe (AAL). B + C = total (total 14) | B. The detection number with probe (AAL) from healthy serum (total 2) | C. The detection number with probe (AAL) from medium 2 + serum (total 10) | D. The detection number from HCC related specimen representative specimen (total 7) | E. The detection number from HCC specimen after surgery (fibrosis specimen) (total 5) | F. The detection number with RCA from serum (total 11) | G. The number of protein candidate derived |
|---|---|---|---|---|---|---|---|---|---|
| 125 | 125 | KAENSSNEEETSSEGNMR/000040000000000000 | 1 | 0 | 1 | 1 | 0 | 0 | 1 |
| 126 | 126 | KTTCNPCPLGYKEENNTGECCGR/00000000000004000000000000 | 1 | 0 | 1 | 1 | 0 | 0 | 1 |
| 127 | 127 | LDAPTNLQFVNETDSTVLVR/000000000000040000000000 | 1 | 0 | 1 | 1 | 0 | 0 | 1 |
| 128 | 128 | LEPEGPAPHMLGLVAGWGISNPNVTVDEIISSGTR/00000000002000000000040000000000000000 | 1 | 0 | 1 | 1 | 0 | 0 | 1 |
| 129 | 129 | LNAENNATFYFKIDNVKJ0000004000000000000 | 1 | 0 | 1 | 1 | 0 | 0 | 1 |
| 130 | 130 | LQQDVLQFQKNQTNLER/00000000000040000000000 | 1 | 0 | 1 | 1 | 0 | 0 | 2 |
| 131 | 131 | LSHNELADSGIPGNSFNVSSLVELDLSYNK/000000000000000040000000000000 | 1 | 0 | 1 | 1 | 0 | 0 | 1 |
| 132 | 132 | LSNISHLNYCEPDLR/000400000000000 | 1 | 0 | 1 | 1 | 0 | 0 | 1 |
| 133 | 133 | LTDTICGVGNMSANASDQER/000000000000040040000000 | 1 | 0 | 1 | 1 | 0 | 0 | 1 |
| 134 | 134 | REGDHEFLEVPEAQEDVEATFPVHQPGNYSCSYR/000000000000000000000000040000000 | 1 | 0 | 1 | 1 | 0 | 0 | 1 |
| 135 | 135 | SGPKNMTFDLPSDATVVLNR/000040000000000000400 | 1 | 0 | 1 | 1 | 0 | 0 | 1 |
| 136 | 136 | TYNVLDMKNTTCQDLQIEVTVK/000000002040000000000000 | 1 | 0 | 1 | 1 | 0 | 0 | 2 |
| 137 | 137 | VASVININPNTTHSTGSCR/0000000000004000000000 | 1 | 0 | 1 | 1 | 0 | 0 | 2 |

TABLE 5-continued

Hepatic disease-state indicating marker glycopeptide

Peptide sequence and modification information
The initial position of a sequence of numbers represents the terminal amino group and the end position there of represents the terminal carboxyl group. The numerals between them represent modification states of residue side-chains. "0" means not modified: "1" represents deamidation or cyclization of an N-terminal Gln: "2" represents oxidation of a Met side-chain: "3" represents deamidation or cyclization of an N-tide terminal carbamidemethylated Cys: "4" represents a glycosylation site (Asnlabel)

| SEQ. ID. NO.: | Pep-tide No. | Sequence | A. The detection number with probe (AAL). (B+C = total 14) | B. The detection number with probe (AAL) from healthy serum (total 2) | C. The detection number with probe (AAL) from HCC related specimen (total 12) | D. The detection number from HCC representative specimen (total 7) | E. The detection number from HCC specimen after surgery (fibrosis specimen) (total 5) | F. The detection number with RCA from serum (total 11) | G. The number of protein candidate derived |
|---|---|---|---|---|---|---|---|---|---|
| 138 | 138 | VTVQSLLITVETLEHNQTYECR/00000000000000040000000 | 1 | 0 | 1 | 1 | 0 | 0 | 1 |
| 139 | 139 | WVNYSCLDQAR/00040000000000 | 1 | 0 | 1 | 1 | 0 | 0 | 3 |
| 140 | 140 | YKVDYESQSTDTQNFSSESKR/00000000000000040000000 | 1 | 0 | 1 | 1 | 0 | 0 | 2 |

Fourth group: Hepatic cellfibrosis marker peptide (marker peptide present in a relative lower amount in serum)

| 141 | 141 | GCVLLSYLNETVTVSASLESVR/00000000000040000000000000 | 6 | 0 | 6 | 4 | 2 | 0 | 1 |
| 142 | 142 | ALVLEQLTPALHSTNFSCVLVDPEQVVQR/000000000000000004000000000000 | 4 | 0 | 4 | 2 | 2 | 0 | 3 |
| 143 | 143 | WFYIASAFRNEEYNK/000000000000400 | 4 | 0 | 4 | 2 | 2 | 0 | 2 |
| 144 | 144 | SEGTNSTLTLSPVSFENEHSYLCTVTCGHK/0000040000000000000000000000000 | 4 | 0 | 4 | 1 | 3 | 0 | 1 |
| 145 | 145 | QNQCFYNSSYLNVQRENGTVSR/1000040000000000000000 | 4 | 0 | 4 | 1 | 3 | 0 | 1 |
| 146 | 146 | VDLEDFENNTAYAK/00000000040000 | 4 | 0 | 4 | 1 | 3 | 0 | 1 |
| 147 | 147 | IGEADFNRSKEFMEEVIQR/00000004000000000000 | 3 | 0 | 3 | 1 | 2 | 0 | 1 |
| 148 | 148 | SHAASDAPENLTLLAETADAR/00000000004000000000000 | 3 | 0 | 3 | 1 | 2 | 0 | 2 |
| 149 | 149 | DFYVDENTTVR/00000004000 | 3 | 0 | 3 | 1 | 2 | 0 | 1 |

TABLE 5-continued

Hepatic disease-state indicating marker glycopeptide

Peptide sequence and modification information

The initial position of a sequence of numbers represents the terminal amino group and the end position there of represents the terminal carboxyl group. The numerals between them represent modification states of residue side-chains. "0" means not modified: "1" represents deamidation or cyclization of an N-terminal Gln: "2" represents oxidation of a Met side-chain: "3"

Pep- represents deamidation or cyclization of an N-tide terminal carbamidemethylated Cys: "4" represents a No. glycosylation site (Asnlabel)

| SEQ. ID. NO.: | Pep-tide No. | Peptide sequence and modification | A. The detection number with probe (AAL). B + C = total (total 14) | B. The detection number with probe (AAL) from healthy serum specimen (total 2) | C. The detection number with probe (AAL) from medium 2+ serum specimen (total 10) | D. The detection number from HCC related specimen (total 7) | E. The detection number from HCC specimen after surgery (fibrosis specimen) (total 5) | F. The detection number with RCA from serum specimen (total 11) | G. The number of protein candidate derived |
|---|---|---|---|---|---|---|---|---|---|
| 150 | 150 | VQNVTEFDDSLLR/0004000000000000 | 3 | 0 | 3 | 1 | 2 | 0 | 1 |
| 151 | 151 | HGVIISSTVDTYENGSSVEYR/000000000000400000000 | 2 | 0 | 2 | 1 | 1 | 0 | 1 |
| 152 | 152 | YTGNASALFILPDQDKMEEVEAMLLPETLKR/00004000000000000000020000000 | 2 | 0 | 2 | 1 | 1 | 0 | 1 |
| 153 | 153 | AFGQFFSPGEVIYNKTDR/000000000400000000 | 2 | 0 | 2 | 1 | 1 | 0 | 2 |
| 154 | 154 | EAPYFYNDTVTFK/000000040000000 | 2 | 0 | 2 | 1 | 1 | 0 | 2 |
| 155 | 155 | EHEAQSNASLDVFLGHTNVEELMK/000000040000000000000200 | 2 | 0 | 2 | 1 | 1 | 0 | 1 |
| 156 | 156 | ELDREVYPWNLTVEAK/000000000040000000 | 2 | 0 | 2 | 1 | 1 | 0 | 1 |
| 157 | 157 | LGSYPVGGNVSFECEDGFILR/000000004000000000000 | 2 | 0 | 2 | 1 | 1 | 0 | 1 |

Fifth group: Peptide identified with AAL from the serum of a healthy person but not identified with AAL from the patient after surgery and being possible HCC marker candidate (note that rank is low)

| 158 | 158- | GCVLLSYLNETVTVSASLESVRGNR/000000000400000000000000400 | 3 | 1 | 2 | 2 | 0 | 2 | 1 |
| 159 | 159- | VYKPSAGNNSLYR/0000000040000000 | 5 | 2 | 3 | 3 | 0 | 1 | 1 |
| 160 | 160- | NGTGHGNSTHHGPEYMR/04000004000000000200 | 3 | 1 | 2 | 2 | 0 | 1 | 1 |

TABLE 5-continued

| SEQ. ID. NO.: | Pep- tide No. | Hepatic disease-state indicating marker glycopeptide Peptide sequence and modification information The initial position of a sequence of numbers represents the terminal amino group and the end position there of represents the terminal carboxyl group. The numerals between them represent modification states of residue side-chains. "0" means not modified: "1" represents deamidation or cyclization of an N-terminal Gln: "2" represents oxidation of a Met side-chain: "3" represents deamidation or cyclization of an N-tide terminal carbamidemethylated Cys: "4" represents a glycosylation site (Asnlabel) | A. The de- tec- tion num- ber with probe (AAL). (B + C = total 14) | B. The de- tec- tion num- ber with probe (AAL) from heal- thy serum (total 2) | C. The de- tec- tion num- ber with probe (AAL) from HCC relat- ed serum (total 12) | D. The detec- tion number from HCC spec- imen (total 7) | E. The detec- tion number from HCC spec- imen after sur- gery (fibro- sis spec- imen) (total 5) | F. The de- tec- tion num- ber with RCA from serum (total 11) | G. The num- ber of pro- tein can- di- date de- rived |
|---|---|---|---|---|---|---|---|---|---|
| 161 | 161- | NGTGHGNSTHHGPEYMR/0400000400000000000 | 3 | 1 | 2 | 2 | 0 | 1 | 1 |
| 162 | 162- | AAIPSALDTNSSK/00000000040000 | 3 | 1 | 2 | 2 | 0 | 11 | 1 |
| 163 | 163- | LGNWSAMPSCK/00040002000000 | 3 | 1 | 2 | 2 | 0 | 11 | 1 |
| 164 | 164- | VVGVPYQGNATALFILPSEGK/000000004000000000000 | 2 | 1 | 1 | 1 | 0 | 11 | 1 |
| 165 | 165- | GLNLTEDTYKPR/000400000000000 | 3 | 1 | 2 | 2 | 0 | 10 | 1 |
| 166 | 166- | SIPACVPWSPYLFQPNDTCIVSGWGR/00000000004000000000000000 | 2 | 1 | 1 | 1 | 0 | 2 | 1 |
| 167 | 167- | YNSQNQSNNQFVLYR/000040000000000 | 2 | 1 | 1 | 1 | 0 | 2 | 1 |
| 168 | 168- | KLPPGLLANFTLLR/00000000040000 | 2 | 1 | 1 | 1 | 0 | 1 | 1 |
| 169 | 169- | LGNWSAMPSCK/00040000000000 | 2 | 1 | 1 | 1 | 0 | 10 | 1 |
| 170 | 170- | LHINHNNLTESVGPLPK/00000000040000000 | 2 | 1 | 1 | 1 | 0 | 8 | 1 |
| 171 | 171- | GICNSSDVR/000040000 | 2 | 1 | 1 | 1 | 0 | 7 | 2 |
| 172 | 172- | HERDAGVVCTNETR/00000000004000 | 2 | 1 | 1 | 1 | 0 | 5 | 1 |
| 173 | 173- | ASPPSSSCNISSGEMQK/000000000400000000 | 2 | 1 | 1 | 1 | 0 | 4 | 1 |
| 174 | 174- | KEDALNETRESETK/00000004000000000 | 2 | 1 | 1 | 1 | 0 | 4 | 2 |

TABLE 5-continued

Hepatic disease-state indicating marker glycopeptide

Peptide sequence and modification information

The initial position of a sequence of numbers represents the terminal amino group and the end position there of represents the terminal carboxyl group. The numerals between them represent modification states of residue side-chains. "0" means not modified: "1" represents deamidation or cyclization of an N-terminal Gln: "2" represents oxidation of a Met side-chain: "3" Pep- represents deamidation or cyclization of an N-tide terminal carbamidemethylated Cys: "4" represents a No. glycosylation site (Asnlabel)

| SEQ. ID. NO. | Pep- tide No. | Peptide | A. The detection number with probe (AAL). (B + C = total 14) | B. The detection number with probe (AAL). healthy serum (total 2) | C. The detection number with probe (AAL) from relate ed specimen (medium 2 + serum 10) (total 12) | D. The detection number from HCC representative specimen (total 7) | E. The detection number from HCC specimen after surgery (fibrosis specimen) (total 5) | F. The detection number with RCA from serum specimen (total 11) | G. The number of protein candidate derived |
|---|---|---|---|---|---|---|---|---|---|
| 175 | 175-LR | ESKPLTAQQTTKLDAPTNLQFVNETDSTVLVR/ 000000000000000000000000004000000000 | 2 | 1 | 1 | 1 | 0 | 3 | 6 |
| 176 | 176-LR | EIRHNSTGCLR/0000004000000000 | 4 | 1 | 3 | 3 | 0 | 0 | 2 |
| 177 | 177-LR | MLNTSSLLEQLNEQFNWVSRLANLTQGEDQYYLR/ 0004000000000000000000040000000000000 | 2 | 1 | 1 | 1 | 0 | 0 | 2 |
| 178 | 178-LR | NFTENDLLVR/0400000000000 | 2 | 1 | 1 | 1 | 0 | 0 | 1 |
| 179 | 179-LR | NLASRPYTFHSHGITYYKEHEGAIYPDNTTDFQR/ 000000000000000000000000000000400000000 | 2 | 1 | 1 | 1 | 0 | 0 | 1 |
| 180 | 180-LR | YPPTVSMVEGQGEKNVTFWGRPLPR/ 0000000000000000000040000000000 | 2 | 1 | 1 | 1 | 0 | 0 | 1 |
| 181 | 181-LR | FCRDNYTDLVAIQNK/00000040000000000 | 2 | 1 | 1 | 1 | 0 | 0 | 1 |
| 182 | 182-LR | INATDADEPNTLNSK/00400000000000000 | 2 | 1 | 1 | 1 | 0 | 0 | 1 |
| 183 | 183-LR | TVVTYHIPQNSSLENVDSR/000000000004000000000000 | 2 | 1 | 1 | 1 | 0 | 0 | 1 |

4. Marker Glycoprotein

From the sequences of the marker glycopeptides identified and selected in the section 3, the glycoproteins containing the sequences can be defined. In detail, a table (Table 6) was prepared where each serial No. of glycoprotein having a sequence of glycopeptide listed in Table 5 were linked to its corresponding No. of glycopeptides. In this manner, a list of marker glycoproteins can be easily prepared. These glycoproteins are listed in Table 2 above.

TABLE 6

| Protein No. | Marker protein | Number of derived marker peptides | Peptide No. of derived marker peptide | | | |
|---|---|---|---|---|---|---|
| 1 | ADAM metallopeptidase domain 9 isoform 1 precursor | 1 | 68 | | | |
| 2 | ADAM metallopeptidase domain 9 isoform 2 precursor | 1 | 68 | | | |
| 3 | ADAM metallopeptidase with thrombospondin type 1 motif, 13 isoform 1 preproprotein | 1 | 139 | | | |
| 4 | ADAM metallopeptidase with thrombospondin type 1 motif, 13 isoform 2 preproprotein | 1 | 139 | | | |
| 5 | ADAM metallopeptidase with thrombospondin type 1 motif, 13 isoform 3 preproprotein | 1 | 139 | | | |
| 6 | ADAM metallopeptidase with thrombospondin type 1 motif, 9 preproprotein | 1 | 97 | | | |
| 7 | ADAMTS-like 2 | 1 | 111 | | | |
| 8 | alpha 1B-glycoprotein | 2 | 26 | 134 | | |
| 9 | alpha-2-glycoprotein 1, zinc | 3 | 25 | 32 | 57 | |
| 10 | alpha-2-macroglobulin precursor | 3 | 56 | 117 | 141 | |
| 11 | alpha-2-macroglobulin-like 1 | 1 | 110 | | | |
| 12 | alpha-fetoprotein precursor | 2 | 6 | 30 | | |
| 13 | apolipoprotein B precursor | 4 | 1 | 11 | 38 | 99 |
| 14 | asialoglycoprotein receptor 1 | 2 | 90 | 91 | | |
| 15 | attractin isoform 1 | 1 | 124 | | | |
| 16 | attractin isoform 2 | 1 | 124 | | | |
| 17 | basigin isoform 1 | 1 | 84 | | | |
| 18 | basigin isoform 2 | 1 | 84 | | | |
| 19 | biotinidase precursor | 1 | 59 | | | |
| 20 | cadherin 5, type 2 preproprotein | 1 | 156 | | | |
| 21 | carboxypeptidase E precursor | 1 | 83 | | | |
| 22 | carboxypeptidase N, polypeptide 2, 83 kD | 1 | 7 | | | |
| 23 | cat eye syndrome critical region protein 1 isoform a precursor | 1 | 150 | | | |
| 24 | CD163 antigen isoform a | 1 | 118 | | | |
| 25 | CD163 antigen isoform b | 1 | 118 | | | |
| 26 | ceruloplasmin precursor | 3 | 79 | 113 | 122 | |
| 27 | clusterin isoform 1 | 2 | 17 | 43 | | |
| 28 | clusterin isoform 2 | 2 | 17 | 43 | | |
| 29 | coagulation factor C homolog, cochlin precursor | 1 | 104 | | | |
| 30 | coagulation factor V precursor | 1 | 72 | | | |
| 31 | coagulation factor XIII B subunit precursor | 1 | 151 | | | |
| 32 | colony stimulating factor 1 receptor precursor | 2 | 42 | 138 | | |
| 33 | complement component (3d/Epstein Barr virus) receptor 2 isoform 1 | 1 | 154 | | | |
| 34 | complement component (3d/Epstein Barr virus) receptor 2 isoform 2 | 1 | 154 | | | |
| 35 | complement component 1, q subcomponent, A chain | 1 | 50 | | | |
| 36 | complement component 1, r subcomponent | 2 | 58 | 155 | | |
| 37 | complement component 2 precursor | 2 | 133 | 157 | | |
| 38 | complement component 4 binding protein, alpha chain precursor | 2 | 53 | 116 | | |
| 39 | complement component 4 binding protein, beta chain isoform 1 precursor | 1 | 19 | | | |
| 40 | complement component 4 binding protein, beta chain isoform 1 precursor | 1 | 19 | | | |
| 41 | complement component 4 binding protein, beta chain isoform 1 precursor | 1 | 19 | | | |
| 42 | complement component 4 binding protein, beta chain isoform 2 precursor | 1 | 19 | | | |
| 43 | complement component 4 binding protein, beta chain isoform 2 precursor | 1 | 19 | | | |
| 44 | complement component 4A preproprotein | 2 | 8 | 136 | | |
| 45 | complement component 4B preproprotein | 2 | 8 | 136 | | |
| 46 | complement factor B preproprotein | 1 | 39 | | | |
| 47 | complement factor H isoform a precursor | 1 | 9 | | | |
| 48 | cytokine receptor-like factor 1 | 2 | 77 | 95 | | |
| 49 | dopamine beta-hydroxylase precursor | 1 | 28 | | | |
| 50 | EMI domain containing 2 | 1 | 102 | | | |
| 51 | fibrinogen, beta chain preproprotein | 2 | 3 | | | |
| 52 | fibrinogen, gamma chain isoform gamma-A precursor | 1 | 64 | | | |
| 53 | fibrinogen, gamma chain isoform gamma-B precursor | 1 | 64 | | | |

TABLE 6-continued

| Protein No. | Marker protein | Number of derived marker peptides | Peptide No. of derived marker peptide | | | | | | |
|---|---|---|---|---|---|---|---|---|---|
| 54 | fibronectin 1 isoform 1 preproprotein | 7 | 4 | 5 | 10 | 12 | 31 | 67 | 127 |
| 55 | fibronectin 1 isoform 2 preproprotein | 7 | 4 | 5 | 10 | 12 | 31 | 67 | 127 |
| 56 | fibronectin 1 isoform 3 preproprotein | 7 | 4 | 5 | 10 | 12 | 31 | 67 | 127 |
| 57 | fibronectin 1 isoform 4 preproprotein | 7 | 4 | 5 | 10 | 12 | 31 | 67 | 127 |
| 58 | fibronectin 1 isoform 5 preproprotein | 7 | 4 | 5 | 10 | 12 | 31 | 67 | 127 |
| 59 | fibronectin 1 isoform 6 preproprotein | 7 | 4 | 5 | 10 | 12 | 31 | 67 | 127 |
| 60 | fibronectin 1 isoform 7 preproprotein | 6 | 4 | 5 | 10 | 12 | 31 | 67 | |
| 61 | fibulin 1 isoform A precursor | 1 | 86 | | | | | | |
| 62 | fibulin 1 isoform B precursor | 1 | 86 | | | | | | |
| 63 | fibulin 1 isoform C precursor | 1 | 86 | | | | | | |
| 64 | fibulin 1 isoform D | 1 | 86 | | | | | | |
| 65 | galectin 3 binding protein | 1 | 114 | | | | | | |
| 66 | glucosamine (N-acetyl)-6-sulfatase precursor | 1 | 107 | | | | | | |
| 67 | golgi phosphoprotein 2 | 2 | 24 | 130 | | | | | |
| 68 | golgi phosphoprotein 2 | 2 | 24 | 130 | | | | | |
| 69 | haptoglobin | 1 | 18 | | | | | | |
| 70 | hypothetical protein LOC196463 | 1 | 101 | | | | | | |
| 71 | immunoglobulin J chain | 1 | 20 | | | | | | |
| 72 | immunoglobulin superfamily, member 1 isoform 1 | 1 | 82 | | | | | | |
| 73 | insulin-like growth factor binding protein 3 isoform a precursor | 1 | 140 | | | | | | |
| 74 | insulin-like growth factor binding protein 3 isoform b precursor | 1 | 140 | | | | | | |
| 75 | inter-alpha (globulin) inhibitor H4 | 1 | 120 | | | | | | |
| 76 | inter-alpha globulin inhibitor H2 polypeptide | 2 | 13 | | | | | | |
| 77 | intercellular adhesion molecule 2 precursor | 1 | 119 | | | | | | |
| 78 | interleukin 18 binding protein precursor | 1 | 142 | | | | | | |
| 79 | interleukin 18 binding protein precursor | 1 | 142 | | | | | | |
| 80 | interleukin 18 binding protein precursor | 1 | 142 | | | | | | |
| 81 | kininogen 1 | 4 | 23 | 48 | 62 | 129 | | | |
| 82 | laminin, gamma 1 precursor | 3 | 74 | 75 | 93 | | | | |
| 83 | legumain preproprotein | 1 | 89 | | | | | | |
| 84 | legumain preproprotein | 1 | 89 | | | | | | |
| 85 | lumican precursor | 2 | 109 | 131 | | | | | |
| 86 | lunatic fringe isoform a | 1 | 96 | | | | | | |
| 87 | lunatic fringe isoform b | 1 | 96 | | | | | | |
| 88 | lysosomal-associated membrane protein 1 | 3 | 70 | 71 | 135 | | | | |
| 89 | lysosomal-associated membrane protein 2 precursor | 1 | 137 | | | | | | |
| 90 | lysosomal-associated membrane protein 2 precursor | 1 | 137 | | | | | | |
| 91 | mannan-binding lectin serine protease 1 isoform 2 precursor | 1 | 128 | | | | | | |
| 92 | mannosidase, alpha, class 2B, member 2 | 1 | 106 | | | | | | |
| 93 | MHC class I chain-related gene A protein | 1 | 94 | | | | | | |
| 94 | microfibrillar-associated protein 4 | 1 | 146 | | | | | | |
| 95 | neuronal cell adhesion molecule isoform A precursor | 1 | 103 | | | | | | |
| 96 | neuronal cell adhesion molecule isoform B precursor | 1 | 103 | | | | | | |
| 97 | orosomucoid 1 precursor | 4 | 34 | 35 | 63 | 143 | | | |
| 98 | orosomucoid 2 | 5 | 27 | 63 | 78 | 143 | 145 | | |
| 99 | oxygen regulated protein precursor | 1 | 80 | | | | | | |
| 100 | palmitoyl-protein thioesterase 1 (ceroid-lipofuscinosis, neuronal 1, infantile) | 1 | 65 | | | | | | |
| 101 | peptidoglycan recognition protein 2 precursor | 1 | 15 | | | | | | |
| 102 | phospholipid transfer protein isoform a precursor | 1 | 2 | | | | | | |
| 103 | plasma carboxypeptidase B2 isoform a preproprotein | 1 | 29 | | | | | | |
| 104 | plasma carboxypeptidase B2 isoform b | 1 | 29 | | | | | | |
| 105 | polymeric immunoglobulin receptor | 2 | 51 | 60 | | | | | |
| 106 | PREDICTED: similar to ADAMTS-like 2 | 1 | 111 | | | | | | |
| 107 | PREDICTED: similar to Carboxypeptidase N subunit 2 precursor (Carboxypeptidase N polypeptide 2) | 1 | 7 | | | | | | |
| 108 | PREDICTED: similar to HEG homolog 1 | 1 | 148 | | | | | | |
| 109 | PREDICTED: similar to HEG homolog 1 | 1 | 148 | | | | | | |
| 110 | PREDICTED: similar to Mucin-5B precursor (Mucin 5 subtype B, tracheobronchial) (High molecular weight salivary mucin MG1) (Sublingual gland mucin) | 1 | 153 | | | | | | |

TABLE 6-continued

| Protein No. | Marker protein | Number of derived marker peptides | Peptide No. of derived marker peptide | | | | | | |
|---|---|---|---|---|---|---|---|---|---|
| 111 | PREDICTED: similar to Mucin-5B precursor (Mucin 5 subtype B, tracheobronchial) (High molecular weight salivary mucin MG1) (Sublingual gland mucin) (4390) | 1 | 153 | | | | | | |
| 112 | prion protein preproprotein | 1 | 81 | | | | | | |
| 113 | prion protein preproprotein | 1 | 81 | | | | | | |
| 114 | prion protein preproprotein | 1 | 81 | | | | | | |
| 115 | prion protein preproprotein | 1 | 81 | | | | | | |
| 116 | prion protein preproprotein | 1 | 81 | | | | | | |
| 117 | procollagen-lysine, 2-oxoglutarate 5-dioxygenase 3 precursor | 1 | 100 | | | | | | |
| 118 | prosaposin isoform a preproprotein | 1 | 73 | | | | | | |
| 119 | prosaposin isoform b preproprotein | 1 | 73 | | | | | | |
| 120 | prosaposin isoform c preproprotein | 1 | 73 | | | | | | |
| 121 | selectin L precursor | 1 | 112 | | | | | | |
| 122 | selenoprotein P isoform 1 precursor | 1 | 22 | | | | | | |
| 123 | selenoprotein P isoform 1 precursor | 1 | 22 | | | | | | |
| 124 | selenoprotein P isoform 2 | 1 | 22 | | | | | | |
| 125 | serine (or cysteine) proteinase inhibitor, clade A (alpha-1 antiproteinase, antitrypsin), member 4 | 2 | 36 | 149 | | | | | |
| 126 | serine (or cysteine) proteinase inhibitor, clade A, member 7 | 2 | 33 | 115 | | | | | |
| 127 | serine (or cysteine) proteinase inhibitor, clade C (antithrombin), member 1 | 3 | 16 | 40 | 108 | | | | |
| 128 | serpin peptidase inhibitor, clade A, member 3 | 7 | 37 | 41 | 44 | 46 | 52 | 55 | 152 |
| 129 | sex hormone-binding globulin | 2 | 49 | 85 | | | | | |
| 130 | SPARC-like 1 | 1 | 125 | | | | | | |
| 131 | TP53-target gene 5 protein | 1 | 87 | | | | | | |
| 132 | transferrin | 3 | 45 | 54 | 98 | | | | |
| 133 | transmembrane 4 superfamily member 6 | 1 | 88 | | | | | | |
| 134 | transmembrane 4 superfamily member 8 isoform 1 | 1 | 92 | | | | | | |
| 135 | transmembrane 4 superfamily member 8 isoform 2 | 1 | 92 | | | | | | |
| 136 | tripeptidyl-peptidase I preproprotein | 1 | 66 | | | | | | |
| 137 | tumor rejection antigen (gp96) 1 | 1 | 121 | | | | | | |
| 138 | UDP-GlcNAc: betaGal beta-1,3-N-acetylglucosaminyltransferase 1 | 2 | 69 | 76 | | | | | |
| 139 | UDP-GlcNAc: betaGal beta-1,3-N-acetylglucosaminyltransferase 2 | 1 | 132 | | | | | | |
| 140 | vascular cell adhesion molecule 1 isoform a precursor | | 144 | | | | | | |
| 141 | vitronectin precursor | | 47 | | | | | | |
| 142 | von Willebrand factor preproprotein | 5 | 21 | 61 | 123 | 126 | 147 | | |
| 143-LR | apolipoprotein H precursor | 1 | 159-LR | | | | | | |
| 144-LR | coagulation factor II precursor | 1 | 178-LR | | | | | | |
| 145-LR | complement factor I | 1 | 166-LR | | | | | | |
| 146-LR | complement factor properdin | 1 | 180-LR | | | | | | |
| 147-LR | desmoglein 2 preproprotein | 1 | 182-LR | | | | | | |
| 148-LR | hemopexin | 2 | 160-LR | 161-LR | | | | | |
| 149-LR | inducible T-cell co-stimulator ligand | 1 | 183-LR | | | | | | |
| 150-LR | leucine-rich alpha-2-glycoprotein 1 | 1 | 168-LR | | | | | | |
| 151-LR | serine (or cysteine) proteinase inhibitor, clade A (alpha-1 antiproteinase, antitrypsin), member 5 | 1 | 164-LR | | | | | | |

(with the proviso that No. 97 and No. 98 (AGP) and No. 65 (M2BP) in Table 6 above are eliminated)

5. Demonstration by Comparison of Mass Spectrometry Signal Intensities of Glycopeptides in IGOT-LC/MS Analysis Cases where a hepatic disease-state was detected by using the glycopeptides identified in the section 3 (those peptides were detected as peptides labeled with stable isotope(s) at their glycosylation site(s) in IGOT-LC/MS analysis) as markers will be shown below. Proteins contained in the sera of healthy volunteers and the patients (taken before and after surgery) were fragmented into peptides by the aforementioned method and then subjected to IGOT-LC/MS analysis. The resultant signal intensities of the glycopeptides were compared between the sera samples of healthy volunteers and patients (the sera were taken before and after surgery). As a result, marker glycopeptides showing a significant signal only in the serum before surgery were found. Part of them is shown in FIG. 9. Among the hepatic disease-state-indicating marker glycopeptides, these are expected to be useful as a "marker glycopeptide for hepatocellular carcinoma" of the present invention for detecting an early-detection of hepatocellular carcinoma.

Example 2

Use of Hepatic Disease-State-Indicating Glycan Marker Candidate Glycoprotein in Hepatic Disease Detection Of the glycoproteins (glycoproteins containing the sequences of glycopeptides) collected from the sera of a (viral) hepatitis patient, a hepatic cirrhosis patient and a hepatocarcinoma patient, and verified during comparative glycan profiling performed by an antibody overlay lectin microarray etc. in verification and screening of the hepatic disease-state-indicating glycan marker candidates, CPN2 was applied to detection of a hepatic disease using a novel hepatic disease-state-indicating glycan marker candidate using an antibody overlay lectin array. The Example thereof will be shown below. Note that the strategy of comparative analysis of glycans on the marker glycoproteins derived from the sera of a (viral) hepatitis patient (CH), a hepatic cirrhosis patient (LC), a hepatocarcinoma patient (HCC) and a healthy volunteer (HV) according to the method is shown in FIG. 7.

1. Enrichment of Marker Protein from the Serum

The marker glycoproteins derived from the sera of a (viral) hepatitis patient (CH), a hepatic cirrhosis patient (LC), a hepatocarcinoma patient (HCC) and a healthy volunteer (HV) were enriched in accordance with "Kuno A, Kato Y, Matsuda A, Kaneko M K, Ito H, Amano K, Chiba Y, Narimatsu H, Hirabayashi J. Mol. Cell Proteomics. 8, 99-108 (2009)". Note that to clarify that the obtained results are dependent upon the disease-state, five cases for each disease-state were analyzed. The serum of each patient was diluted 10 fold with a 0.2% SDS-containing PBS buffer solution, heated for 10 minutes at 95° C., dispensed in a 25 µL reaction tube in the case of CPN2. To the reaction tube, 500 ng of an antibody (biotinylated compound) against CPN2 was added. Each reaction solution was adjusted to be 45 µL with a reaction buffer (Tris-buffered saline (TBSTx) containing 1% Triton X-100) and then the reaction was performed at 4° C. for 2 hours with shaking. After completion of an antigen-antibody reaction, 5 µL (corresponding to 10 µl of the original beads solution) of a streptoavidin immobilized magnetic beads solution (Dynabeads MyOne Streptavidin T1, DYNAL, manufactured by Biotech ASA), which was preliminarily washed three times with a reaction buffer and adjusted to be 2 fold concentration, was added to the above reaction solution and a reaction was performed further for 1 hour. Owing to the reaction, the glycoprotein forms into a complex with magnetic beads via the biotinylated antibody. After the complex was allowed to adsorb to a magnet for recovering magnetic beads, the solution was discarded. The complex recovered was washed three times with a reaction buffer (500 µL) and then suspended in a 10 µL elution buffer (TBS containing 0.2% SDS). The suspended solution was treated with heat at 95° C. for 5 minutes to dissociate and elute the glycoprotein from magnetic beads. The obtained solution was used as an eluate. Since a biotinylated antibody denatured with heat was contaminated in the elute at this time, 10 µL of a magnetic beads solution (corresponding to 20 µl of the original beads solution), which was adjusted to be 2 fold concentration by the aforementioned method, was added to the eluate and allowed to react for 1 hour to remove the biotinylated antibody by adsorption. The resultant solution was used in the later experiments as the serum-derived glycoprotein solution.

2. Antibody Overlay Lectin Array

An appropriate amount of the glycoprotein solution obtained as described above was taken and adjusted with a lectin array reaction buffer, i.e., a 1% Triton X-100-containing phosphate-buffered saline containing 1% TritonX-100 (PBSTx) to 60 µl. This solution was added to each of reaction vessels of a lectin microarray (8 reaction vessels are formed per a single glass) and reacted at 20° C. for 10 hours or more. A lectin microarray substrate formed of 8 reaction vessels was prepared in accordance with the method described by Uchiyama et al. (Proteomics 8, 3042-3050 (2008)). In this manner, the binding reaction between glycans on the glycoprotein and 43 types of lectins immobilized onto an array substrate reaches an equilibrium state. Thereafter, to avoid generation of noise formed by binding glycan on a detection antibody to lectins remaining unreacted on the substrate, 2 µL of human serum derived IgG solution (manufactured by Sigma) was added and reacted for 30 minutes. Each reaction vessel was washed three times with 60 µL of PBSTx and then the human serum derived IgG solution (2 µL) was added again, slightly stirred and then a detection antibody (biotinylated compound) against the glycoprotein was added in an amount corresponding to 100 ng and reacted at 20° C. for 1 hour. After the antigen-antibody reaction, each reaction vessel was washed three times with 60 µL of PBSTx. Subsequently, a Cy3 labeled streptoavidin (corresponding to 200 ng)—in PBSTx solution was added and further reacted at 20° C. for 30 minutes. After completion of the reaction, each reaction vessel was washed three times with 60 µL of PBSTx and the array was scanned by an array scanner, GlycoStation manufactured by MORITEX Corporation.

Of the obtained results, typical examples of individual disease-states (CPN2) are shown in FIG. 8. As is apparent from the figure, the signal on lectin AAL, used in Example 1 "large-scale identification method of glycoprotein, 2) Collection and purification of glycopeptide" and the signal on AOL lectin having similar sugar binding property had a tendency of increasing in chronic hepatitis, hepatic cirrhosis, and hepatocarcinoma and as the severity of hepatic disease increases in each candidate molecule.

From the results, it was demonstrated that, of the AAL-bound glycopeptides identified by the aforementioned large-scale analysis, a glycoprotein containing the sequence of a glycopeptide that presented in a hepatocarcinoma patient but not identified in a healthy volunteer could be a hepatic disease-state marker in the same as the glycopeptide.

Furthermore, These experiments of this time revealed that some lectins other than AAL and the lectins having similar binding property also increase or decrease in accordance with a change in hepatic disease-state. This means that if a plurality of lectin signals for a glycoprotein are combined in various ways, disease-states of various-phases can be more accurately detected.

Example 3

Study on Separation/Fractionation of Fucose-Containing Glycoprotein by Serial Column Chromatography and Quantitative Comparative Analysis Procedure of a verification method of a marker candidate molecule by serial column chromatography using two different fucose recognizing lectins shown in FIG. 10 will be described.

1. Separation/Fractionation of Fucose-Containing Glycoprotein by LCA-AAL Continuous Column Chromatography Fifty µl of a healthy volunteer's pooled serum (NHS) and hepatitis C virus positive hepatocarcinoma patient's serum (HCC) were diluted 10 fold with a 0.2% SDS-containing PBS buffer and heated at 95° C. for 20 minutes to inactivate the virus. Each of the heat-treated samples was applied to an LCA lectin column (manufactured by Seikagaku Corporation) (5 mL, φ7.0 mm, height: 100.0 mm) which was preliminarily equilibrated by an initiation buffer (PBS containing 0.1% SDS and 1% Triton X-100). The flow rate during the chromatography was adjusted to 200 µL/min. After injection of the sample, the column was washed with the initiation buffer (3 fold column amount) and then with a washing buffer of 3-fold column amount (0.2% SDS-containing PBS). The glycoproteins adsorbed to the LCA column was eluted with elution buffer A (PBS containing 0.02% SDS and 200 mM methyl-α-mannoside). The solution was collected by a fraction collector by 1.0 mL per tube. The position at which the LCA-unbound fraction and the bound fraction were separated was determined by protein quantitation. Next, the LCA-unbound fraction was applied to an AAL lectin column (manufactured by Wako Pure Chemical Industries Ltd.) (0.5 mL, φ5.0 mm, height: 20.0 mm), which was previously equilibrated by an initiation buffer (PBS containing 0.1% SDS and 1% Triton X-100). The flow rate during the chromatography was adjusted to 40 µL/min. After application of the sample, the column was washed with the initiation buffer (3 fold column amount) and then with a washing buffer of 6-fold column amount (0.02% SDS-containing PBS). The glycoproteins adsorbed to the AAL column were eluted by elution buffer B (PBS containing 0.02% SDS and 200 mM fucose). The solution was collected by a fraction collector by 1.0 mL per tube. The position at which the AAL-unbound fraction and the bound fraction were separated was determined by protein quantitation. After individual fractions (LCA-bound fraction (LE), LCA-unbound/AAL-bound fraction (AE) and LCA/AAL-unbound fraction (LTAT)) were determined, separation states were confirmed by SDS-PAGE. Note that, the liquid amounts of individual fractions during the chromatography were as follows. In the case of NHS, LE was 7.7 mL, AE was 1.34 mL and LTAT was 9.25 mL. In the case of HCC, LE was 12.48 mL, AE was 1.79 mL and LTAT was 11.91 mL.

2. Qualitative and Quantitative Comparison of Fractions by Lectin Array

Sugar-chain profiling of heat treated serum and glycoproteins in each fragment by a lectin array was basically performed in accordance with the method of Kuno et al. (Literature 1: Kuno et al., Nature Method 2005) and the method of Uchiyama et al. (Literature 2: Uchiyama et al. Proteomics 2008). The heat treated serum proteins (corresponding to a protein amount of 1 µg) were labeled with a fluorescent substance in accordance with the following method. After serial column chromatography, a glycoprotein in each fraction was labeled with a fluorescent substance by using a liquid whose amount was calculated assuming that the serum protein corresponding to 1 µg was fractionated based on the ratio of solution amounts after fractionation. Furthermore, an elution fraction contains a competitive sugar. To remove the competitive sugar, dilution with PBS containing 0.1% SDS and centrifugal concentration using an ultrafiltration column [Millipore Amicon Ultra™ 0.5 mL 3K cut] were repeated. The sample was prepared to a volume of 10 µL with a PBS buffer containing 1% Triton X-100. To this, 10 µg of a fluorescent labeling reagent (Cy3-SE, GE Healthcare) was added and a fluorescent labeling reaction was performed for 1 hour at room temperature. To a reaction product, a glycine-containing buffer solution (90 µL) was added and a masking reaction was performed for 2 hours at room temperature to inactivate the excessive fluorescent labeling reagent. This solution was subjected to a lectin array as fluorescent labeled glycoprotein solution. The lectin array herein had 43 types of immobilized lectins shown in Table 4. The fluorescent labeled glycoprotein solution was applied to the lectin array so as to bring a final concentration up to 2.0 µg/mL. An AE fraction sample alone was applied so as to bring a final concentration up to 8.0 µg/mL. The binding reaction between a lectin and an analysis target, i.e., glycoprotein was performed at 20° C. for 12 hours. After completion of the reaction, the sample solution on the array was removed, washed three times with a buffer for exclusive use, and scanned by a scanner for a lectin array, i.e., GlycoStation™ Reader 1200 manufactured by GP Bioscience, Ltd. Data obtained by scanning were stored as jpeg file and TIFF file. Numerical conversion of signals was performed by use of the TIFF file and by means of special software, ArrayPro Analyzer.

A sugar-chain profile of individual fragments are shown in FIG. 11. The effect of chromatography using each lectin (LCA, AAL) column can be validated referring to signal variation of each of LCA and AAL, and the signal intensity ratio of the two lectins. For example, the LCA signal observed during the serum analysis was maintained in an LE fraction and rarely observed in an LT fraction. This means that most of glycoproteins to be bonded to LCA were adsorbed to the LCA column and eluted by elution buffer. Furthermore, the AAL column adsorbs sugar fucose-containing glycoprotein which does not bind to LCA or only has poor interaction with LCA. Therefore, the LCA signal of the elution fraction is lower than the AAL signal; whereas the LCA signal of the LCA-bound fraction is more intensive than the AAL signal. Also in the AAL-unbound fraction herein, LCA and AAL signals were observed. This means that there was a molecule which interacts with each of the lectins even if the interaction is poor but fails to bind to a lectin column during chromatographic analysis. As a typical molecule thereof, IgG is conceivable. IgG is one of the N-glycosylated glycoprotein and at least seven out of ten of IgG has core fucosylation modification glycan. However, since the N-linked sugar-chain of IgG is present in the proximity of an IgG molecule, it has been revealed that it is difficult for the N-linked sugar-chain to interact with lectin. Because of this, IgG cannot bind to the lectin column. Nevertheless, the lectin array is analysis for observing even poor interaction. Therefore, it is considered that a signal was observed even in an LCA/AAL-unbound fraction.

Next, signal patterns of NHS and HCC were compared. In the serum, substantially no difference was observed in the patterns; however, a little difference was observed in fucose recognizing lectins, LCA, PSA, AAL, AOL, etc. In contrast, in the case of the LCA-bound fraction, an intensive signal tends to be observed in HCC as a whole. The tendency was significantly observed in the AAL-bound fraction. Interestingly, in the LCA/AAL-unbound fraction, no substantial difference was observed between NHS and HCC. From the foregoing, the amount of fucose-containing glycoprotein is higher in HCC than in NHS. This fact suggests that both LCA-bound fucose-containing glycoprotein and LCA-unbound/AAL-bound fucose-containing glycoprotein increased.

3. Quantitative Comparison Between LCA-Bound Fucose-Containing Molecule and LCA-Unbound/AAL-Bound Fucose-Containing Molecule of Specific Glycoprotein With respect to a specific glycoprotein, how much an LCA-bound fucose-containing molecule and an LCA-unbound/AAL-bound fucose-containing molecule increase with the development of hepatocarcinoma was investigated. The LCA-bound fraction (LE) and the LCA-unbound/AAL-bound fraction (AE) of NHS and HCC obtained as mentioned above each were mixed with a Laemmli sample buffer, heated and thereafter subjected to SDS/PAGE using 5 to 20% gradient polyacrylamide gel. After electrophoresis, the separated protein was transferred to a PVDF membrane. The protein on the membrane was detected in accordance with a customary method. At this time, as the blocking agent, Block Ace (DS Pharma Biomedical, Osaka, Japan) was used; as a primary antibody, a biotinylated antibody was used; as a detection reagent, alkaline phospatase-conjugated streptavidin (1/5000 diluted with TBST; ProZyme, Inc., San Leandoro, Calif.) and Wetern Blue™ stabilized substrate for alkaline phosphatase (Promega, Madison, Wis.) were used.

Herein, the results of an analysis for AGP, α1-anti-trypsin (AAT), and α1-antichymotrypsin (ACT), which have been so far reported to increase fucose modification with the progress of hepatic fibrosis and HCC carcinogenesis (J Proteome Res. 2006 February; 5 (2): 308-15.), are shown in FIG. 12. When quantitative comparison was performed based on the band intensity of Western blot, it is found that, in AGP, a fucose-containing molecule is not present in an LCA-bound fraction at all and present only in an AAL-bound fraction. Furthermore, the amount thereof is found to be significantly high in HCC compared to in NHS. In the case of AAT, a fucose-containing molecule is divided into the LCA-bound fraction and the AAL-bound fraction. More specifically, it suggests that AAT molecules, although they are the same, are differently modified with fucose. When NHS is compared to HCC, in the LCA-bound fraction, slightly presence thereof was confirmed in NHS; whereas, significant presence was confirmed in HCC. Furthermore, in the AAL-bound fraction, it is rarely present in NHS, whereas, it is significantly present in HCC. In the case of ACT, fucose-containing molecules are divided into an LCA-bound fraction and an AAL-bound fraction; however the present ratio thereof differed from that of AAT. More specifically, when NHS is compared to HCC, in the LCA-bound fraction, it is confirmed that the presence thereof is confirmed in both NHS and HCC; however, there is no significant quantitative difference between them. In contrast, in the AAL-bound fraction, the presence thereof is confirmed in both NHS and HCC; however it is found that the amount thereof in HCC is significantly high.

As is apparent form the above results, the N-linked glycan structure (e.g., degree of branching) and fucose modification (core fucose, blood-type antigen, etc.) differ depending upon the protein type. Furthermore, even if molecules, although they are the same type of molecules, are sometimes differently modified with fucose. These phenomena differently increase in different timing depending upon the type of disease and degree of progression thereof. In this respect, the operation where separation/fractionation is performed by serial column chromatography using two different fucose recognizing lectins and thereafter quantitative comparative analysis is performed has an advantage. To explain more specifically, by virtue of this operation, an increase or decrease of fucosylation on the same protein with a disease can be evaluated for every modification type. Hereinafter, comparative analysis of marker candidate molecules will be made by this approach.

Example 4

Identification and Validation of Hepatocarcinoma Indicating Biomarker

Screening and identification method for a hepatocarcinoma marker using serial column chromatography treatment described in Example 3 will be described. More specifically, optimization of e.g., a washing buffer (Triton X-100 concentration is optimized from 1.0% to 0.1%) and an elution buffer (SDS concentration is optimized from 0.02% to 0.1%) will be described. A fractionation method for the serum will be more specifically described below. The serum was diluted with PBS [pH7.4] 10 fold and then treated with heat in the presence of 0.2% SDS at 100° C. for 15 minutes. The heat treated serum specimen (10 µL) was diluted with a washing buffer [0.1% SDS, 0.1% TritonX-100, in PBS] 10 fold to adjust a total amount to 100 µL (crude).

One hundred µL of LCA agarose beads (J-oil mills Inc.) and 100 µL of the diluted and heat-treated serum specimen (crude) were mixed in an microtube and shaken in a shaker at 1,400 rpm and at 4° C. for 5 hours. After shaking, centrifugation was performed at 2,000 rpm and at 4° C. for 2 minutes to obtain the supernatant (100 µL). To LCA agarose beads, a washing buffer (100 µL) was added. The mixture was lightly mixed by a vortex and centrifuged at 2,000 rpm and at 4° C. for 2 minutes to obtain the supernatant (100 µL). This operation was repeated twice. The obtained supernatants were combined to obtain 300 µL of an LCA-unbound fraction (LT).

The LCA agarose beads remaining in the microtube was washed twice with 1 mL of PBS and thereafter 100 µL of elution buffer 1 [0.1% SDS, 0.2M Methyl α-D-Mannose in PBS] was added. The mixture was shaken (O/N) by a shaker at 1,400 rpm and at 4° C. On the other hand, LT (300 µL) and 50 µL of AAL agarose beads (J-oil mills Inc.) were mixed in a microtube and shaken (O/N) by a shaker at 1,400 rpm and at 4° C.

To LCA agarose beads, elution buffer 1 was added. The mixture was shaken overnight and centrifuged at 2,000 rpm and at 4° C. for 2 minutes to obtain the supernatant (90 µL). Subsequently, to the LCA agarose beads, elution buffer 1 (100 µL) was added. The mixture was gently mixed by a vortex and centrifuged at 2,000 rpm and at 4° C. for 2 minutes to obtain the supernatant (100 µL). This operation was repeated twice and then elution buffer 1 (50 µL) was added. The same operation was repeated to obtain the supernatant (40 µL). The obtained supernatants were combined to obtain 330 µL of LCA elution fraction (LE).

AAL agarose beads shaken overnight were centrifuged at 2,000 rpm and at 4° C. for 2 minutes to obtain the supernatant (300 µL). To the AAL agarose beads, a washing buffer (50 µL) was added. The mixture was gently mixed by a vortex and centrifuged at 2,000 rpm and at 4° C. for 2 minutes to obtain the supernatant (50 µL). This operation was repeated twice. The obtained supernatants were combined to obtain 400 µL of an LCA/AAL-unbound fraction (LTAT).

The AAL agarose beads remaining in the microtube was washed twice with PBS (500 µL) and thereafter 50 µL of elution buffer 2 [0.1% SDS, 0.2M L-(-)-Fucose in PBS] was added. The mixture was shaken by a shaker at 1,400 rpm and at 4° C. for 5 hours. After shaken, the mixture was centrifuged at 2,000 rpm and at 4° C. for 2 minutes to obtain the supernatant (50 µL). To AAL agarose beads, elution buffer 2 (50 µL) was added. The mixture was gently mixed by a vortex and centrifuged at 2,000 rpm and at 4° C. for 2 minutes to obtain the supernatant (50 µL). This operation was repeated twice. The obtained supernatants were combined to obtain 150 µL of AAL elution fraction (AE).

The fractionation operations with LCA and AAL mentioned above were repeated twice to obtain respective fractions (2 fold). The obtained LTAT (600 µL), LE (660 µL) and AE (300 µL) were each concentrated in an ultrafiltration column [Millipore Amicon Ultra™ 0.5 mL 3K cut] to obtain a final volume of 40 µL. After concentrated, 10 µL of 5×SDS sample buffer [250 mM Tris-HCl (pH6.8), 10% SDS, 5% β-ME, 50% glycerol, 0.05% BPB] was added. The mixture was treated with heat at 98° C. for 5 minutes and stored at −20° C. as a specimen to be used in SDS-PAGE.

Example 5

Screening of Hepatocarcinoma Indicating Biomarker

The pooled sera of healthy volunteers (14 individuals) and the pooled sera of hepatocellular carcinoma patients (4 patients having AFP-L3 values in the sera taken from them of 1855.4, 130.1, 171420.0 and 1562.0, respectively) were used as a sample set. Of the proteins shown in a table (Table 2), SHBG SEPP1, pIgR, SPARCL1, CSF1R, SERPINA7 and MANA2 were compared for expression levels thereof in the serum fractionations (the serum Crude, LCA-bound fractionation, LCA-unbound/AAL-bound fractionation, unbound fractionation) by the aforementioned serial column chromatography (FIGS. 13A to H). In consideration of the results together with the finding of specificity (also described in Example 3) or trajectory of each lectin so far obtained, the marker proteins whose expression levels in an LCA fraction are higher in a hepatocellular carcinoma patient than in a healthy volunteer are SHBG, pIgR and CSF1R. This fact demonstrates that in the serum of a hepatocellular carcinoma patient compared to that of a healthy volunteer, in part of these proteins, the amount of hypo-branched N-linked sugar-chain containing core fucose added to the protein increases. On the other hand, the marker proteins whose expression levels in LCA-unbound/AAL-bound fraction are higher in a hepatocellular carcinoma patient than in a healthy volunteer are SEPP1, pIgR, SPARCL1, CSF1R, SERPINA7 and MANA2. This fact demonstrates that in the serum of a hepatocarcinoma patient compared to that of a healthy volunteer, in part of these proteins, the amount of hyper-branched (at least triantennary) N-linked glycan containing core fucose added to the protein or an N-linked glycan having a fucose modification on the side of a non-reducing end increases. In a hepatocarcinoma patient, it is demonstrated that in part of these proteins, a hyper-branched (at least three branches) N-linked glycan containing core fucose added to the protein or an N-linked glycan having a fucose modification on the side of a non-reducing end increases.

Example 6

Screening 2 for Hepatocarcinoma Indicating Biomarker

Comparative analysis was performed using a sample set consisting of the sera of three healthy volunteers (Healthy), three hepatic cirrhosis patients (LC), and three hepatocellular carcinoma patients (HCC) by the aforementioned serial column chromatography (FIG. 14). As a result, in the LCA-bound fraction of pIgR, LCA-unbound/AAL-bound fraction of pIgR, LCA-unbound/AAL-bound fraction of CPB2, the LCA fractionation of CSF1R and LCA-unbound/AAL-bound fraction of CSF1R, the expression level was significantly high in the hepatic cirrhosis or hepatocellular carcinoma patients compared to in the healthy individuals. Particularly, in the LCA fractionation of pIgR, LCA fractionation of CSF1R and LCA-unbound/AAL-bound fraction of CSF1R, the expression level was higher in the hepatocellular carcinoma patients than in hepatic cirrhosis patients. It was demonstrated that these molecules are useful markers to specify a hepatocellular carcinoma patient. It was demonstrated that the aforementioned fractions of these molecules (molecule complex) are extremely effective to distinguish the disease state of the liver.

Example 7

Screening 3 of Hepatocarcinoma Indicating Biomarker

Comparative analysis was performed using a sample set consisting of the sera of five healthy volunteers (Healthy), five (viral) hepatitis patients (CH), five hepatic cirrhosis patients (LC) and five hepatocellular carcinoma patients (HCC) by the aforementioned serial column chromatography (FIG. 15). As a result, in the LCA-unbound/AAL-bound fractionation of pIgR, the expression level was significantly high in hepatic cirrhosis or hepatocellular carcinoma patients compared to in healthy volunteers and hepatitis patients. In the LCA fractionation of CSF1R, the expression level was significantly high in the hepatocellular carcinoma patients compared to in healthy volunteers, hepatitis patients and cirrhosis patients. Furthermore, in the LCA-unbound/AAL-bound fractionation of CSF1R, the expression level in the healthy volunteers was as low as in that of the hepatitis patients and significantly higher in the hepatic cirrhosis patients than them and further higher in the hepatocellular carcinoma patients. It was demonstrated that the quantitative determination of individual fractions of these molecules (molecule complex) is extremely effective to distinguish the states of these hepatic diseases.

Example 8

Screening in Connection with Fibrosis Progression

To validate the relationship with fibrosis progression, comparative analysis was performed using a sample set consisting of the sera of mild chronic hepatitis (F1), moderate chronic hepatitis (F2), severe chronic hepatitis (F3) and hepatic cirrhosis (F4) patients by the aforementioned serial column chromatography. As a result, in the LCA-unbound/AAL-bound fractionation of pIgR, the expression level in the sera of F3 or F4 patients was high compared to in F1 and F2 (FIG. 16). In contrast, in the LCA-bound fractionation of CSF1R, the expression level increased with the progression from F1 to F4 (FIG. 17). Furthermore, in the AAL-bound fractionation of CSF1R, the expression level in F3 was high compared to those in F1 and F2 and further higher in the serum of F4 patient (FIG. 17). By quantitative determination and comparison of a change of a glycan on these molecules (molecule complex), particularly, an LCA-bound or an LCA-unbound/AAL-bound glycan, it is considered that the disease state of the liver, particularly, the progress of hepatic fibrosis or early-stage hepatocellular carcinoma can be predicted.

Example 9

Preparation of pIgR from Biological Specimen by Immunoprecipitation

The serum was diluted 10-fold with PBS [pH7.4] and treated with heat in the presence of 0.2% SDS at 100° C. for 15 minutes.

Subsequently, the heat treated serum specimen (40 µL) was mixed with 0.2 µg of an affinity-purified and biotinylated goat anti-human pIgR antibody [R&D Cat#BAF2717, Lot#WZN01] and an antigen-antibody reaction was performed by a shaker at 1,400 rpm and at 20° C. for 2 hours. After completion of the reaction, to the solution, 20 µL of magnetic beads [Invitrogen Dynabeads™ MyOne™ Streptavidin T1 Cat#656.02] equilibrated with a washing buffer [20 mM Tris-HCl pH8.0, 1% TritonX100, 0.1% Na3N] were added. The mixture was gently mixed and shaken by a shaker at 1,400 rpm and at 20° C. for 1 hour. After shaking, magnetic beads and the supernatant were separated by a magnet stand [Invitrogen Dynal MPCTM-S Cat#120.20D]. After the supernatant separated was removed, magnetic beads were washed three times with PBS (1 mL). To the magnetic beads already washed, 20 µL of an elution buffer [0.2% SDS in PBS] was added. The mixture was lightly mixed by a vortex and an elution reaction was performed at 70° C. for 5 minutes. Thereafter, an microtube was allowed to stand still for 5 minutes at room temperature and centrifuged at 6,400 rpm for about 3 seconds. To the solution centrifuged, a washing buffer (20 µL) was added to bring the amount of solution to 40 µL. The mixture was gently mixed by a vortex. The supernatant and the beads were separated by a magnet stand. The supernatant was taken and used as an elution fraction. The pIgR amount of the elution fraction was quantified by Western blot. The above operation was repeated several times to obtain a solution containing pIgR (12.5 ng or more). This solution was precipitated with TCA/acetone by using a 2D-Clean up kit [GE Healthcare, Code#80-6484-51] and finally dissolved in a PBS solution to perform concentration and purification. The final concentration was adjusted to 10 ng/20 µL.

Example 10

Analysis of Glycan Profile of Immuno-Precipitated pIgR Specimen by Lectin Microarray By the aforementioned method, pIgR protein was purified and concentrated from the pooled sera of healthy volunteers (NHS: 14 individuals) and the pooled sera of hepatocellular carcinoma patients (HCC: 4 patients). This was subjected to lectin microarray to analyze a glycan profile of the pIgR protein (anti-pIgR antibody precipitate) (FIG. 18). As a result, a signal was observed in 19 types of lectins. Of them, in AOL, AAL, SNA, SSA, TJA-I, BPL, and ABA lectins, it was found that the signal derived from hepatocellular carcinoma patients (HCC) is high compared to that of healthy volunteers (NHS). In contrast, in MAL, DSA, EEL, WFA, and HPA lectins, it was found that the signal derived from hepatocellular carcinoma patients (HCC) was low compared to healthy volunteers (NHS).

Furthermore, with respect to a hepatocellular carcinoma patient (HCC), verification was performed again using a plurality of pooled sera (HCC, HCC-K1, HCC-K2, and HCC-K3). Similarly, pIgR protein was purified and concentrated and the glycan profile of the pIgR protein (anti-pIgR antibody precipitate) was analyzed (FIG. 19). As a result, the same results as in FIG. 18 were obtained. In MAL, SSA, SNA, TJA-I, EEL, ABA, and WFA, signal change was confirmed with good reproducibility.

Example 11

Simple Purification of CSF1R from Biological Specimen by Immunoprecipitation

The serum was diluted with PBS [pH7.4] 10 fold and treated with heat in the presence of 0.2% SDS at 100° C. for 15 minutes. Subsequently, the heat treated serum specimen (40 µL) and 0.2 µg of affinity-purified and biotinylated goat anti-human CSF1R antibody [R&D Cat#BAF329, Lot#BXD03] were mixed and an antigen-antibody reaction was performed by a shaker at 1,400 rpm and at 20° C. for 2 hours. After completion of the reaction, to the solution, 20 µL of magnetic beads [Invitrogen Dynabeads™ MyOne™ Streptavidin T1 Cat#656.02] equilibrated with a washing buffer [20 mM Tris-HCl pH8.0, 1% Triton X100, 0.1% Na3N] were added. The mixture was gently mixed and shaken by a shaker at 1,400 rpm and at 20° C. for 1 hour. After shaking, the magnetic beads and the supernatant were separated by use of a magnet stand [Invitrogen Dynal MPCTM-S Cat#120.20D]. After the supernatant separated was removed, the magnetic beads were washed three times with PBS (1 mL). To the magnetic beads washed, 20 µL of an elution buffer [0.2% SDS in PBS] was added. The mixture was gently mixed by a vortex and an elution reaction was performed at 70° C. for 5 minutes. Thereafter, a microtube was allowed to stand still for 5 minutes at room temperature and centrifuged at 6,400 rpm for about 3 seconds. To the solution centrifuged, a washing buffer (20 µL) was added to bring the amount of solution to 40 µL. The mixture was gently mixed by a vortex. The supernatant and the beads were separated by a magnet stand and the supernatant was taken and used as an elution fraction. The CSF1R amount of the elution fraction was quantified by Western blot.

Example 12

Analysis of Glycan Profile of Immuno-Precipitated CSF1R Specimen by Lectin Microarray By the aforementioned method, CSF1R protein was purified and concentrated each from the pooled sera of healthy volunteers (NHS) and the pooled sera of hepatocellular carcinoma patients (HCC). This was subjected to lectin microarray to analyze a glycan profile of the CSF1R protein (anti-pIgR antibody precipitate) (FIG. 20). As a result, a signal was observed in 20 types of lectins. Of them, in AOL, AAL, ECA, ABA, and WFA lectins, it was found that the signal from CSFR1 derived from hepatocellular carcinoma patients (HCC) is high compared to CSFR1 derived from healthy volunteers (NHS). It is considered that disease state of the liver, particularly, hepatocellular carcinoma, can be predicted by quantification and comparison of signals of these lectins.

Example 13

Analysis of Comparative Glycan Profile of Immuno-Precipitated CSF1R Specimen by Lectin Microarray Furthermore, CSF1R protein was purified and concentrated in the same manner from each of the pooled sera of healthy volunteers (NHS: 14 individuals), relatively advanced-age healthy volunteers (GP: 5 individuals), (viral) hepatitis patients (CH: 5 individuals), cirrhosis patients (LC: 5 individuals) and hepatocellular carcinoma patients (HCC: 5 individuals, K1: 2 individuals, K2: 6 individuals, K3: 2 individuals) and the glycan profile of CSF1R protein (anti-CSF1R antibody precipitate) was analyzed (FIGS. 21-1 and 21-2). As a result, the same lectin-profile results as the above results shown in FIG. 20 were obtained. However, signal intensity differed depending upon the state of a disease. More specifically, WFA lectin signal was not virtually detected in CSFR1 derived from the healthy volunteers (NHS), relatively advanced-age healthy volunteers (GP), (viral) hepatitis patients (CH) and cirrhosis patients (LC), whereas, a significant signal was observed in (HCC, K1, K2, K3) derived from the hepatocellular carcinoma patients (HCC). It is considered that disease state of the liver, particularly, hepatocellular carcinoma, can be predicted by quantification and comparison of signals of these lectins.

Example 14

Butch Fractionation Method by WFA Derived from the Serum

In the analysis so far made, it has been clarified that the signal of WFA lectin increases in e.g., CSFR1 derived from a hepatocellular carcinoma patient (HCC). This was validated in accordance with FIG. 22A. More specifically, WFA lectin-bound protein was captured from the serum by lectin affinity-chromatography, etc. The bound fraction was electrophoresed and subjected to Western blot analysis using an anti-CSF1R antibody, together with an input (untreated sample). In this manner, the ratio of WFA-bound target protein was computed. Finally, the amount of CSF1R having a WFA-bound glycan present in the serum was tested as shown in FIG. 22B.

A specific method for capturing and recovering WFA-bound protein will be described below.

First, 5 μg of biotinylated WFA [Vector biotinilated WFA Cat#B-1355] was diluted with 40 μL of PBS [pH 7.4] to obtain a lectin dilution solution. To the lectin dilution solution, 204 of magnetic beads [Invitrogen Dynabeads™ MyOne™ Streptavidin T1 Cat#656.02] equilibrated with PBS were added. The mixture was gently mixed and shaken by a shaker at 1,400 rpm and 20° C., for 30 minutes. After shaking, magnetic beads and the supernatant were separated by a magnet stand [Invitrogen Dynal MPCTM-S Cat#120.20D]. After the supernatant separated was removed, magnetic beads were washed three times with PBS (100 μL). After the serum was diluted with PBS [pH7.4] 10 fold, the serum was treated with heat in the presence of 0.2% SDS at 100° C. for 15 minutes. The heat treated serum specimen (10 μL) was diluted with PBS 10 fold and adjusted a total amount to 100 μL (crude). The magnetic beads (20 μL) with WFA bounded thereto and the serum (100 μL) prepared were mixed in a microtube and stirred by a shaker at 1,400 rpm and at 4° C., O/N. After shaking, the magnetic beads and the supernatant were separated by use of a magnet stand. After the supernatant separated was removed (WFA-unbound fraction), the magnetic beads were washed three times with PBS (500 μL). To the magnetic beads washed, 20 μL of an elution buffer [0.1% SDS 0.2M lactose in PBS] was added. The mixture was gently mixed by a vortex and an elution reaction was performed at 1,400 rpm and at 20° C. for 2 hours. Thereafter, the magnetic beads and the supernatant were separated by a magnet stand to recover the supernatant (WFA bound fraction).

Example 15

The amount of WFA-bound CSF1R present in the sera was checked using a sample set consisting of the sera of five healthy volunteers (Normal), five (viral) hepatitis patients (CHC), five hepatic cirrhosis patients (LC) and five hepatocellular carcinoma patients (HCC) by the aforementioned method (method of Example 14). As a result, as shown in FIG. 22C, in the cirrhosis patients (LC), the amount of WFA-bound CSF1R present in the sera was high compared to those of the healthy volunteers (Normal) and (viral) hepatitis patients (CHC). Furthermore, in the hepatocellular carcinoma patients (HCC), the amount of WFA-bound CSF1R present in the sera was significantly high compared to those of the healthy volunteers (Normal), (viral) hepatitis patients (CHC) and hepatic cirrhosis patients (LC). In the hepatic cirrhosis patients (LC), a significantly high amount was observed as an exception. In the hepatic cirrhosis patients, since there is a risk of hepatocarcinoma (bud), it was suggested that these may possibly reflect hepatocellular carcinoma. As described above, it is considered that disease state of the liver, particularly, hepatocellular carcinoma, can be predicted by quantification and comparison of WFA lectin signal (WFA-bound glycans) on CSF1R.

Example 16

Screening in Connection with Fibrosis Progression

To validate the relationship with fibrosis progression, WFA-bound CSF1R amount was analyzed using a sample set consisting of the sera of mild chronic hepatitis (F1), moderate chronic hepatitis (F2), severe chronic hepatitis (F3) and hepatic cirrhosis (F4) patients by the aforementioned method (method of Example 14). In the WFA-bound fractionation, CSF1R was virtually not detected in F1 to F3 and detected in part of the patient's serum of F4 (one out of two cases) (FIG. 22D). Furthermore, the amount of CSF1R in the serum was checked by use of crude serum without fractionation. As a result, the amount of CSF1R protein in the serum increased with the progress of F1 to F4. This fact suggests a possibility of quantifying the progress of fibrosis by the protein amount. In addition to this, if a change of a glycan structure on CSF1R (LCA-bound glycan or LCA-unbound/AAL-bound glycan) as described in Example 8 is used in combination, it is considered that the accuracy of differential identification can be increased. In addition, from the results of two cases of F4 patients, it was found that the amount of CSF1R in the serum is relatively large in both cases; however, the amount of CSF1R having a WFA-bound glycan significantly differ. This is considered to reflect a phenomenon other than fibrosis. In the stage of F4, most cases have hepatic cirrhosis and the possibility that patients already have hepatocarcinoma (bud) is high. Therefore, hepatocellular carcinoma is highly possibly reflected by this. It is considered that disease state of the liver, particularly, early-stage hepatocellular carcinoma, can be predicted by quantification and comparison of WFA-bound glycan on CSF1R.

INDUSTRIAL APPLICABILITY

The present invention can be used in manufacturing an apparatus, tool or kit for determining a hepatic disease or hepatic disease-state, in determination of a hepatic disease-state or detection of hepatic cirrhosis.

The invention claimed is:

1. A method for detecting hepatocarcinoma in a subject, comprising analyzing a glycosylation change associated with the progress of hepatocarcinoma in at least one hepatic disease-state-indicating glycan marker glycoprotein in a specimen taken from the subject, wherein the hepatic disease-state-indicating glycan marker glycoprotein is
protein CSF1R having a glycosylation change including fucosylation;
wherein the analyzing comprises measurement of an amount of the hepatic disease-state-indicating glycan marker glycoprotein in combination with measurement of LCA binding the hepatic disease-state-indicating glycan marker glycoprotein or AAL binding the hepatic disease-state-indicating glycan marker glycoprotein,
wherein elevated hepatic disease-state-indicating glycan marker glycoprotein in combination with elevated LCA binding the hepatic disease-state-indicating glycan marker glycoprotein or AAL binding the hepatic disease-state-indicating glycan marker glycoprotein is indicative of hepatocarcinoma in the subject,
provided that the hepatocarcinoma is not one arisen from metastasis.

2. A method for detecting hepatocarcinoma in a subject, comprising analyzing a glycosylation change associated with the progress of hepatocarcinoma in CSF1R in a specimen taken from the subject, wherein the analyzing comprises measurement of an amount of CSF1R binding to a lectin selected from a group consisting of AOL, AAL, ECA, ABA and WFA, wherein increased CSF1R binding to a lectin selected from a group consisting of AOL, AAL, ECA, ABA and WFA is indicative of hepatocarcinoma in the subject.

3. A method for determining progress of fibrosis in a subject, comprising analyzing a glycosylation change associated with the progress of fibrosis in CSF1R in a specimen taken from the subject, wherein the analyzing comprises measurement of an amount of CSF1R binding to LCA or AAL in the specimen taken from the subject and in a specimen from a healthy subject, and comparing the amount of CSF1R binding to LCA or AAL in the specimen from the subject and the specimen from the healthy subject, wherein increased CSF1R binding to LCA or AAL in the specimen taken from the subject is indicative of progress of fibrosis in the subject.

4. A method for determining progress of fibrosis, detecting hepatic cirrhosis, or predicting incidence and recurrence of hepatocarcinoma in a subject comprising analyzing a glycosylation change associated with the progress of fibrosis, hepatic cirrhosis, or hepatocarcinoma in CSF1R in a specimen taken from the subject, wherein the analyzing comprises measurement of an amount of CSF1R binding to WFA in the specimen taken from the subject and in a specimen from a healthy subject, and comparing the amount of CSF1R binding to WFA in the specimen from the subject and the specimen from the healthy subject, wherein increased CSF1R binding to WFA in the specimen taken from the subject is indicative of progress of fibrosis, hepatic cirrhosis, or predicting incidence and recurrence of hepatocarcinoma in the subject.

5. A method for detecting hepatocarcinoma in a subject, comprising analyzing a glycosylation change associated with the progress of hepatocarcinoma in at least one hepatic disease-state-indicating glycan marker glycoprotein in a specimen taken from the subject, wherein the hepatic disease-state-indicating glycan marker glycoprotein is protein CSF1R having a glycosylation change including fucosylation;

wherein the analyzing comprises measurement of an amount of the hepatic disease-state-indicating glycan marker glycoprotein in the specimen taken from the subject in combination with measurement of LCA binding the hepatic disease-state-indicating glycan marker glycoprotein or AAL binding the hepatic disease-state-indicating glycan marker glycoprotein in the specimen taken from the subject wherein an elevated amount of the hepatic disease-state-indicating glycan marker glycoprotein in the specimen taken from the subject in combination with elevated LCA binding the hepatic disease-state-indicating glycan marker glycoprotein or AAL binding the hepatic disease-state-indicating glycan marker glycoprotein in the specimen taken from the subject is indicative of hepatocarcinoma in the subject.

* * * * *